(12) United States Patent
Abreu

(10) Patent No.: US 8,914,089 B2
(45) Date of Patent: Dec. 16, 2014

(54) NONINVASIVE MEASUREMENT OF CHEMICAL SUBSTANCES

(75) Inventor: Marcio Marc Abreu, North Haven, CT (US)

(73) Assignee: Geelux Holdings, Ltd., Tortola (VG)

( * ) Notice: Subject to any disclaimer, the term of this patent is extended or adjusted under 35 U.S.C. 154(b) by 1661 days.

(21) Appl. No.: 12/213,093

(22) Filed: Jun. 13, 2008

(65) Prior Publication Data

US 2009/0036761 A1 Feb. 5, 2009

Related U.S. Application Data

(62) Division of application No. 10/423,056, filed on Apr. 25, 2003, now Pat. No. 7,403,805, which is a division (Continued)

(51) Int. Cl.
*A61B 5/1455* (2006.01)
*A61B 5/00* (2006.01)
(Continued)

(52) U.S. Cl.
CPC ....... *A61B 5/1455* (2013.01); *A61B 2560/0214* (2013.01); *A61B 2562/12* (2013.01);
(Continued)

(58) Field of Classification Search
USPC .......................................... 600/310, 318, 319
See application file for complete search history.

(56) References Cited

U.S. PATENT DOCUMENTS

| 3,545,260 A | 12/1970 | Lichtenstein et al. |
| 3,585,849 A | 6/1971 | Grolman |

(Continued)

FOREIGN PATENT DOCUMENTS

| DE | 4433104 | 5/1996 |
| EP | 0236028 | 9/1987 |

(Continued)

OTHER PUBLICATIONS

RCA Technical Notes, Contact Lens Tonometer by Robert E. Morey, RCA TN No. 602, dated Dec. 1964, 2 pages.

(Continued)

*Primary Examiner* — Eric Winakur
(74) *Attorney, Agent, or Firm* — Studebaker & Brackett PC

(57) ABSTRACT

Utilization of a contact device placed on the eye in order to detect physical and chemical parameters of the body as well as the non-invasive delivery of compounds according to these physical and chemical parameters, with signals being transmitted continuously as electromagnetic waves, radio waves, infrared and the like. One of the parameters to be detected includes non-invasive blood analysis utilizing chemical changes and chemical products that are found in the conjunctiva and in the tear film. A transensor mounted in the contact device laying on the cornea or the surface of the eye is capable of evaluating and measuring physical and chemical parameters in the eye including non-invasive blood analysis. The system utilizes eye lid motion and/or closure of the eye lid to activate a microminiature radio frequency sensitive transensor mounted in the contact device. The signal can be communicated by wires or radio telemetered to an externally placed receiver. The signal can then be processed, analyzed and stored. Several parameters can be detected including a complete non-invasive analysis of blood components, measurement of systemic and ocular blood flow, measurement of heart rate and respiratory rate, tracking operations, detection of ovulation, detection of radiation and drug effects, diagnosis of ocular and systemic disorders and the like.

11 Claims, 84 Drawing Sheets

Related U.S. Application Data of application No. 10/359,254, filed on Feb. 6, 2003, now Pat. No. 7,041,063, which is a division of application No. 09/790,653, filed on Feb. 23, 2001, now Pat. No. 6,544,193.

(51) Int. Cl.

| | | |
|---|---|---|
| *A61B 5/145* | (2006.01) | |
| *A61B 3/12* | (2006.01) | |
| *A61F 9/00* | (2006.01) | |
| *A61B 8/00* | (2006.01) | |
| *A61B 3/16* | (2006.01) | |
| *A61B 5/18* | (2006.01) | |
| *A61B 8/06* | (2006.01) | |
| *A61B 5/01* | (2006.01) | |
| *A61B 5/03* | (2006.01) | |
| *A61B 5/1486* | (2006.01) | |

(52) U.S. Cl.
CPC .............. *A61B 5/18* (2013.01); *A61B 5/0002* (2013.01); *A61B 5/6814* (2013.01); *A61B 5/412* (2013.01); *A61B 5/14555* (2013.01); *A61B 5/14532* (2013.01); *A61B 5/416* (2013.01); *A61B 2562/0238* (2013.01); *A61B 2560/0219* (2013.01); *A61B 8/06* (2013.01); *A61B 5/4839* (2013.01); *A61B 2560/0252* (2013.01); *A61B 5/445* (2013.01); *A61B 3/1241* (2013.01); *A61B 5/14539* (2013.01); *A61B 5/01* (2013.01); *A61B 2560/0418* (2013.01); *A61B 5/14546* (2013.01); *A61B 5/031* (2013.01); *A61F 9/0017* (2013.01); *A61B 8/56* (2013.01); *A61B 3/16* (2013.01); *A61B 5/1486* (2013.01)
USPC ........................................ 600/319; 600/318

(56) References Cited

U.S. PATENT DOCUMENTS

| | | | |
|---|---|---|---|
| 3,724,263 | A | 4/1973 | Rose et al. |
| 3,769,961 | A | 11/1973 | Fatt |
| 3,893,444 | A | 7/1975 | Fatt |
| 3,963,019 | A | 6/1976 | Quandt |
| 4,186,184 | A | 1/1980 | Zaffaroni |
| 4,305,399 | A | 12/1981 | Beale |
| 4,321,261 | A | 3/1982 | Ellis et al. |
| 4,330,299 | A | 5/1982 | Cerami |
| 4,344,438 | A | 8/1982 | Schultz |
| 4,386,831 | A | 6/1983 | Grounauer |
| 4,485,820 | A | 12/1984 | Flower |
| 4,597,392 | A | 7/1986 | Opitz et al. |
| 4,628,938 | A | 12/1986 | Lee |
| 4,629,424 | A | 12/1986 | Lauks et al. |
| 4,771,792 | A | 9/1988 | Seale |
| 4,836,206 | A * | 6/1989 | Maxwell et al. ............. 600/340 |
| 4,860,755 | A | 8/1989 | Erath |
| 4,922,913 | A | 5/1990 | Waters et al. |
| 4,944,303 | A | 7/1990 | Katsuragi |
| 4,947,849 | A | 8/1990 | Takahashi et al. |
| 4,951,671 | A | 8/1990 | Coan |
| 5,005,577 | A | 4/1991 | Frenkel |
| 5,040,539 | A * | 8/1991 | Schmitt et al. ................. 600/340 |
| 5,076,274 | A | 12/1991 | Matsumoto |
| 5,109,852 | A | 5/1992 | Kaye et al. |
| 5,115,815 | A | 5/1992 | Hansen |
| 5,148,807 | A | 9/1992 | Hsu |
| 5,165,409 | A | 11/1992 | Coan |
| 5,179,953 | A | 1/1993 | Kursar |
| 5,183,044 | A | 2/1993 | Nishio et al. |
| 5,209,231 | A | 5/1993 | Cote et al. |
| 5,217,015 | A | 6/1993 | Kaye et al. |
| 5,222,495 | A | 6/1993 | Clarke et al. |
| 5,246,867 | A | 9/1993 | Lakowicz et al. |
| 5,251,627 | A | 10/1993 | Morris |
| 5,295,495 | A | 3/1994 | Maddess |
| 5,297,554 | A | 3/1994 | Glynn et al. |
| 5,313,941 | A | 5/1994 | Braig et al. |
| 5,341,805 | A | 8/1994 | Stavridi et al. |
| 5,342,283 | A | 8/1994 | Good |
| 5,342,789 | A | 8/1994 | Chick et al. |
| 5,352,411 | A | 10/1994 | Khuri |
| 5,356,780 | A | 10/1994 | Robinson et al. |
| 5,375,595 | A | 12/1994 | Sinha et al. |
| 5,383,452 | A | 1/1995 | Buchert |
| 5,433,197 | A | 7/1995 | Stark |
| 5,435,307 | A | 7/1995 | Friauf et al. |
| 5,503,770 | A | 4/1996 | James et al. |
| 5,636,635 | A | 6/1997 | Massie et al. |
| 5,666,956 | A | 9/1997 | Buchert |
| 5,673,692 | A | 10/1997 | Schulze et al. |
| 5,676,143 | A | 10/1997 | Simonsen et al. ............. 128/633 |
| 5,711,915 | A | 1/1998 | Siegmund et al. |
| 5,728,281 | A | 3/1998 | Holmström et al. .......... 204/403 |
| 5,769,791 | A * | 6/1998 | Benaron et al. ............... 600/473 |
| 5,813,982 | A | 9/1998 | Baratta |
| 5,820,557 | A | 10/1998 | Hattori et al. |
| 5,830,139 | A | 11/1998 | Abreu |
| 5,854,078 | A | 12/1998 | Asher et al. |
| 5,898,004 | A | 4/1999 | Asher et al. |
| 5,995,860 | A * | 11/1999 | Sun et al. ....................... 600/322 |
| 6,011,984 | A | 1/2000 | Van Antwerp et al. |
| 6,040,194 | A | 3/2000 | Chick et al. |
| 6,072,180 | A | 6/2000 | Kramer et al. |
| 6,120,460 | A | 9/2000 | Abreu |
| 6,123,668 | A | 9/2000 | Abreu |
| 6,152,875 | A | 11/2000 | Hakamata |
| 6,178,346 | B1 | 1/2001 | Amundson et al. |
| 6,181,957 | B1 * | 1/2001 | Lambert et al. ............... 600/319 |
| 6,187,599 | B1 | 2/2001 | Asher et al. |
| 6,197,534 | B1 | 3/2001 | Lakowicz et al. |
| 6,197,928 | B1 | 3/2001 | Tsien et al. |
| 6,213,943 | B1 | 4/2001 | Abreu |
| 6,226,089 | B1 | 5/2001 | Hakamata ....................... 356/432 |
| 6,256,522 | B1 | 7/2001 | Schultz |
| 6,312,393 | B1 | 11/2001 | Abreu |
| 6,319,540 | B1 | 11/2001 | Van Antwerp et al. |
| 6,423,001 | B1 | 7/2002 | Abreu |
| 6,544,193 | B2 | 4/2003 | Abreu |
| 6,594,518 | B1 * | 7/2003 | Benaron et al. ............... 600/342 |
| 6,681,127 | B2 | 1/2004 | March |

FOREIGN PATENT DOCUMENTS

| | | |
|---|---|---|
| JP | 9168602 | 6/1997 |
| JP | 200037355 | 2/2000 |
| WO | 93/01745 | 2/1993 |
| WO | 93/07801 | 4/1993 |
| WO | 97/19188 | 5/1997 |
| WO | 98/22820 | 5/1998 |
| WO | 99/51142 | 10/1999 |
| WO | 00/10007 | 2/2000 |
| WO | 00/13580 | 3/2000 |
| WO | 00/16099 | 3/2000 |
| WO | 00/18237 | 4/2000 |
| WO | 00/64492 | 11/2000 |
| WO | 02/03855 | 1/2002 |
| WO | 02/067688 | 9/2002 |

OTHER PUBLICATIONS

Ophthal. Phsyiol. Opt., 1989, vol. 9, April, Research Note, Multiple Applications of the NCT: An Assessment of Instrument's Effect on IOP by G.E. Russell and J.P.G. Bergmanson, pp. 212-214.

Arch Ophthalmol—vol. 97, Mar. 1979, The Pneumatonograph—A Laboratory Study, by Robert A. Moses, M.D. and Walter J. Grodzki Jr., D.D.S., pp. 547-552.

IEEE Transactions on bio-Medical Engineering, vol. BME-14, No. 2, Apr. 1967, Miniature Passive Pressure Transensor for Implanting in the Eye, by C.C. Collins, pp. 74-83.

Trans. Amer. Acad. of O. & O., Jan.-Feb. 1957, Tonometer Calibra-

(56) References Cited

OTHER PUBLICATIONS tion, An Attempt to Remove Discrepancies Found in the 1954 Calibration Scale for Schiotz Tonometers by Jonas S. Friedenwald, M.D., pp. 108-123.

Investigative Ophthalmology, Feb. 1962, The Relationship Between Pressure and Volume Changes in Living and Dead Rabbit Eyes, by John E. Eisenlohr and Maurice E. Langham, pp. 63-77.

Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.

The British Journal of Ophthalmology, Jun. 1920, Communications—Tonometry, by HJ. Schiötz, pp. 249-261.

American Journal of Opthalmology, vol. 20, No. 10, Oct. 1937, Contribution to the Theory and Practice of Tonometry by Jonas S. Friedenwald, M.D., pp. 985-1024.

Ophthalmologica vol. 150, No. 5, (1965), Rheology of the Human Sclera, Unifying Formulation of Ocular Rigidity, by W.K. McEwen and Roger St. Helen, pp. 321-346.

A.M.A. Archives of Ophthalmology, vol. 57, Apr. 1957, Tonometer Calibration, by Earle H. McBain, M.D., pp. 520-531.

The Photonics Dictionary, 1996 Book 4, $42^{nd}$ Edition, pp. D-24, D153.

Manual of Skin Diseases, Fifth Edition, Gordon C. Sauer, MD., 1985, pp. 204, 373.

Fm-2 Fluorotron™ Master Ocular Fluorophotometer Specifications, 1994 OcuMetrics, Inc.

Textbook of Biochemistry With Clinical Correlations, Second Edition, Thomas M. Devlin, Ph.D., 1986, pp. 118, 139.

Physical Optics, Third Revised Edition, Robert W. Wood, 1961, pp. 650-651.

\* cited by examiner

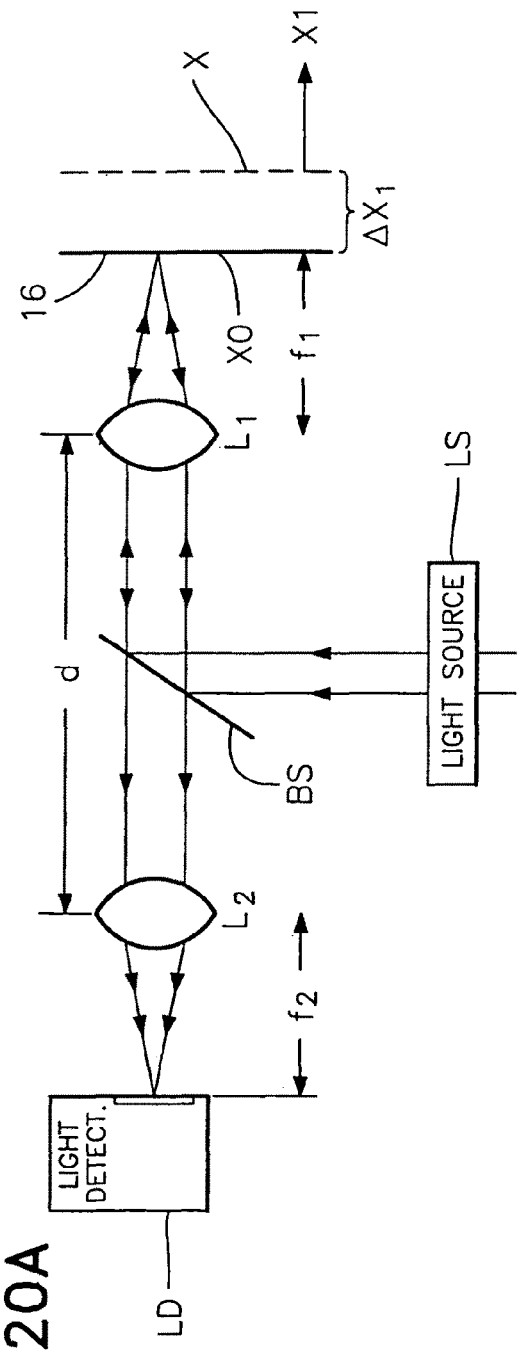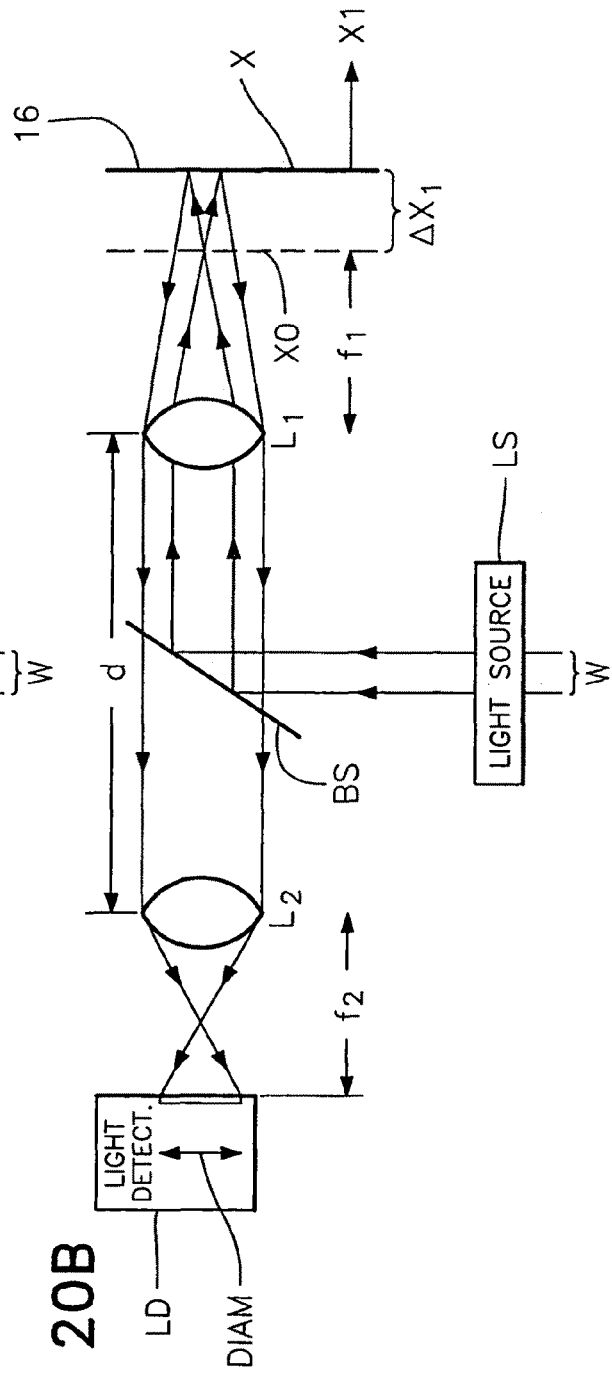
FIG. 20A
FIG. 20B

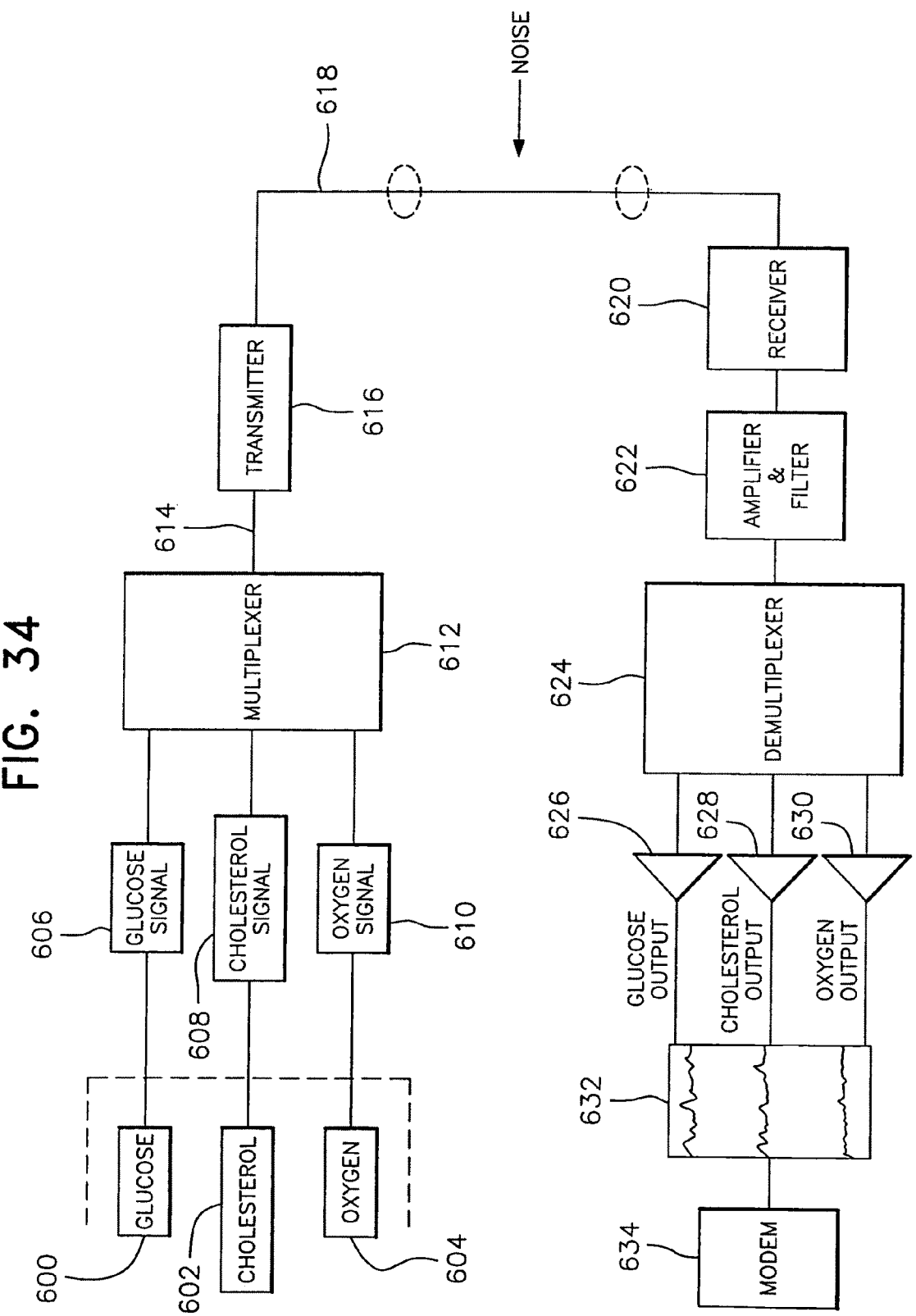

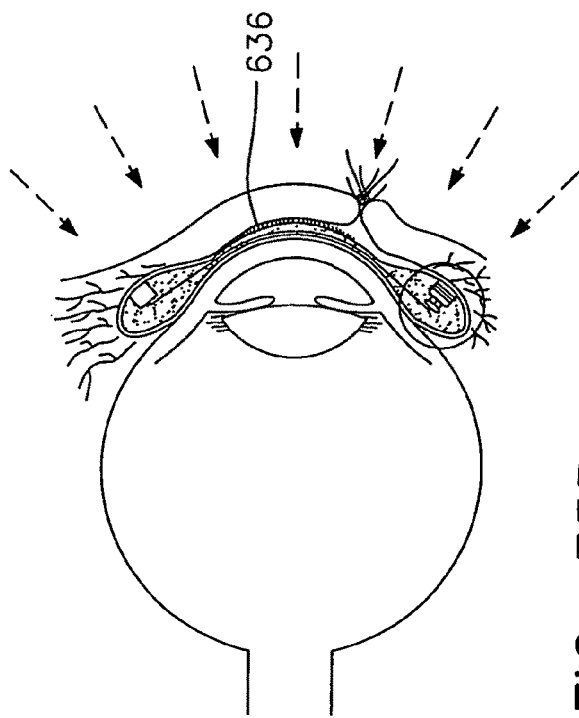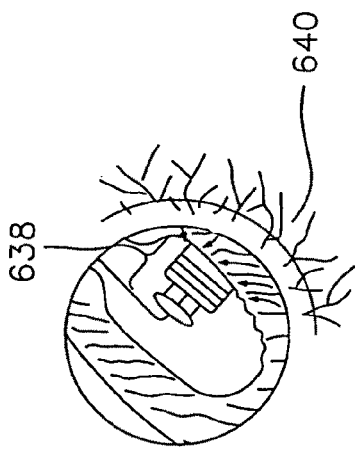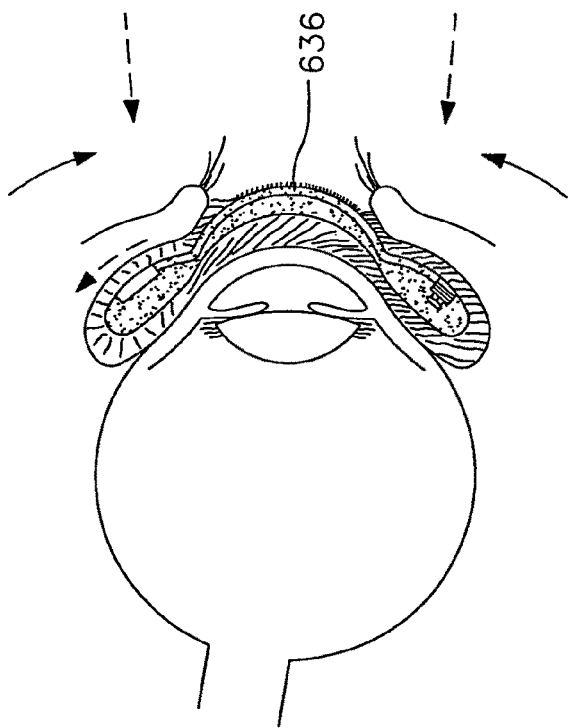

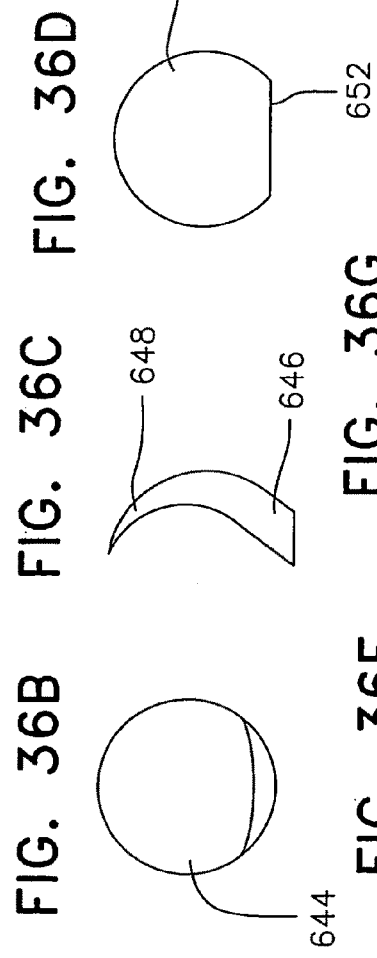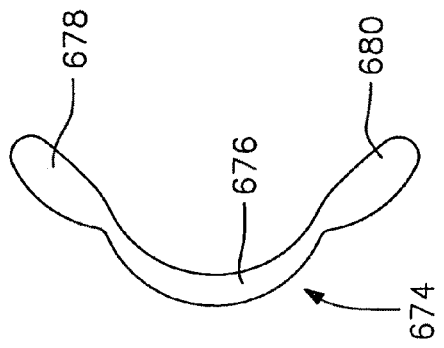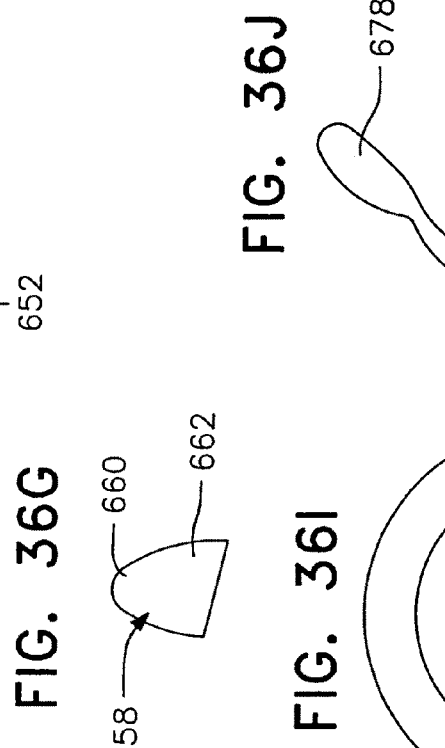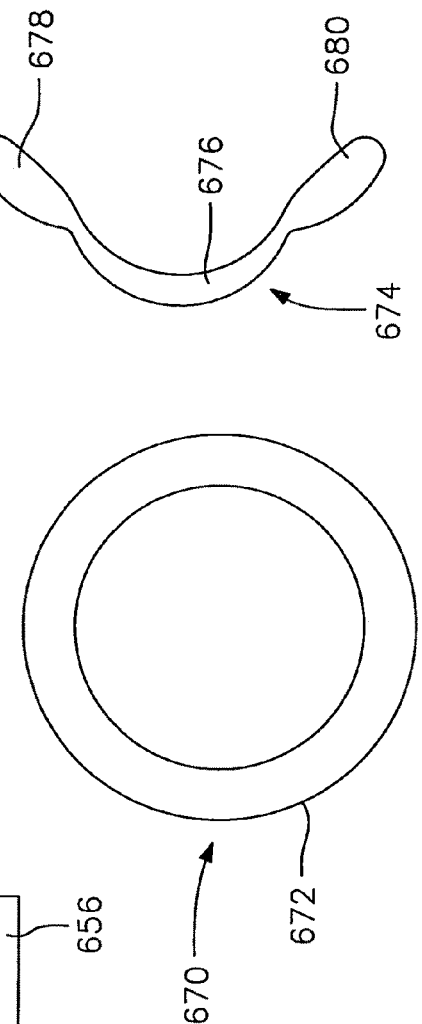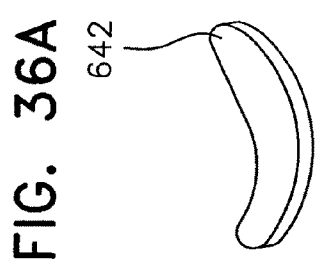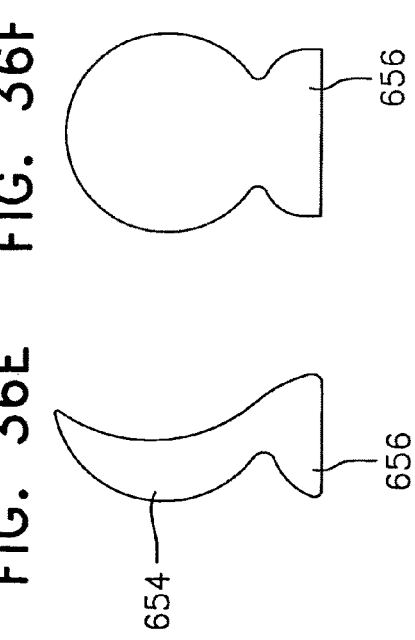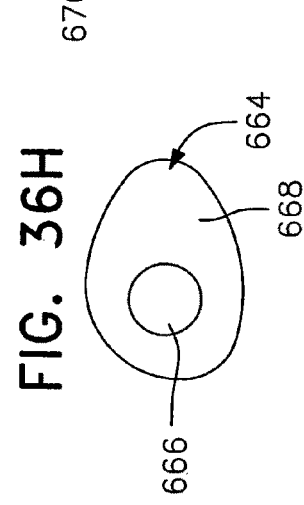

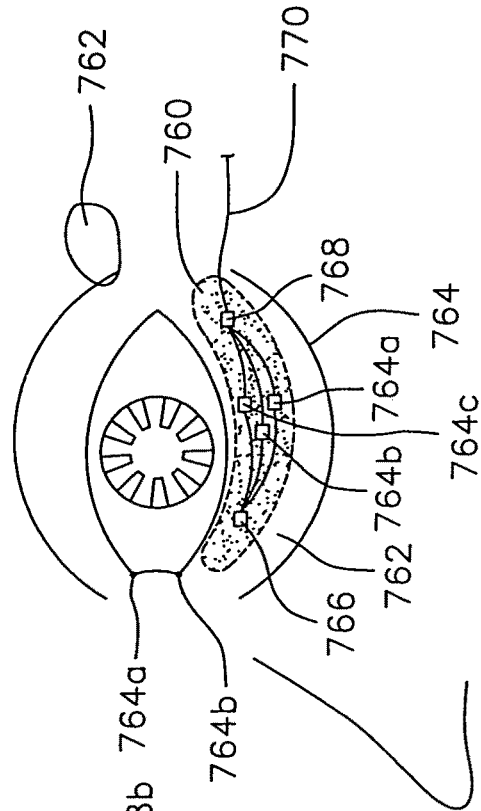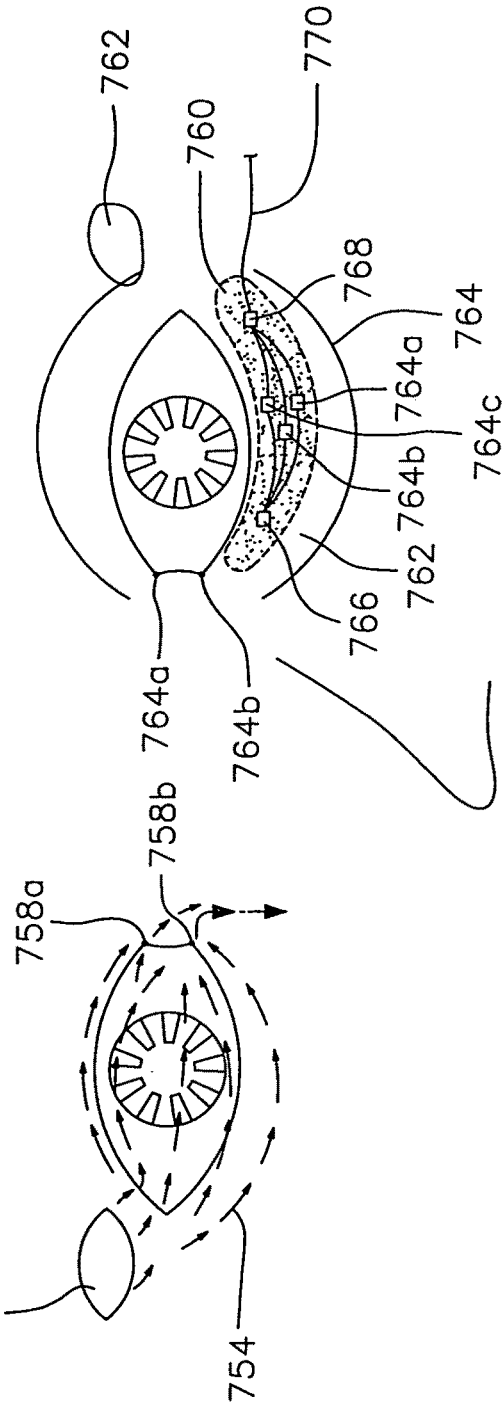

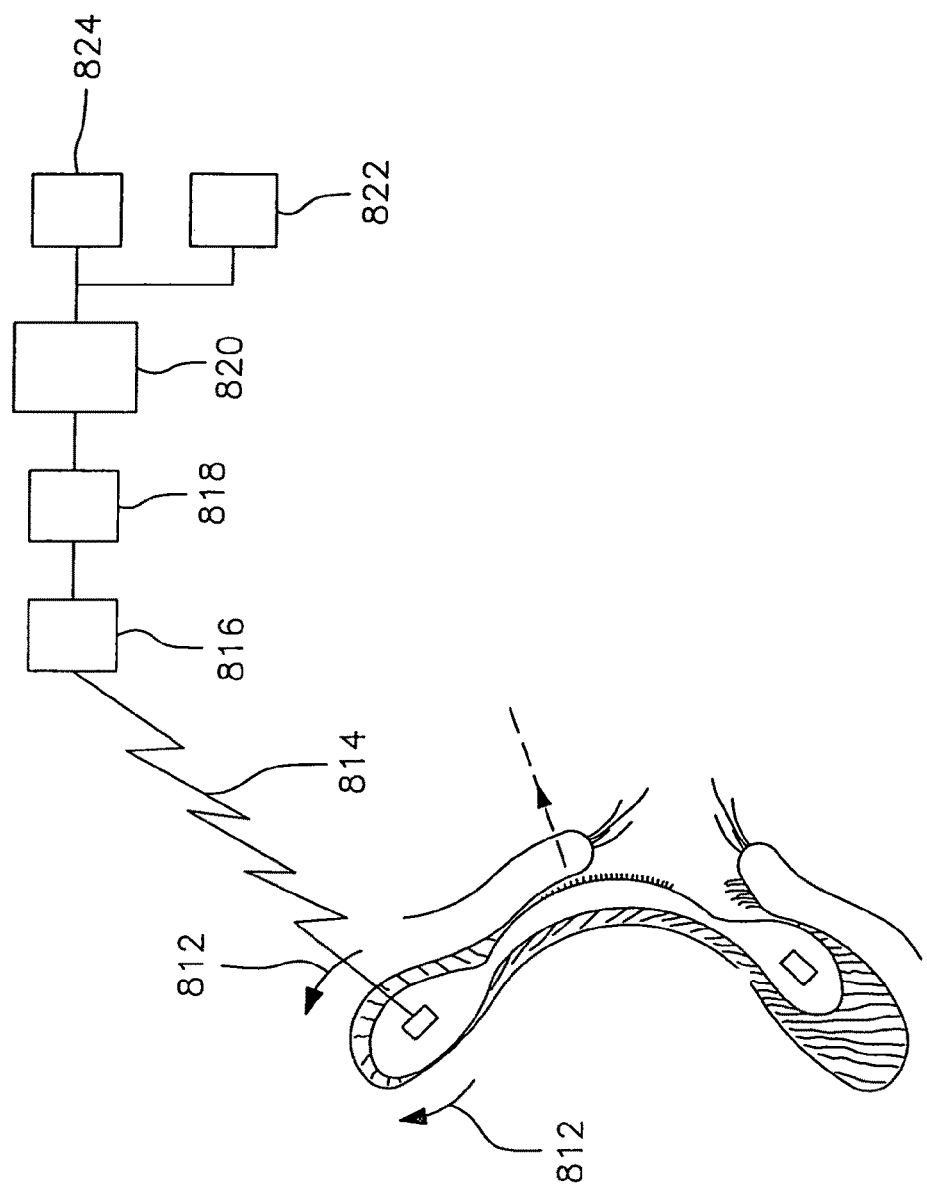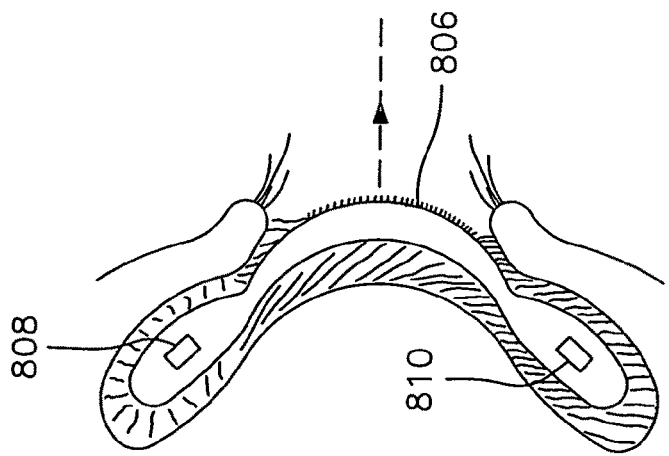

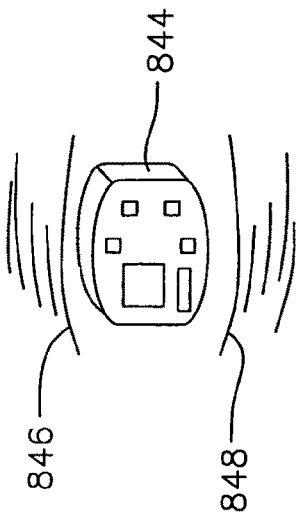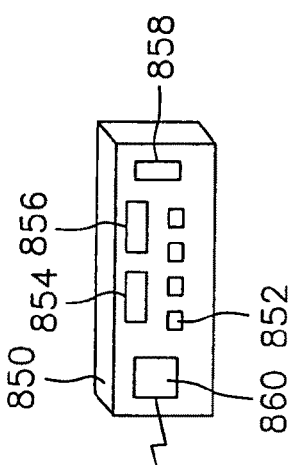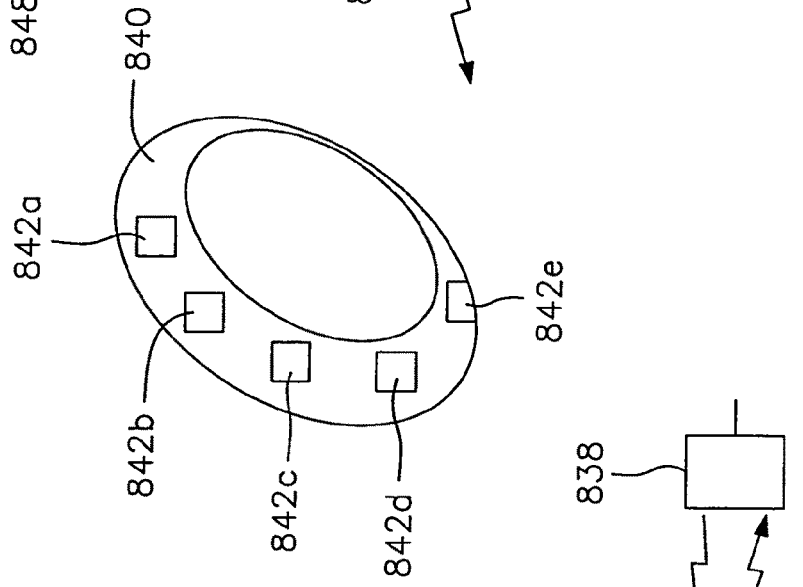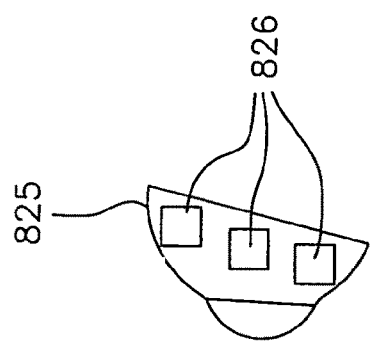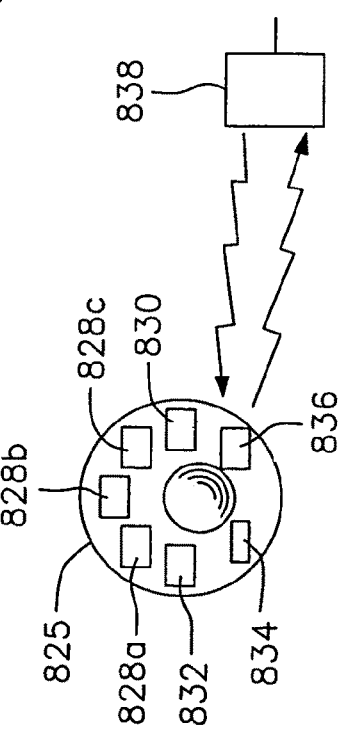

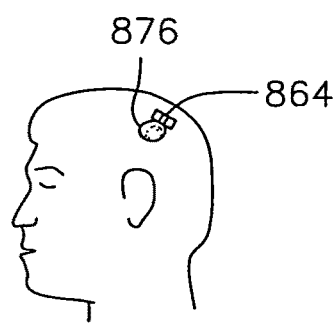
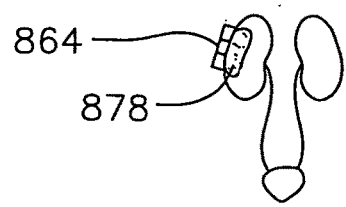
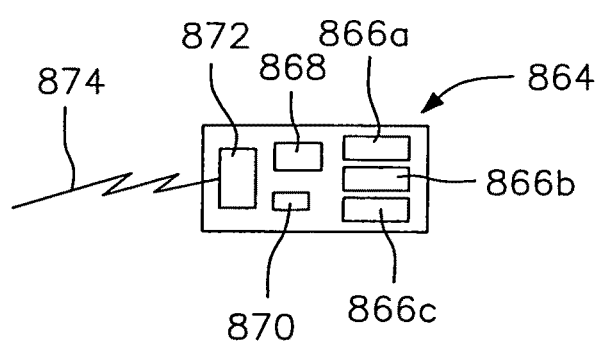
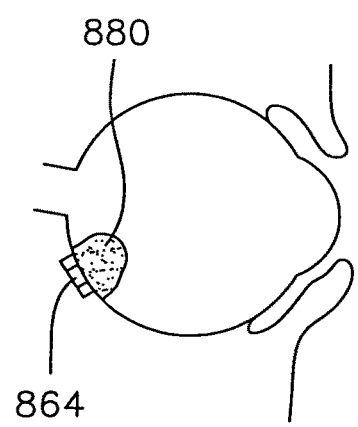
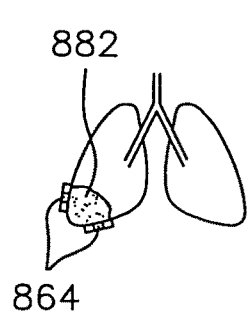
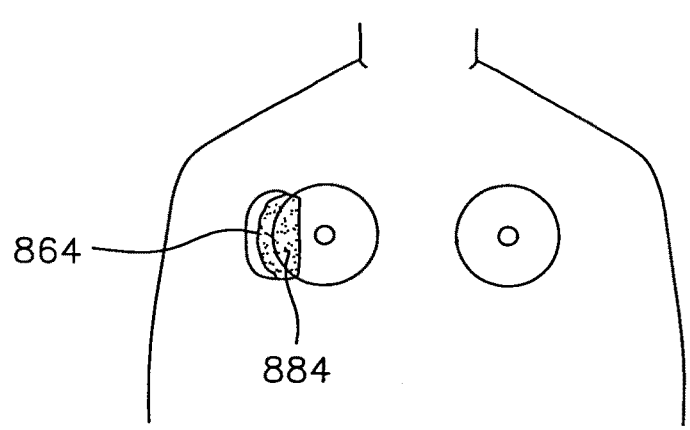

- Superior forux
- Upper Lid Pocket
- 1188
- 1180
- 10–12 mm
- 1186
- 1182
- 1188
- 8–10 mm
- Lower Lid Pocket
- 1184
- 40 mm ▨ Palpebral Conjuctiva    ▧ Bulbar Conjuctiva

1192

1190

1204  1196
1198        1202
1202
1206  1194

Apposition and fluid flow created by the presence of the ICL

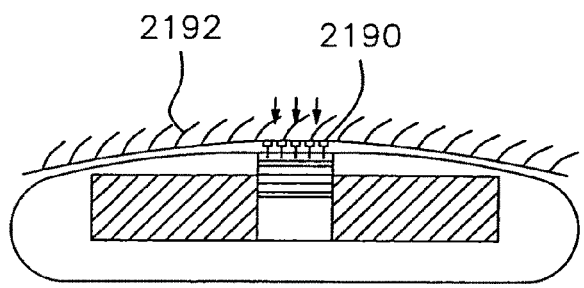
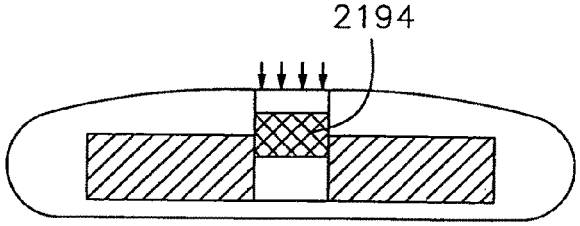
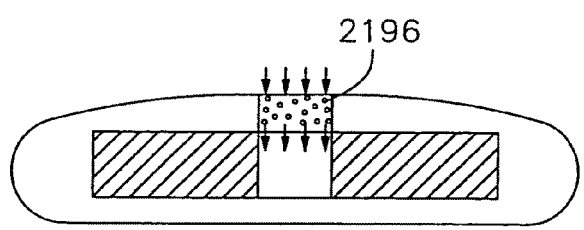
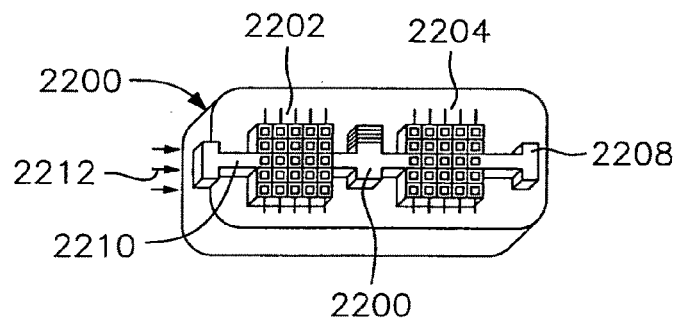
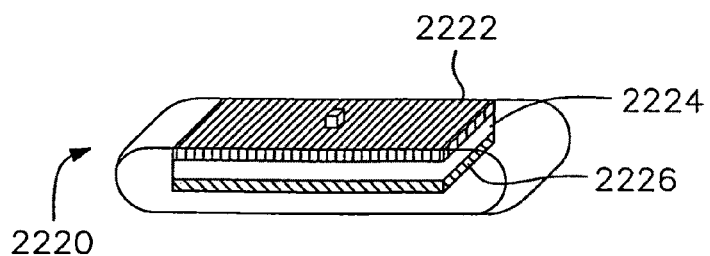

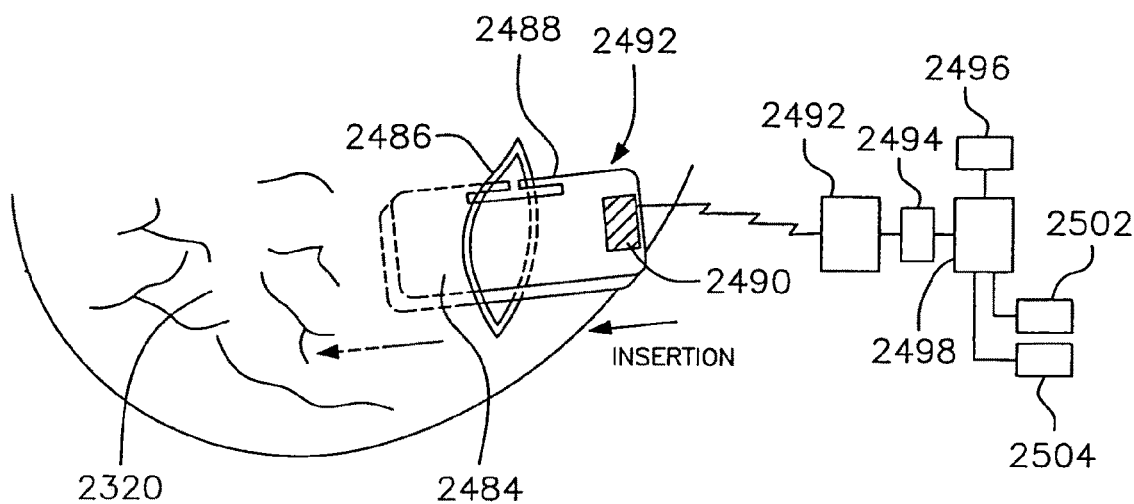
FIG. 93A
FIG. 93B
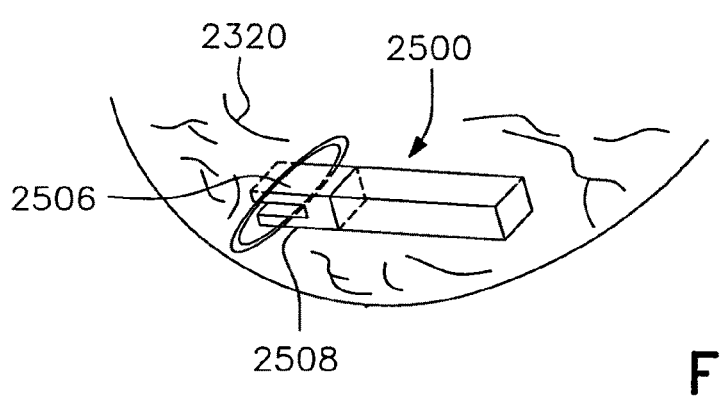
FIG. 94
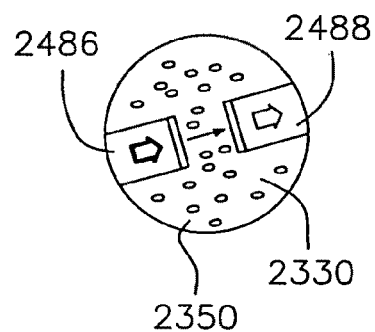
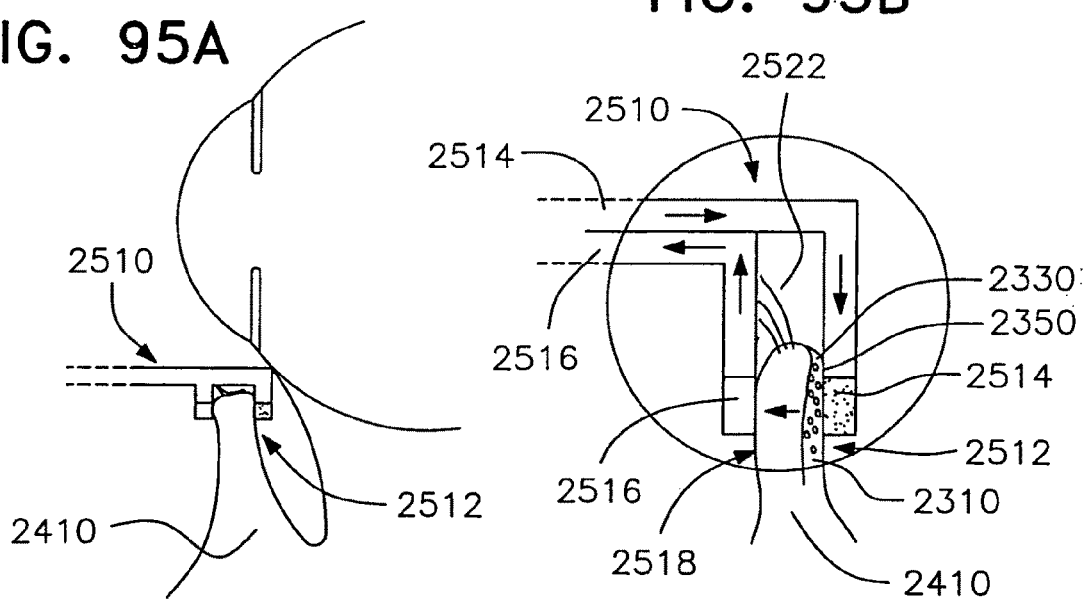
FIG. 95A
FIG. 95B

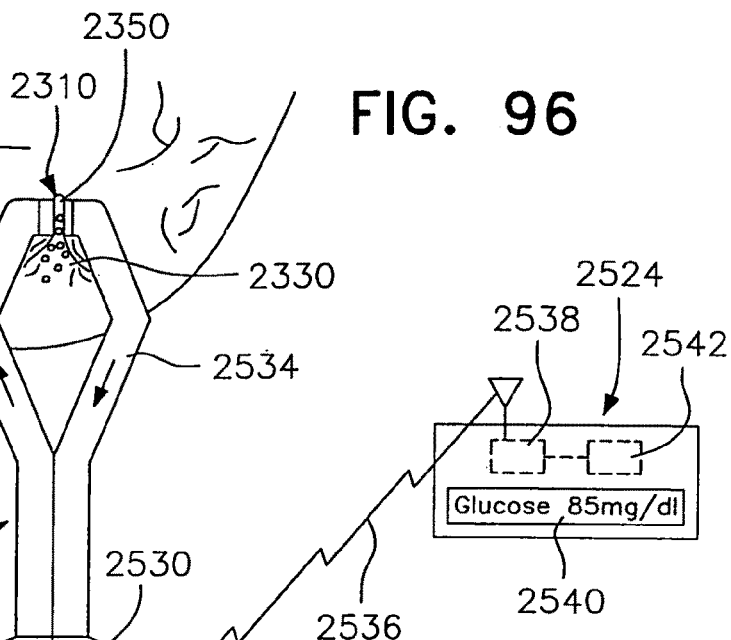
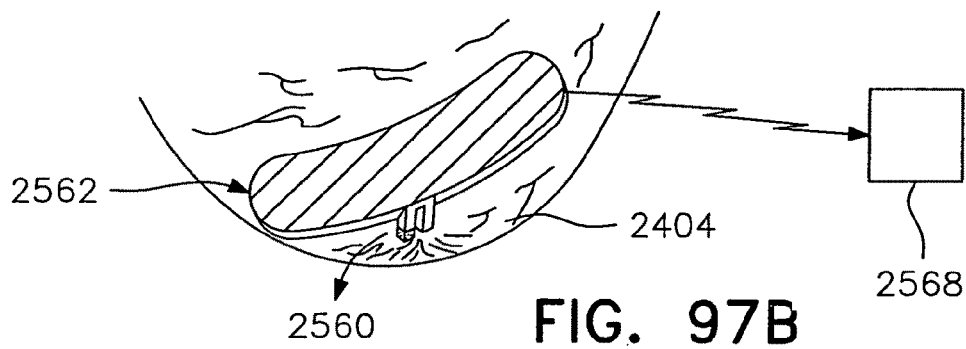
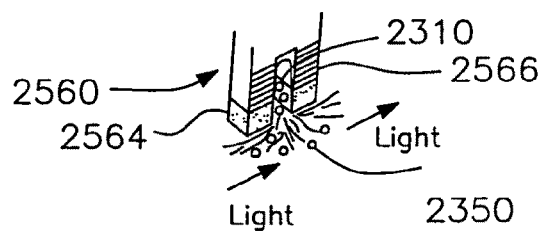
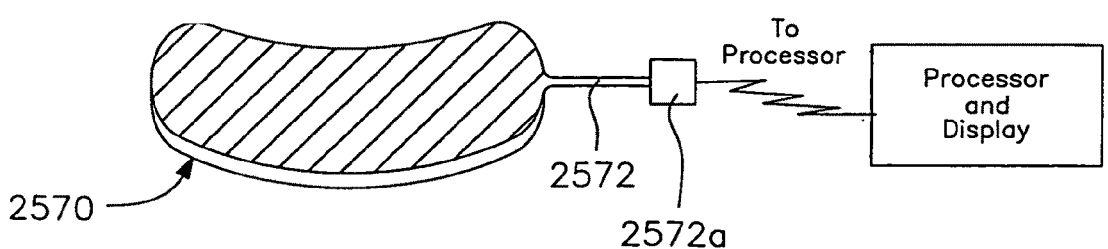
FIG. 96
FIG. 97A
FIG. 97B
FIG. 97C

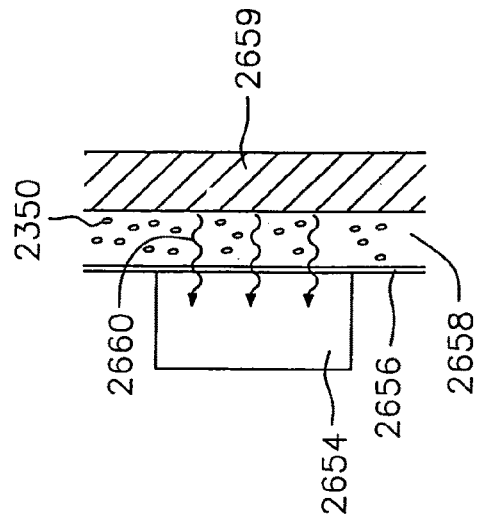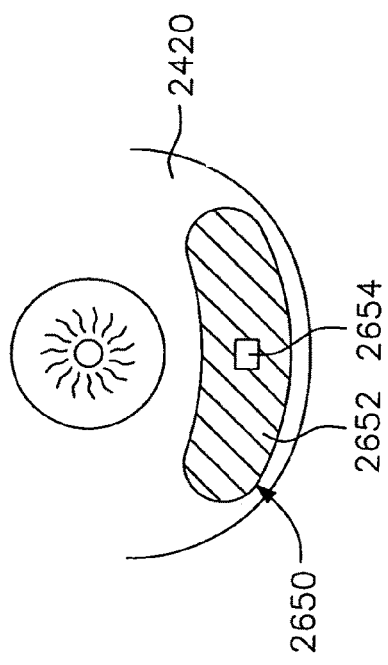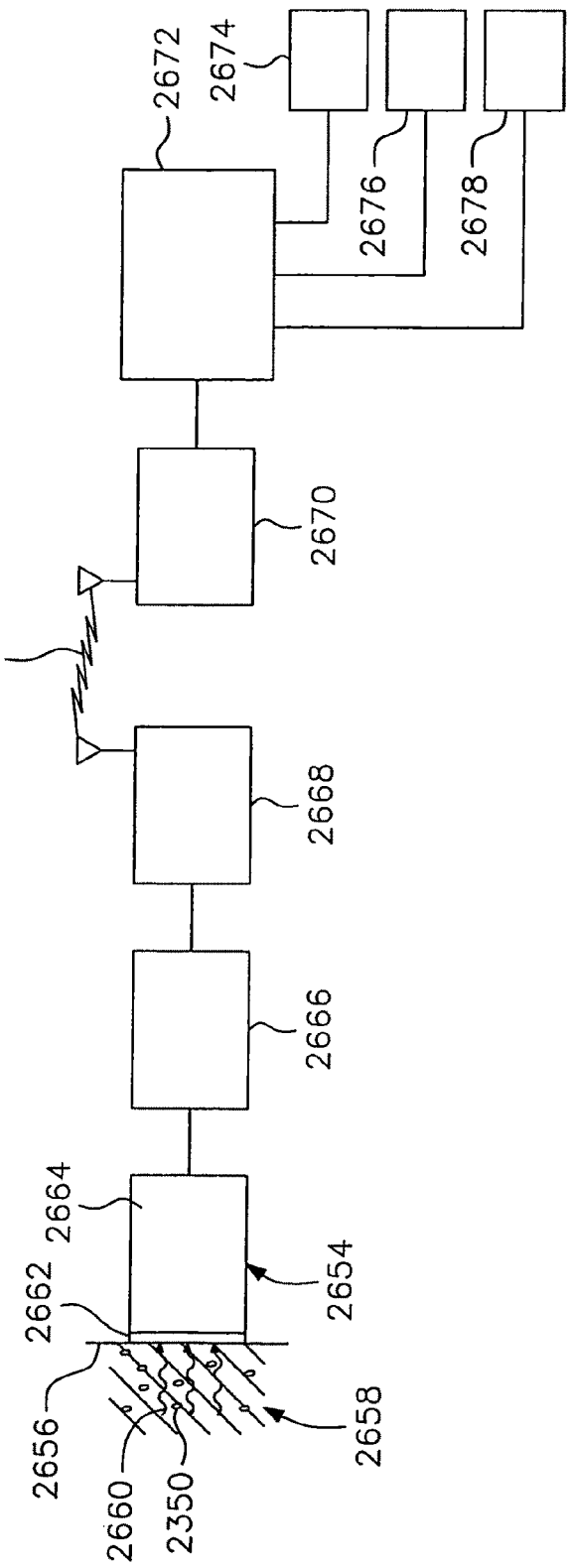

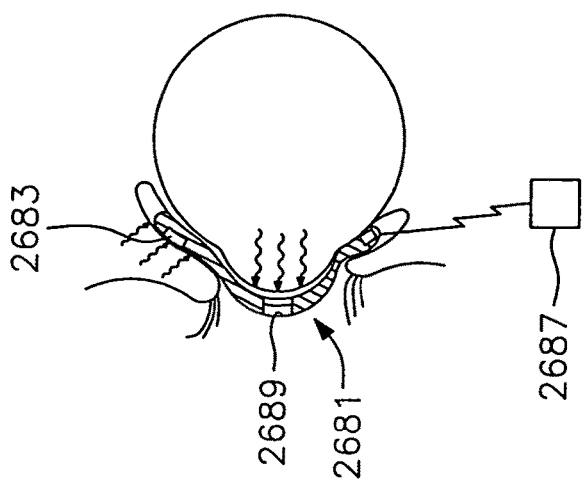
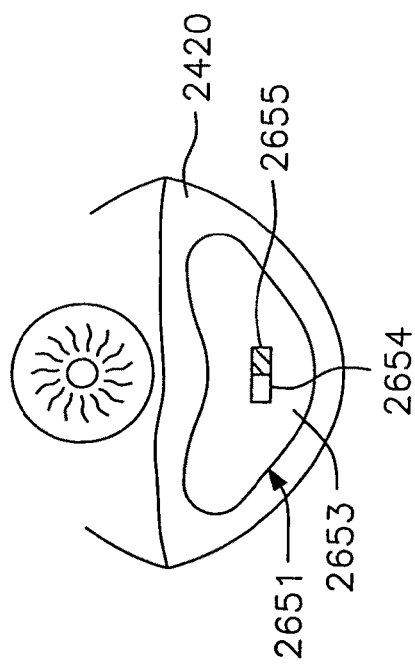
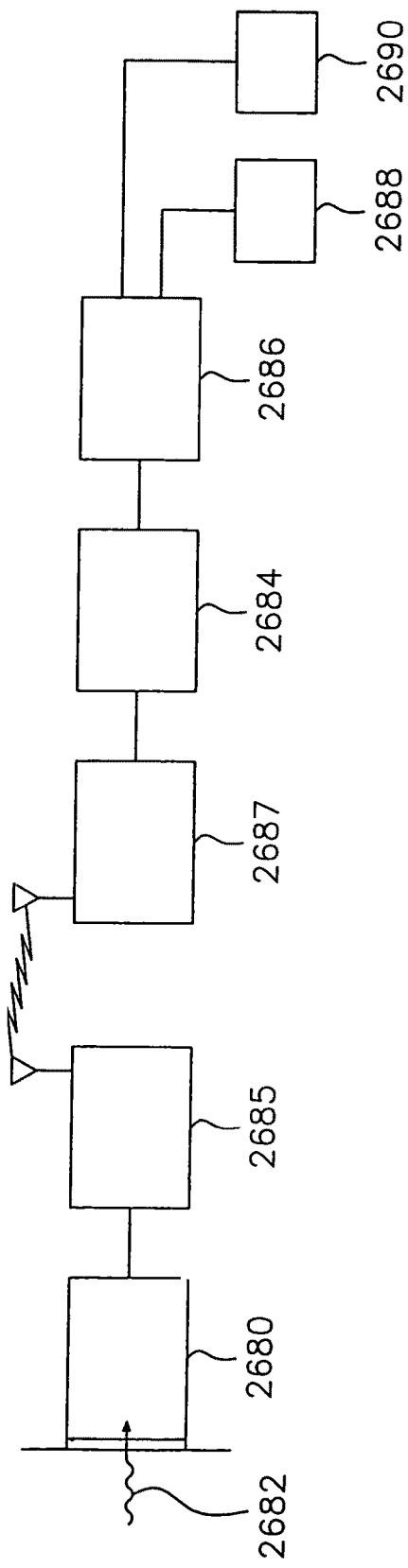
FIG. 101B
FIG. 101A
FIG. 100D

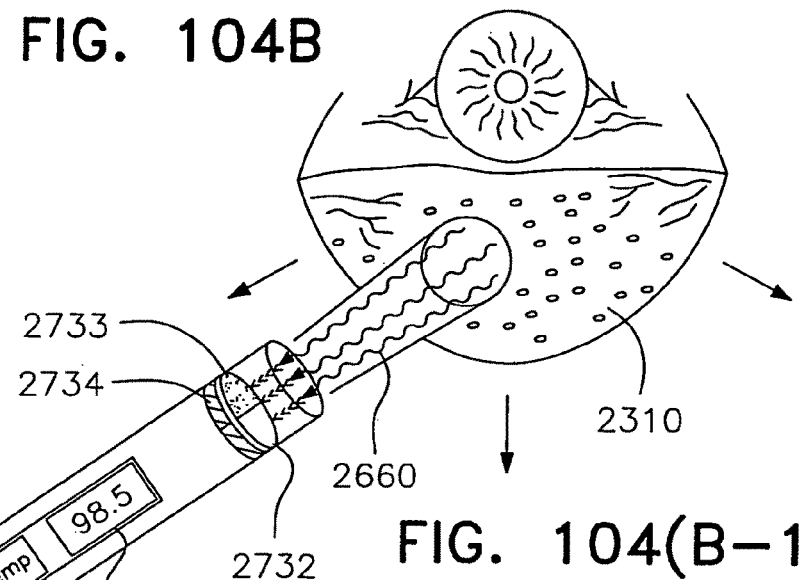
FIG. 104B
FIG. 104(B-1)
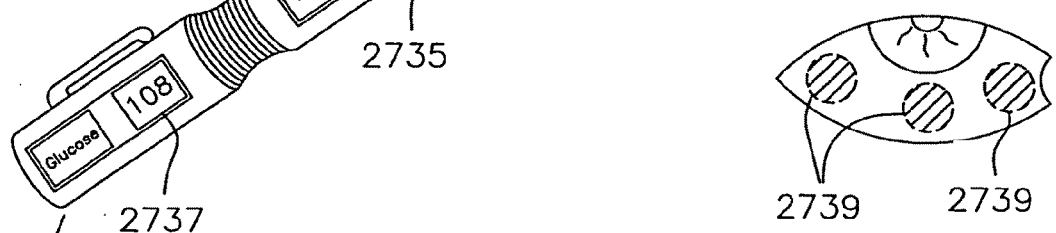
FIG. 104(B-2)  FIG. 104(B-3)
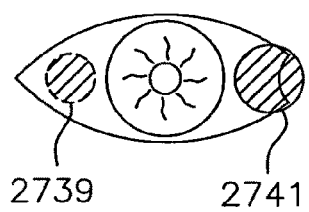
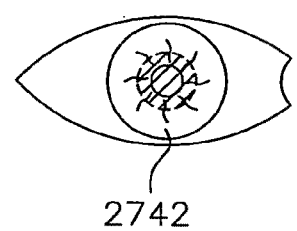
FIG. 104C
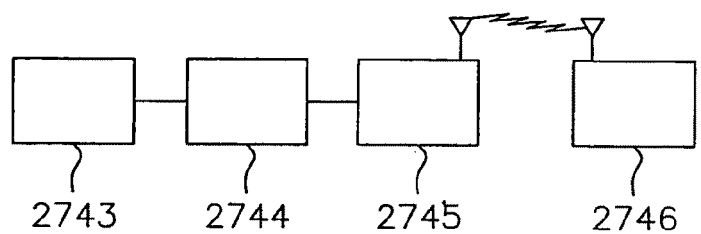
FIG. 104D
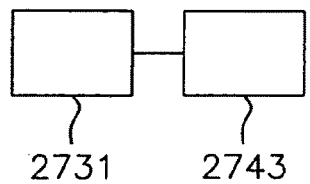

FIG. 104E
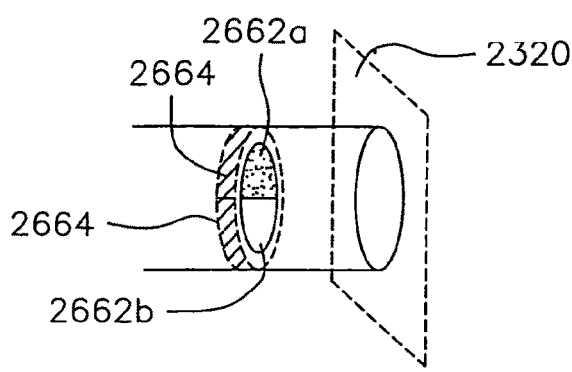
FIG. 104F
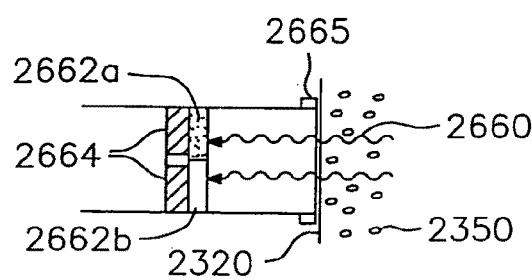
FIG. 104G
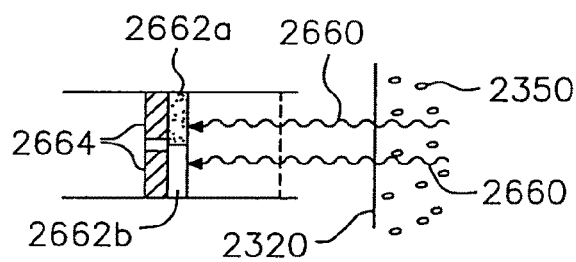
FIG. 104H
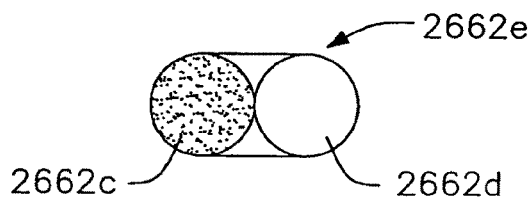
FIG. 104I
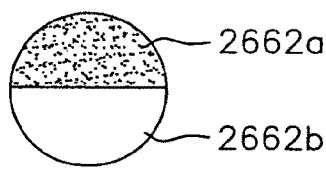
FIG. 104J
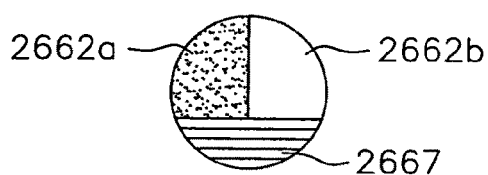
FIG. 104K-2   FIG. 104K-1
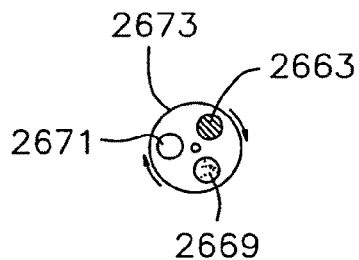 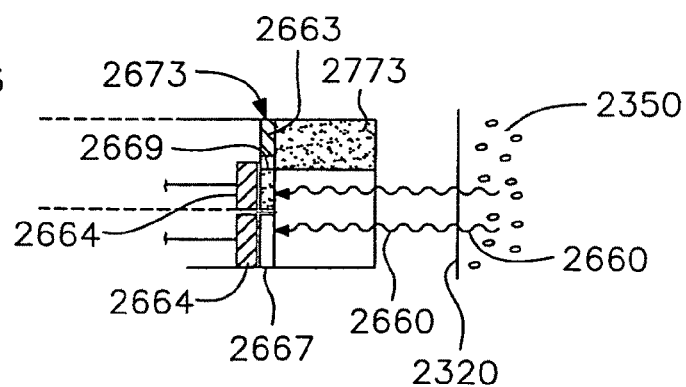

FIG. 104Q(1A)
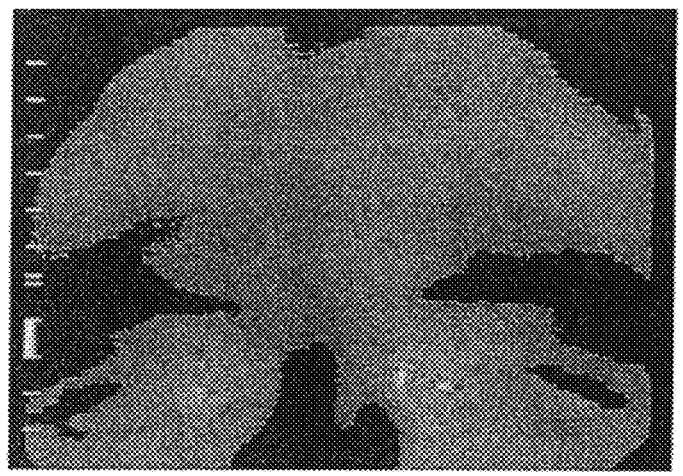
FIG. 104Q(1B)
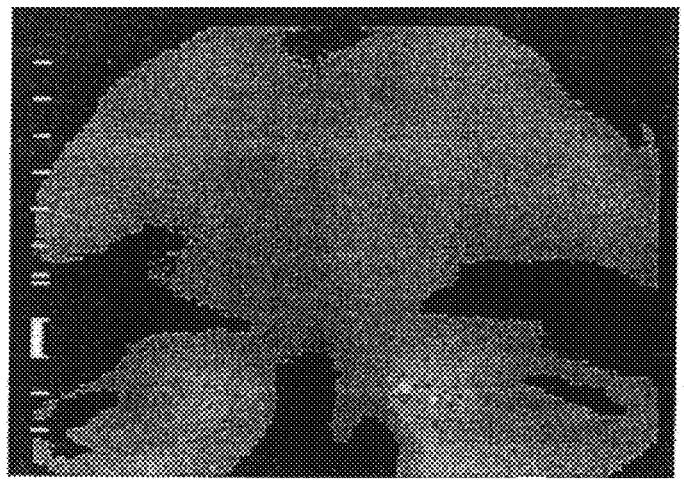

FIG. 104Q(2A)
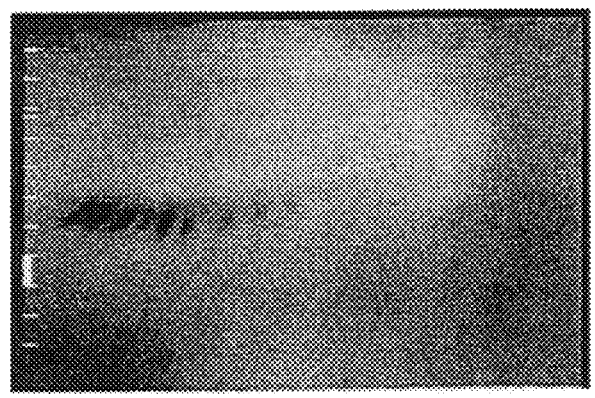
FIG. 104Q(2B)
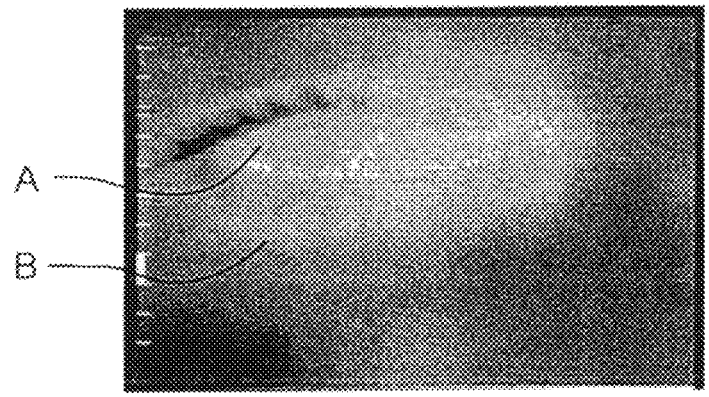

FIG. 104Q(3)
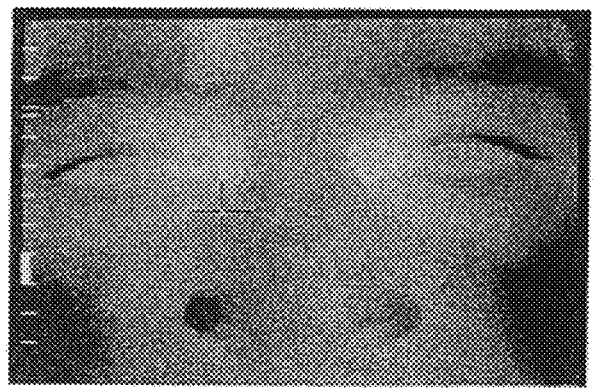

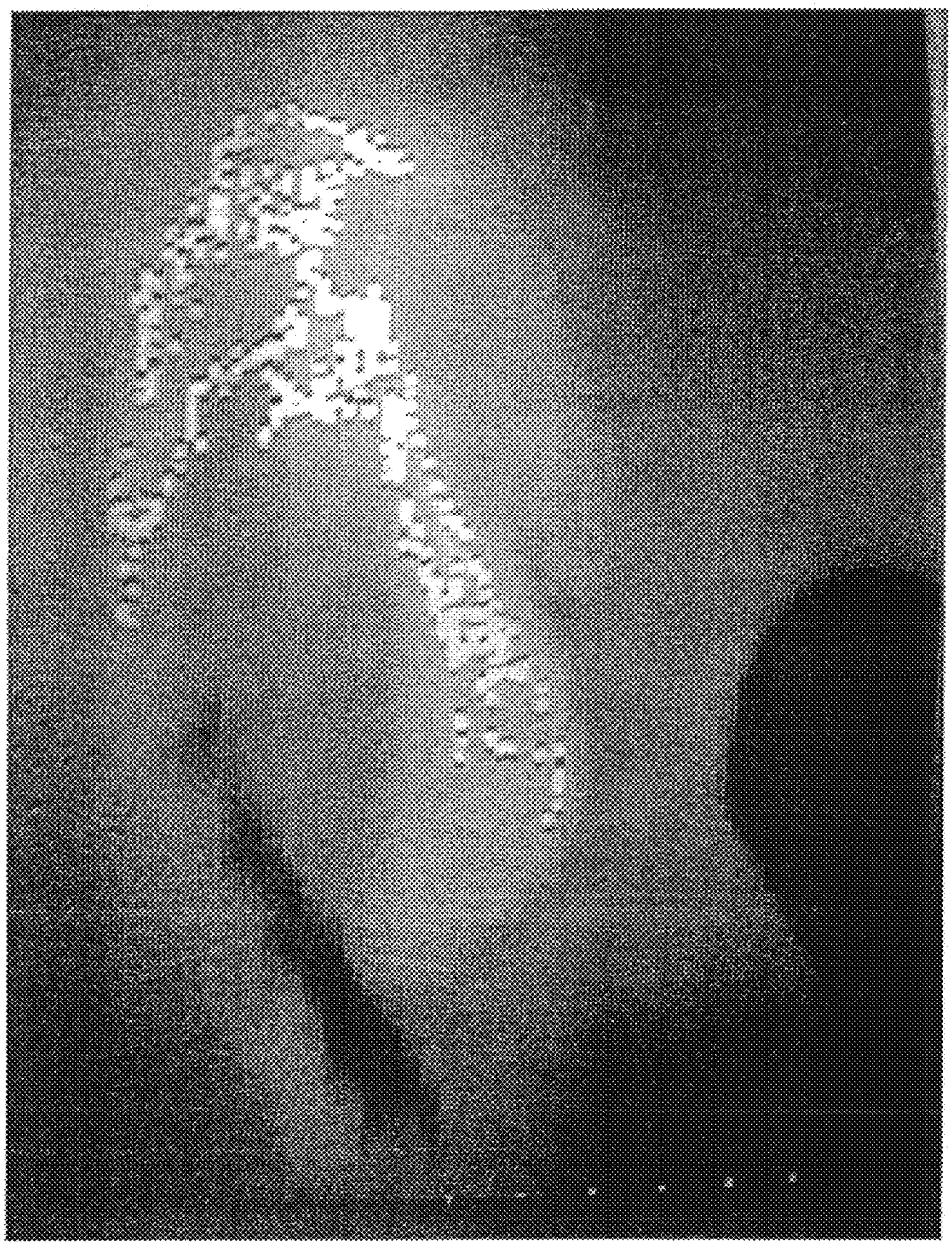
FIG. 104Q(4)

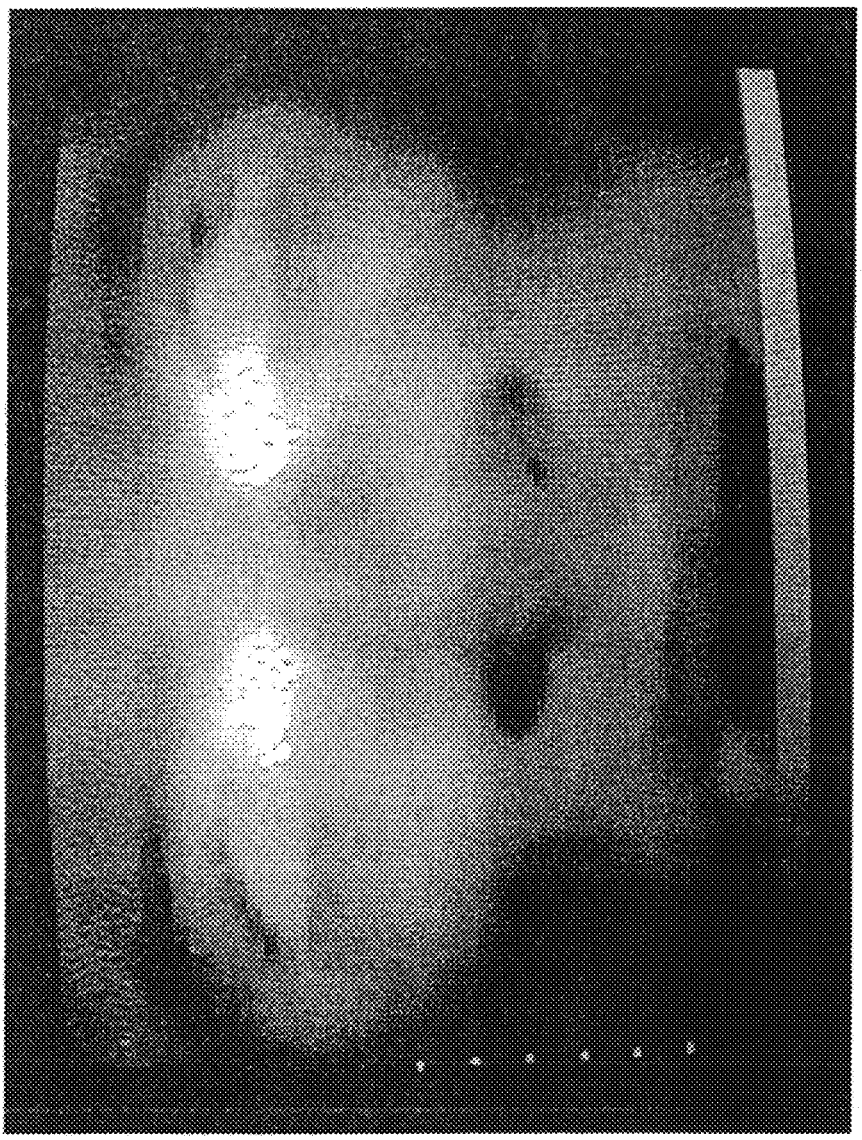
FIG. 104Q(5)

NONINVASIVE MEASUREMENT OF CHEMICAL SUBSTANCES

This is a Divisional of application Ser. No. 10/423,056 filed Apr. 25, 2003, now U.S. Pat. No. 7,403,805 which in turn is a divisional application of application Ser. No. 10/359,254, filed Feb. 6, 2003, now U.S. Pat. No. 7,041,063 which is a divisional application of U.S. Ser. No. 09/790,653, filed Feb. 23, 2001, now U.S. Pat. No. 6,544,193, all of which are incorporated herein in their entirety by reference.

FIELD OF THE INVENTION

The present invention includes a contact device for mounting on a part of the body to measure bodily functions and to treat abnormal conditions indicated by the measurements.

BACKGROUND OF THE INVENTION

The present invention relates to a tonometer system for measuring intraocular pressure by accurately providing a predetermined amount of applanation to the cornea and detecting the amount of force required to achieve the predetermined amount of applanation. The system is also capable of measuring intraocular pressure by indenting the cornea using a predetermined force applied using an indenting element and detecting the distance the indenting element moves into the cornea when the predetermined force is applied, the distance being inversely proportional to intraocular pressure. The present invention also relates to a method of using the tonometer system to measure hydrodynamic characteristics of the eye, especially outflow facility.

The tonometer system of the present invention may also be used to measure hemodynamics of the eye, especially ocular blood flow and pressure in the eye's blood vessels. Additionally, the tonometer system of the present invention may be used to increase and measure the eye pressure and evaluate, at the same time, the ocular effects of the increased pressure.

Glaucoma is a leading cause of blindness worldwide and, although it is more common in adults over age 35, it can occur at any age. Glaucoma primarily arises when intraocular pressure increases to values which the eye cannot withstand.

The fluid responsible for pressure in the eye is the aqueous humor. It is a transparent fluid produced by the eye in the ciliary body and collected and drained by a series of channels (trabecular meshwork, Schlemm's canal and venous system). The basic disorder in most glaucoma patients is caused by an obstruction or interference that restricts the flow of aqueous humor out of the eye. Such an obstruction or interference prevents the aqueous humor from leaving the eye at a normal rate. This pathologic condition occurs long before there is a consequent rise in intraocular pressure. This increased resistance to outflow of aqueous-humor is the major cause of increased intraocular pressure in glaucoma-stricken patients.

Increased pressure within the eye causes progressive damage to the optic nerve. As optic nerve damage occurs, characteristic defects in the visual field develop, which can lead to blindness if the disease remains undetected and untreated. Because of the insidious nature of glaucoma and the gradual and painless loss of vision associated therewith, glaucoma does not produce symptoms that would motivate an individual to seek help until relatively late in its course when irreversible damage has already occurred. As a result, millions of glaucoma victims are unaware that they have the disease and face eventual blindness. Glaucoma can be detected and evaluated by measuring the eye's fluid pressure using a tonometer and/or by measuring the eye fluid outflow facility. Currently, the most frequently used way of measuring facility of outflow is by doing indentation tonography. According to this technique, the capacity for flow is determined by placing a tonometer upon the eye. The weight of the instrument forces aqueous humor through the filtration system, and the rate at which the pressure in the eye declines with time is related to the ease with which the fluid leaves the eye.

Individuals at risk for glaucoma and individuals who will develop glaucoma generally have a decreased outflow facility. Thus, the measurement of the outflow facility provides information which can help to identify individuals who may develop glaucoma, and consequently will allow early evaluation and institution of therapy before any significant damage occurs.

The measurement of outflow facility is helpful in making therapeutic decisions and in evaluating changes that may occur with time, aging, surgery, or the use of medications to alter intraocular pressure. The determination of outflow facility is also an important research tool for the investigation of matters such as drug effects, the mechanism of action of various treatment modalities, assessment of the adequacy of antiglaucoma therapy, detection of wide diurnal swings in pressure and to study the pathophysiology of glaucoma.

There are several methods and devices available for measuring intraocular pressure, outflow facility, and/or various other glaucoma-related characteristics of the eye. The following patents disclose various examples of such conventional devices and methods:

| PATENT NO. | PATENTEE |
|---|---|
| 5,375,595 | Sinha et al. |
| 5,295,495 | Maddess |
| 5,251,627 | Morris |
| 5,217,015 | Kaye et al. |
| 5,183,044 | Nishio et al. |
| 5,179,953 | Kursar |
| 5,148,807 | Hsu |
| 5,109,852 | Kaye et al. |
| 5,165,409 | Coan |
| 5,076,274 | Matsumoto |
| 5,005,577 | Frenkel |
| 4,951,671 | Coan |
| 4,947,849 | Takahashi et al. |
| 4,944,303 | Katsuragi |
| 4,922,913 | Waters, Jr. et al. |
| 4,860,755 | Erath |
| 4,771,792 | Seale |
| 4,628,938 | Lee |
| 4,305,399 | Beale |
| 3,724,263 | Rose et al. |
| 3,585,849 | Grolman |
| 3,545,260 | Lichtenstein et al. |

Still other examples of conventional devices and/or methods are disclosed in Morey, Contact Lens Tonometer, RCA Technical Notes, No. 602, December 1964; Russell & Bergmanson, Multiple Applications of the NCT: An Assessment of the Instrument's Effect on IOP, Ophthal. Physiol. Opt., Vol. 9, April 1989, pp. 212-214; Moses & Grodzki, The Pneumatonograph: A Laboratory Study, Arch. Ophthalmol., Vol. 97, March 1979, pp. 547-552; and C. C. Collins, Miniature Passive Pressure Transensor for Implanting in the Eye, IEEE Transactions on Bio-medical Engineering, April 1967, pp. 74-83.

In general, eye pressure is measured by depressing or flattening the surface of the eye, and then estimating the amount of force necessary to produce the given flattening or depression. Conventional tonometry techniques using the principle of applanation may provide accurate measurements of intraocular pressure, but are subject to many errors in the way they are currently being performed. In addition, the present devices either require professional assistance for their use or are too complicated, expensive or inaccurate for individuals to use at home. As a result, individuals must visit an eye care professional in order to check their eye pressure. The frequent self-checking of intraocular pressure is useful not only for monitoring therapy and self-checking for patients with glaucoma, but also for the early detection of rises in pressure in individuals without glaucoma and for whom the elevated pressure was not detected during their office visit.

Pathogens that cause severe eye infection and visual impairment such as herpes and adenovirus as well as the virus that causes AIDS can be found on the surface of the eye and in the tear film. These microorganisms can be transmitted from one patient to another through the tonometer tip or probe. Probe covers have been designed in order to prevent transmission of diseases but are not widely used because they are not practical and provide less accurate measurements. Tonometers which prevent the transmission of diseases, such as the "air-puff" type of tonometer also have been designed, but they are expensive and provide less accurate measurements. Any conventional direct contact tonometers can potentially transmit a variety of systemic and ocular diseases.

The two main techniques for the measurement of intraocular pressure require a force that flattens or a force that indents the eye, called "applanation" and "indentation" tonometry respectively.

Applanation tonometry is based on the Imbert-Fick principle. This principle states that for an ideal dry, thin walled sphere, the pressure inside the sphere equals the force necessary to flatten its surface divided by the area of flattening. $P=F/A$ (where $P$=pressure, $F$=force, $A$=area). In applanation tonometry, the cornea is flattened, and by measuring the applanating force and knowing the area flattened, the intraocular pressure is determined.

By contrast, according to indentation tonometry (Schiotz), a known weight (or force) is applied against the cornea and the intraocular pressure is estimated by measuring the linear displacement which results during deformation or indentation of the cornea. The linear displacement caused by the force is indicative of intraocular pressure. In particular, for standard forces and standard dimensions of the indenting device, there are known tables which correlate the linear displacement and intraocular pressure.

Conventional measurement techniques using applanation and indentation are subject to many errors. The most frequently used technique in the clinical setting is contact applanation using Goldman tonometers. The main sources of errors associated with this method include the addition of extraneous pressure on the cornea by the examiner, squeezing of the eyelids or excessive widening of the lid fissure by the patient due to the discomfort caused by the tonometer probe resting upon the eye, and inadequate or excessive amount of dye (fluorescein). In addition, the conventional techniques depend upon operator skill and require that the operator subjectively determine alignment, angle and amount of depression. Thus, variability and inconsistency associated with less valid measurements are problems encountered using the conventional methods and devices.

Another conventional technique involves air-puff tonometers wherein a puff of compressed air of a known volume and pressure is applied against the surface of the eye, while sensors detect the time necessary to achieve a predetermined amount of deformation in the eye's surface caused by application of the air puff. Such a device is described, for example, in U.S. Pat. No. 3,545,260 to Lichtenstein et al. Although the non-contact (air-puff) tonometer does not use dye and does not present problems such as extraneous pressure on the eye by the examiner or the transmission of diseases, there are other problems associated therewith. Such devices, for example, are expensive, require a supply of compressed gas, are considered cumbersome to operate, are difficult to maintain in proper alignment and depend on the skill and technique of the operator. In addition, the individual tested generally complains of pain associated with the air discharged toward the eye, and due to that discomfort many individuals are hesitant to undergo further measurement with this type of device. The primary advantage of the non-contact tonometer is its ability to measure pressure without transmitting diseases, but they are not accepted in general as providing accurate measurements and are primarily useful for large-scale glaucoma screening programs.

Tonometers which use gases, such as the pneumotonometer, have several disadvantages and limitations. Such device are also subject to the operator errors as with Goldman's tonometry. In addition, this device uses freon gas, which is not considered environmentally safe. Another problem with this device is that the gas is flammable and as with any other aerosol-type can, the can may explode if it gets too hot. The gas may also leak and is susceptible to changes in cold weather, thereby producing less accurate measurements. Transmission of diseases is also a problem with this type of device if probe covers are not utilized.

In conventional indentation tonometry (Schiotz), the main source of errors are related to the application of a relatively heavy tonometer (total weight at least 16.5 g) to the eye and the differences in the distensibility of the coats of the eye. Experience has shown that a heavy weight causes discomfort and raises the intraocular pressure. Moreover the test depends upon a cumbersome technique in which the examiner needs to gently place the tonometer onto the cornea without pressing the tonometer against the globe. The accuracy of conventional indentation may also be reduced by inadequate cleaning of the instrument as will be described later. The danger of transmitting infectious diseases, as with any contact tonometer, is also present with conventional indentation.

A variety of methods using a contact lens have been devised, however, such systems suffer from a number of restrictions and virtually none of these devices is being widely utilized or is accepted in the clinical setting due to their limitations and inaccurate readings. Moreover, such devices typically include instrumented contact lenses and/or cumbersome and complex contact lenses.

Several instruments in the prior art employ a contact lens placed in contact with the sclera (the white part of the eye). Such systems suffer from many disadvantages and drawbacks. The possibility of infection and inflammation is increased due to the presence of a foreign body in direct contact with a vascularized part of the eye. As a consequence, an inflammatory reaction around the device may occur, possibly impacting the accuracy of any measurement. In addition, the level of discomfort is high due to a long period of contact with a highly sensitive area of the eye. Furthermore, the device could slide and therefore lose proper alignment, and again, preventing accurate measurements to be taken. Moreover, the sclera is a thick and almost non-distensible coat of the eye which may further impair the ability to acquire accurate readings. Most of these devices utilize expensive sensors and complicated electric circuitry imbedded in the lens which are expensive, difficult to manufacture and sometimes cumbersome.

Other methods for sensing pressure using a contact lens on the cornea have been described. Some of the methods in this prior art also employ expensive and complicated electronic circuitry and/or transducers imbedded in the contact lens. In addition, some devices use piezoelectric material in the lens and the metalization of components of the lens overlying the optical axis decreases the visual acuity of patients using that type of device. Moreover, accuracy is decreased since the piezoelectric material is affected by small changes in temperature and the velocity with which the force is applied. There are also contact lens tonometers which utilize fluid in a chamber to cause the deformation of the cornea; however, such devices lack means for alignment and are less accurate, since the flexible elastic material is unstable and may bulge forward. In addition, the fluid therein has a tendency to accumulate in the lower portion of the chamber, thus failing to produce a stable flat surface which is necessary for an accurate measurement.

Another embodiment uses a coil wound about the inner surface of the contact lens and a magnet subjected to an externally created magnetic field. A membrane with a conductive coating is compressed against a contact completing a short circuit. The magnetic field forces the magnet against the eye and the force necessary to separate the magnet from the contact is considered proportional to the pressure. This device suffers from many limitations and drawbacks. For example, there is a lack of accuracy since the magnet will indent the cornea and when the magnet is pushed against the eye, the sclera and the coats of the eye distort easily to accommodate the displaced intraocular contents. This occurs because this method does not account for the ocular rigidity, which is related to the fact that the sclera of one person's eye is more easily stretched than the sclera of another. An eye with a low ocular rigidity will be measured and read as having a lower intraocular pressure than the actual eye's pressure. Conversely, an eye with a high ocular rigidity distends less easily than the average eye, resulting in a reading which is higher than the actual intraocular pressure. In addition, this design utilizes current in the lens which, in turn, is in direct contact with the body. Such contact is undesirable. Unnecessary cost and complexity of the design with circuits imbedded in the lens and a lack of an alignment system are also major drawbacks with this design.

Another disclosed contact lens arrangement utilizes a resonant circuit formed from a single coil and a single capacitor and a magnet which is movable relative to the resonant circuit. A further design from the same disclosure involves a transducer comprised of a pressure sensitive transistor and complex circuits in the lens which constitute the operating circuit for the transistor. All three of the disclosed embodiments are considered impractical and even unsafe for placement on a person's eye. Moreover, these contact lens tonometers are unnecessarily expensive, complex, cumbersome to use and may potentially damage the eye. In addition none of these devices permits measurement of the applanated area, and thus are generally not very practical.

The prior art also fails to provide a sufficiently accurate technique or apparatus for measuring outflow facility. Conventional techniques and devices for measuring outflow facility are limited in practice and are more likely to produce erroneous results because both are subject to operator, patient and instrument errors.

With regard to operator errors, the conventional test for outflow facility requires a long period of time during which there can be no tilting of the tonometer. The operator therefore must position and keep the weight on the cornea without moving the weight and without pressing the globe.

With regard to patient errors, if during the test the patient blinks, squeezes, moves, holds his breath, or does not maintain fixation, the test results will not be accurate. Since conventional tonography takes about four minutes to complete and generally requires placement of a relatively heavy tonometer against the eye, the chances of patients becoming anxious and therefore reacting to the mechanical weight placed on their eyes is increased.

With regard to instrument errors, after each use, the tonometer plunger and foot plate should be rinsed with water followed by alcohol and then wiped dry with lint-free material. If any foreign material drys within the foot plate, it can detrimentally affect movement of the plunger and can produce an incorrect reading.

The conventional techniques therefore are very difficult to perform and demand trained and specialized personnel: The pneumotonograph, besides having the problems associated with the pneumotonometer itself, was considered "totally unsuited to tonography." (Report by the Committee on Standardization of Tonometers of the American Academy of Ophthalmology; Archives Ophthalmol., 97:547-552, 1979). Another type of tonometer (Non Contact "Air Puff" Tonometer—U.S. Pat. No. 3,545,260) was also considered unsuitable for tonography. (Ophthalmic & Physiological Optics, 9 (2):212-214, 1989). Presently there are no truly acceptable means for self-measurement of intraocular pressure and outflow facility.

In relation to an additional embodiment of the present invention, blood is responsible not only for the transport of oxygen, food, vitamins, water, enzymes, white and red blood cells, and genetic markers, but also provides an enormous amount of information in regards to the overall health status of an individual. The prior art related to analysis of blood relies primarily on invasive methods such as with the use of needles to draw blood for further analysis and processing. Very few and extremely limited methods for non-invasive evaluating blood components are available.

In the prior art for example, oxygenated hemoglobin has been measured non-invasively. The so called pulse oximeter is based on traditional near infrared absorption spectroscopy and indirectly measures arterial blood oxygen with sensors placed over the skin utilizing LEDs emitting at two wave lengths around 940 and 660 nanometers. As the blood oxygenation changes, the ratio of the light transmitted by the two frequencies changes indicating the amount of oxygenated hemoglobin in the arterial blood of the finger tip. The present systems are not accurate and provide only the amount of oxygenated hemoglobin in the finger tip.

The skin is a thick layer of tissue with a thick epithelium. The epithelium is the superficial layers of tissue and vary according to the organ or location in the body. The skin is thick because it is in direct contact with the environment and it is the barrier between the internal organs and the external environment. The skin is exposed and subject to all kind of noxious external agents on a daily basis. Stratified squamous keratinizing epithelium layers of the skin have a strong, virtually impermeable layer called the stratum corneum and keratin. The keratin that covers the skin is a thick layer of a hard and dead tissue which creates another strong barrier of protection against pathogenic organisms but also creates a barrier to the proper evaluation of bodily functions such as non-invasive blood analysis and cell analysis.

Another drawback in using the skin is due to the fact that the superficial layer of tissue covering the skin does not allow acquisition of important information, only present in living tissue. In addition, the other main drawback in using the skin is because the blood vessels are not easily accessible. The main vascular supply to the skin is located deep and distant from the superficial and still keratinized impermeable skin layer.

Prior art attempts to use the skin and other areas of the body to perform non-invasive blood analysis, diagnostics and evaluations of bodily functions such as oral, nasal and ear mucosa. These areas have been found to be unsuitable for such tasks. Moreover, placement of an object in oral or nasal mucosa can put the user at risk of aspiration and obstructing the airway which is a fatal event.

Another drawback in using the skin is the presence of various appendages and glands which prevent adequate measurements from being acquired such as hair, sweat glands, and sebaceous glands with continuous outflowing of sebum. Moreover, the layers of the skin vary in thickness in a random fashion. Furthermore, the layers of the skin are strongly attached to each other, making the surgical implantation of any device extremely difficult. Furthermore the skin is a highly innervated area which is highly sensitive to painful stimuli.

In order to surgically implant a device under the skin there is need for invasive application of anesthetic by injection around the area to be incised and the obvious risk of infection. Moreover, the structure of the skin creates electrical resistance and makes acquisition of electrical signals a much more difficult procedure.

Attempts to use electroosmosis as a flux enhancement by iontophoresis with increased passage of fluid through the skin with application of electrical energy, do not provide accurate or consistent signals and measurements due to the skin characteristics described above. Furthermore there is a significant delay in the signal acquisition when electroosmosis-based systems are used on the skin because of the anatomy and physiology of the skin which is thick and has low permeability.

Previously, a watch with sensing elements in apposition to the skin has been used in order to acquire a signal to measure glucose. Because of the unsuitable characteristics of the skin the watch has to actually shock the patient in order to move fluid. The fluid measured provides inconsistent, inaccurate and delayed results because of the unsuitable characteristics of the skin as described above. It is easy to see how unstable the watch is if one were to observe how much their own watch moves up and down and around one=s pulse during normal use. There is no natural stable nor consistent correct apposition of the sensor surface to the tissue, in this case the dead keratin layer of the thick skin.

Previously invasive means were used with tearing of the skin in the tip of the fingers to acquire whole blood, instead of plasma, for glucose measurement. Besides being invasive, whole blood from the fingers is used which has to be corrected for plasma levels. Plasma levels provide the most accurate evaluation of blood glucose.

The conventional way for blood analysis includes intense labor and many expenses using many steps including cumbersome, expensive and bulky laboratory equipment. A qualified medical professional is required to remove blood and this labor is certainly costly. The professionals expose themselves to the risk of acquiring infections and fatal diseases such as AIDS, hepatitis, and other viral and prion diseases. In order to prevent that possible contamination a variety of expensive measures and tools are taken, but still only providing partial protection to the medical professional and the patient. A variety of materials are used such as alcohol swabs, syringes, needles, sterile vials, gloves as well as time and effort. Moreover, effort, time and money must be spent with the disposal of biohazard materials such as the disposal of the sharps and related biohazard material used to remove blood. These practices negatively affect the environment as those biohazard materials are non-degradable and obviously made of non-recycled material.

In addition, these practices comprise a painful procedure with puncturing the skin and putting the patient and nurse at risk for infection, fatal diseases, contamination, and blood borne diseases. After all of this cumbersome, costly, time-consuming and hazardous procedure, the vials with blood have to be transported by a human attendant to the laboratory which is also costly. At the laboratory the blood is placed in other machines by a trained human operator with all of the risks and costs associated with the procedure of dealing with blood.

The conventional laboratory instruments then have to separate the blood using special and expensive machines and then materials are sent for further processing and analysis by a trained human operator. Subsequent to that the result is printed and sent to the patient and/or doctor, most frequently by regular mail. All of this process in laboratories is risky, complex, cumbersome, and expensive; and this is only for one test.

If a patient is admitted to a hospital, this very laborious and expensive process could happen several times a day. Only one simple blood test result can be over $100 dollars and this cost is easily explained by the labor and materials associated with the cost related to manipulation of blood and protection against infections as described above. If four tests are needed over 24 hours, as may occur with admitted patients, the cost then can increase to $400 dollars.

The world and in particular the United States face challenging health care costs with a grim picture of rapidly rising health care expenditures with a rapid increase in the number and frequency of testing. Today, the worldwide diabetic population alone is over 125 million and is expected to reach 250 million by the year 2008. The United States spent over $140 billion dollars on diabetes alone in 1998. More frequent control of blood glucose is known to prevent complications and would substantially reduce the costs of the disease.

According to the projections by the Health Care Financing Administration of the United States Department of Health and Human Services, health care spending as a share of U.S. gross domestic product (GDP) is estimated to increase from 13 percent to potentially and amazingly close to 20% of the United States GDP in the near future, reaching over $2 trillion dollars a year, which clearly demonstrates how unwise health care spending can affect the overall economy of a nation.

The World Health Organization reported in 1995, the percentage of total spending on health by various governments clearly indicating health care costs as a serious global problem and important factor concerning the overall utilization of public money. Public spending on health by the United States government was 47%, while United Kingdom was 84%, France was 81%, Japan was 78%, Canada was 71%, Italy was 70% and Mexico was 55%.

Infrared spectroscopy is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred as fingerprint or signature which can be used to identify each of such substances.

Radiation containing various infrared wavelengths is emitted at the substance or constituent to be measured, referred to herein as "substance of interest", in order to identify and quantify said substance according to its absorption spectra. The amount of absorption of radiation is dependent upon the concentration of said chemical substance being measured according to Beer-Lambert's Law.

When electromagnetic energy is emitted an enormous amount of interfering constituents, besides the substance of interest, are also irradiated such as skin, fat, wall of blood vessels, bone, cartilage, water, blood, hemoglobin, albumin, total protein, melanin, and various other interfering substances. Those interfering constituents and background noise such as changes in pressure and temperature of the sample irradiated drastically reduce the accuracy and precision of the measurements when using infrared spectroscopy. Those many constituents and variables including the substance of interest form then an absorption spectrum for each wavelength. The sum of the absorption for each wavelength of radiation by all of the constituents and variables generates the total absorption with said total absorption spectrum being measured at two or more wavelengths of emission.

In order then to achieve the concentration of the substance of interest, a procedure must be performed to subtract the statistical absorption spectra for each of the various intervening tissues and interfering constituents, with the exception of the substance of interest being measured. It is then assumed that all of the interfering constituents were accounted for and completely eliminated and that the remainder is the real spectra of the substance of interest. It has been very difficult to prove this assumption in vivo as no devices or methods in the prior art have yet shown to be clinically useful.

In the prior art the interfering constituents and variables introduce significant source of errors which are particularly critical since the background noise as found in the prior art tremendously exceeds the signal of the substance of interest which is found in minimal concentrations relative to the whole sample irradiated. Furthermore, in the prior art, the absorption of a solute such as glucose is very small compared to the other various interfering constituents which leads to many statistical errors preventing the accurate statistical measurement of glucose concentration. A variety of other techniques using infrared devices and methods have been described but all of them suffer from the same limitation due to the great amount of interference and noise.

Other techniques based on comparison with a known reference signal as with phase sensitive techniques have also the same limitations and drawbacks due to the great number of interfering constituents and generation of only a very weak signal. The interfering constituents are source of many artifacts, errors, and variability which leads to inadequate signal and severe reduction of the signal to noise ratio. Besides, calculation errors are common because of the many interfering substances and because the spectra of interfering constituents can overlap with the spectra of the substance of the interest being measured. If adequate signal to noise can be achieved, infrared spectroscopy should be able to provide a clinically useful device and determine the concentration of the substance of interest precisely and accurately.

Attempts in the prior art using infrared spectroscopy for noninvasive measurement of chemical substances have failed to accurately and precisely measure chemical substances such as for example glucose. The prior art have used transcutaneous optical means, primarily using the skin non-invasively, to determine the concentration of chemical substances. The prior art has also used invasive means with implant of sensors inside blood vessels or around the blood vessels. The prior art used polarized light directed at the aqueous humor of the eye, which is located inside the eye, in an attempt to measure glucose in said aqueous humor. However, precise measurements are very difficult to achieve particularly when there is substantial background noise and minimal concentration of the substance of interest as it occurs in the aqueous humor of the eye. Besides, polarized light techniques as used in the aqueous humor of the eye can only generate a very weak signal and there is low concentration of the solute in the aqueous sample. The combination of those factors and presence of interfering constituents and variables prevent accurate measurements to be achieved when using the aqueous humor of the eye.

The most frequent optical approaches in the prior art were based on measuring chemical substances using the skin. Other techniques include measuring substances in whole blood in the blood vessel (either non-invasively transcutaneously or invasively around or inside the blood vessel). Yet attempts were made to measure substances present in interstitial fluid with devices implanted under the skin. Attempts were also made by the prior art using the oral mucosa and tongue.

Mucosal surfaces such as the oral mucosa are made to stand long wear and tear as occurs during mastication. If the oral mucosa or tongue lining were thin with exposed vessels, one would easily bleed during chewing. Thus, those areas have rather thick lining and without plasma leakage. Furthermore these mucosal areas have no natural means for apposition of a sensor such as a natural pocket formation.

Since there is still a low signal with an enormous amount of interfering constituents, useful devices using the oral mucosal, tongue, and other mucosa such as genito-urinary and gastrointestinal have not been developed. The prior art also attempted to measure glucose using far infrared thermal emission from the body, but a clinically useful device has not been developed due to the presence of interfering elements and great thermal instability of the sample. Near infrared spectroscopy and far-infrared techniques have been tried by the prior art as means to non-invasively measure glucose, but accuracy and precision for clinical application has not been achieved.

Therefore remains a need to provide a method and apparatus capable of delivering a higher signal to noise by reducing or eliminating interfering constituents, noise, and other variables, which will ultimately provide the accuracy and precision needed for useful clinical application.

SUMMARY OF THE INVENTION

In contrast to the various prior art devices, the apparatus of the present invention offers an entirely new approach for the measurement of intraocular pressure and eye hydrodynamics. The apparatus offers a simple, accurate, low-cost and safe means of detecting and measuring the earliest of abnormal changes taking place in glaucoma, and provides a method for the diagnosis of early forms of glaucoma before any irreversible damage occurs. The apparatus of this invention provides a fast, safe, virtually automatic, direct-reading, comfortable and accurate measurement utilizing an easy-to-use, gentle, dependable and low-cost device, which is suitable for home use.

Besides providing a novel method for a single measurement and self-measurement of intraocular pressure, the apparatus of the invention can also be used to measure outflow facility and ocular rigidity. In order to determine ocular rigidity it is necessary to measure intraocular pressure under two different conditions, either with different weights on the tonometer or with the indentation tonometer and an applanation tonometer. Moreover, the device can perform applanation tonography which is unaffected by ocular rigidity because the amount of deformation of the cornea is so very small that very little is displaced with very little change in pressure. Large variations in ocular rigidity, therefore, have little effect on applanation measurements.

According to the present invention, a system is provided for measuring intraocular pressure by applanation. The system includes a contact device for placement in contact with the cornea and an actuation apparatus for actuating the contact device so that a portion thereof projects inwardly against the cornea to provide a predetermined amount of applanation. The contact device is easily sterilized for multiple use, or alternatively, can be made inexpensively so as to render the contact device disposable. The present invention, therefore, avoids the danger present in many conventional devices of transmitting a variety of systemic and ocular diseases.

The system further includes a detecting arrangement for detecting when the predetermined amount of applanation of the cornea has been achieved and a calculation unit responsive to the detecting arrangement for determining intraocular pressure based on the amount of force the contact device must apply against the cornea in order to achieve the predetermined amount of applanation.

The contact device preferably includes a substantially rigid annular member, a flexible membrane and a movable central piece. The substantially rigid annular member includes an inner concave surface shaped to match an outer surface of the cornea and having a hole defined therein. The subsannular member preferably has a maximum thickness at the hole and a progressively decreasing thickness toward a periphery of the substantially rigid annular member.

The flexible membrane is preferably secured to the inner concave surface of the substantially rigid annular member. The flexible membrane is coextensive with at least the hole in the annular member and includes at least one transparent area. Preferably, the transparent area spans the entire flexible membrane, and the flexible membrane is coextensive with the entire inner concave surface of the rigid annular member.

The movable central piece is slidably disposed within the hole and includes a substantially flat inner side secured to the flexible membrane. A substantially cylindrical wall is defined circumferentially around the hole by virtue of the increased thickness of the rigid annular member at the periphery of the hole. The movable central piece is preferably slidably disposed against this wall in a piston-like manner and has a thickness which matches the height of the cylindrical wall. In use, the substantially flat inner side flattens a portion of the cornea upon actuation of the movable central piece by the actuation apparatus.

Preferably, the actuation apparatus actuates the movable central piece to cause sliding of the movable central piece in the piston-like manner toward the cornea. In doing so, the movable central piece and a central portion of the flexible membrane are caused to project inwardly against the cornea. A portion of the cornea is thereby flattened. Actuation continues until a predetermined amount of applanation is achieved.

Preferably, the movable central piece includes a magnetically responsive element arranged so as to slide along with the movable central piece in response to a magnetic field, and the actuation apparatus includes a mechanism for applying a magnetic field thereto. The mechanism for applying the magnetic field preferably includes a coil and circuitry for producing an electrical current through the coil in a progressively increasing manner. By progressively increasing the current, the magnetic field is progressively increased. The magnetic repulsion between the actuation apparatus and the movable central piece therefore increases progressively, and this, in turn, causes a progressively greater force to be applied against the cornea until the predetermined amount of applanation is achieved.

Using known principles of physics, it is understood that the electrical current passing through the coil will be proportional to the amount of force applied by the movable central piece against the cornea via the flexible membrane. Since the amount of force required to achieve the predetermined amount of applanation is proportional to intraocular pressure, the amount of current required to achieve the predetermined amount of applanation will also be proportional to the intraocular pressure.

The calculation unit therefore preferably includes a memory for storing a current value indicative of the amount of current passing through the coil when the predetermined amount of applanation is achieved and also includes a conversion unit for converting the current value into an indication of intraocular pressure.

The magnetically responsive element is circumferentially surrounded by a transparent peripheral portion. The transparent peripheral portion is aligned with the transparent area and permits light to pass through the contact device to the cornea and also permits light to reflect from the cornea back out of the contact device through the transparent peripheral portion.

The magnetically responsive element preferably comprises an annular magnet having a central sight hole through which a patient is able to see while the contact device is located on the patient's cornea. The central sight hole is aligned with the transparent area of the flexible membrane.

A display is preferably provided for numerically displaying the intraocular pressure detected by the system. Alternatively, the display can be arranged so as to give indications of whether the intraocular pressure is within certain ranges.

Preferably, since different patients may have different sensitivities or reactions to the same intraocular pressure, the ranges are calibrated for each patient by an attending physician. This way, patients who are more susceptible to consequences from increased intraocular pressure may be alerted to seek medical attention at a pressure less than the pressure at which other less-susceptible patients are alerted to take the same action.

The detecting arrangement preferably comprises an optical applanation detection system. In addition, a sighting arrangement is preferably provided for indicating when the actuation apparatus and the detecting arrangement are properly aligned with the contact device. Preferably, the sighting arrangement includes the central sight hole in the movable central piece through which a patient is able to see while the device is located on the patient's cornea. The central sight hole is aligned with the transparent area, and the patient preferably achieves a generally proper alignment by directing his vision through the central sight hole toward a target mark in the actuation apparatus.

The system also preferably includes an optical distance measuring mechanism for indicating whether the contact device is spaced at a proper axial distance from the actuation apparatus and the detecting arrangement. The optical distance measurement mechanism is preferably used in conjunction with the sighting arrangement and preferably provides a visual indication of what corrective action should be taken whenever an improper distance is detected.

The system also preferably includes an optical alignment mechanism for indicating whether the contact device is properly aligned with the actuation apparatus and the detecting arrangement. The optical alignment mechanism preferably provides a visual indication of what corrective action should be taken whenever a misalignment is detected, and is preferably used in conjunction with the sighting arrangement, so that the optical alignment mechanism merely provides indications of minor alignment corrections while the sighting arrangement provides an indication of major alignment corrections.

In order to compensate for deviations in corneal thickness, the system of the present invention may also include an arrangement for multiplying the detected intraocular pressure by a coefficient (or gain) which is equal to one for corneas of normal thickness, less than one for unusually thick corneas, and a gain greater than one for unusually thin corneas.

Similar compensations can be made for corneal curvature, eye size, ocular rigidity, and the like. For levels of corneal curvature which are higher than normal, the coefficient would be less than one. The same coefficient would be greater than one for levels of corneal curvature which are flatter than normal.

In the case of eye size compensation, larger than normal eyes would require a coefficient which is less than one, while smaller than normal eyes require a coefficient which is greater than one.

For patients with "stiffer" than normal ocular rigidities, the coefficient is less than one, but for patients with softer ocular rigidities, the coefficient is greater than one.

The coefficient (or gain) may be manually selected for each patient, or alternatively, the gain may be selected automatically by connecting the apparatus of the present invention to a known pachymetry apparatus when compensating for corneal thickness, a known keratometer when compensating for corneal curvature, and/or a known biometer when compensating for eye size.

The contact device and associated system of the present invention may also be used to detect intraocular pressure by indentation. When indentation techniques are used in measuring intraocular pressure, a predetermined force is applied against the cornea using an indentation device. Because of the force, the indentation device travels in toward the cornea, indenting the cornea as it travels. The distance traveled by the indentation device into the cornea in response to the predetermined force is known to be inversely proportional to intraocular pressure. Accordingly, there are various known tables which, for certain standard sizes of indentation devices and standard forces, correlate the distance traveled and intraocular pressure.

Preferably, the movable central piece of the contact device also functions as the indentation device. In addition, the circuit is switched to operate in an indentation mode. When switched to the indentation mode, the current producing circuit supplies a predetermined amount of current through the coil. The predetermined amount of current corresponds to the amount of current needed to produce one of the aforementioned standard forces.

In particular, the predetermined amount of current creates a magnetic field in the actuation apparatus. This magnetic field, in turn, causes the movable central piece to push inwardly against the cornea via the flexible membrane. Once the predetermined amount of current has been applied and a standard force presses against the cornea, it is necessary to determine how far the movable central piece moved into the cornea.

Accordingly, when measurement of intraocular pressure by indentation is desired, the system of the present invention further includes a distance detection arrangement for detecting a distance traveled by the movable central piece, and a computation portion in the calculation unit for determining intraocular pressure based on the distance traveled by the movable central piece in applying the predetermined amount of force.

Preferably, the computation portion is responsive to the current producing circuitry so that, once the predetermined amount of force is applied, an output voltage from the distance detection arrangement is received by the computation portion. The computation portion then, based on the displacement associated with the particular output voltage, determines intraocular pressure.

In addition, the present invention includes alternative embodiments, as will be described hereinafter, for performing indentation-related measurements of the eye. Clearly, therefore, the present invention is not limited to the aforementioned exemplary indentation device.

The aforementioned indentation device of the present invention may also be utilized to non-invasively measure hydrodynamics of an eye including outflow facility. The method of the present invention preferably comprises several steps including the following:

According to a first step, an indentation device is placed in contact with the cornea. Preferably, the indentation device comprises the contact device of the present invention.

Next, at least one movable portion of the indentation device is moved in toward the cornea using a first predetermined amount of force to achieve indentation of the cornea. An intraocular pressure is then determined based on a first distance traveled toward the cornea by the movable portion of the indentation device during application of the first predetermined amount of force. Preferably, the intraocular pressure is determined using the aforementioned system for determining intraocular pressure by indentation.

Next, the movable portion of the indentation device is rapidly reciprocated in toward the cornea and away from the cornea at a first predetermined frequency and using a second predetermined amount of force during movement toward the cornea to thereby force intraocular fluid out from the eye. The second predetermined amount of force is preferably equal to or more than the first predetermined amount of force. It is understood, however, that the second predetermined amount of force may be less than the first predetermined amount of force.

The movable portion is then moved in toward the cornea using a third predetermined amount of force to again achieve indentation of the cornea. A second intraocular pressure is then determined based on a second distance traveled toward the cornea by the movable portion of the indentation device during application of the third predetermined amount of force. Since intraocular pressure decreases as a result of forcing intraocular fluid out of the eye during the rapid reciprocation of the movable portion, it is generally understood that, unless the eye is so defective that no fluid flows out therefrom, the second intraocular pressure will be less than the first intraocular pressure. This reduction in intraocular pressure is indicative of outflow facility.

Next, the movable portion of the indentation device is again rapidly reciprocated in toward the cornea and away from the cornea, but at a second predetermined frequency and using a fourth predetermined amount of force during movement toward the cornea. The fourth predetermined amount of force is preferably equal to or greater than the second predetermined amount of force; however, it is understood that the fourth predetermined amount of force may be less than the second predetermined amount of force. Additional intraocular fluid is thereby forced out from the eye.

The movable portion is subsequently moved in toward the cornea using a fifth predetermined amount of force to again achieve indentation of the cornea. Thereafter, a third intraocular pressure is determined based on a third distance traveled toward the cornea by the movable portion of the indentation device during application of the fifth-predetermined amount of force.

The differences are then preferably calculated between the first, second, and third distances, which differences are indicative of the volume of intraocular fluid which left the eye and therefore are also indicative of the outflow facility. It is understood that the difference between the first and last distances may be used, and in this regard, it is not necessary to use the differences between all three distances. In fact, the difference between any two of the distances will suffice.

Although the relationship between the outflow facility and the detected differences varies when the various parameters of the method and the dimensions of the indentation device change, the relationship for given parameters and dimensions can be easily determined by known experimental techniques and/or using known Friedenwald Tables.

Preferably, the method further comprises the steps of plotting the differences between the first, second, and third distance to a create a graph of the differences and comparing the resulting graph of differences to that of a normal eye to determine if any irregularities in outflow facility are present;

Additionally, the present invention relates to the utilization of a contact device placed on the front part of the eye in order to detect physical and chemical parameters of the body as well as the non-invasive delivery of compounds according to these-physical and chemical parameters, with signals preferably being transmitted continuously as electromagnetic waves, radio waves, infrared and the like. One of the parameters to be detected includes non-invasive blood analysis utilizing chemical changes and chemical products that are found in the front part of the eye and in the tear film. The non-invasive blood analysis and other measurements are done using the system of my co-pending prior application, characterized as an intelligent contact lens system.

The word lens is used here to define an eyepiece which fits inside the eye regardless of the presence of optical properties for correction of imperfect vision. The word intelligent used here defines a lens capable of signal-detection and/or signal-transmission and/or signal-reception and/or signal-emission and/or signal-processing and analysis as well as the ability to alter physical, chemical, and or biological variables. When the device is placed in other parts of the body other than the eye, it is referred to as a contact device or intelligent contact device (ICD).

An alternative embodiment of the present invention will now be described. The apparatus and method is based on a different and novel concept originated by the inventor in which a transensor mounted in the contact device laying on the cornea or the surface of the eye is capable of evaluating and measuring physical and chemical parameters in the eye including non-invasive blood analysis. The alternative embodiment preferably utilizes a transensor mounted in the contact device which is preferably laying in contact with the cornea and is preferably activated by the process of eye lid motion and/or closure of the eye lid. The system preferably utilizes eye lid motion and/or closure of the eye lid to activate a microminiature radio frequency sensitive transensor mounted in the contact device. The signal can be communicated by cable, but is preferably actively or passively radio telemetered to an externally placed receiver. The signal can then be processed, analyzed and stored.

This eye lid force and motion toward the surface of the eye is also capable to create the deformation of any transensor/electrodes mounted on the contact device. During blinking, the eye lids are in full contact with the contact device and the transensor's surface is in contact with the cornea/tear film and/or inner surface of the eye lid and/or blood vessels on the surface of the conjunctiva. It is understood that the transensor used for non-invasive blood analysis is continuously activated when placed on the eye and do not need closure of the eyelid for activation. It is understood that after a certain amount of time the contact device will adhere to tissues in the conjunctiva optimizing flow of tissue fluid to sensors for measurement of blood components.

The present invention includes apparatus and methods that utilizes a contact device laying on the surface of the eye called intelligent contact lens (ICL) which provides means for transmitting physiologic, physical, and chemical information from one location as for instance living tissue on the surface of the eye to another remote location accurately and faithfully reproducing the event at the receiver. In my prior copending application, the whole mechanism by which the eye lid activate transensors is described and a microminiature passive pressure-sensitive radio frequency transducer is disclosed to continuously measure intraocular pressure and eye fluid outflow facility with both open and closed eyes.

The present invention provides a new method and apparatus to detect physical and chemical parameters of the body and the eye utilizing a contact device placed on the eye with signals being transmitted continuously as electromagnetic waves, radio waves, sound waves, infrared and the like. Several parameters can be detected with the invention including a complete non-invasive analysis of blood components, measurement of systemic and ocular blood flow, measurement of heart rate and respiratory rate, tracking operations, detection of ovulation, detection of radiation and drug effects, diagnosis of ocular and systemic disorders and the like. The invention also provides a new method and apparatus for somnolence awareness, activation of devices by disabled individuals, a new drug delivery system and new therapy for ocular and neurologic disorders, and treatment of cancer in the eye or other parts of the body, and an evaluation system for the overall health status of an individual. The device of the present invention quantifies non-invasively the amount of the different chemical components in the blood using a contact device with suitable electrodes and membranes laying on the surface of the eye and in direct contact with the tear film or surface of the eye, with the data being preferably transmitted utilizing radio waves, but alternatively sound waves, light waves, wire, or telephone lines can be used for transmission.

The system comprises a contact device in which a microminiature radio frequency transensor, actively or passively activated, such as endoradiosondes, are mounted in the contact device which in turn is preferably placed on the surface of the eye. A preferred method involves small passive radio telemetric transducers capable of detecting chemical compounds, electrolytes, glucose, cholesterol, and the like on the surface of the eye. Besides using passive radio transmission or communication by cable, active radio transmission with active transmitters contained a microminiature battery mounted in the contact device can also be used.

Several means and transensors can be mounted in the contact device and used to acquire the signal. Active radio transmitters using transensors which are energized by batteries or using cells that can be recharged in the eye by an external oscillator, and active transmitters which can be powered from a biologic source can also be used and mounted in the contact device. The preferred method to acquire the signal involves passive radio frequency transensors, which contain no power source. They act from energy supplied to it from an external source. The transensor transmits signals to remote locations using different frequencies indicative of the levels of chemical and physical parameters. These intraocular recordings can then be transmitted to remote extra ocular radio frequency monitor stations with the signal sent to a receiver for amplification and analysis. Ultrasonic micro-circuits can also be mounted in the contact device and modulated by sensors which are capable of detecting chemical and physical changes in the eye. The signal may be transmitted using modulated sound signals particularly under water because sound is less attenuated by water than are radio waves. The sonic resonators can be made responsive to changes in temperature and voltage which correlate to the presence and level of molecules such as glucose and ions in the tear film.

Ocular and systemic disorders may cause a change in the pH, osmolarity, and temperature of the tear film or surface of the eye as well as change in the tear film concentration of substances such as acid-lactic, glucose, lipids, hormones, gases, enzymes, inflammatory mediators, plasmin, albumin, lactoferrin, creatinin, proteins and so on. Besides pressure, outflow facility, and other physical characteristics of the eye, the apparatus of the invention is also capable of measuring the above physiologic parameters in the eye and tear film using transensor/electrodes mounted in the contact device. These changes in pressure, temperature, pH, oxygen level, osmolality, concentration of chemicals, and so on can be monitored with the eyes opened or closed or during blinking. In some instance such as with the evaluation of pH, metabolites, and oxygen concentration, the device does not need necessarily eye lid motion because just the contact with the transensor mounted in the contact device is enough to activate the transensor/electrodes.

The presence of various chemical elements, gases, electrolytes, and pH of the tear film and the surface of the eye can be determined by the use of suitable electrodes and a suitable permeable membrane. These electrodes, preferably microelectrodes, can be sensitized by several reacting chemicals which are in the tear film or the surface of the eye, in the surface of the cornea or preferably the vascularized areas in the surface of the eye. The different chemicals and substances diffuse through suitable permeable membranes sensitizing suitable sensors. Electrodes and sensors to measure the above compounds are available from several manufacturers.

The level of oxygen can be measured in the eye with the contact device, and in this case just the placement of the contact device would be enough to activate the system and eye lid motion and/or closure of the eye lid may not be necessary for its operation. Reversible mechanical expansion methods, photometric, or electrochemical methods and electrodes can be mounted in the device and used to detect acidity and gases concentration. Oxygen gas can also be evaluated according to its magnetic properties or be analyzed by micro-polarographic sensors mounted in the contact device. Moreover, the same sensor can measure different gases by changing the cathode potential. Carbon dioxide, carbon monoxide, and other gases can also be detected in a similar fashion.

Microminiature glass electrodes mounted in the contact device can be used to detect divalent cations such as calcium, as well as sodium and potassium ion and pH. Chloride-ion detector can be used to detect the salt concentration in the tear film and the surface of the eye. The signal can be radio transmitted to a receiver and then to a screen for continuous recording and monitoring. This allows for the continuous non-invasive measurement of electrolytes, chemicals and pH in the body and can be very useful in the intensive care unit setting.

A similar transensor can also be placed not in the eye, but in contact with other mucosas and secretions in the body, such as the oral mucosa, and the concentration of chemicals measured in the saliva or even sweat or any other body secretion with signals being transmitted to a remote location via ultrasonic or radio waves and the like. However, due to the high concentration of enzymes in the saliva and in other secretion, the electrodes and electronics could be detrimentally affected which would impact accuracy. Furthermore, there is a weak correlation between concentration of chemicals in body secretions and blood.

The tear fluid proves to be the most reliable location and indicator of the concentration of chemicals, both organic and inorganic, but other areas of the eye can be utilized to measure the concentration of chemicals. The tear fluid and surface of the eye are the preferred location for these measurements because the tear film and aqueous humor (which can be transmitted through the intact cornea) can be considered an ultrafiltrate of the plasma.

The apparatus and method of the present invention allows the least traumatic way of measuring chemicals in the body without the need of needle stick and the manipulation of blood. For instance, this may be particularly important as compared to drawing blood from infants because the results provided by the drawn blood sample may not be accurate. There is a dramatic change in oxygen and carbon dioxide levels because of crying, breath holding and even apnea spells that occur during the process of restraining the baby and drawing blood. Naturally, the ability to painlessly measure blood components without puncturing the vessel is beneficial also to any adult who needs a blood work-up, patients with diabetes who need to check their glucose level on a daily basis, and health care workers who would be less exposed to severe diseases such as AIDS and hepatitis when manipulating blood. Patients in intensive care units would benefit by having a continuous painless monitoring of electrolytes, gases, and so on by non-invasive means using the intelligent contact lens system. Moreover, there is no time wasted transporting the blood sample to the laboratory, the data is available immediately and continuously.

The different amounts of eye fluid encountered in the eye can be easily quantified and the concentration of substances calibrated according to the amount of fluid in the eye. The relationship between the concentration of chemical substances and molecules in the blood and the amount of said chemical substances in the tear fluid can be described mathematically and programmed in a computer since the tear film can be considered an ultrafiltrate of the plasma and diffusion of chemicals from capillaries on the surface of the eye have a direct correspondence to the concentration in the blood stream.

Furthermore, when the eyes are closed there is an equilibrium between the aqueous humor and the tear fluid allowing measurement of glucose in a steady state and since the device can send signals through the intervening eyelid, the glucose can be continuously monitored in this steady state condition. Optical sensors mounted in the contact device can evaluate oxygen and other gases in tissues and can be used to detect the concentration of compounds in the surface of the eye and thus not necessarily have to use the tear film to measure the concentration of said substances. In all instances, the signals can be preferably radio transmitted to a monitoring station. Optical, acoustic, electromagnetic, micro-electromechanical systems and the like can be mounted in the contact device and allow the measurement of blood components in the tear film, surface of the eye, conjunctival vessels, aqueous humor, vitreous, and other intraocular and extraocular structures.

Any substance present in the blood can be analyzed in this way since as mentioned the fluid measured is a filtrate of the blood. Rapidly responding microelectrodes with very thin membranes can be used to measure these substances providing a continuous evaluation. For example, inhaled anesthetics become blood gases and during an experiment the concentration of anesthetics present in the blood could be evaluated in the eye fluid. Anesthetics such as nitrous oxide and halothane can be reduced electrochemically at noble metal electrodes and the electrodes can be mounted in the contact device. Oxygen sensors can also used to measure the oxygen of the sample tear film. Measurement of oxygen and anesthetics in the blood has been performed and correlated well with the amount of the substances in the eye fluid with levels in the tear fluid within 85-95% of blood levels. As can be seen, any substances not only the ones naturally present, but also artificially inserted in the blood can be potentially measured in the eye fluid. A correction factor may be used to account for the differences between eye fluid and blood. In addition, the non-invasive measurement and detection by the ICL of exogenous substances is a useful tool to law enforcement agents for rapidly testing and detecting drugs and alcohol.

The evaluation of systemic and ocular hemodynamics can be performed with suitable sensors mounted in the contact device. The measurements of blood pulsations in the eye can be done through electrical means by evaluating changes in impedance. Blood flow rate can be evaluated by several techniques including but not limited to ultrasonic and electromagnetic meters and the signals then radio transmitted to an externally placed device. For the measurement of blood flow, the contact device is preferably placed in contact with the conjunctiva, either bulbar or palpebral, due to the fact that the cornea is normally an avascular structure. Changing in the viscosity of blood can also be evaluated from a change in damping on a vibrating quartz micro-crystal mounted in the contact device.

The apparatus of the invention may also measure dimension such as the thickness of the retina, the amount of cupping in the optic nerve head, and so on by having a microminiature ultrasound device mounted in the contact device and placed on the surface of the eye. Ultra sonic timer/exciter integrated circuits used in both continuous wave and pulsed bidirectional Doppler blood flowmeters are in the order few millimeters in length and can be mounted in the apparatus of the invention.

For the measurement of hemodynamics, the contact device should preferably be placed in contact with the conjunctiva and on top of a blood vessel. Doppler blood microflowmeters are available and continuous wave (CW) and pulsed Doppler instruments can be mounted in the contact device to evaluate blood flow and the signal radio transmitted to an external receiver. The Doppler flowmeters may also use ultrasonic transducers and these systems can be fabricated in miniature electronic packages and mounted in the contact device with signals transmitted to a remote receiver.

Illumination of vessels, through the pupil, in the back of the eye can be used to evaluate blood flow velocity and volume or amount of cupping (recess) in the optic nerve head. For this use the contact device has one or more light sources located near the center and positioned in a way to reach the vessels that exit the optic nerve head, which are the vessels of largest diameter on the surface of the retina. A precise alignment of beam is possible because the optic nerve head is situated at a constant angle from the visual axis. Sensors can be also positioned on the opposite side of the illumination source and the reflected beam reaching the sensor. Multioptical filters can be housed in the contact device with the light signal converted to voltage according to the angle of incidence of reflected light.

Moreover, the intracranial pressure could be indirectly estimated by the evaluation of changes and swelling in the retina and optic nerve head that occurs in these structures due to the increased intracerebral pressure. Fiber optics from an external light source or light sources built in the contact device emit a beam of plane-polarized light from one side at three o=clock position with the beam entering through the cornea and passing through the aqueous humor and exiting at the nine o=clock position to reach a photodetector. Since glucose can rotate the plane of polarization, the amount of optical rotation would be compared to a second reference beam projected in the same manner but with a wavelength that it is insensitive to glucose with the difference being indicative of the amount of glucose present in the aqueous humor which can be correlated to plasma glucose by using a correction factor.

A dielectric constant of several thousand can be seen in blood and a microminiature detector placed in the contact device can identify the presence of blood in the surface of the cornea. Moreover, blood causes the decomposition of hydrogen peroxide which promotes an exothermic reaction that can be sensed with a temperature-sensitive transensor. Small lamps energized by an external radio-frequency field can be mounted in the contact device and photometric blood detectors can be used to evaluate the presence of blood and early detection of neovascularization in different parts of the eye and the body.

A microminiature microphone can be mounted in the contact device and sounds from the heart, respiration, flow, vocal and the environment can be sensed and transmitted to a receiver. In cases of abnormal heart rhythm, the receiver would be carried by the individual and will have means to alert the individual through an alarm circuit either by light or sound signals of the abnormality present. Changes in heart beat can be detected and the patient alerted to take appropriate action.

The contact device can also have elements which produce and radiate recognizable signals and this procedure could be used to locate and track individuals, particularly in military operations. A permanent magnet can also be mounted in the contact device and used for tracking as described above.

Life threatening injuries causing change in heart rhythm and respiration can be detected since the cornea pulsates according to heartbeat. Motion sensitive microminiature radio frequency transensors can be mounted in the contact device and signals indicative of injuries can be radio transmitted to a remote station particularly for monitoring during combat in military operations.

In rocket or military operations or in variable g situations, the parameters above can be measured and monitored by utilizing materials in the transensor such as light aluminum which are less sensitive to gravitational and magnetic fields. Infrared emitters can be mounted in the contact device and used to activate distinct photodetectors by ocular commands such as in military operations where fast action is needed without utilizing hand movement.

Spinal cord injuries have lead thousands of individuals to complete confinement in a wheel chair. The most unfortunate situation occurs with quadriplegic individuals who virtually only have useful movement of their mouth and eyes. The apparatus of the invention allows these individuals to use their remaining movement ability to become more independent and capable of indirect manipulation of a variety of hardware. In this embodiment, the ICL uses blinking or closure of the eyes to activate remotely placed receptor photodiodes through the activation of an LED drive coupled with a pressure sensor.

The quadriplegic patient focuses on a receptor photo diode and closes their eyes for 5 seconds, for example. The pressure exerted by the eyelid is sensed by the pressure sensor which is coupled with a timing chip. If the ICL is calibrated for 5 sec, after this amount of time elapses with eyes closed, the LED drive activates the LED which emits infrared light though the intervening eyelid tissue reaching suitable receptor photodiodes or suitable optical receivers connected to a power on or off circuit. This allows quadriplegics to turn on, turn off, or manipulate a variety of devices using eye motion. It is understood that an alternative embodiment can use more complex integrated circuits connected by fine wires to the ICL placed on the eye in order to perform more advanced functions such as using LED-s of different wavelengths.

Another embodiment according to the present invention includes a somnolence alert device using eye motion to detect premonitory signs of somnolence related to a physiologic condition called Bell phenomena in which the eye ball moves up and slightly outwards when the eyes are closed. Whenever an individual starts to fall asleep, the eye lid comes down and the eyes will move up.

A motion or pressure sensor mounted in the superior edge of the ICL will cause, with the Bell phenomena, a movement of the contact device upwards. This movement of the eye would position the pressure sensitive sensor mounted in the contact device against the superior cul-de-sac and the pressure created will activate the sensor which modulates a radio transmitter. The increase in pressure can be timed and if the pressure remains increased for a certain length of time indicating closed eyes, an alarm circuit is activated. The signal would then be transmitted to a receiver coupled with an alarm circuit and speaker creating a sound signal to alert the individual at the initial indication of falling asleep. Alternatively, the pressure sensor can be positioned on the inferior edge of the ICL and the lack of pressure in the inferiorly placed sensor would activate the circuit as described above.

It is also understood that other means to activate a circuit in the contact device such as closing an electric circuit due to motion or pressure shift in the contact device which remotely activate an alarm can be used as a somnolence awareness device. It is also understood that any contact device with sensing elements capable of sensing Bell phenomena can be used as a somnolence awareness device. This system, device and method are an important tool in diminishing car accidents and machinery accidents by individuals who fall sleep while operating machinery and vehicles.

If signs of injury in the eye are detected, such as increased intraocular pressure (IOP), the system can be used to release medication which is placed in the cul-de-sac in the lower eye lid as a reservoir or preferably the contact lens device acts as a reservoir for medications. A permeable membrane, small fenestrations or a valve like system with micro-gates, or micro-electronic systems housed in the contact device structure could be electrically, magnetically, electronically, or optically activated and the medication stored in the contact device released. The intelligent lenses can thus be used as non-invasive drug delivery systems. Chemical composition of the tear film, such as the level of electrolytes or glucose, so that can be sensed and signals radio transmitted to drug delivery pumps carried by the patient so that medications can be automatically delivered before symptoms occur.

A part of the contact transducer can also be released, for instance if the amount of enzymes increases. The release of part of the contact device could be a reservoir of lubricant fluid which will automatically be released covering the eye and protecting it against the insulting element. Any drugs could be automatically released in a similar fashion or through transmission of signal to the device.

An alternative embodiment includes the contact device which has a compartment filled with chemical substances or drugs connected to a thread which keeps the compartments sealed. Changes in chemicals in the tear fluid or the surface of the eye promote voltage increases which turns on a heater in the circuit which melts the thread allowing discharge of the drug housed in the compartment such as insulin if there is an increase in the levels of glucose detected by the glucose sensor.

To measure temperature, the same method and apparatus applies, but in this case the transmitter is comprised of a temperature-sensitive element. A microminiature temperature-sensitive radio frequency transensor, such as thermistor sensor, is mounted in the contact device which in turn is placed on the eye with signals preferably radio transmitted to a remote station. Changes in temperature and body heat correlate with ovulation and the thermistor can be mounted in the contact device with signals telemetered to a remote station indicating optimum time for conception.

The detection and transmission to remote stations of changes in temperature can be used on animals for breeding purposes. The intelligent contact lens can be placed on the eye of said animals and continuous monitoring of ovulation achieved. When this embodiment is used, the contact device with the thermistor is positioned so that it lodges against the palpebral conjunctiva to measure the temperature at the palpebral conjunctiva. Monitoring the conjunctiva offers the advantages of an accessible tissue free of keratin, a capillary level close to the surface, and a tissue layer vascularized by the same arterial circulation as the brain. When the lids are closed, the thermal environment of the cornea is exclusively internal with passive prevention of heat loss during a blink and a more active heat transfer during the actual blink.

In carotid artery disease due to impaired blood supply to the eye, the eye has a lower temperature than that of the fellow eye which indicates a decreased blood supply. If a temperature difference greater than normal exists between the right and left eye, then there is an asymmetry in blood supply. Thus, this embodiment can provide information related to carotid and central nervous system vascular disorders. Furthermore, this embodiment can provide information concerning intraocular tumors such as melanoma. The area over a malignant melanoma has an increase in temperature and the eye harboring the malignant melanoma would have a higher temperature than that of the fellow eye. In this embodiment the thermistor is combined with a radio transmitter emitting an audio signal frequency proportional to the temperature.

Radiation sensitive endoradiosondes are known and can be used in the contact device to measure the amount of radiation and the presence of radioactive corpuscules in the tear film or in front of the eye which correlates to its presence in the body. The amount of hydration and humidity of the eye can be sensed with an electrical discharge and variable resistance moisture sensor mounted in the contact device. Motion and deceleration can be detected by a mounted accelerometer in the contact device. Voltages accompanying the function of the eye, brain, and muscles can be detected by suitable electrodes mounted in the device and can be used to modulate the frequency of the transmitter. In the case of transmission of muscle potentials, the contact device is placed not on the cornea, but next to the extraocular muscle to be evaluated and the signals remotely transmitted. A fixed frequency transmitter can be mounted in the contact device and used as a tracking device which utilizes a satellite tracking system by noting the frequency received from the fixed frequency transmitter to a passing satellite A surface electrode mounted in the contact device may be activated by optical or electromagnetic means in order to increase the temperature of the eye. This increase in temperature causes a dilation of the capillary bed and can be used in situations in which there is hypoxia (decreased oxygenation) in the eye. The concept and apparatus called heat stimulation transmission device (HSTD) is based upon my experiments and in the fact that the eye has one of largest blood supply per gram of tissue in the body and has the unique ability to be overpefused when there is an increase in temperature. The blood flow to the eye can thus be increased with a consequent increase in the amount of oxygen. The electrode can be placed in any part of the eye, inside or outside, but is preferably placed on the most posterior part of the eye. The radio frequency activated heating elements can be externally placed or surgically implanted according to the area in need of increase in the amount of oxygen in the eye. It is understood that the same heating elements could be placed or implanted in other parts of the body. Naturally, means that promote an increase in temperature of the eye without using electrodes can be used as long as the increase in temperature is sufficient to increase blood flow without promoting any injury.

The amount of increase varies from individual to individual and according to the status of the vascular bed of the eye. The increase in temperature of blood in the eye raises its oxygen level about 6% per each one degree Celsius of increase in temperature allowing precise quantification of the increase in oxygen by using a thermistor which simultaneously indicates temperature, or alternatively an oxygen sensor can be used in association with the heating element and actual amount of increase in oxygen detected.

This increase in blood flow can be timed to occur at predetermined hours in the case of chronic hypoxia such as in diabetes, retinal degenerations, and even glaucoma. These devices can be externally placed or surgically implanted in the eye or other parts of the body according to the application needed.

Another embodiment is called over heating transmission device (OHTD) and relates to a new method and apparatus for the treatment of tumors in the eye or any other part of the body by using surgically implanted or externally placed surface electrodes next to a tumor with the electrodes being activated by optical or electromagnetic means in order to increase the temperature of the cancerous tissue until excessive localized heat destroys the tumor cells. These electrodes can be packaged with a thermistor and the increase in temperature sensed by the thermistor with the signal transmitted to a remote station in order to evaluate the degree of temperature increase.

Another embodiment concerning therapy of eye and systemic disorders include a neurostimulation transmission device (NSTD) which relates to a system in which radio activated microphotodiodes or/and micro-electric circuits and electrodes are surgically implanted or externally placed on the eye or other parts of the body such as the brain and used to electrically stimulate non-functioning neural or degenerated neural tissue in order to treat patients with retinal degeneration, glaucoma, stroke, and the like. Multiple electrodes can be used in the contact device, placed on the eye or in the brain for electrical stimulation of surrounding tissues with consequent regeneration of signal transmission by axonal and neural cells and regeneration of action potential with voltage signals being transmitted to a remote station.

Radio and sonic transensors to measure pressure, electrical changes, dimensions, acceleration, flow, temperature, bioelectric activity and other important physiologic parameters and power switches to externally control the system have been developed and are suitable systems to be used in the apparatus of the invention. The sensors can be automatically turned on and off with power switches externally controlling the intelligent contact lens system. The use of integrated circuits and advances occurring in transducer, power source, and signal processing technology allow for extreme miniaturization of the components which permits several sensors to be mounted in one contact device. For instance, typical resolutions of integrated circuits are in the order of a few microns and very high density circuit realization can be achieved. Radio frequency and ultrasonic microcircuits are available and can be used and mounted in the contact device. A number of different ultrasonic and pressure transducers are also available and can be used and mounted in the contact device.

Technologic advances will occur which allow full and novel applications of the apparatus of the invention such as measuring enzymatic reactions and DNA changes that occur in the tear fluid or surface of the eye, thus allowing an early diagnosis of disorders such as cancer and heart diseases. HIV virus is present in tears and AIDS could be detected with the contact device by sensors coated with antibodies against the virus which would create a photochemical reaction with appearance of colorimetric reaction and potential shift in the contact device with subsequent change in voltage or temperature that can be transmitted to a monitoring station.

A variety of other pathogens could be identified in a similar fashion. These signals can be radio transmitted to a remote station for further signal processing and analysis. In the case of the appearance of fluorescent light, the outcome could be observed on a patient=s eye simply by illuminating the eye with light going through a cobalt filter and in this embodiment the intelligent contact lens does not need to necessarily have signals transmitted to a station.

The system further comprises a contact device in which a microminiature gas-sensitive, such as oxygen-sensitive, radio frequency transensor is mounted in the contact device which in turn is placed on the cornea and/or surface of the eye. The system also comprises a contact device in which a microminiature blood velocity-sensitive radio frequency transensor is mounted in the contact device which in turn is placed on the conjunctiva and is preferably activated by eye lid motion and/or closure of the eye lid. The system also comprises a contact device in which a radio frequency transensor capable of measuring the negative resistance of nerve fibers is mounted in the contact device which in turn is preferably placed on the cornea and/or surface of the eye. By measuring the electrical resistance, the effects of microorganisms, drugs, poisons and anesthetics can be evaluated. The system also comprises a contact device in which a microminiature radiation-sensitive radio frequency transensor is mounted in the contact device which in turn is preferably placed on the cornea.

The contact device preferably includes a rigid or flexible annular member in which a transensor is mounted in the device. The transensor is positioned in a way to allow passage of light through the visual axis. The annular member preferably includes an inner concave surface shaped to match an outer surface of the eye and having one or more holes defined therein in which transensors are mounted. It is understood that the contact device conforms in general shape to the surface of the eye with its dimensions and size chosen to achieve optimal comfort level and tolerance. It is also understood that the curvature and shape of the contact device is chosen to intimately and accurately fit the contact device to the surface of the eye for optimization of sensor function. The surface of the contact device can be porous or microporous as well as with micro-protuberances on the surface. It is also understood that fenestrations can be made in the contact device in order to allow better oxygenation of the cornea when the device is worn for a long period of time. It is also understood that the shape of the contact device may include a ring-like or band-like shape without any material covering the cornea. It is also understood that the contact device may have a base down prism or truncated edge for better centration. It is also understood that the contact device preferably has a myoflange or a minus carrier when a conventional contact lens configuration is used. It is also understood that an eliptical, half moon shape or the like can be used for placement under the eyelid. It is understood that the contact device can be made with soft of hard material according to the application needed. It is also understood that an oversized corneal scleral lens covering the whole anterior surface of the eye can be used as well as hourglass shaped lenses and the like. It is understood also that the external surface of the contact device can be made with polymers which increases adherence to tissues or coating which increases friction and adherence to tissues in order to optimize fluid passage to sensors when measuring chemical components. It is understood that the different embodiments which are used under the eyelids are shaped to fit beneath the upper and/or eyelids as well as to fit the upper or lower cul-de-sac.

The transensor may consist of a passive or active radio frequency emitter, or a miniature sonic resonator, and the like which can be coupled with miniature microprocessor mounted in the contact device. The transensors mounted in the contact device can be remotely driven by ultrasonic waves or alternatively remotely powered by electromagnetic waves or by incident light. They can also be powered by microminiature low voltage batteries which are inserted into the contact device.

As mentioned, preferably the data is transmitted utilizing radio waves, sound waves, light waves, by wire, or by telephone lines. The described techniques can be easily extrapolated to other transmission systems. The transmitter mounted in the contact device can use the transmission links to interconnect to remote monitoring sites. The changes in voltage or voltage level are proportional to the values of the biological variables and this amplified physiologic data signal from the transducers may be frequency modulated and then transmitted to a remote external reception unit which demodulates and reconstitutes the transmitted frequency modulated data signal preferably followed by a low pass filter with the regeneration of an analog data signal with subsequent tracing on a stripchart recorder.

The apparatus of the invention can also utilize a retransmiter in order to minimize electronic components and size of the circuit housed in the contact device. The signal from a weak transmitter can be retransmitted to a greater distance by an external booster transmitter carried by the subject or placed nearby. It is understood that a variety of noise destruction methods can be used in the apparatus of the invention.

Since the apparatus of the invention utilizes externally placed elements on the surface of the eye that can be easily retrieved; there is no tissue damage due to long term implantation and if drift occurs it is possible to recalibrate the device. There are a variety of formats that can be used in the apparatus of the invention in which biologic data can be encoded and transmitted. The type of format for a given application is done according to power requirement, circuit complexity, dimensions and the type of biologic data to be transmitted. The general layout of the apparatus preferably includes an information source with a variety of biological variables, a transducer, a multiplexer, a transmitter, a transmission path and a transmission medium through which the data is transmitted preferably as a coded and modulated signal.

The apparatus of the invention preferably includes a receiver which receives the coded and modulated signal, an amplifier and low pass filter, a demultiplexer, a data processing device, a display and recording equipment, and preferably an information receiver, a CPU, a modem, and telephone connection. A microprocessor unit containing an autodialing telephone modem which automatically transmits the data over the public telephone network to a hospital based computer system can be used. It is understood that the system may accept digitally coded information or analog data.

When a radio link is used, the contact device houses a radio frequency transmitter which sends the biosignals to a receiver located nearby with the signals being processed and digitized for storage and analysis by microcomputer systems. When the apparatus of the invention transmits data using a radio link, a frequency carrier can be modulated by a subcarrier in a variety of ways: amplitude modulation (AM), frequency modulation (FM), and code modulation (CM). The subcarriers can be modulated in a variety of ways which includes AM, FM, pulse amplitude modulation (PAM), pulse duration modulation (PDM), pulse position modulation (PPM), pulse code modulation (PCM), delta modulation (DM), and the like.

It is understood that the ICL structure and the transducer/transmitter housing are made of material preferably transparent to radio waves and the electronic components coated with materials impermeable to fluids and salts and the whole unit encased in a biocompatable material. The electronics, sensors, and battery (whenever an active system is used), are housed in the contact device and are hermetically sealed against fluid penetration. It is understood that sensors and suitable electrodes such as for sensing chemicals, pH and the like, will be in direct contact with the tear fluid or the surface of the eye. It is also understood that said sensors, electrodes and the like may be covered with suitable permeable membranes according to the application needed. The circuitry and electronics may be encased in wax such as beeswax or paraffin which is not permeable to body fluid. It is understood that other materials can be used as a moisture barrier. It is also understood that various methods and materials can be used as long as there is minimal frequency attenuation, insulation, and biocompatibility. The components are further encased by biocompatible materials as the ones used in conventional contact lenses such as Hydrogel, silicone, flexible acrylic, sylastic, or the like.

The transmitter, sensors, and other components can be mounted and/or attached to the contact device using any known attachment techniques, such as gluing, heat-bonding, and the like. The intelligent contact lens can use a modular construction in its assembly as to allow tailoring the number of components by simply adding previously constructed systems to the contact device.

It is understood that the transmission of data can be accomplished using preferably radio link, but other means can also be used. The choice of which energy form to be used by the ICL depends on the transmission medium and distance, channel requirement, size of transmitter equipment and the like. It is understood that the transmission of data from the contact device by wire can be used but has the disadvantage of incomplete freedom from attached wires. However, the connection of sensors by wires to externally placed electronics, amplifiers, and the like allows housing of larger sensors in the contact device when the application requires as well as the reduction of mechanical and electrical connections in the contact device. The transmission of data by wire can be an important alternative when there is congested space due to sensors and electronics in the contact device. It is understood that the transmission of data in water from the contact device can be preferably accomplished using sound energy with a receiver preferably using a hydrophone crystal followed by conventional audio frequency FM decoding.

It is also understood that the transmission of data from the contact device can be accomplished by light energy as an alternative to radio frequency radiation. Optical transmission of signals using all sorts of light such as visible, infrared, and ultraviolet can be used as a carrier for the transmission of data preferably using infrared light as the carrier for the transmission system. An LED can be mounted in the contact device and transmit modulated signals to remotely placed receivers with the light emitted from the LED being modulated by the signal. When using this embodiment, the contact device in the receiver unit has the following components: a built in infrared light emitter (950 nm), an infrared detector, decoder, display, and CPU. Prior to transmission, the physiologic variables found on the eye or tear fluid are multiplexed and encoded by pulse interval modulation, pulse frequency modulation, or the like. The infrared transmitter then emits short duration pulses which are sensed by a remotely placed photodiode in the infrared detector which is subsequently decoded, processed, and recorded. The light transmitted from the LED is received at the optical receiver and transformed into electrical signals with subsequent regeneration of the biosignals. Infrared light is reflected quite well including surfaces that do not reflect visible light and can be used in the transmission of physiological variables and position/motion measurement. This embodiment is particularly useful when there is limitations in bandwidth as in radio transmission. Furthermore, this embodiment may be quite useful with closed eyes since the light can be transmitted through the skin of the eyelid.

It is also understood that the transmission of data from the contact device can be accomplished by the use of sound and ultrasound being the preferred way of transmission underwater since sound is less strongly attenuated by water than radio waves. The information is transmitted using modulated sound signals with the sound waves being transmitted to a remote receiver. There is a relatively high absorption of ultrasonic energy by living tissues, but since the eye even when closed has a rather thin intervening tissue the frequency of the ultrasonic energy is not restricted. However, soundwaves are not the preferred embodiment since they can take different paths from their source to a receiver with multiple reflections that can, alter the final signal. Furthermore, it is difficult to transmit rapidly changing biological variables because of the relatively low velocity of sound as compared to electromagnetic radiation. It is possible though to easily mount an ultrasonic endoradiosonde in the contact device such as for transmitting pH values or temperature. An ultrasonic booster transmitter located nearby or carried by the subject can be used to transmit the signal at a higher power level. An acoustic tag with a magnetic compass sensor can be used with the information acoustically telemetered to a sector scanning sonar.

A preferred embodiment of the invention consists of electrodes, FM transmitter, and a power supply mounted in the contact device. Stainless steel micro cables are used to connect the electronics to the transducers to the battery power supply. A variety of amplifiers and FM transmitters including Colpitts oscillator, crystal oscillators and other oscillators preferably utilizing a custom integrated circuit approach with ultra density circuitry can be used in the apparatus of the invention.

Several variables can be simultaneously transmitted using different frequencies using several transmitters housed in the contact device. Alternatively, a single transmitter (3 channel transmitter) can transmit combined voltages to a receiver, with the signal being subsequently decoded, separated into three parts, filtered and regenerated as the three original voltages (different variables such as glucose level, pressure and temperature). A multiple channel system incorporating all signal processing on a single integrated circuit minimizes interconnections and can be preferably mounted in the apparatus of the invention when multiple simultaneous signal transmission is needed such as transmitting the level of glucose, temperature, bioelectrical, and pressure. A single-chip processor can be combined with a logic chip to also form a multichannel system for the apparatus of the invention allowing measurement of several parameters as well as activation of transducers.

It is understood that a variety of passive, active, and inductive power sources can be used in the apparatus of the invention. The power supply may consist of micro batteries, inductive power link, energy from biological sources, nuclear cells, micro power units, fuel cells which use glucose and oxygen as energy sources, and the like. The type of power source is chosen according to the biological or biophysical event to be transmitted.

A variety of signal receivers can be used such a frame aerial connected to a conventional FM receiver from which the signal is amplified decoded and processed. Custom integrated circuits will provide the signal processing needed to evaluate the parameters transmitted such as temperature, pressure flow dimensions, bioelectrical activity, concentration of chemical species and the like. The micro transducers, signal processing electronics, transmitters and power source can be built in the contact device.

Power for the system may be supplied from a power cell activated by a micropower control switch contained in the contact device or can be remotely activated by radio frequency means, magnetic means and the like. Inductive radio frequency powered telemetry in which the same coil system used to transfer energy is used for the transmission of data signal can be used in the apparatus of the invention. The size of the system relates primarily to the size of the batteries and the transmitter. The size of conventional telemetry systems are proportional to the size of the batteries because most of the volume is occupied by batteries. The size of the transmitter is related to the operating frequency with low frequencies requiring larger components than higher frequency circuits. Radiation at high frequencies are more attenuated than lower frequencies by body tissues. Thus a variety of systems implanted inside the body requires lower frequency devices and consequently larger size components in order for the signal to be less attenuated. Since the apparatus of the invention is placed on the surface of the eye there is little to no attenuation of signals and thus higher frequency small devices can be used. Furthermore, very small batteries can be used since the contact device can be easily retrieved and easily replaced. The large volume occupied by batteries and power sources in conventional radio telemetry implantable devices can be extremely reduced since the apparatus of the invention is placed externally on the eye and is of easy access and retrieval, and thus a very small battery can be utilized and replaced whenever needed.

A variety of system assemblies can be used but the densest system assembly is preferred such as a hybrid assembly of custom integrated circuits which permits realization of the signal processing needed for the applications. The typical resolution of such circuits are in the order of a few microns and can be easily mounted in the contact device. A variety of parameters can be measured with one integrated circuit which translates the signals preferably into a transmission bandwidth. Furthermore, a variety of additional electronics and a complementary metal oxide semiconductor (CMOS) chip can be mounted in the apparatus of the invention for further signal processing and transmission.

The micropower integrated circuits can be utilized with a variety of transmitter modalities mounted in the intelligent contact lens including radio links, ultrasonic link and the like. A variety of other integrated circuits can be mounted in the contact device such as signal processors for pressure and temperature, power switches for external control of implanted electronics and the like. Pressure transducers such as a capacitive pressure transducer with integral electronics for signal processing can be incorporated in the same silicon structure and can be mounted in the contact device. Evolving semiconductor technology and more sophisticated encoding methods as well as microminiature integrated circuits amplifiers and receivers are expected to occur and can be housed in the contact device. It is understood that a variety of transmitters, receivers, and antennas for transmitting and receiving signals in telemetry can be used in the apparatus of the invention, and housed in the contact device and/or placed remotely for receiving, processing, and analyzing the signal.

The fluid present on the front surface of the eye covering the conjunctiva and cornea is referred as the tear film or tear fluid. Close to 100% of the tear film is produced by the lacrimal gland and secreted at a rate of 2 µl/min. The volume of the tear fluid is approximately 10 µl. The layer of tear fluid covering the cornea is about 8-10 µm in thickness and the tear fluid covering the conjunctiva is about 15 µm thick. The pre-corneal tear film consists of three layers: a thin lipid layer measuring about 0.1 µm consisting of the air tear interface, a mucin layer measuring 0.03 µm which is in direct contact with the corneal epithelium, and finally the remaining layer is the thick aqueous layer which is located between the lipid and mucin layer. The aqueous layer is primarily derived from the secretions of the lacrimal gland and its chemical composition is very similar to diluted blood with a reduced protein content and slightly greater osmotic pressure. The secretion and flow of tear fluid from the lacrimal gland located in the supero-temporal quadrant with the subsequent exit through the lacrimal puncta located in the infero-medial quadrant creates a continuous flow of tear fluid providing the ideal situation by furnishing a continuous supply of substrate for one of the stoichiometric reactions which is the subject of a preferred embodiment for evaluation of glucose levels. The main component of the tear fluid is the aqueous layer which is an ultrafiltrate of blood containing electrolytes such as sodium, potassium, chloride, bicarbonate, calcium, and magnesium as well as amino acids, proteins, enzymes, DNA, lipids, cholesterol, glycoproteins, immunoglobulins, vitamins, minerals and hormones. Moreover, the aqueous layer also holds critical metabolites such as glucose, urea, catecholamines, and lactate, as well as gases such as oxygen and carbon dioxide. Furthermore, any exogenous substances found in the blood stream such as drugs, radioactive compounds and the like are present in the tear fluid. Any compound present in the blood can potentially noninvasively be evaluated with the apparatus of the invention with the data transmitted and processed at a remotely located station.

According to one preferred embodiment of the invention, the non-invasive analysis of glucose levels will be described:

Glucose Detection:—The apparatus and methods for measurement of blood components and chemical species in the tear fluid and/or surface of the eye is based on electrodes associated with enzymatic reactions providing an electrical current which can be radio transmitted to a remote receiver providing continuous data on the concentration of species in the tear fluid or surface of the eye. The ICL system is preferably based on a diffusion limited sensors method that requires no reagents or mechanical/moving parts in the contact device. The preferred method and apparatus of the glucose detector using ICL uses the enzyme glucose oxidase which catalyze a reaction involving glucose and oxygen in association with electrochemical sensors mounted in the contact device that are sensitive to either the product of the reaction, an endogenous coreactant, or a coupled electron carrier molecule such as the ferrocene-mediated glucose sensors, as well as the direct electrochemical reaction of glucose at the contact device membrane-covered catalytic metal electrode.

Glucose and oxygen present in the tear fluid either derived from the lacrimal gland or diffused from vessels on the surface of the eye will diffuse into the contact device reaching an immobilized layer of enzyme glucose oxidase mounted in the contact device. Successful operation of enzyme electrodes demand constant transport of the substrate to the electrode since the substrate such as glucose and oxygen are consumed enzymatically. The ICL is the ideal device for using enzyme electrodes since the tear fluid flows continuously on the surface of the eye creating an optimal environment for providing substrate for the stoichiometric reaction. The ICL besides being a noninvasive system solves the critical problem of sensor lifetime which occurs with any sensors that are implanted inside the body. The preferred embodiment refers to amperometric glucose biosensors with the biosensors based on biocatalytic oxidation of glucose in the presence of the enzyme oxidase. This is a two step process consisting of enzymatic oxidation of glucose by glucose oxidase in which the co-factor flavin-adenine dinucleotide (FAD) is reduced to $FADH_2$ followed by oxidation of the enzyme co-factor by molecular oxygen with formation of hydrogen peroxide.

$$Glucose + O_2 + H_2O \xrightarrow{glucose\ oxidase} gluconic\ acid + H_2O_2$$

$$H_2O_2 \rightarrow 2O_2 + H_2O$$

With catalase enzyme the overall reaction is $$glucose + 2O_2 \rightarrow gluconic\ acid$$

Glucose concentration can be measured either by electrochemical detection of an increase of the anodic current due to hydrogen peroxide (product of the reaction) oxidation or by detection of the decrease in the cathodic current due to oxygen (co-reactant) reduction. The ICL glucose detection system preferably has an enzyme electrode in contact with the tear fluid and/or surface of the eye capable of measuring the oxidation current of hydrogen peroxide created by the stoichiometric conversion of glucose and oxygen in a layer of glucose oxidase mounted inside the contact device. The ICL glucose sensor is preferably electrochemical in nature and based on a hydrogen peroxide electrode which is converted by immobilized glucose oxidase which generates a direct current depending on the glucose concentration of the tear fluid.

The glucose enzyme electrode of the contact device responds to changes in the concentration of both glucose and oxygen, both of which are substrates of the immobilized enzyme glucose oxidase. It is also understood that the sensor in the contact device can be made responsive to glucose only by operating in a differential mode. The enzymatic electrodes built in the contact device are placed in contact with the tear fluid or the surface of the eye and the current generated by the electrodes according to the stoichiometric conversion of glucose, are subsequently converted to a frequency audio signal and transmitted to a remote receiver, with the current being proportional to the glucose concentration according to calibration factors.

The signals can be transmitted using the various transmission systems previously described with an externally placed receiver demodulating the audio frequency signal to a voltage and the glucose concentration being calculated from the voltage and subsequently displayed on a LED display. An interface card can be used to connect the receiver with a computer for further signal processing and analysis. During oxidation of glucose by glucose oxidase an electrochemically oxidable molecule or any other oxidable species generated such as hydrogen peroxide can be detected amperometrically as a current by the electrodes. A preferred embodiment includes a tree electrode setup consisting of a working electrode (anode) and auxiliary electrode (cathode) and a reference electrode connected to an amperometric detector. It should be noted though, that a glucose sensor could function well using two electrodes. When appropriate voltage difference is applied between the working and auxiliary electrode, hydrogen peroxide is oxidized on the surface of the working electrode which creates a measurable electric current. The intensity of the current generated by the sensor is proportional to the concentration of hydrogen peroxide which is proportional to the concentration of glucose in the tear film and the surface of the eye.

A variety of materials can be used for the electrodes such as silver/silver chloride coded cathodes. Anodes may be preferably constructed as a platinum wire coated with glucose oxidase or preferably covered by a immobilized glucose oxidase membrane. Several possible configurations for sensors using amperometric enzyme electrodes which involves detection of oxidable species can be used in the apparatus of the invention. A variety of electrodes and setups can be used in the contact device which are capable of creating a stable working potential and output current which is proportional to the concentration of blood components in the tear fluid and surface of the eye. It is understood that a variety of electrode setups for the amperometric detection of oxidable species can be accomplished with the apparatus of the invention. It is understood that solutions can be applied to the surface of the electrodes to enhance transmission.

Other methods which use organic mediators such as ferrocene which transfers electrons from glucose oxidase to a base electrode with subsequent generation of current can be utilized. It is also understood that needle-type glucose sensors can be placed in direct contact with the conjunctiva or encased in a contact device for measurement of glucose in the tear fluid. It is understood that any sensor capable of converting a biological variable to a voltage signal can be used in the contact device and placed on the surface of the eye for measurement of the biological variables. It is understood that any electrode configuration which measures hydrogen peroxide produced in the reaction catalysed by glucose oxidase can be used in the contact device for measurement of glucose levels. It is understood that the following oxygen based enzyme electrode glucose sensor can be used in the apparatus of the invention which is based on the principal that the oxygen not consumed by the enzymatic reactions by catalase enzyme is electrochemically reduced at an oxygen sensor producing a glucose modulated oxygen dependent current. This current is compared to a current from a similar oxygen sensor without enzymes.

It is understood that the sensors are positioned in a way to optimize the glucose access to the electrodes such as by creating micro traumas to increase diffusion of glucose across tissues and capillary walls, preferably positioning the sensors against vascularized areas of the eye. In the closed eye about two-thirds of oxygen and glucose comes by diffusion from the capillaries. Thus positioning the sensors against the palpebral conjunctiva during blinking can increase the delivery of substrates to the contact device biosensor allowing a useful amount of substrates to diffuse through the contact device biosensor membranes.

There are several locations on the surface of the eye in which the ICL can be used to measure glucose: such as: the tear film laying on the surface of the cornea which is an ultrafiltrate of blood derived from the main lacrimal gland; the tear meniscus which is a reservoir of tears on the edge of the eye lid; the supero-temporal conjunctival fornix which allows direct measurement of tears at the origin of secretion; the limbal area which is a highly vascularized area between cornea and the sclera; and preferably the highly vascularized conjunctiva. The contact device allows the most efficient way of acquiring fluid by creating micro-damage to the epithelium with a consequent loss of the blood barrier function of said epithelium, with the subsequent increase in tissue fluid diffusion. Furthermore, mechanical irritation caused by an intentionally constructed slightly rugged surface of the contact device can be used in order to increase the flow of substrates. Furthermore, it is understood that a heating element can be mounted in association with the sensor in order to increase transudation of fluid.

The samples utilized for noninvasive blood analysis may preferably be acquired by micro-traumas to the conjunctiva caused by the contact device which has micro projections on its surface in contact with the conjunctiva creating an increase in the diffusion rate of plasma components through the capillary walls toward the measuring sensors. Moreover, the apparatus of the invention may promote increased vascular permeability of conjunctival vessels through an increase in temperature using surface electrodes as heating elements. Furthermore, the sensors may be located next to the exit point of the lacrimal gland duct in order to collect tear fluid close to its origin. Furthermore, the sensors may be placed inferiorly in contact with the conjunctival tear meniscus which has the largest volume of tear fluid on the surface of the eye. Alternatively, the sensors may be placed in contact with the limbal area which is a substantially vascularized surface of the eye. Any means that create a micro-disruption of the integrity of the ocular surface or any other means that cause transudation of tissue fluid and consequently plasma may be used in the invention. Alternatively, the sensors may be placed against he vascularized conjunctiva in the cul-de-sac superiorly or inferiorly.

It is also understood that the sensors can be placed on any location on the surface of the eye to measure glucose and other chemical compounds. Besides the conventional circular shape of contact lenses, the shape of the contact device also includes a flat rectangular configuration, ring like or half moon like which are used for applications that require placement under the palpebral conjunctiva or cul-de-sac of the eye.

A recessed region is created in the contact device for placement of the electrodes and electronics with enzyme active membranes placed over the electrodes. A variety of membranes with different permeabilities to different chemical species are fitted over the electrodes and enzyme-active membranes. The different permeability of the membranes allows selection of different chemicals to be evaluated and to prevent contaminants from reaching the electrodes. Thus allowing several electroactive compounds to be simultaneously evaluated by mounting membranes with different permeabilities with suitable electrodes on the contact device.

It is also understood that multilayer membranes with preferential permeability to different compounds can be used. The contact device encases the microelectrodes forming a bioprotective membrane such that the electrodes are covered by the enzyme active membrane which is covered by the contact device membrane such as polyurethane which is biocompatible and permeable to the analytes. A membrane between the electrodes and the enzyme membrane can be used to block interfering substances without altering transport of peroxide ion. The permeability of the membranes are used to optimize the concentration of the compounds needed for the enzymatic reaction and to protect against interfering elements.

It is understood that the diffusion of substrate to the sensor mounted in the contact device is preferably perpendicular to the plane of the electrode surface. Alternatively, it is understood that the membrane and surface of the contact device can be constructed to allow selective non-perpendicular diffusion of the substrates. It is also understood that membranes such as negatively charged perfluorinated ionomer Nafion membrane can be used in order to reduce interference by electroactive compounds such as ascorbate, urate and acetaminophen. It is also understood that new polymers and coatings under development which are capable of preferential selection of electroactive compounds and that can prevent degradation of electrodes and enzymes can be used in the apparatus of the invention.

The sensors and membranes coupled with radio transmitters can be positioned in any place in the contact device but may be placed in the cardinal positions in a pie like configuration, with each sensor transmitting its signal to a receiver. For example, if four biological variables are being detected simultaneously the four sensors signals A, B, C, and D are simultaneously transmitted to one or more receivers. Any device utilizing the tear fluid to non-invasively measure the blood components and signals transmitted to a remote station can be used in the apparatus of the invention. Preferably a small contact device, however any size or shape of contact devices can be used to acquire the data on the surface of the eye.

An infusion pump can be activated according to the level of glucose detected by the ICL system and insulin injected automatically as needed to normalize glucose levels as an artificial pancreas. An alarm circuit can also be coupled with the pump and activated when low or high levels of glucose are present thus alerting the patient. It is understood that other drugs, hormones, and chemicals can be detected and signals transmitted in the same fashion using the apparatus of the invention.

A passive transmitter carrying a resonance circuit can be mounted in the contact device with its frequency altered by a change in reactance whose magnitude changes in response to the voltage generated by the glucose sensors. As the signal from passive transmitters falls off extremely rapidly with distance, the antenna and receiver should be placed near to the contact device such as in the frame of regular glasses.

It is also understood that active transmitters with batteries housed in the contact device and suitable sensors as previously described can also be used to detect glucose levels. It is also understood that a vibrating micro-quartz crystal connected to a coil and capable of sending both sound and radio impulses can be mounted in the contact device and continuously transmit data signals related to the concentration of chemical compounds in the tear fluid.

An oxygen electrode consisting of a platinum cathode and a silver anode loaded with polarographic voltage can be used in association with the glucose sensor with the radio transmission of the two variables. It is also understood that sensors which measure oxygen consumption as indirect means of evaluating glucose levels can be used in the apparatus of the invention. The membranes can be used to increase the amount of oxygen delivered to the membrane enzyme since all glucose oxidase systems require oxygen and can potentially become oxygen limited. The membranes also can be made impermeable to other electroactive species such as acetamymophen or substances that can alter the level of hydrogen peroxide produced by the glucose oxidase enzyme membrane.

It is understood that a polarographic Clark-type oxygen detector electrode consisting of a platinum cathode in a silver-to-silver-chloride anode with signals telemetered to a remote station can be used in the apparatus of the invention. It is also understood that other gas sensors using galvanic configuration and the like can be used with the apparatus of the invention. The oxygen sensor is preferably positioned so as to lodge against the palpebral conjunctiva. The oxygen diffusing across the electrode membrane is reduced at the cathode which produces a electrical current which is converted to an audio frequency signal and transmitted to a remote station. The placement of the sensor in the conjunctiva allows intimate contact with an area vascularized by the same arterial circulation as the brain which correlates with arterial oxygen and provides an indication of peripheral tissue oxygen. This embodiment allows good correlation between arterial oxygen and cerebral blood flow by monitoring a tissue bed vascularized by the internal carotid artery, and thus, reflects intracranial oxygenation.

This embodiment can be useful during surgical procedures such as in carotid endarterectomy allowing precise detection of the side with decreased oxygenation. This same embodiment can be useful in a variety of heart and brain operations as well as in retinopathy of prematurity which allows close observation of the level of oxygen administered and thus prevention of hyperoxia with its potentially blinding effects while still delivering adequate amount of oxygen to the infant.

Cholesterol secreted in the tear fluid correlates with plasma cholesterol and a further embodiment utilizes a similar system as described by measurement of glucose. However, this ICL as designed by the inventor involves an immobilized cholesterol esterase membrane which splits cholesterol esters into free cholesterol and fatty acids. The free cholesterol passes through selectively permeable membrane to both free cholesterol and oxygen and reaches a second membrane consisting of an immobilized cholesterol oxidase. In the presence of oxygen the free cholesterol is transformed by the cholesterol oxidase into cholestenone and hydrogen peroxide with the hydrogen peroxide being oxidized on the surface of the working electrode which creates a measurable electric current with signals preferably converted into audio frequency signals and transmitted to a remote receiver with the current being proportional to the cholesterol concentration according to calibration factors. The method and apparatus described above relates to the following reaction or part of the following reaction.

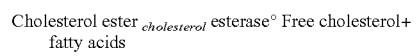

A further embodiment utilizes an antimone electrode that can be housed in the contact device and used to detect the pH and other chemical species of the tear fluid and the surface of the eye. It is also understood that a glass electrode with a transistor circuit capable of measuring pH, pH endoradiosondes, and the like can be used and mounted in the contact device and used for measurement of the pH in the tear fluid or surface of the eye with signals preferably radio transmitted to a remote station.

In another embodiment, catalytic antibodies immobilized in a membrane with associated pH sensitive electrodes can identify a variety of antigens. The antigen when interacting with the catalytic antibody can promote the formation of acetic acid with a consequent change in pH and current that is proportional to the concentration of the antigens according to calibration factors. In a further embodiment an immobilized electrocatalytic active enzyme and associated electrode promote, in the presence of a substrate (meaning any biological variable), an electrocatalytic reaction resulting in a current that is proportional to the amount of said substrate. It is understood that a variety of enzymatic and nonenzymatic detection systems can be used in the apparatus of the invention.

It is understood that any electrochemical sensor, thermoelectric sensors, acoustic sensors, piezoelectric sensors, optical sensors, and the like can be mounted in the contact device and placed on the surface of the eye for detection and measurement of blood components and physical parameters found in the eye with signals preferably transmitted to a remote station. It is understood that electrochemical sensors using amperometric, potentiometric, conductometric, gravimetric, impedimetric, systems, and the like can be used in the apparatus of the invention for detection and measurement of blood components and physical parameters found in the eye with signals preferably transmitted to a remote station.

Some preferable ways have been described; however, any other miniature radio transmitters can be used and mounted in the contact device and any microminiature sensor that modulates a radio transmitter and send the signal to a nearby radio receiver can be used. Other microminiature devices capable of modulating an ultrasound device, or infrared and laser emitters, and the like can be mounted in the contact device and used for signal detection and transmission to a remote station. A variety of methods and techniques and devices for gaining and transmitting information from the eye to a remote receiver can be used in the apparatus of the invention.

It is an object of the present invention to provide an apparatus and method for the non-invasive measurement and evaluation of blood components.

It is also an object of the present invention to provide an intelligent contact lens system capable of receiving, processing, and transmitting signals such as electromagnetic waves, radio waves, infrared and the like being preferably transmitted to a remote station for signal processing and analysis, with transensors and biosensors mounted in the contact device.

It is a further object of the present invention to detect physical changes that occur in the eye, preferably using optical emitters and sensors.

It is a further object of the present invention to provide a novel drug delivery system for the treatment of eye and systemic diseases.

The above and other objects and advantages will become more readily apparent when reference is made to the following description taken in conjunction with the accompanying drawings.

The preferred way for evaluation of bodily functions such as diagnostics and non-invasive blood analysis according to the present invention includes placing an intelligent contact lens on the A highly vascularized conjunctiva@. By the present invention it has been discovered that the surface of the eye and surrounding tissues, in particular the conjunctiva, is the ideal place for diagnostic studies, non-invasive blood analysis, and health status evaluation. This area provides all of the requirements needed for such diagnostics and evaluations including the presence of superficially located fenestrated blood vessels. This is the only area in the body which allows the undisturbed direct view of blood vessels in their natural state. The present invention allows fluid and cell evaluation and diagnostics to be naturally done using the normal physiology of the eye and conjunctiva.

The fenestrated blood vessels in the conjunctiva are superficially located and leak plasma. Fenestrated blood vessels have pores and/or openings in the vessel wall allowing free flow of fluid through its vessel walls.

According to the principles of the invention, the surface of the eye and the conjunctiva and surrounding tissues provides the ideal location in the human body for non-invasive analysis and other fluid and cellular diagnostics and the preferred way for evaluation of bodily functions and non-invasive blood analysis. The conjunctiva is the extremely thin continuous membrane which covers the anterior portion of the eye and eye lid and ends in the limbus at the junction with the cornea and at the junction of the skin of the eye lid. The conjunctiva is a thin transparent membrane that covers the Awhite@ of the eye as the bulbar conjunctiva and lines the eye lids as the palpebral conjunctiva. The conjunctiva has a vast network of blood vessels and lies on a second network of blood vessels on the episclera. The episcleral network is much less voluminous than the conjunctival vessel network.

The epithelium of the conjunctiva is a stratified columnar epithelium made up of only three or less layers of cells, and the middle layer (polygonal cells) is absent in most of the palpebral conjunctiva. Physiologic, anatomic and in-vitro studies by the inventor demonstrated that the blood vessels in the conjunctiva are fenestrated, meaning have pores, and leak plasma to the surface of the eye and that this plasma can be evaluated when a device is placed in contact with the conjunctiva. The sensing device can be held by any part of the eye lids, partially when the device is not placed in the cul-de-sac or totally when the sensing device is placed in the conjunctival pocket under the eye lid (lower or upper cul-de-sac).

Unlike other tissues covering the body the conjunctiva has a vast network of blood vessels which are superficially located and easily accessible. This can be seen by pulling down the lower eye lid and looking at the red tissue with the actual blood vessels being visualized. Those blood vessels and thin membrane are protected by the eye lid and the palpebral conjunctiva is normally hidden behind the eye lids. The blood vessels are in close proximity to the surface and the redness in the tissue is due to the presence of the vast network of superficial blood vessels. This area of the body allows the undisturbed direct view of the blood vessels. Besides the fact that the blood vessels have thin walls and are superficially located, those vessels have a very important and peculiar feature fenestration with continuous leakage of plasma to the surface of the eye. The plasma continuously leaks from the conjunctival blood vessels, and since they are superficially located, only a few micrometers have to be traveled by this fluid to reach the surface of the eye, with the fluid being then acquired by the diagnostic system of the intelligent contact lens of the present invention in apposition to the tissue surface.

Besides the presence of such superficial and fenestrated vessels, the conjunctiva, contrary to the skin, has a thin epithelium with no keratin which makes acquisition of signals a much easier process. Moreover, the conjunctiva has little electrical resistance due to the lack of a significant lipid layer as found in the skin such as the stratum corneum with a good rate of permeation of substances.

It is important to note that the acquisition of the signal as disclosed by the invention involves a natural occurrence in which the eye lid and surrounding ocular structures hold the sensing device in direct apposition to the conjunctiva. The simple apposition of the intelligent contact lens to the conjunctiva can create a stimuli for flow toward the sensor and the eye lid; muscular function works as a natural pump. Furthermore, the lack of keratin in the conjunctiva also eliminates a critical barrier creating the most suitable place for evaluation of bodily functions and non-invasive cell analysis with epithelial, white blood cells, and the like being naturally or artificially pumped into the intelligent contact lens for analysis.

The contact lens according to the principles of the present invention provides the ideal structure which is stable, continuous and correctly positioned against the tissue, in this case the living thin superficial layer of the thin conjunctiva of the eye. The eye lids provide the only natural and superficial means in the body for sensor apposition to the tissues being evaluated without the need for other supporting systems creating a perfect, continuous and undisturbed natural and physiologic contact between the sensing devices and tissues due to the natural anatomy and tension present in the cul-de-sac of the eye lids.

The natural pocket that is formed by the eye lids provides the ideal location for the undisturbed placement of sensing devices such as the intelligent contact lens of the present invention. Besides providing an undisturbed place for sensor placement and apposition, the natural eye lid pocket provides a place that is out of sight allowing a more desirable cosmetic appearance in which no hardware is exposed or visible to another person.

The eye lids are completely internally covered by the conjunctiva allowing a vast double surface, both anterior and posterior surface, to be used as an area to acquire signals for chemicals, protein and cell evaluation. Furthermore and of vital importance is the fact that the eye lid is also the only place in the body that work as a natural pump of fluid to sensing devices.

The eye lid creates a natural pump effect with a force of 25,000 dynes. The force generated by the eye lids is used by the present invention to move fluids and cells toward sensing devices and works as the only natural enhancer to increase fluid transport and cell motion toward a sensing device. The pumping and/or tension effect by the eye lid allows the fluid or cells to more rapidly reach and permeate the sensor surface.

The presence of the intelligent contact lens against the conjunctiva in the conjunctival pocket creates physiologic changes which increases flow and permeation of fluid flux towards the sensor. The lens can be made irregular which creates friction against the thin and loosely arranged cell layers of the conjunctiva providing a further increase of flow of fluid and cells to the sensor. Since the blood vessels in the conjunctiva are fenestrated and superficial the fluid flows freely from the vessels to the surface. This rate of flow can be enhanced by the presence of the lens and the friction that is created between lens surface and conjunctiva due to the tension and muscular activity present in the eye lid. The free flow of fluid associated with the natural pump action of the eye lid moves fluid toward the intelligent contact lens which can be used to store such fluid and cells for immediate or later processing.

When the later processing method is used, the partial or complete intelligent contact lens is removed from the eye for further evaluation. A variety of ionization storage areas can be housed in the intelligent contact lens with the flow of fluid being continuously carried out by the eye lid pumping action. Furthermore, the conjunctiva provides a large area for housing the diagnostic systems of the intelligent contact lens with its microchips, microsensors, and hardware for signal acquisition, evaluation, processing and transmission. There is a surprising amount of space in the conjunctiva and its natural pockets under the eye lid in each eye. An average of 16 square centimeters of conjunctival area in the human eye allows enough area for housing the necessary lens hardware including two natural large pocket formations under the lower and upper eye lid. Since the superficial layer of the conjunctiva is a living tissue, contrary to the skin which is dead tissue, a variety of materials can be used in the lens to create the apposition needed by combining hydrophilic and hydrophobic biocompatible material lens surfaces such as hydroxyethylmethacrylate and silicone which allow precise balance of material to create the apposition and isolation from contaminants while even creating a suction cup effect to increase fluid flow.

An exemplary housing of the intelligent contact lens can consist of a surrounding silicone surface which creates adherence around the sensor surface and thus prevents contaminants to reach the sensor. The fluid or cells to be evaluated are then kept isolated from the remaining environment of the eye and any potential contaminant. The remaining portion of the contact lens can be made with hydrogel such as hydroxyethylmethacrylate which is physiologic for the eye. It is understood that a variety of lens materials presently used for or later developed for contact lenses can be used as housing material. Any other new materials used in conventional contact lenses or intraocular lenses can be used as the housing for the diagnostic systems of the intelligent contact lens of the present invention. Moreover since the diagnostic intelligent contact lens is preferably placed in the cul-de-sac or conjunctival pocket, there is no problem with oxygen transmissibility and corneal swelling as occurs with contact lenses placed on the cornea.

Contact lenses placed on the cornea generally cause hypoxic stress leading to corneal swelling when said contact lenses are worn for extended periods of time. The conjunctiva is highly vascularized with internal supply of oxygen allowing extended wear of the contact lenses placed in the conjunctival pocket. Contrary to that, the cornea is avascular and requires external supply of oxygen to meet its metabolic needs.

The high oxygen content present in the conjunctiva is also an advantage for amperometric sensing systems in which oxygen is used as a substrate. Oxygen is present in lower concentrations in the skin creating an important limiting factor when using amperometric systems placed on or under the skin. Similar to the skin, mucosal areas in the body such as oral or gastrointestinal, ear, and nasal passages suffer from equivalent drawbacks and limitations.

Therefore, preferably, by utilizing a natural physiologic action in which there is continuous free flow of fluid through blood vessels associated with the continuous tension effect by the lid and a thin permeable tissue layer such as the conjunctival epithelium, the system of the invention is capable of providing continuous measurement of fluids allowing the creation of a continuous feed-back system. The intelligent contact lens as described can have magnetic and/or electric elements which are actuated by electrical force or external magnetic forces in order to enhance the performance and/or augment the functions of the system. The dimensions and design for the lens are made in order to optimize function, comfort, and cosmesis. For example, a length of less than 4 mm and a height of less than 7 mm for the lower pocket and less than 10 mm for the upper pocket may be used. A thickness of less than 2.5 mm, and preferably less than 1.0 mm, would be used. The diagnostic systems of the intelligent contact lens of the present invention is referred to herein as any AICL@ which is primarily used for fluid, chemicals, proteins, molecular or cell diagnosis and the like.

The epithelium of the conjunctiva is very thin and easily accessible both manually and surgically. The layers of the conjunctiva are loosely adherent to the eyeball allowing easy implantation of sensing devices underneath said conjunctiva. The intelligent implant of the present invention is an alternative embodiment to be used in patients who want continuous measurement of blood components without having to place an ICL on the surface of the conjunctiva. The surgical implantation can be done in the most simple way with a drop of local anesthetic followed by a small incision in the conjunctiva with subsequent placement of the sensing device. The sensing device with its hardware for sensing and transmission of signals is implanted underneath the conjunctiva or in the surface of the eye and is continuously bathed by the plasma fluid coming from the fenestrated conjunctival blood vessels. Although, a conventional power source can be housed in the ICL, the implanted ICL can be powered by biological sources with energy being acquired from the muscular contraction of the eye muscles. The eye muscles are very active metabolically and can continuously generate energy by electromechanical means. In this embodiment the eye lid muscle and/or extra-ocular muscle which lies underneath the conjunctiva is connected to a power transducer housed in the ICL which converts the muscular work into electrical energy which can be subsequently stored in a standard energy storage medium.

Besides the exemplary electromechanical energy source, other power sources that are suitable for both implanted and externally placed ICLs would include lightweight thin plastic batteries. These batteries use a combination of plastics such as fluorophenylthiophenes as electrodes and are flexible allowing better conformation with the anatomy of the eye.

Another exemplary suitable power source includes a light weight ultra-thin solid state lithium battery comprised of a semisolid plastic electrolyte which are about 150 µm thick and well suited for use in the ICL. The power supply can also be inactive in order to preserve energy with a switch triggered by muscle action whenever measurement is needed according to patient=s individual condition.

The implanted ICL provides continuous measurement of analytes creating a continuous feed-back system. A long-term implanted ICL can be used without the need for replacement of reagents. As an alternative implanted ICLs can use enzymatic systems that require replacement of enzymes and when such alternative embodiment is used the whole implanted ICL can be removed or simply a cartridge can be exchanged or enzymatic material inserted through the ICL housing into its appropriate place. All of this manipulation for implanted ICLs can be easily done with a simple drop of anesthetic since the conjunctival area is easily accessible. Contrary to the skin which is non-transparent, the conjunctiva is transparent allowing easy visualization of the implanted ICL. Contrary to other parts of the body the procedure can be done in a virtually bloodless manner for both insertion, removal and replacement if needed.

It is important to note that previously, after removing blood from a patient, major laboratory analysis was required consisting of the separation of blood components to acquire plasma. In the case of the conjunctiva and the eye, according to the principles of the invention, the body itself deliver the plasma already separated for measurement and freely flowing to the ICL sensing device externally or internally (surgically) placed. To further create the perfect location for evaluation of bodily functions, the conjunctival area is poorly innervated which allows placement of the ICL in the conjunctival sac for long periods of time with no sensation of discomfort by the user. There are only few pain fibers, but no pressure fibers in the conjunctiva. Furthermore, as mentioned, there is a vast amount of space under the lids allowing multiple sensing devices and other hardware to be placed in the conjunctival area.

To further provide the perfect location for measurements of fluid and cells, the sensing device can be held in place by the eye lid creating the perfect apposition between the surface of the eye and the ICL sensor. Since the blood vessels are superficially located, only a few micrometers have to be traveled by the fluid to reach the surface of the eye, with the fluid being then acquired by the ICL in apposition to the tissue surface. No other organ has the advantage of the natural pocket of the eye lid to secure a sensor in position and apposition naturally without need of other devices or external forces. A combination of a hydrophobic and a hydrophilic surface of the ICL housing creates the stability that is needed for the ICL to remain in any type of apposition to the conjunctival surface, meaning more tightly adherent or less adherent to the conjunctival surface according to the evaluation being carried out. To further create the prefect environment for evaluation of blood components, the eye lid during blinking or closure, creates a pump effect which is an adjunctive in directing the plasma components toward the sensor.

The present invention uses plasma, but non-invasively. Furthermore, contrary to the finger, the ocular surface evaluated by the system of the present invention is irrigated by a direct branch from the carotid artery allowing the direct evaluation of brain analyte level. The brain analyte level is the most important value for the evaluation of the metabolic state of a patient.

The cells of the epithelium of the conjunctiva are alive and loosely adherent allowing cell analysis to be performed using the ICL, contrary to the skin surface which is dead. The ICL can naturally remove the cells from the surface during the action of the eye lid or by mechanical pumping means or electrical means and then living cells can then be extracted for further evaluation within the ICL or outside the ICL. Appropriate membrane surfaces are used to separate cells components and fluid components. Different permeabilities of membranes in apposition to the conjunctiva are used according to the function that is carried out or the function of a particular ICL.

The present invention brings not only innovation but also a cost-effective system allowing diagnostic and blood evaluation to be done in a way never possible before. The current invention allows unbelievable savings for the patient, government and society in general. An ICL can be disposable and provide continuous measurement over 24 hours and costs to the user around $5 to $8 dollars for one single or multiple testing ICL (meaning more than one analyte is evaluated). The material used in the ICL includes an inexpensive polymer. The reagents and/or enzymatic membranes are used in very small quantities and are also thus inexpensive, and the electronics, integrated circuits and transmitter are common and fairly inexpensive when mass produced as is done with conventional chips.

The current invention provides means to better control health care expenditure by delivering systems that are astonishingly 20 times cheaper than the prior art using a variety of means ranging from low-cost amperometric systems to disposable microfluidic chips and integration of biochemical and disposable silicon chip technologies into the ICLs. The ICLs can perform numerous analysis per lens and if just one more test is performed the cost of ICL remains about the same since the new reagents are used in minute quantities and the similar electronics can be used in the same ICL. In this case, with dual testing (two tests per lens, four times a day) the ICL is a staggering 100 times cheaper.

The system of the invention allows a life-saving technological innovation to help contain health care costs and thus enhance the overall economy of the nation, as well as to not only provide a technological innovation that can be used in industrialized nations but also in economically challenged countries, ultimately allowing life-saving diagnostic and monitoring biological data to be accessible in a cost-effective and wide-spread manner. Moreover, this affordable system allows not only individual measurements but also continuous 24 hour non-invasive measurement of analytes including during sleeping, allowing thus the creation of an artificial organ with precisely tailored delivery of medications according to the analyte levels.

Although the ICL externally placed is the preferred way, a surgical implant for continuous monitoring is a suitable alternative embodiment as described above. Furthermore, it is understood that a small rod with sensing devices housed in the tip can be used. In that embodiment the patient places the sensor against the conjunctiva after pulling the eye lid down and exposing the red part and then applying the sensing device against it for measurement. Alternatively, the tip of the rod is lightly rubbed against the conjunctiva to create microdisruption as naturally caused by the eyelid tension, and then the sensing device is applied and the sensor activated for measurement. It is understood that any other means to promote or increase transudation of plasma in the conjunctiva can be used with the ICL, including, but not limited to heating systems, creating a reverse electroosmotic flow, electrophoresis, application of current, ultrasonic waves as well as chemical enhancers of flow, electroporation and other means to increase permeation.

An exemplary embodiment of the diagnostic ICLs provides a continuous measurement of the analyte by means of biosensing technology. These ICL biosensors are compact analytical devices combining a biological sensing element coupled with a physicochemical transducer which produces a continuous or discrete electronic signal that is proportional to the concentration of the elements or group of elements being evaluated. The diagnostic ICLs then can continuously measure the presence or the absence of organic and inorganic elements in a rapid, accurate, compact and low-cost manner. A variety of biosensors can be used as previously described including amperometric with other conventional parts as high impedance amplifiers with associated power supply as well as potentiometric, conductometric, impedimetric, optical, immunosensors, piezoimmunobiosensor, other physicocehmical biosensors and the like.

Some of the amperometric systems described produce a current generated when electrons are exchanged between a biological system and an electrode as the non-invasive glucose measuring system referred to herein as AGlucoLens@. The potentiometric ICLs measure the accumulation of charge density at the surface of an electrode as in ion-selective field-effect transistors (ISFET) such as for measuring sodium, potassium, ionized calcium, chloride, gases as carbon dioxide, pH, and the like present in the eye.

Optical diagnostic biosensors ICL correlates the changes in the mass or concentration of the element with changes in the characteristic of the light. It is also understood that the diagnostic ICLs can utilize other forms for biosensing such as changes in ionic conductance, enthalpy, mass as well as immunobiointeractions and the like.

The miniaturization and integration of biochemical/chemical systems and microelectronic technologies can provide the microscopic analytical systems with integrated biochemical processing that are housed in the ICLs for fluid and cell evaluation. ICLs can then perform all of the steps used in a conventional laboratory using minute amounts of reagents being capable of evaluating any blood, plasma or tissue components. Advances in nanotechnology, micro and nanoscale fabrication, nanoelectronics, Asmart dust@ and the like will create systems of infinitely small dimensions which can be used in ICLs allowing multiple fluid and cell evaluation to be done simultaneously in one single ICL. Therefore, thicknesses of less than 0.5 mm for the ICL are likely.

Another exemplary embodiment of the diagnostic ICLs provide chemical, genetic, and other analytical evaluations using microfabricated bioelectronic chips with the acquisition of biochemical and chemical information using microsystems with microfabrication of chemical integrated circuits and other silicon chip biochemical technologies. ICLs can house a variety of microscopic means for fluid and cell handling and biochemical processing devices. Diagnostic ICLs provide a complete analysis of the fluid and cells being acquired from the eye with elements being transported into the ICL for analysis according to the principles of the invention.

In this embodiment the ICL comprises a microchip using microfluidics and chemical/biochemical microchip technology creating a complete chemical processing system. Using electrical impulses the ICLs can actively direct small quantities of fluid to different parts of the ICL structure in fractions of a second for further analysis in a completely automated way with the detectable signal result being preferably radiotransmitted to a remote station according to the principles of the invention.

The ICL biomicrochips can be produced using photolithography, chemical etching techniques and silicon chip technologies similar to those used in the manufacture of computer chips. The ICL system thus achieve the miniaturization needed for the ICL dimensions with microchannels etched into the chip substrate measuring up to 100 micrometers, and preferably up to 10 micrometers in depth, by 1 to 500 micrometers, and preferably 10 to 100 micrometers wide.

The microchannels carry the fluid and cells from the eye and have reservoirs and chambers with the reagents and sample solutions needed for analysis. The ICL radio frequency transceivers comprise microelectronic systems with radio frequency integrated circuits allowing the small dimensions to be achieved for incorporation into the ICL.

A variety of power sources have been described, but in order to minimize hardware and cost of the ICL, an ultracapacitor charged externally through electromagnetic induction coupling can be used instead of the polymer microbatteries or rechargeable batteries. Although there is an enormous amount of space in the conjunctival area, with two large pockets in each eye as described, allowing much larger systems to be used, it is preferable that the most miniaturized system be used which then allows multiple tests to be simultaneously performed.

The exemplary ICL embodiments contain on a microscopic scale equivalent elements to all of the elements found in conventional laboratories such as pumps, valves, beakers, separation equipment, and extractors, allowing virtually any chemical preparation, manipulation and detection of analytes to be performed in the ICLs. The pumps, reactors, electrical valves, filters, sample preparation can be created preferably by the application of electrical charges and piezoelectric charges to the channels and structure of the ICL allowing directing of fluid to any part of the ICL structure as needed, coupled to the analysis of the material with the completion of numerous biochemical, cell-based assays, and nucleic acid assays. Current and future advances in microfluidics, electrically conducting liquids, microcapillary electrophoresis, electrospray technology, nanofluidics, ultrafine particles, and nanoscale fabrication allows the creation of several analytical system within one single ICL with the concomitant analysis of cancer markers, heart markers, DNA mutations, glucose level, detection of infectious agents such as bacteria, virus, and the like using samples from the eye in the microliter and picoliter scales.

Diagnostic ICLs can perform molecular separations using numerous techniques. Complete clinical chemistry, biochemical analysis, nucleic acid separation, immunoassays, and cellular processing, can be performed on a continuous manner by using the appropriate integration of chip with biochemical processing and associated remote transmission associated with the continuous flow of fluid and cells from the eye. ICLs contain numerous elements for a variety of microfluidic manipulation and separation of plasma or fluid components acquired from the surface of the eye for chemical analysis. Since there is a continuous flow of fluid from the conjunctival surface to the sensing devices and systems in the ICL, the sensing devices and systems can perform continuous biochemical evaluation while moving minute amounts of fluid through the microscopic channels present in a microchip contained in the structure of the ICL.

A variety of chemical microchips can be used creating motion of fluid through microchannels using electrokinetic forces generated within the structure of the ICL. Microwires, power sources, electrical circuits and controllers with the associated electronics generate certain changes in electrical voltage across portions of the microchip which controls the flow rate and direction of the fluid in the various channels and parts of the microchip housed in the structure of the ICL creating an automated handling of fluids within the ICL and a complete chemical processing systems within the ICL, preferably without any moving parts within the ICL structure. However, micropumps, microvalves, other microelectrical and mechanical systems (MEMS) and the like can be used in the present invention.

The ICLs provide a cost-effective system which can be broadly and routinely used for a range of classical screening applications, functional cell-based assays, enzyme assays, immunoassays, clinical chemistry such as testing for glucose, electrolytes, enzymes, proteins, and lipids; as well as toxicology and the like in both civilian and military environments. A critical element in the battlefield in the future will be the detection of biological or chemical weapons. One of the ways to detect the use of weapons by enemy forces unfortunately relies on detection of immediate illness and most often, later after illness is spreading, since some of the damaging effects do not elicit immediate symptoms and cause serious damage until time goes on. Troops can use an ICL with detection systems for the most common chemical/biological weapons. The ICLs create a 24 hour surveillance system identifying any insulting element, even in minute amounts, allowing proper actions and preventive measures to be taken before irreversible or more serious damage occur.

A dual system ICL with tracking and chemical sensing can be an important embodiment in the battlefield as troops exposed to chemical weapons are not only identified as exposed to chemical weapons but also immediately located. In this exemplary embodiment the ICL position can be located using for instance Global Positioning System (GPS), fixed frequency, or the like. The GPS is a sophisticated satellite-based positioning system initially built in the mid-1970s by the United States Department of Defense to be used primarily in military operations to indicate the position of a receiver on the ground. Radio pulses as spheres of position from the satellites in orbit intersect with the surface of the earth marking the transceiver exact position. ICL transceivers for instance in one eye determines position and a chemical sensing ICL in the other eye determines a chemical compound. Besides being placed externally in the eye, during military use, the ICL, both tracking and chemical sensing, can be easily and temporarily surgically implanted in the conjunctival pocket.

A surveillance system can be used in the civilian environment as for instance detecting the presence of tumor markers, cardiac markers, infectious agents and the like. Very frequently the body provides information in the form of markers before some serious illnesses occur but unfortunately those markers are not identified on a timely fashion. It is known that certain tumors release markers and chemicals before going out of control and creating generalized damage and spread. If patients could have access to those blood tests on a timely fashion, many cancers could be eliminated before causing irreversible and widespread damage.

For example patients at risk for certain cancers can use the ICL on a routine basis for the detection of markers related to the cancers. The markers that appear when the cancer is spreading or becoming out of control by the body immune system can then be detected.

The same applies to a variety of disorders including heart attacks. Thus, if a patient has a family history of heart disease, has high cholesterol or high blood pressure, the patient uses the ICL for cardiac markers on a periodic basis in order to detect the presence of markers before a potentially fatal event, such as a heart attack, occurs.

A temperature sensing ICL, as previously described, can be coupled with an infection detecting system in patients at risk for infection such as post-transplant recovery or undergoing chemotherapy. The temperature sensing ICL continuously monitors the temperature and as soon as a temperature spike occurs it activates the cell sensing ICL to detect the presence of infectious agents. The conjunctival surface is an ideal place for continuous temperature measurement by allowing measurement of core temperature without the need to use a somehow invasive and/or uncomfortable means.

As micro and nanofabrication evolves, a variety of analytes and physical changes, such as for instance temperature changes, can be evaluated with one single ICL with fluid and tissue specimens being directed to parallel systems allowing multiple assays and chemical analysis to be performed in one individual ICL. By using both eyes and the upper and lower eye lid pockets of each eye a large of number of testing and monitoring means can be achieved at the same time by each patient, ultimately replacing entire conventional laboratories while providing life-saving information.

While sleeping chemical and physical signs can be identified with the ICL which can remain in place in the eye in intimate contact with not only the body, chemically and physically, but also in direct contact with the two main vital organs, the brain and the heart. A single ICL or a combination of an ICL to detect physical changes and a chemical ICL can detect markers related to sudden death and/or changes in blood gas, brain and heart activity, and the like. If timely identified many of those situations related to unexplained death or sudden death can be treated and lives preserved.

The type of ICL can be tailored to the individual needs of a patient, for instance a patient with heart disease or family history of heart disease or sudden death can use an ICL for detection of elements related to the heart. Since the ICLs are primarily designed to be placed on the conjunctiva in the eye lid pocket, there is virtually no risk for the eye or decreased oxygenation in the cornea due to sleeping with a lens. Thus, another advantage of the present invention is to provide physical and chemical analysis while the user is sleeping.

Another combination of ICLs systems concerns the ICL which identifies the transition between sleep and arousal states. It is impossible for human beings to know the exact time one falls asleep. One may know what time one went to bed, but the moment of falling asleep is not part of the conscious mind. The reticular formation in the brain controls the arousal state. Interestingly, that brain function is connected with an eye function, the Bell phenomena. An alarm system to prevent the user from falling asleep (referred herein as Alert ICL), for example while driving or operating machinery may be used. In another exemplary embodiment, the Alert ICL is coupled to a Therapeutic ICL to release minute-amounts of a-drug that keeps the patient alert and oriented;

The fluid in the tissue or surface of the eye is continuously loaded into the ICL chip preferably associated with the pump action of the eye lid but alternatively by diffusion or electrokinetically at preset periods, of time such as every 30 minutes in order to preserve reagents present in the ICL microchip. A selective permeable membrane and/or a one-way microvalve can separate the compounds before they are loaded into the microchannels in the ICL chip. Plasma and other fluids and cells can be electrically directed from the ocular tissue to the ICL sensing system and using electrical charges present or artificially created in the molecules or by electromagnetic means multiple or individual compounds can be directed to the ICL. The fluid and/or cell with its individual substances reaches and selectively permeates the ICL surface for analysis allowing specific compounds to be acquired according to the ICL analytical system and reagents present. One of the principles related to the movement of fluid through the microchannels is based on capillary electrophoresis.

The eye fluid for analysis flow through microscopic channels housed in the ICL with the direction of flow being controlled by electrical or electromagnetic means with changes in the configuration of electrical fields dynamically moving substances to a particular direction and the voltage gradient determining the concentration and location of the substance along the channels. In an exemplary embodiment microelectrophoresis is used for chemical analysis with separation of the molecules according to their electrical charge and mass as well as simple diffusion with the consequent motion and separation of the substances for analysis.

Besides performing complete chemical processing and analysis, the system of the invention uses DNA or genetic chips in the micro and nanoarray dimensions and microfabricated capillary electrophoresis chips to diagnose genetically based diseases using the fluid and cells flowing to the ICL present in the conjunctival pocket. The ICL provides a cost-effective and innovative way to do screening and monitor therapy. DNA-chip systems in the ICL can perform all the processing and analysis of fluids preferably using capillary electrophoresis. A variety of known DNA chips and other emerging technology in DNA chips can be used in the ICL including, but not limited to, sequencing chips, expression chips, and the like. PCR (polymerase chain reaction) can be done much more rapidly on a micro scale as with the ICL design.

The ICL microchip can have an array of DNA probes and use electrical fields to move and concentrate the sample DNA to specific sites on the ICL microchip. These genetic ICLs can be used for diagnosing diseases linked to particular genetic expressions or aberrant genetic expressions using cells and/or fluid acquired by the ICL according to the principles of the invention.

For instance, the gene p450 and its eight different expressions, or mutations have been associated with a variety of cancers. Numerous oncogenes and tumor-suppressor genes can be detected by using the prior art with the conventional removal of blood, although the yield is very low because of the limitation of sample collected at only one point in time. It is very difficult to find a tumor cell, chemical change or marker among millions of cells or chemical compounds present in one blood sample acquired at one point in time. The prior art collects one blood sample and analyzes the sample in an attempt to find markers or other chemical and cell changes. As one can see it is by chance that one can actually find a marker. Thus even after removing blood, sending it to the laboratory and analyzing the sample the result of this expensive procedure may be negative regardless of the fact of the patient actually has the occult cancer or risk for a heart attack. These false negatives occur because the sample is acquired in one point in time. Furthermore even if several blood samples are acquired over several hours which is practically impossible and painful, the prior art has to detect compounds and cells at very low concentrations and would have thus to perform several analysis isolating small samples to try to increase the yield.

With the system of the present invention there is continuous flow of analytes, cell and fluid to the ICL chips with the ICLs working on a continuous mode to search for the marker 24 hours a day. The fluid is continuously acquired, processed within the ICL with subsequent reabsorption of the fluid and cells by the surface of the eye.

Please note that because the surface of the eye is composed of living tissue, contrary to the skin in which the keratin that covers said skin is dead, a completely recycled system can be created. The fluid and cells move to the ICL and are analyzed in microamounts as they pass through the microchannels, network of channels, and detection systems, and if for instance a marker is found, the signal is wirelessly transmitted to a remote receiver. The fluid then continues its movement toward the place for reabsorption according to its diffusing properties or moved by electrokinetic forces applied within the structure and channels of the ICL chip. In this manner, large amounts of sample fluid (although still nanoliters going through the microchannels) can be very precisely and finely analyzed as an ultrafiltrate going through a fine sieve. The fluid flows through the chip with the chip continuously capturing fluid and cells for a variety of chemical analysis including genetic analysis since the continuous flow allows concentrating nucleic acid for analysis as it passes, for example, through the array structure in the chip.

Although selectively permeable membranes can be used to retain any toxic reagent, and those reagents are used in the picoliter and nanoliter range, alternatively, a disposal chamber can be used with the fluid and cells remaining in the ICL until being removed from the eye, for instance after 24 to 48 hours. In the case of a very complex DNA analysis still not available in the ICL, the ICL can be alternatively transferred to conventional macro equipment after the eye fluid is acquired, but preferably the complete analysis is done within the ICL with signals transmitted to a remote station.

A variety of matrix and membranes with different permeabilities and pore sizes are used in the channels in order to size and separate cells and pieces of DNA. The continuous analysis provided by the system provides a reliable way for the detection of oncogenes and tumor suppressing genes establishing a correlation between measurable molecular changes and critical clinical findings such as cancer progression and response to therapy allowing a painless and bloodless surveillance system to be created. As the Human Genome Project further identify markers and genes, the system of the invention can provide a noninvasive, inexpensive, widespread analysis and detection system by comfortably using a cosmetically acceptable device being hidden under the eye lids or placed on the surface of the eye, but preferably placed in any of the pockets naturally formed by the anatomy of the eye lids.

The control of electrical signals applied within the structure of the ICLs are microprocessor-based allowing an enormous amount of combinations of fluid and cell motion to be achieved and the finest control of fluid motion within precise and specific time frames such as moving positive charges to a certain microchannel and waiting a certain amount of time until reaction and processing occurs, and then redirecting the remaining fluid for further processing at another location within the ICL, then mixing reagents and waiting a fixed amount of time until a new electrical signal is applied, in the same manner as with semiconductor chips. The processing then is followed by separation of the products of the reaction and/or generation of a detectable signal, and then further electrical energy is applied redirecting the remaining fluid to a disposal reservoir or to be reabsorbed by the ocular surface. The cycle repeats again and as fluid is reabsorbed or leaves the system, more fluid on the other end is moved toward the ICL according to the principles described.

The ICLs accomplish these repetitive functions and analysis quickly and inexpensively using the charged or ionic characteristics of fluid, cells and substances with electrodes applying a certain voltage to move cells and fluids through the ICL microchannels and reservoirs. The ICLs can be designed according to the type of assay performed with electrical signals being modified according to the function and analysis desired as controlled by the microprocessor including the timing of the reactions, sample preparation and the like. An ICL can be designed with certain sensor and reagent systems such as for instance amperometric, optical, immunologic, and the like depending on the compound being analyzed. The only limiting factor is consumption of reagents which can be replaced, or a cartridge-based format used, or preferably as a disposable unit. Since the ICL is low-cost and is easily accessible manually simply by pulling down the eyelid, the complete ICL can work as a disposable unit and be replaced as needed.

The design of the ICL is done in a way to optimize fluid flow and liquid-surface interaction and the channels can be created photolithographically in either silicon, glass, or plastic substrates and the like as well as combining chip technology and microbiosensors with microelectronics and mechanical systems. Each ICL is preloaded with reagents, antigens, antibodies, buffer, and the like according to the analysis to be performed and each reservoir on an ICL chip can be a source of enzymatic membranes, buffers, enzymes, ligand inhibitors, antigens, antibodies, substrates, DNA inhibitor, and the like. The movement of fluids in the ICL can be accomplished mechanically as with the lid pumping action, non-mechanically, electrically or as a combination.

The microstructures incorporated in the ICLs can efficiently capture and move fluids and/or cells using the physiological pump action of the eye lids and/or by using electrical-charges to move and direct specific compounds toward specific sensors or detection units using nanoliter volume of the biological sample and taking these minute sample volumes and then moving them through the various stages of sample preparation, detection, and analysis. The ICL system moves a measured and precise volume of fluid according to the time that the voltage is applied to the channels and the size of the channels. In the ICL microfluidics chips the fluid motion is primarily derived from electrokinetic forces as a result of voltages that are applied to specific parts of the chip.

A combination of electroosmosis and electrophoresis moves bulk amounts of fluid along the channels according to the application of an electrical field along the channel while molecules are moved to a particular microelectrode depending on the charge of the molecule or/and according to its transport and diffusion properties. In electrophoresis the application of voltage gradient causes the ions present in the eye fluid to migrate toward an oppositely charged electrode.

Electroosmosis relates to the surface charge on the walls of the microchannels with a negative wall attracting positive ions. Then when voltage is applied across the microchannel the cations migrate in the direction of the cathode resulting in a net flow of the fluid in the direction of the negative electrode with a uniform flow velocity across the entire channel diameter.

By applying voltages to various channel intersections, the ICL chip moves the eye fluid through the system of microchannels and/or micro array systems, adjusting its concentration, diluting, mixing it with buffers, fragmenting cells by electrical discharge, separating out the constituents, adding fluorescent tags and directing the sample past detection devices. The eye fluid can then, after processing, be moved to the detection units within the ICL. Numerous sensing devices and techniques can be used as part of the analysis/detection system with creation of an optically detectable or encoded substance, chromatographic techniques, electrochemical, reaction with antibodies placed within the structure of the ICL with the subsequent creation of an end signal such as electrical current, change in voltage, and the like, with the signal wirelessly transmitted to a remote receiver. The current invention allows all of the steps to be performed for data generation including acquisition, processing, transmission and analysis of the signal with one device, the ICL.

A variety of processes and apparatus can be used for manufacturing ICLs including casting, molding, spin-cast, lathing and the like. An exemplary embodiment for low-cost mass production of the ICL consists of production of the detection and transmission hardware (chemical microchips, processor, transmitter, power supply) as one unit (sheet-like) for instance mounted in polyamide or other suitable material. The sheet then, which can have different shapes, but preferably a rectangular or ring-like configuration, is placed inside a cavity defined between moulding surfaces of conventional contact lens manufacturing apparatus. The moulding surfaces and cavity determine the shape and thickness of the ICL to be produced according to the function needed.

However, an ICL placed in an eye lid pocket or an annular ring contact lens will have a maximum thickness of 2.5 mm, preferably less than 1.0 mm. An oversized round or regular round contact lens configuration having a diameter of less than 3 cm for an oversize contact lens and a diameter less than 12 mm for a regular contact lens, will have a maximum thickness of 1.0 mm, and preferably less than 0.5 mm.

After the hardware above is in the cavity, the lens polymer is dispensed into the cavity with subsequent polymerization of the lens material as for instance with the use of heat, ultra-violet light, or by using two materials which in contact trigger polymerization. Accordingly, the ICLs can be manufactured in very large quantities and inexpensively using moulding techniques in which no machining is necessary. Although one exemplary preferred embodiment is described it is understood that a variety of manufacturing means and processes for manufacturing of lenses can be used and other materials such as already polymerized plastic, thermoplastic, silicone, and the like can be used.

The ICL diagnostic system of the exemplary embodiment above described consists of an integration of chemical chips, microprocessors, transmitters, chemical sensing, tracking, temperature and other detecting devices incorporated within the structure of the contact device placed in the eye. Although the system preferably uses tissue fluid and cells, and plasma for analysis, it is understood that there are certain markers, cells or chemical compounds present in the actual tear film that can be analyzed in the same fashion using a contact lens based system.

The present invention allows the user to perform life-saving testing while doing their daily routines: one can have an ICL in the eye detecting an occult breast cancer marker while driving, or diagnosing the presence of an infectious agent or mutation of a viral gene while doing groceries (if the mutation is detected in the patient, it can be treated on a timely fashion with the appropriate drug), while working having routine clinical chemistry done, or while eating in a restaurant detecting a marker for prostate cancer in one eye and a marker for heart attack in the other eye before heart damage and sudden death occurs, or one can have an ICL placed in the eye detecting genetic markers while checking their GPI e-mail with a computer arrangement. In this last embodiment, the computer screen can power the ICL electromagnetically while the user checks their GPI e-mail.

Furthermore, diabetics can monitor their disease while playing golf, and a parent with high blood pressure can have ICLs in their eyes detecting stroke and heart markers while playing with their children in the comfort of their homes and without having to spend time, money, and effort to go to a hospital for testing with drawing of blood as is conventionally done.

The ICL can besides performing tests in-situ also collect the eye fluid for further analysis as one is working in the office over an eight hour period in a comfortable and undisturbed manner by having the ICL in the eye lid pocket. In this last exemplary embodiment the user sends the ICL to the laboratory for further processing if needed, but still sampling was done without the user having to go to a doctor, devote time exclusively for the test, endure pain with a needle stick, endure the risk of infection and the costs associated with the procedure.

Moreover, the ICL system provides a 24 hour continuous surveillance system for the presence of, for instance, cancer markers before the cancer is clinically identifiable, meaning identified by the doctor or by symptoms experienced by the patient. The ICL system of the current invention can pump eye fluid and cells into the ICL continuously for many days at a time creating thus a continuous monitoring system and as soon as the marker is identified a signal is transmitted. For example if a reaction chamber X in the ICL is coated with electrocatalytic antibodies for a breast cancer marker, then once the marker is present an electrical signal is created in the chamber X indicating that a breast cancer or prostate cancer for instance was identified.

Most cancers kill because they are silent and identified only when in advanced stages. Thus the ICL system provides the ideal surveillance system potentially allowing life-expectancy in general to increase associated with the extra benefit of the obvious decrease in health care costs related which occurs when treating complicated and advanced cancers. In addition, the present invention provides all of these life-saving, cost-saving and time-saving features in a painless manner without anyone even knowing one is checking for a cancer marker, heart disease marker, infectious agent, blood sugar levels and so forth since the ICL is conveniently and naturally hidden under the eye lid working as your Personal Invisible Laboratory (PIL).

It is an object of the present invention to address the above needs in the art and provide the accuracy and precision needed for clinical application by being able to eliminate or substantially reduce the sources of errors, interference, and variability found in the prior art. By greatly reducing or eliminating the interfering constituents and providing a much higher signal to noise ratio, the present invention can provide the answers and results needed for accurate and precise measurement of chemical components in vivo using optical means such as infrared spectroscopy. Moreover, the apparatus and methods of the present invention by enhancing the signal allows clinical useful readings to be obtained with various techniques and using different types of electromagnetic radiation. Besides near-infrared spectroscopy, the present invention provides superior results and higher signal to noise ratio when using any other form of electromagnetic radiation such as for example mid-infrared radiation, radio wave impedance, photoacoustic spectroscopy, Raman spectroscopy, visible spectroscopy, ultraviolet spectroscopy, fluorescent spectroscopy, scattering spectroscopy, and optical rotation of polarized light as well as other techniques such as fluorescent (including Maillard reaction, light induced fluorescence, and induction of glucose fluorescence by ultraviolet light), colorimetric, refractive index, light reflection, thermal gradient, Attenuated Total Internal Reflection, molecular imprinting, and the like.

It is a further object of the present invention to provide methods and apparatus for measuring a substance of interest using natural body far-infrared emissions which occur in a thermally stable environment such as in the eyelid pocket.

Still a further object of the invention is to provide an apparatus and method that allows direct application of Beer-Lambert's law in-vivo.

Yet a further object is to provide a method and apparatus for continuous measurement of core temperature in a thermally stable environment.

By the present invention, the discovery of plasma present in and on the surface of the conjunctiva can be used for a complete analysis of blood components. Plasma corresponds to the circulating chemistry of the body and it is the standard used in laboratories for sample testing. Interstitial fluid for instance is tested in labs only from corpses but never from a living person.

Laboratories also do not use whole blood for measuring compounds such as for example, glucose. Laboratories separate the plasma and then measure the glucose present in plasma.

Measurement of glucose in whole blood is subject to many errors and inaccuracies. For example changes in hematocrit that occur particularly in women, certain metabolic states, and in many diseases can have an important effect on the true value of glucose levels. Moreover, the cellular component of blood alters the value of glucose levels.

Many of the machines which use whole blood (invasive means using finger prick) give a fictitious value which attempts to indicate the plasma value. Measurements in interstitial fluid also give fictitious values which tries to estimate what the plasma values of glucose would be if measured in plasma.

Measurement of substances in the plasma gives the most accurate and precise identification and concentration of said substances and reflects the true metabolic state of the body. In addition, the optical properties of plasma are stable and homogeneous in equivalent sample population.

Evaluations have been made of the external surfaces and mucosal areas of the human body and only one area has been identified with superficial vessels and leakage of plasma. This area with fenestrations and plasma leakage showed to be suitable for noninvasive measurements. This preferred area is the conjunctival lining of the eye including the tear punctum lining.

Another area identified but with leakage of lymphatic fluid is in the oral mucosa between teeth, but leakage is of only a small amount, not constant, and not coming from superficial vessels with fenestrations and plasma leakage as it occurs in the conjunctiva.

The methods and apparatus using superficially flowing plasma adjacent to the conjunctiva as disclosed in the present invention provides an optimal point for diagnostics and a point of maximum detected value and maximum signal for determination of concentration or identification of substances independent of the type of electromagnetic radiation being directed at or through the substance of interest in the sample.

These areas in the eye provide plasma already separated from the cellular component of blood with said plasma available superficially on the surface of the eye and near the surface of the eye. The plasma fills the conjunctival interface in areas with blood vessels and without blood vessels. Plasma flowing through fenestrations rapidly leaks and permeates the whole conjunctival area, including areas denuded from blood vessels.

The plasma can be used for non-invasive or minimally invasive analysis, for instance, using chemical, electrochemical, or microfluidic systems. The conjunctiva and plasma can also be used for evaluation and identification of substances using electromagnetic means such as with the optical techniques of the present invention. The measurement provided by the present invention can determine the concentration of any constituent in the eye fluid located adjacent to the conjunctiva. A variety of optical approaches such as infrared spectroscopy can be used in the present invention to perform the measurements in the eye including transmission, reflectance, scattering measurement, frequency domain, or for example phase shift of modulated light transmitted through the substance of interest, or a combination of these.

The methods, apparatus, and systems of the present invention can use spectroscopic analysis of the eye fluid including plasma present on, in, or preferably under the conjunctiva to determine the concentration of chemical species present in such eye fluid while removing or reducing all actual or potential sources of errors, sources of interference, variability, and artifacts.

The method and apparatus of the present invention overcomes all of the issues and problems associated with previous techniques and devices. In accordance with the present invention, plasma containing the substance to be measured is already separated and can be used for measurement including simultaneous and continuous measurement of multiple substances present in said plasma or eye fluid. One of the approaches includes non-invasive and minimally invasive means to optically measure the substance of interest located in the eye fluid adjacent to the conjunctiva.

An electromagnetic measurement, such as optical, is based on eye fluid including plasma flowing in a living being on the surface of the eye. The method and apparatus involves directing electromagnetic radiation at or through the conjunctiva with said radiation interacting with the substance of interest and being collected by a detector. The data collected is then processed for obtaining a value indicative of the concentration of the substance of interest.

It is very important to note that measurements using the electromagnetic technique as described in the present invention do not require any flow of fluid to reach the sensor in order to determine the concentration of the substance of interest. The system is reagentless and determination of the concentration of the substance of interest is accomplished simply by detecting and analyzing radiation that interacts with the substance of interest present adjacent to the conjunctiva The method and apparatus of the present invention include for example glucose measurement in the near infrared wavelength region between 750 and 3000 nm and preferably in the region where the highest absorption peaks are known to occur, for glucose for example in the region between 2080 to 2200 nm and for cholesterol centered around 2300 nm. The spectral region can also include infrared or visible wavelength to detect other chemical substances besides glucose or cholesterol.

The apparatus includes at least one radiation source from infrared to visible light which interacts with the substance of interest and is collected by a detector. The number and value of the interrogation wavelengths from the radiation source depends upon the chemical substance being measured and the degree of accuracy required. As the present invention provides reduction or elimination of sources of interference and errors, it is possible to reduce the number of wavelengths without sacrificing accuracy. Previously, the mid-infrared region has not been considered viable for measurement in humans because of the high water absorption that reduces penetration depths to microns. The present invention can use this mid-infrared region since the plasma with the substance of interest is already separated and located very superficially and actually on the surface of the eye which allows sufficient penetration of radiation to measure said substance of interest.

The present invention reduces variability due to tissue structure, interfering constituents, and noise contribution to the signal of the substance of interest, ultimately substantially reducing the number of variables and the complexity of data analysis, either by empirical or physical methods. The empirical methods including Partial Least squares (PLS), principal component analysis, artificial neural networks, and the like while physical methods include chemometric techniques, mathematical models, and the like. Furthermore, algorithms were developed using in-vitro data which does not have extraneous tissue and interfering substances completely accounted for as occurs with measurement in deep tissues or with excess background noise such as in the skin and with blood in vivo. Conversely, standard algorithms for in-vitro testing correlates to the in vivo testing of the present invention since the structures of the eye approximates a Lambertian surface and the conjunctiva is a transparent and homogeneous structure that can fit with the light-transmission and light-scattering condition characterized by Beer-Lambert's law.

The enormous amount of interfering constituents, source of errors, and variables in the sample which are eliminated or reduced with the present invention include:

Sample with various layers of tissue
Sample with scattering tissue
Sample with random thickness
Sample with unknown thickness
Sample with different thickness among different individuals
Sample that changes in thickness with aging
Sample that changes in texture with aging
Sample with keratin
Sample that changes according to exposure to the environment
Sample with barriers to penetration of radiation
Sample that changes according to the local ambient
Sample with fat
Sample with cartilage
Sample with bone
Sample with muscle
Sample with high water content
Sample with walls of vessels
Sample with non-visible medium that is the source of the signal
Sample with opaque interface
Sample interface made out of dead tissue
Sample with interface that scars
Sample highly sensitive to pain and touch
Sample with melanin
Sample interface with different hue
Sample with hemoglobin
Sample medium which is in motion
Sample medium with cellular components
Sample with red blood cells
Sample with uneven distribution of the substance being measured
Sample with unsteady supply of the substance being measured
Non-homogeneous sample
Sample with low concentration of the substance being measured
Sample surrounded by structures with high-water content
Sample surrounded by irregular structures
Sample medium that pulsates
Sample with various and unknown thickness of vessel walls
Sample with unstable pressure
Sample with variable location
Sample filled with debris
Sample located deep in the body
Sample with unstable temperature
Sample with thermal gradient
Sample in no direct contact with thermal energy
Sample with no active heat transfer
Sample with heat loss
Sample influenced by external temperature
Sample with no-isothermic conditions
Sample with self-absorption of thermal energy An exemplary representation of some of the interfering constituents present in the sample irradiated that are reduced or eliminated by the present invention.

a) Radiation directed at a target tissue can be absorbed by the various constituents including several layers of the skin, various blood cellular components, fat, bone, walls of the blood vessel, and the like. This drastically reduces the signal and processing requires subtracting all of those intervening elements. All of the named interfering constituents in the sample irradiated are eliminated with the present invention.

b) Skin alone as the target tissue creates reduction of signal to noise because skin by itself is an additional scattering tissue. The present invention eliminates interfering scattering structures in the sample irradiated.

c) Thickness of the skin (which includes the surface of the tongue) is random within the same individual even in an extremely small area with changes in thickness depending on location. It is very difficult to know the exact thickness of the skin from point to point without histologic (tissue removal) studies. There is great variability in signal due to skin thickness. All of those, sources of errors and variability such as random thickness and unknown thickness of the structure in the sample irradiated are eliminated.

d) Thickness of the skin also varies from individual to individual at the exact same location in the skin and thus the signal has to be individually considered for each living being. Individual variation in thickness of the structure in the sample irradiated is also eliminated.

e) Changes in texture and thickness in the skin that occurs with aging have a dramatic effect in acquiring accurate measurements. Changes in texture and thickness due to aging of the structure in the sample irradiated are also eliminated.

f) Changes in the amount of keratin in the skin and tongue lining which occurs in different metabolic and environmental conditions also prevent accurate signal acquisition. Keratin and variability in the sample irradiated are both also eliminated.

g) Skin structure such as amount of elastin also varies greatly from person to person, according to the amount of sun exposure, pollution, changes in the ozone layer, and other environmental factors which lead to great variability in signal acquisition. There is elimination of the sample irradiated being susceptible to most of the environmental factors by being naturally shielded from said environmental factors.

h) Due to the structure and thickness of the skin the radiation can fail to penetrate and reach the location in which the substance of interest is present. There is elimination of a structure in the sample irradiated that can work as a barrier to radiation.

i) Measurements are also affected by the day-to-day variations in skin surface temperature and hydration in the same individual according to ambient conditions and metabolic status of said individual. There is elimination of structures in the sample irradiated that is susceptible to changes in temperature and hydration according to ambient conditions.

j) The intensity of the reflected or transmitted signal can vary drastically from patient to patient depending on the individual physical characteristics such as the amount of fat. A thin and obese person will vary greatly in the amount of fat and thus will vary greatly in the radiation signal for the same concentration of the substance of interest. There is elimination of fat in the sample area being irradiated.

k) The amount of protein such as muscle mass also varies greatly from person to person. There is elimination of muscle mass variability in the sample area being irradiated.

l) The level of water content and hydration of skin and surrounding structures varies from individual to individual and in the same individual over time with evaporation. There is elimination of variability from person to person and over time due to changes in water evaporation in the sample area being irradiated.

m) Thickness and texture of walls of blood vessels also change substantially with aging and greatly vary from location to location. There is elimination in the sample being irradiated of signal variability due to presence of walls which change substantially with aging and location.

n) The deep blood vessels location and structure within the same age group still varies greatly from person to person and anatomic variation is fairly constant with different depth and location of blood vessel in each individual. Since those blood vessels are located deep and covered by an opaque structure like the skin it is impossible to precisely determine the position of said blood vessels. There is elimination of source medium for the signal which is not visible during irradiation of the sample.

The use of conjunctiva and plasma present adjacent to said conjunctiva and the eyelid pocket provides an optimum location for measurement by electromagnetic means in a stable environment which is undisturbed by internal or external conditions.

Signal to noise is greatly improved since the thin transparent conjunctiva is the only intervening tissue in the optical path to be traversed from source to detector.

The conjunctiva does not age like the skin or blood vessels. Both the thickness and texture of the conjunctiva remain without major changes throughout the lifespan of a person. That can be easily noted by looking at the conjunctiva of a normal person but with different ages, such as a 25 year old and a 65 year old person.

The conjunctiva is a well vascularized tissue, but still leaves most of its area free from blood vessels which allows measurement of plasma to be performed without interference by blood components. Those areas free of vessels are easily identified and the eyeball of a normal person is white with few blood vessels. Furthermore, the conjunctiva in the cul-de-sac rim is free of blood vessels and plasma is collected there due to gravity, and measurement of substance of interest in the cul-de-sac is one of the preferred embodiments of the present invention.

Moreover, the conjunctiva is capable of complete regeneration without scarring. Furthermore, the conjunctiva can provide easy coupling with the surface of the sensing means since the conjunctiva surface is a living tissue contrary to the skin surface and tongue lining which is made out of dead tissue (keratin). In: addition, the conjunctiva is easily accessible manually or surgically. Besides, the conjunctiva has only a few pain fibers and no tactile fibers creating minimal sensation to touch and to any hardware in contact with the conjunctival tissue.

Skin has various layers with random and inconstant thickness. The skin has several layers including: the epidermis which varies in thickness depending on the location from approximately 80 to 250µ, the dermis with thickness between approximately 1 to 2 mm, and the subcutaneous tissue which varies substantially in thickness according to area and physical constitution of the subject and which falls in the centimeter range reaching various centimeters in an obese person. The conjunctiva is a few micrometers thick mono-layer structure with constant thickness along its entire structure. The thickness of the conjunctiva remains the same regardless of the amount of body fat. Normal conjunctiva does not have fat tissue.

In the present invention the superficial and the only interface radiated, involves the conjunctiva, a very thin layer of transparent homogenous epithelial tissue. Wavelengths of less than 2000 nm do not penetrate well through skin. Contrary to that, due to the structure and thickness of the conjunctiva, a broad range of wavelengths can be used and will penetrate said conjunctiva.

Melanin is a cromophore and there is some amount of melanin in the skin of all normal individuals, with the exception of pathologic status as in complete albinos. The skin with melanin absorbs near-infrared light which is the spectral region of interest in near-infrared spectroscopy and the region, for example, where glucose absorbs light. The present invention eliminates surface barriers and sources of error and variability such as melanin present in the skin and which varies from site to site and from individual to individual. Normal conjunctiva does not have melanin.

There are variations from person to person in thickness and color of skin and texture of skin. Normal conjunctiva is transparent in all normal individuals and has the equivalent thickness and texture.

The present invention eliminates enormous sample variability due to location as occur in the skin with different thickness and structure according to the area measured in said skin. The conjunctiva is a thin and homogeneous tissue across its entire surface area.

There is elimination of variability due to changes in texture and structure as occur in the skin due to aging. The conjunctiva is homogeneous and does not age like the skin. There is also elimination of variability found in the skin surface due to the random presence of various glands such as sweat glands, hair follicles, and the like.

There is elimination of an optically-opaque structure like the skin. It is very difficult to apply Beer-Lambert's law when using the skin. The law describes the relationship between light absorption and concentration and according to Beer-Lambert's law the absorbance of a constituent is proportional to its concentration in solution. The conjunctiva is a transparent and homogeneous structure which can fit with the light-transmission and light-scattering phenomena characterized by Beer-Lambert's law.

There is elimination of interfering constitutes and light scattering elements such as fat, bone, cartilage and the like. The conjunctiva does not have a fat layer and radiation does not have to go through cartilage or bone to reach the substance of interest.

In the present invention the conjunctiva, which is a thin mono-layer transparent homogeneous structure, is the only interfering tissue before radiation reaches the substance of interest already separated and collected in the plasma adjacent to said conjunctiva. Since the conjunctiva does not absorb the near-infrared light there is no surface barrier as an interfering constituent and since the conjunctiva is very thin and homogeneous there is minimal scattering after penetration.

In addition, the temperature in the eye is fairly constant and the pocket in the eyelid offers a natural and thermally sealed pocket for placement of sensing means.

Presence of whole blood and other tissues such as skin scatters light and further reduces the signal. The present invention eliminates absorption interference by cromophores such as hemoglobin such as present in whole blood. Radiation can be directed at the conjunctival area free of blood and hemoglobin, but with plasma collected underneath. Thus another source of error is eliminated as caused by confusion of hemoglobin spectra with glucose spectra.

The reflective or transmissive measurements of the present invention involve eye fluid and plasma adjacent to the conjunctiva which creates the most homogeneous medium and provides signal to noise useful for clinical applications. The present invention provides plasma which is the most accurate and precise medium for measuring and identifying substances. The present invention provides said plasma covered only by the conjunctiva which is a structure which does not absorb near-infrared light.

The plasma is virtually static or in very slow motion as under the conjunctiva which creates a stable environment for measurement.

The plasma present in the eye provides a sample free of blood constituents which are source of errors and scattering. The plasma being irradiated is free of major cellular components and it is homogeneous with minimal scattering.

The background where the plasma is collected includes the sclera which is a homogeneous and white reflective structure with virtually no water contained in its layers. Thus, there is also elimination of surrounding tissue composed by large amounts of water.

The present invention eliminates light being radiated through a tissue with varying amounts of glucose depending on the location such as the skin with the epidermis, dermis and subcutaneous having different concentrations of glucose. In the present invention glucose is evenly distributed in the plasma adjacent to the conjunctiva.

The plasma present in the eye is a great source of undisturbed and stable signal for glucose as the eye requires a stable supply of glucose since glucose is the only source of energy that can be used by the retina. The retina requires a steady supply of glucose for proper functioning and to process visual information. The eye has a stable supply of glucose and a relative increase in the amount of the substance of interest such as for example glucose which increases the signal to noise ratio and allows fewer wavelengths to be used in order to obtain measurements.

The eye also has the highest amount of blood per gram of tissue in the whole body and thus provide a continuous supply of blood at high rate which is delivered as plasma through the conjunctival vessels.

The concentration of chemical substances in the plasma are high in relation to the whole sample allowing a high signal to noise ratio to be acquired. Glucose is found in very dilute quantities in whole blood and interstitial fluid but it is relatively concentrated in the plasma providing a higher signal as found in the surface of the eye. In complex media such as the blood where there is a great number of overlapping substances, the number of required wavelengths increases substantially. In a homogenous sample such as the plasma adjacent to the conjunctiva, the reduction in the number of wavelengths does not affect accuracy. In addition, it is difficult for a detector to identify the glucose absorption peak due to the variability in scatter as occurs with blood. The present invention can rely on more cost-effective detectors as the absorption peak in the plasma sample can be more easily identified.

Due to the presence of minimal interfering components and high signal to noise ratio, the present invention can detect lower glucose levels (hypoglycemia). The strength of signal for the substance of interest is a function of the concentration and the homogeneity of the sample. Blood and other tissues are highly non-homogeneous. Contrary to that the plasma is highly homogeneous and with higher concentration of the substance of interest in relation to the total sample.

There is elimination of a very low signal source with great background noise as it occurs in the aqueous humor of the eye. Plasma generates a high signal due to the relative high concentration of the substance of interest already naturally separated from cellular components and with minimal background noise.

There is reduction in the amount of interfering elements such as water. The present invention includes water displacement both passively and actively. Passive displacement is observed when the concentration of the substance of interest increases as found in the plasma adjacent to the conjunctiva which decreases water interference and the sample is surrounded by the sclera which is a structure which does not contain water. Active displacement is observed when artificially using a hydrophobic surface for the contact device which displaces water from the surface of the tissue creating a dry interface.

There is elimination of structural and absorption background irregularities as occur in the skin, inside of the eye, blood vessels, and the like. The conjunctiva is positioned against a smooth white homogeneous water-free surface, the sclera.

There is elimination of variability due to the direct pulsation of the wall of blood vessel. Blood by nature is constantly in rapid motion and such rapid motion can create significant variability in the measurements. The present invention eliminates error and variability due rapid motion of the sample as occurs in blood vessels. Plasma flows continuously through fenestrations but not in a pulsatile manner. The plasma collected adjacent to the conjunctiva has insignificant pulsating content.

There is elimination of an important source of variability as occur in moving blood with cellular components in a blood vessel which is not homogeneous and creates further scattering. Plasma flows continuously through fenestrations but without cellular components.

Many and rapid changes occur in flowing blood inside a blood vessel. Due to this phenomena the resulting spectra has to be acquired in an extremely short period of time which is done in an attempt to decrease the number of artifacts and source of errors. Due to the poor signal created by the various and rapid changes in flow, measurements have to be repeated several times within a very short period of time and the total averaged. This leads to complicated construction of devices and controlling systems, but still only delivering a poor signal to noise. The present invention allows the spectra to be acquired over longer periods of time and without the need for such repeat measurements since there is minimal background noise and interfering constituents. This, therefore, allows lower cost and more efficient systems to be made and used.

There are variations from person to person in thickness and texture of blood vessel walls. There is also variability due to changes in texture and structure that occur in the vessel wall due to aging. The apparatus and methods of the present invention include directing radiation that does not need to penetrate through the wall of blood vessels to acquire the signal for the substance of interest. Therefore, the above source of errors and variability are eliminated.

There is reduction or elimination of variability and error due to changes in pressure between the sensor interface and the tissue. Many errors occur when techniques require placement of a body part against the sensor in which the subject or the operator is artificially applying the pressure. An example is when a subject applies his/her skin against the sensor or an operator grasps the tongue or finger of a subject. The pressure applied by either the subject or the operator varies substantially over time and from measurement to measurement and from subject to subject and from operator to operator. The interface between the tissue and sensor changes continuously with contact pressure and manipulation by the subject or operator since those structures such as skin and tongue have several layers that change and yield in reaction to applied pressure. Even if pressure controlled systems are used, there is significant variation because of the different texture and thickness from individual to individual, from location to location, and in the same individual over time which prevents precise measurements from being acquired.

One of the preferred embodiments of the present invention which uses a contact device in the eyelid pocket eliminates this variation in pressure. The pressure applied by the eyelid in the resting state is fairly constant and equal in normal subjects with a horizontal force of 25,000 dynes and a tangential force of 50 dynes. Furthermore, the other embodiments which do not use a contact device in the eyelid pocket, can use a probe resting on the surface of the tissue and also obtain accurate measurements. Examples of those devices are slit-lamps which can be used for precise application of pressure against the surface of the eye and since the thickness and texture of the conjunctiva is homogeneous, accurate and precise measurement can be obtained.

Depending on the amount and time of exposure, infrared radiation directed at the tissue such as skin may prove uncomfortable and promote unwanted heating and or damage to the surface irradiated. In the present invention the substance of interest is separated from most of the background noise and is located superficially and thus less radiation can be used without affecting accuracy. The present invention enhances signal to noise ratio without increasing the amount of radiation emitted and the increased risk of burning the surface being radiated.

Inconsistency in the location of the source and detector can be an important source of error and variability. The eyelid pocket provides a confined environment of fixed dimensions that provides a natural means for providing the consistency needed for accurate measurements. In addition, the measurements are much less sensitive to sensor location since the structure of the conjunctiva is homogeneous and the sensor surface can rest and adhere to the conjunctival surface. The use of a hydrophobic surface in the contact device encasing the radiation source and detector means promotes adherence to the conjunctival surface further allowing precise positioning.

The present invention also discloses minimally invasive techniques for placement of systems under the conjunctiva that uses only one drop of anesthetic for the procedure. The conjunctiva is the only superficial place in the body that allows painless surgical implantation of hardware to be done using simply one drop of anesthetic. Thus, the present invention eliminates the need for high-risk surgical procedures and internal infection. In the minimally invasive embodiment, the device implanted is located and implanted superficially and can be easily removed using just one drop of anesthetic.

Conjunctiva is transparent and thus the implant procedure can be done under direct view. The bulbar conjunctiva is not adherent to underlying tissues and there is a natural space underneath said conjunctiva allowing easy view for placement and removal of an implanted source/detector pair. Thus, there is elimination of the need to surgically implant devices deep in the body such as around blood vessels and inside the abdomen. There is elimination of implanting devices blindly since the skin is not transparent. There is elimination of a major surgical procedure in case of removal from inside the vessels, around the vessels, or inside the body.

In relation to the minimally invasive embodiment in which the optical sensor system is placed under the conjunctiva, the present invention provides a sample, such as plasma, which is free from debris. In the minimally invasive embodiment of the present invention, the system is measuring glucose already separated and present in the plasma collected adjacent to the sensor.

Body temperature such as is found in the surface of the skin is variable according to the environment and shift of spectra can occur with changes in temperature. The eyelid pocket provides an optimum location for temperature measurement which has a stable temperature and which is undisturbed by the ambient conditions. The conjunctival area radiated has a stable temperature derived from the carotid artery. Moreover, when the embodiment uses a contact device which is located in the eyelid pocket, there is a natural, complete thermal seal and stable core temperature. Good control of the temperature also provides increased accuracy and if desired, reduction of the number of wavelengths. Besides, the stable temperature environment allows use of the natural body infrared radiation emission as means to identify and measure the substance of interest.

Far-infrared radiation spectroscopy measures natural thermal emissions after said emissions interact and are absorbed by the substance of interest at the conjunctival surface. The present invention provides a thermally stable medium, insignificant number of interfering constituents, and the thin conjunctival lining is the only structure to be traversed by the thermal emissions from the eye before reaching the detector. Thus there is higher accuracy and precision when converting the thermal energy emitted as heat by the eye into concentration of the substance of interest.

The ideal thermal environment provided by the conjunctiva in the eyelid pocket can be used for non-invasive evaluation of blood components besides the measurement of temperature. Far-infrared spectroscopy can measure absorption of far-infrared radiation contained in the natural thermal emissions present in the eyelid pocket. Natural spectral emissions of infrared radiation by the conjunctiva and vessels include spectral information of blood components. The long wavelength emitted by the surface of the eye as heat can be used as the source of infrared energy that can be correlated with the identification and measurement of the concentration of the substance of interest. Infrared emission traverses only an extremely small distance from the eye surface to the sensor which means no attenuation by interfering constituents.

Spectral radiation of infrared energy from the surface of the eye can correspond to spectral information of the substance of interest. These thermal emissions irradiated as heat at 38 degrees Celsius can include the 4,000 to 14,000 nm wavelength range. For example, glucose strongly absorbs light around the 9,400 nm band. When far-infrared heat radiation is emitted by the eye, glucose will absorb part of the radiation corresponding to its band of absorption. Absorption of the thermal energy by glucose bands is related in a linear fashion to blood glucose concentration in the thermally sealed and thermally stable environment present in the eyelid pocket.

The natural spectral emission by the eye changes according to the presence and concentration of a substance of interest. The far-infrared thermal radiation emitted follow Planck's Law and the predicted amount of thermal radiation can be calculated. Reference intensity is calculated by measuring thermal energy absorption outside the substance of interest band. The thermal energy absorption in the band of substance of interest can be determined via spectroscopic means by comparing the measured and predicted values at the conjunctiva/plasma interface. The signal is then converted to concentration of the substance of interest according to the amount of thermal energy absorbed.

The Intelligent Contact Lens in the eyelid pocket provides optimal means for non-invasive measurement of the substance of interest using natural heat emission by the eye. Below is an exemplary representation of various unique advantages and features provided by the present invention.

higher signal as found in the plasma/conjunctiva interface due to less background interference undisturbed signal since the heat source is in direct apposition to the sensing means stable temperature since the eyelid pocket is thermally sealed the eyelid pocket functions as a cavity since the eyelid edge is tightly opposed to the surface of the eyeball easily observed in the eye. To see the inside of the eyelid pocket it is necessary to actively pull the eyelid.

there is no heat loss inside the cavity there is active heat transfer from the vessels caused by local blood flow in direct contact with the sensor the temperature of the eye, by being supplied directly from the central nervous system circulation, is in direct equilibrium with core temperature.

Temperature is proportional to blood perfusion. The conjunctiva is extremely vascularized and the eye is the organ in the whole body with the highest amount of blood per gram of tissue. The conjunctiva is a thin homogeneous layer of equal composition and the eyelid pocket is a sealed thermal environment without cooling of surface layers. The blood vessels in the conjunctiva are branches of the carotid artery coming directly from the central nervous system which allows measuring the precise core temperature of the body.

The eyelid pocket provides a sealed and homogeneous thermal environment. When the eyelids are closed (during blinking or with eyes closed) or at any time inside the eyelid pockets, the thermal environment of the eye exclusively corresponds to the core temperature of the body. In the eyelid pocket there is prevention of passive heat loss in addition to associated active heat transfer since the conjunctiva is a thin lining of tissue free of keratin and with capillary level on the surface.

Skin present throughout the body, including the tongue, is covered with keratin, a dead layer of thick tissue that alters transmission of infrared energy emitted as heat. The conjunctiva does not have a keratin layer and the sensor can be placed in intimate thermal contact with the blood vessels.

Skin with its various layers and other constituents selectively absorb infrared energy emitted by deeper layers before said energy reaches the surface of said skin. Contrary to that, the conjunctiva is homogeneous with no absorption of infrared energy and the blood vessels are located on the surface. This allows undisturbed delivery of infrared energy to the surface of the conjunctiva and to a temperature detector such as an infrared detector placed in apposition to said surface of the conjunctiva.

In the skin and other superficial parts of the body there is a thermal gradient with the deeper layers being warmer than the superficial layers. In the conjunctiva there is no thermal gradient since there is only a mono-layer of tissue with vessels directly underneath. The thermal energy generated by the conjunctival blood vessels exiting to the surface corresponds to the undisturbed core temperature of the body.

The surface temperature of the skin and other body parts does not correspond to the blood temperature. The surface temperature in the eye corresponds to the core temperature of the body.

Thus, skin is not suitable for creating a thermally sealed and stable environment for measuring temperature and the concentration of the substance of interest. Most important, no other part of the body, but the eye provides a natural pocket structure for direct apposition of the temperature sensor in direct contact with the surface of the blood vessel. The conjunctiva and eyelid pocket provides a thermally sealed environment in which the temperature sensor is in direct apposition to the heat source. Moreover, in the eyelid pocket thermal equilibrium is achieved immediately as soon as the sensor is placed in said eyelid pocket and in contact with the tissue surface.

The method and apparatus of the present invention provides optimal means for measurement of the concentration of the substance of interest from the infrared energy emissions by the conjunctival surface as well as evaluation of temperature with measurement of core temperature.

The temperature sensor, preferably a contact thermosensor, is positioned in the sealed environment provided by the eyelid pocket, which eliminates spurious readings which can occur by accidental reading of ambient temperature.

The apparatus uses the steps of sensing the level of temperature, producing output electrical signals representative of the intensity of the radiation, converting the resulting input, and sending the converted input to a processor. The processor is adapted to provide the necessary analysis of the signal to determine the temperature and concentration of the substance of interest and displaying the temperature level and the concentration of the substance of interest.

The apparatus can provide core temperature, undisturbed by the environment, and continuos measurement in addition to far-infrared spectroscopy analysis for determining the concentration of the substance of interest with both single or continuous measurement.

The present invention includes means for directing preferably near-infrared energy into the surface of the conjunctiva, means for analyzing and converting the reflectance or back scattered spectrum into the concentration of the substance of interest and means for positioning the light source and detector means adjacent to the surface of the eye. The present invention also provides methods for determining the concentration of a substance of interest with said methods including the steps of using eye fluid including plasma present on, in, or below the conjunctiva, directing electromagnetic radiation such as near-infrared at the plasma interface, detecting the near-infrared energy radiated from said plasma interface, taking the resulting spectra and providing an electrical signal upon detection, processing the signal and reporting concentration of the substance of interest according to said signal. The invention also includes means and methods for positioning the light sources and detectors in stable position and with stable pressure and temperature in relation to the surface to which radiation is directed to and received from. The plasma collected underneath the conjunctiva is preferably used as the source medium for determination of the concentration of the substance of interest.

The present invention further includes means for directing near-infrared energy through the conjunctiva/plasma interface, means for positioning radiation source and detector diametrically opposed to each other, and means for analyzing and converting the transmitted resulting spectrum into the concentration of the substance of interest. The present invention also provides methods for determining the concentration of a substance of interest with said methods including the steps of using eye fluid including plasma adjacent to the conjunctiva as the source medium for measuring the substance of interest, directing electromagnetic radiation such as near-infrared through the conjunctiva/plasma interface; collecting the near-infrared energy radiated from said conjunctiva/plasma interface, taking the resulting spectra and providing an electrical signal upon detection, processing the signal and reporting concentration of the substance of interest according to said signal. The invention also includes means and methods for positioning the radiation sources and detectors in a stable position and with stable pressure and temperature in relation to the surface to which radiation is directed through.

The present invention yet includes means for collecting natural far-infrared radiation emitted as heat from the eye, means for positioning a radiation collector to receive said radiation, and means for converting the collected radiation from the eye into the concentration of the substance of interest. The present invention also provides methods for determining the concentration of the substance of interest with said methods including the steps of using the natural far-infrared emission from the eye as the resulting radiation for measuring the substance of interest, collecting the resulting radiation spectra in a thermally stable environment, providing an electrical signal upon detection, processing the signal and reporting the concentration of the substance of interest according to said signal. A thermally stable environment includes open eye or closed eye. The thermal emission collection means are in contact with the conjunctiva in the eyelid pocket with eyes open or closed.

With closed eye, the collection means can also be in contact with the cornea. With closed eyes the cornea is in equilibrium with the aqueous humor inside the eye with transudation of fluid to the surface of the cornea. The cornea during closed eyes or blinking is in thermal equilibrium with core body temperature. When the eyes are closed the equilibrium created allows the evaluation of substances of interest using a contact lens with optical or electrochemical sensors placed on the surface of the cornea. The invention also includes means and methods for positioning the thermal emission collection means in a stable position and with stable pressure and with eyes open or closed.

The present invention further includes measuring the core temperature of the body, both single and continuous measurements. The present invention includes means for collecting thermal radiation from the eye, means for positioning temperature sensitive devices to receive thermal radiation from the eye in a thermally stable environment, and means for converting said thermal radiation into the core temperature of the body. The present invention also provides methods for determining core temperature of the body with said methods including the steps of using thermal emissions from the eye in a thermally stable environment, collecting the thermal emission by the eye, providing an electrical signal upon detection, processing the signal and reporting the temperature level. The invention also includes means and methods for proper positioning of the temperature sensor in a stable position and with stable pressure as achieved in the eyelid pocket. The invention yet includes means to monitor a bodily function and dispense medications or activate devices according to the signal acquired. The invention further includes apparatus and methods for treating vascular abnormalities and cancer. The invention further includes means to dispense medications.

Substances of interest can include any substance present adjacent to the conjunctiva or surface of the eye which is capable of being analyzed by electromagnetic means. For example but not by way of limitation such substances can include any substance present in plasma such as molecular, chemical or cellular, and for example exogenous chemicals such as drugs and alcohol as well as endogenous chemicals such as glucose, oxygen, bicarbonate, cardiac markers, cancer markers, hormones, glutamate, urea, fatty acids, cholesterol, triglycerides, proteins, creatinine, aminoacids and the like and cellular constituents such as cancer cells, and the like. Values such as pH can also be calculated as pH can be related to light absorption using reflectance spectroscopy.

Substances of interest can also include hemoglobin, cytochromes, cellular elements and metabolic changes corresponding to light interaction with said substances of interest when directing electromagnetic radiation at said substances of interest. All of those constituents and values can be optimally detected in the conjunctiva or surface of the eye using electromagnetic means and in accordance with their optical, physical, and chemical characteristics.

For the purpose of the description herein, the sclera is considered as one structure. It is understood however, that the sclera has several layers and surrounding structures including the episclera and Tenon's capsule.

For the purpose of the description herein, light and radiation are used interchangeably and refers to a form of energy contained within the electromagnetic spectrum.

The eye fluid, conjunctival area, methods and apparatus as disclosed by the present invention provides ideal means and sources of signals for measurement of any substance of interest allowing optimal and maximum signals to be obtained. The present invention allows analytical calibration since the structure and physiology of the conjunctiva is stable and the amount of plasma collected adjacent to the conjunctiva is also stable. This type of analytical calibration can be universal which avoids clinical calibration that requires blood sampling individually as a reference.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIGS. 20A and 20B schematically illustrate an alternative embodiment for measuring intraocular pressure by indentation.

FIG. 34 is a schematic block diagram of a system of obtaining sample signal measurements and transmitting and interpreting the results of the sample signals.

FIGS. 35A and 35C schematically represent the actuation of the contact device of the present invention by the opening and closing of the eye lids. FIG. 35B is an enlarged detail view of an area encircled in FIG. 35A.

FIGS. 36A through 36J schematically illustrate various shapes of a contact device incorporating the principles of the present invention.

FIG. 39A illustrates the continuous flow of fluid in the eye.

FIG. 39B schematically illustrates an alternative embodiment of the contact device of the present invention used under the eyelid to produce signals based upon flow of tear fluid through the eye and transmit the signals by a wire connected to an external device.

FIG. 42A illustrates open eye lids positioned over a contact device including a somnolence awareness device, whereas FIG. 42B illustrates the closing of the eyelids and the production of a signal externally transmitted to an alarm device.

FIG. 43 is a detailed view of a portion of an eyeball including a heat stimulation transmission device.

FIG. 44 is a front view of a heat stimulation transmission device mounted on a contact device and activated by a remote hardware device.

FIG. 45 illustrates a band heat stimulation transmission device for external use or surgical implantation in any part of the body.

FIG. 46 illustrates a surgically implantable heat stimulation transmission device for implantation in the eye between eye muscles.

FIG. 47 illustrates a heat stimulation device for surgical implantation in any part of the body.

FIG. 48 schematically illustrates the surgical implantation of an overheating transmission device adjacent to a brain tumor.

FIG. 49 illustrates the surgical implantation of an overheating transmission device adjacent to a kidney tumor.

FIG. 50 illustrates an overheating transmission device and its various components.

FIG. 51 illustrates the surgical implantation of an overheating transmission devices adjacent to an intraocular tumor.

FIG. 52 schematically illustrates the surgical implantation of an overheating transmission device adjacent to a lung tumor.

FIG. 53 schematically illustrates the positioning of an overheating transmission device adjacent to a breast tumor.

FIG. 79A through 79C are schematic illustrations of exemplary embodiments with transport enhancement capabilities.

FIG. 80 illustrates a microfluidic and bioelectronic chip system in accordance with the present invention.

FIG. 81 is a schematic illustration of an integrated microfluidics and electronics system in accordance with the present invention.

FIG. 93A schematically illustrates an alternative embodiment for implantation.

FIG. 93B is an enlarged view of the sensor arrangement shown in FIG. 93A.

FIG. 94 schematically illustrates another alternative embodiment of the present invention.

FIG. 95A schematically illustrates another embodiment of the present invention in cross-sectional view.

FIG. 95B is an enlarged view of the arrangement shown in FIG. 95A.

FIG. 96 schematically illustrates one preferred embodiment of the present invention.

FIG. 97A schematically illustrates one preferred embodiment of the present invention.

FIG. 97B is an enlarged view of the arrangement shown in FIG. 97A.

FIG. 97C schematically shows an alternative embodiment of the present invention.

FIG. 100A schematically illustrates the position of sensor in accordance with a preferred embodiment of the present invention.

FIG. 100B shows an enlarged view of the sensor shown in FIG. 100A.

FIG. 100C is a schematic block diagram of an apparatus according to one preferred embodiment of the present invention and shown schematically in FIGS. 100A-B.

FIG. 100D schematically illustrates a sensor arrangement in accordance with a preferred embodiment of the present invention.

FIG. 101A is a schematic block diagram of an apparatus according to one preferred embodiment of the present invention.

FIG. 101B shows a cross-sectional view of one preferred embodiment of the present invention in accordance with the embodiment of FIG. 101A.

FIG. 104B(1-3) schematically illustrate various positions for directing the probe arrangement in accordance with a preferred embodiment of the present invention.

FIG. 104C is a schematic block diagram for continuous monitoring of chemical substances in accordance with a preferred embodiment of the present invention.

FIG. 104D is a schematic block diagram of a probe arrangement

FIG. 104E schematically illustrates a probe arrangement in accordance with a preferred embodiment of the present invention.

FIG. 104F-G shows cross-sectional views of the probe arrangement in two different positions in relation to the tissue being evaluated.

FIG. 104H-J shows a frontal view of different arrangements for the sensor and filter used in the measuring probe.

Figure 1:
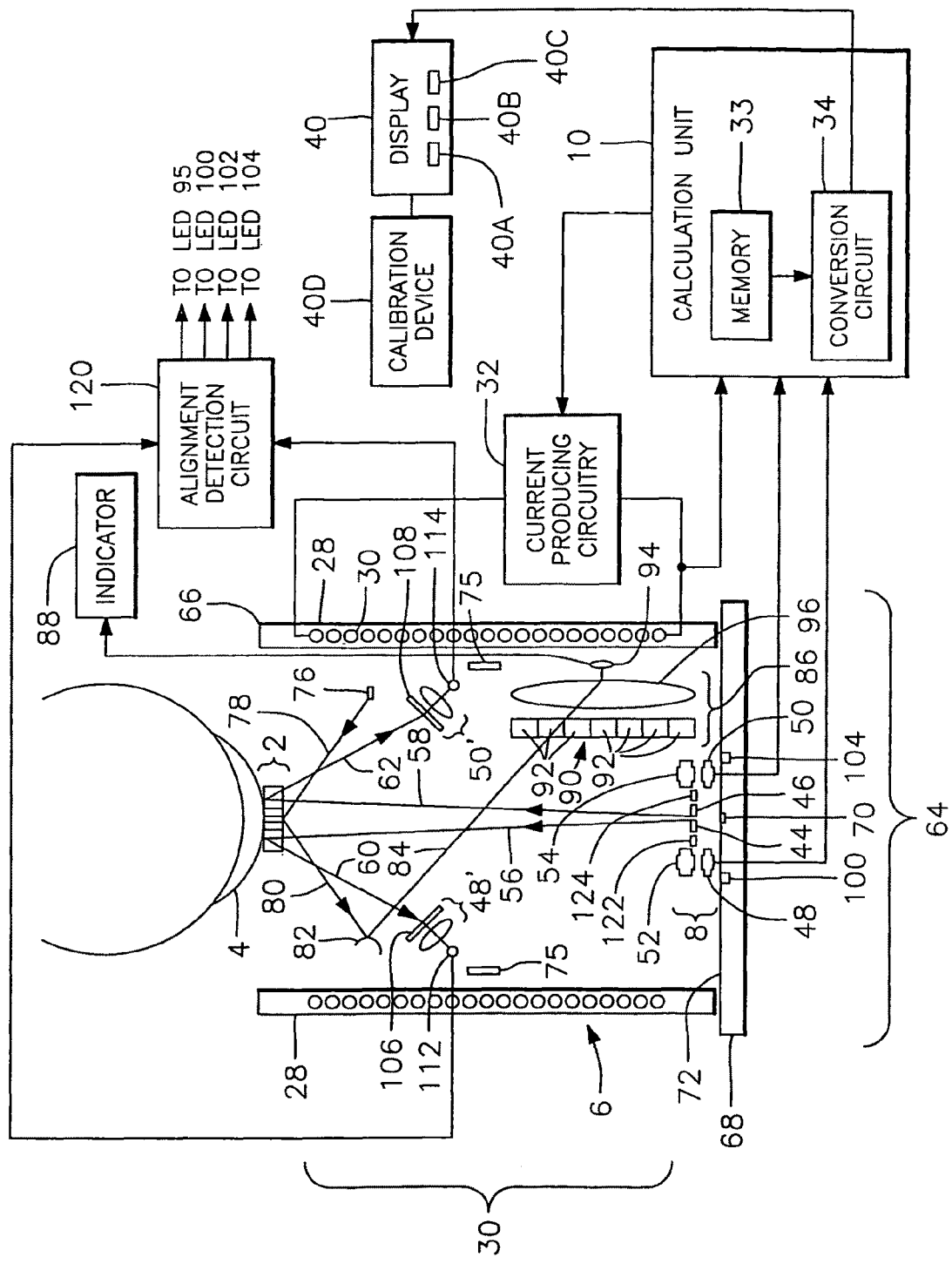
FIG. 1 is a schematic block diagram illustrating a system for measuring intraocular pressure in accordance with a preferred embodiment of the present invention.

FIG. 104K-1 shows a cross-sectional view of the probe arrangement using a rotatable filter system in accordance with a preferred embodiment of the present invention.

Figure 104A:
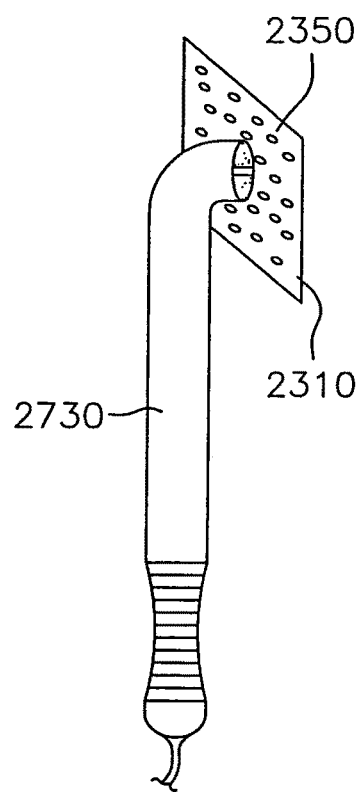
FIG. 104A schematically illustrates a probe arrangement in accordance with a preferred embodiment of the present invention.
Figure 105A:
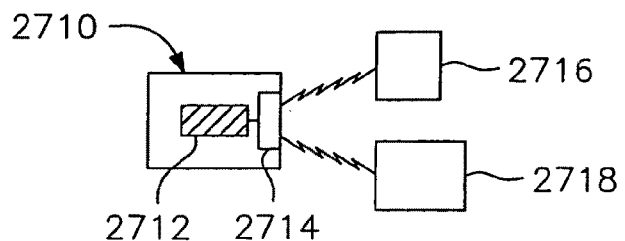
Figure 105B:
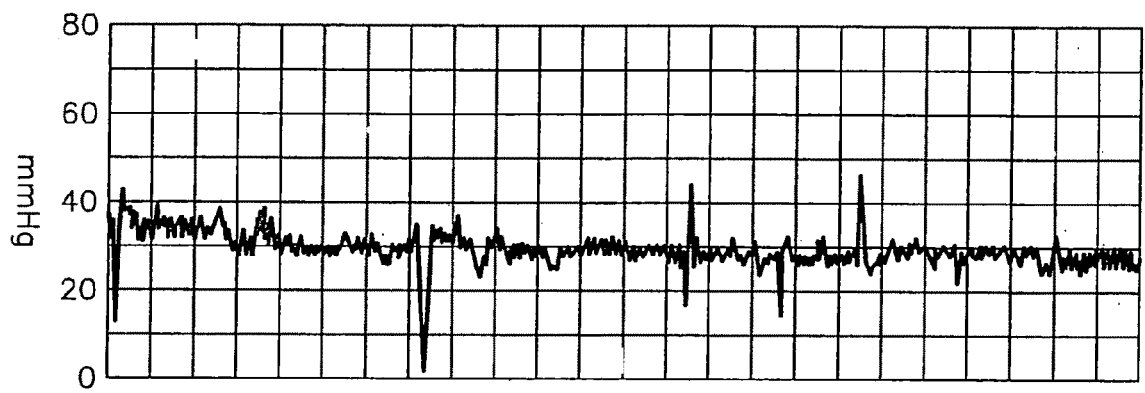
Figure 105C:
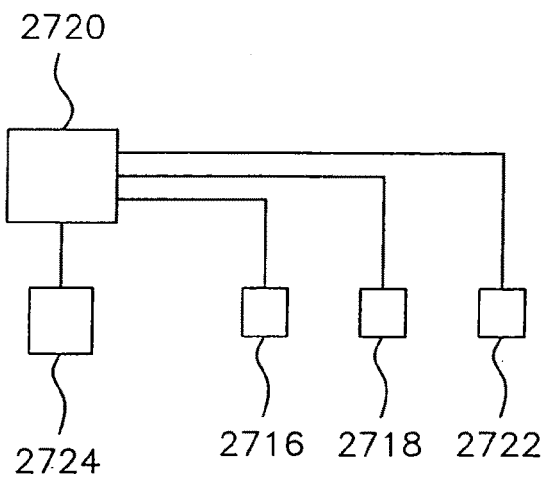
Figures 1, 105D:
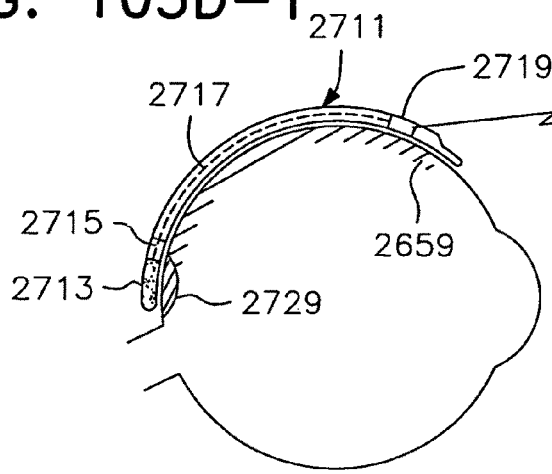
Figures 2, 105D:
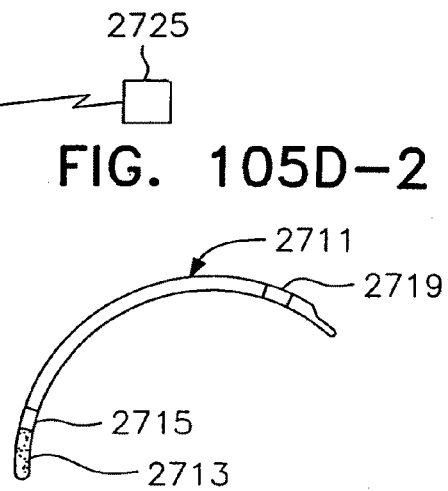
Figures 3, 105D:
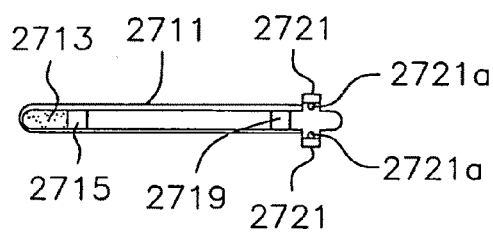
Figures 4, 105D:
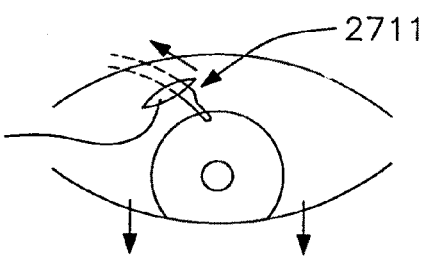
Figures 5, 105D:
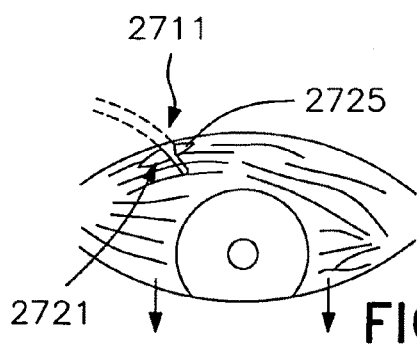
Figures 6, 105D:
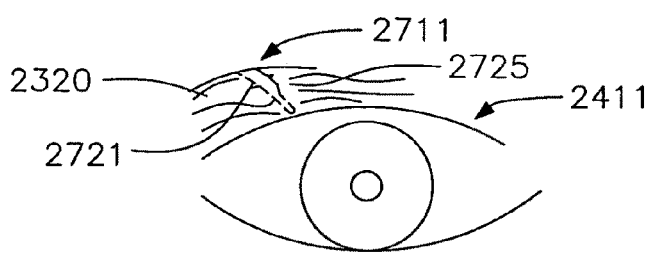
Figures 7, 105D:
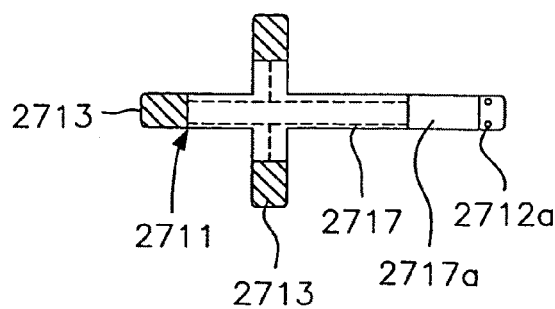

FIG. 104K-2 shows a frontal view of the rotatable filter of FIG. 104K-1.

Figure 104L:
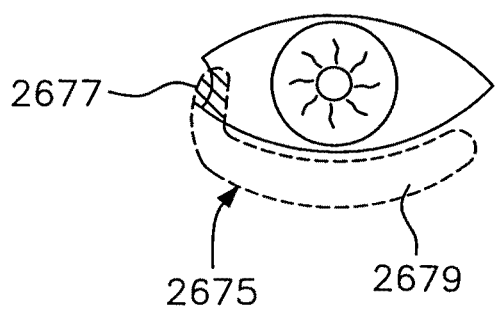
FIG. 104B schematically illustrates a preferred embodiment of the present invention.
Figure 104M:
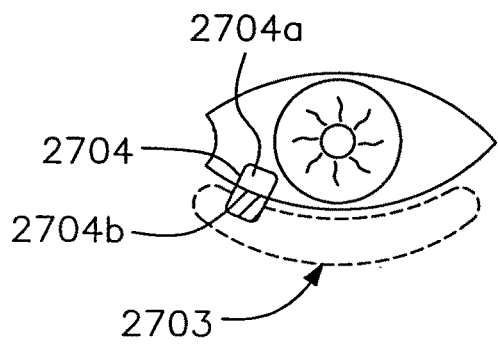
Figure 104N:
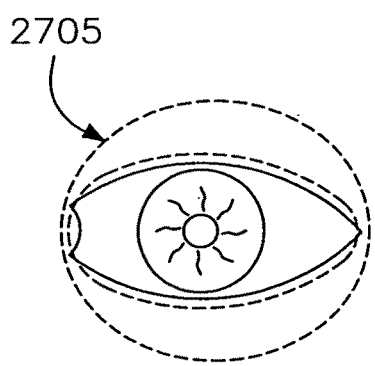

FIG. 104L-N schematically illustrates various measuring arrangements in accordance with an alternative embodiment of the present invention.

Figure 104O:
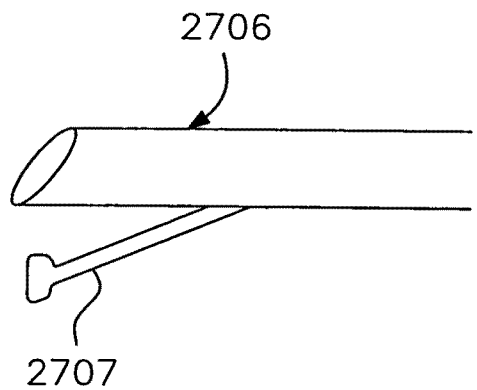

FIG. 104O schematically illustrates a probe arrangement with a supporting arm.

Figure 104P:
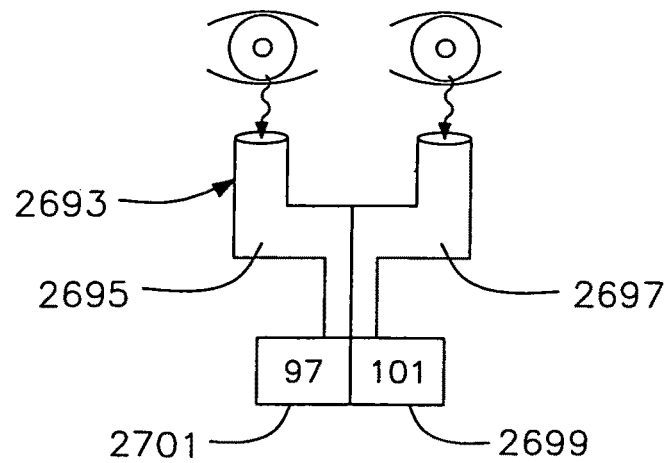

FIG. 104P schematically illustrates a probe arrangement for simultaneous non-contact evaluation of both eyes for detection of abnormalities due to asymmetric measurements.

FIG. 104Q, (1A), (1B), (2A), (2B), (3), (4) and (5) show a series of pictures related to in-vivo evaluation of radiation of the conjunctiva/plasma interface using infrared imaging.

FIG. 105A is a schematic simplified block diagram of one preferred embodiment of the present invention.

FIG. 105B shows a waveform corresponding to heart rhythm achieved by using a contact device and transducer placed on the eye.

FIG. 105C is a schematic block diagram of one preferred embodiment in accordance to FIG. 105B.

FIG. 105(D-1) shows a cross-sectional view of a heating transmission device adjacent to a neovascular membrane in the eye according to a preferred embodiment of the invention.

FIG. 105(D-2) shows a side view of the heating transmission device.

FIG. 105(D-3) shows a frontal view of the overheating transmission device.

FIG. 105(D-4 to D-6) schematically illustrates the surgical implantation of the device in FIG. 105(D-1).

FIG. 105(D-7) shows a frontal view of the overheating transmission device in a cross-shape design.

Figure 106A:
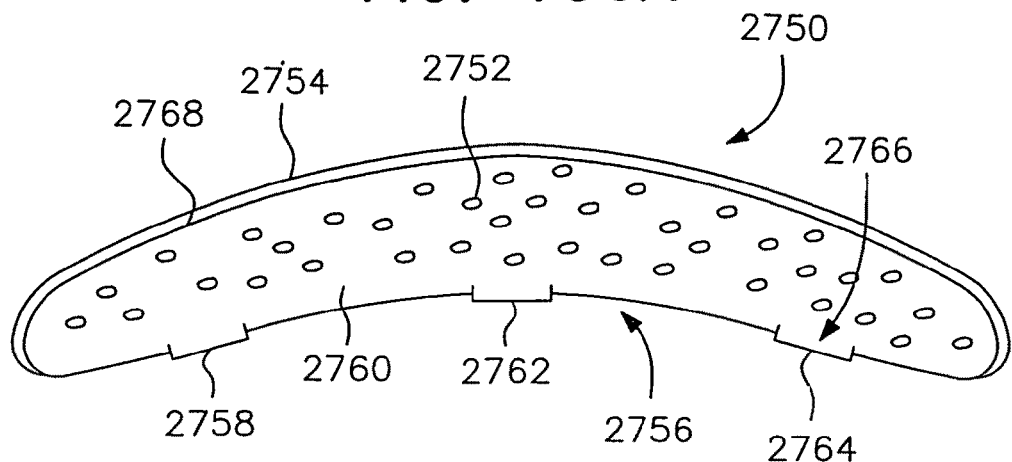

FIG. 106A is a schematic illustration of a dispensation device in accordance with a preferred embodiment of the present invention.

Figure 106B:
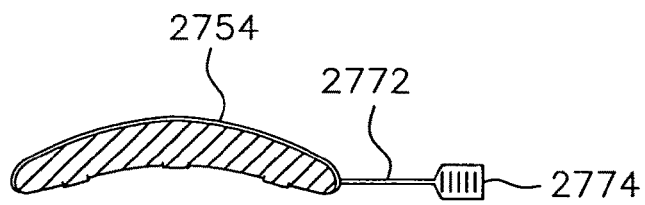

FIG. 106B is a schematic illustration of the preferred embodiment of FIG. 106A with an attached handle.

Figure 107A:
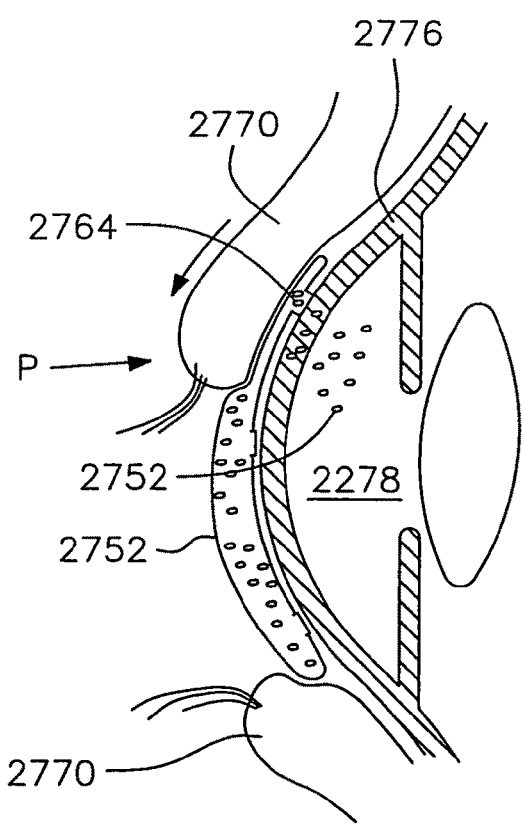
Figure 107B:
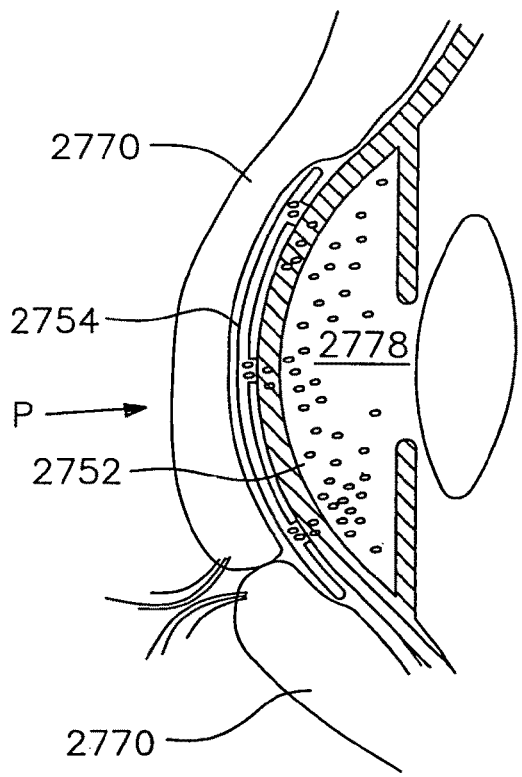

FIGS. 107A-B is a cross sectional view of the embodiment of FIG. 106A-B being actuated by the eyelid.

Figure 108:
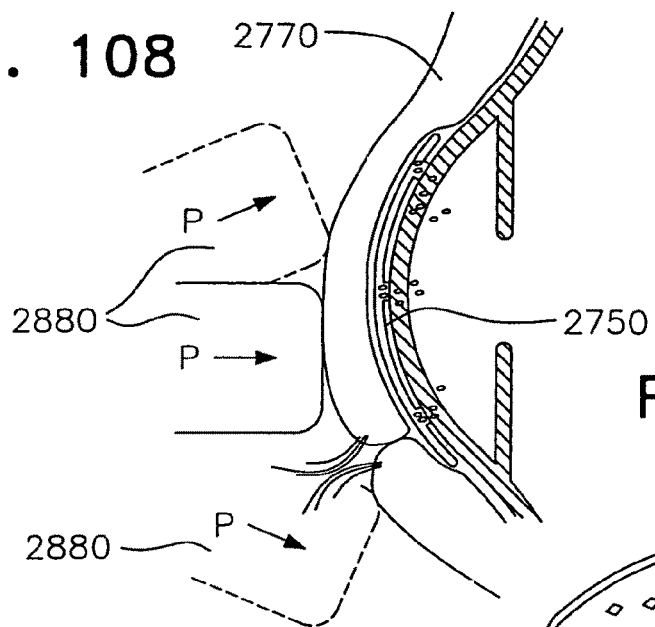

FIG. 108 is a cross-sectional view of an alternative embodiment shown in FIGS. 107A-B.

Figure 109:
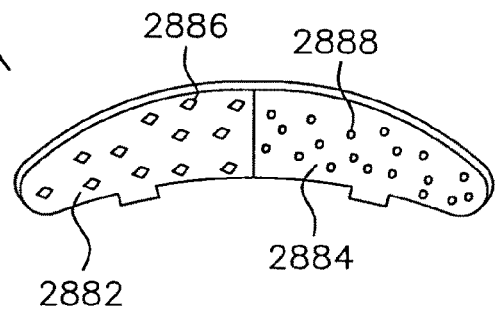

FIG. 109 is a cross sectional view of one preferred embodiment of a dispensation device.

Figure 110A:
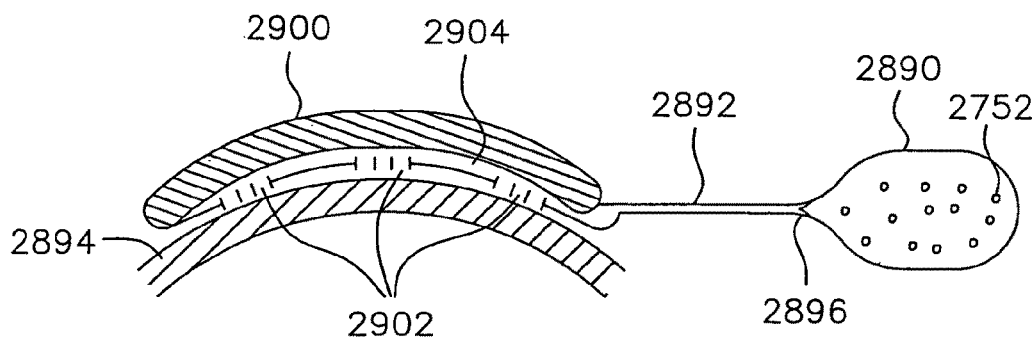
Figure 110B:
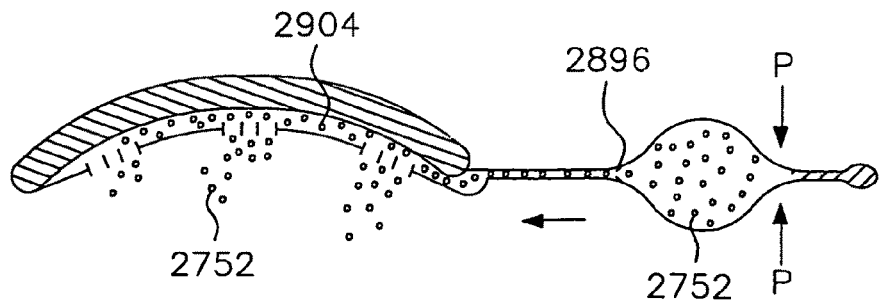

FIGS. 110A-B schematically illustrates an alternative embodiment for the dispensation device.

DESCRIPTION OF THE PREFERRED EMBODIMENTS APPLANATION

A preferred embodiment of the present invention will now be described with reference to the drawings. According to the preferred embodiment illustrated in FIG. 1, a system is provided for measuring intraocular pressure by applanation. The system includes a contact device 2 for placement in contact with the cornea 4, and an actuation apparatus 6 for actuating the contact device 2 so that a portion thereof projects inwardly against the cornea 4 to provide a predetermined amount of applanation. The system further includes a detecting arrangement 8 for detecting when the predetermined amount of applanation of the cornea 4 has been achieved and a calculation unit 10 responsive to the detecting arrangement 8 for determining intraocular pressure based on the amount of force the contact device 2 must apply against the cornea 4 in order to achieve the predetermined amount of applanation.

The contact device 2 illustrated in FIG. 1 has an exaggerated thickness to more clearly distinguish it from the cornea 4. FIGS. 2A-2D more accurately illustrate a preferred embodiment of the contact device 2 which includes a substantially rigid annular member 12, a flexible membrane 14 and a movable central piece 16. The substantially rigid annular member 12 includes an inner concave surface 18 shaped to match an outer surface of the cornea 4 and having a hole 20 defined therein. The substantially rigid annular member 12 has a maximum thickness (preferably approximately 1 millimeter) at the hole 20 and a progressively decreasing thickness toward a periphery 21 of the substantially rigid annular member 12. The diameter of the rigid annular member is approximately 11 millimeters and the diameter of the hole 20 is approximately 5.1 millimeters according to a preferred embodiment. Preferably, the substantially rigid annular member 12 is made of transparent polymethylmethacrylate; however, it is understood that many other materials, such as glass and appropriately rigid plastics and polymers, may be used to make the annular member 12. Preferably, the materials are chosen so as not to interfere with light directed at the cornea or reflected back therefrom.

The flexible membrane 14 is preferably secured to the inner concave surface 18 of the substantially rigid annular member 12 to provide comfort for the wearer by preventing scratches or abrasions to the corneal epithelial layer. The flexible membrane 14 is coextensive with at least the hole 20 in the annular member 12 and includes at least one transparent area 22. Preferably, the transparent area 22 spans the entire flexible membrane 14, and the flexible membrane 14 is coextensive with the entire inner concave surface 18 of the rigid annular member 12. According to a preferred arrangement, only the periphery of the flexible membrane 14 and the periphery of the rigid annular member 12 are secured to one another. This tends to minimize any resistance the flexible membrane might exert against displacement of the movable central piece 16 toward the cornea 4.

According to an alternative arrangement, the flexible membrane 14 is coextensive with the rigid annular member and is heat-sealed thereto over its entire extent except for a circular region within approximately one millimeter of the hole 20.

Although the flexible membrane 14 preferably consists of a soft and thin polymer, such as transparent silicone elastic, transparent silicon rubber (used in conventional contact lens), transparent flexible acrylic (used in conventional intraocular lenses), transparent hydrogel, or the like, it is well understood that other materials may be used in manufacturing the flexible membrane 14.

The movable central piece 16 is slidably disposed within the hole 20 and includes a substantially flat inner side 24 secured to the flexible membrane 14. The engagement of the inner side 24 to the flexible membrane 14 is preferably provided by glue or thermo-contact techniques. It is understood, however, that various other techniques may be used in order to securely engage the inner side 24 to the flexible membrane 14. Preferably, the movable central piece 16 has a diameter of approximately 5.0 millimeters and a thickness of approximately 1 millimeter.

A substantially cylindrical wall 42 is defined circumferentially around the hole 20 by virtue of the increased thickness of the rigid annular member 12 at the periphery of the hole 20. The movable central piece 16 is slidably disposed against this wall 42 in a piston-like manner and preferably has a thickness which matches the height of the cylindrical wall 42. In use, the substantially flat inner side 24 flattens a portion of the cornea 4 upon actuation of the movable central piece 16 by the actuation apparatus 6.

The overall dimensions of the substantially rigid annular member 12, the flexible membrane 14 and the movable central piece 16 are determined by balancing several factors, including the desired range of forces applied to the cornea 4 during applanation, the discomfort tolerances of the patients, the minimum desired area of applanation, and the requisite stability of the contact device 2 on the cornea 4. In addition, the dimensions of the movable central piece 16 are preferably selected so that relative rotation between the movable central piece 16 and the substantially rigid annular member 12 is precluded, without hampering the aforementioned piston-like sliding.

The materials used to manufacture the contact device 2 are preferably selected so as to minimize any interference with light incident upon the cornea 4 or reflected thereby.

Figure 2A:
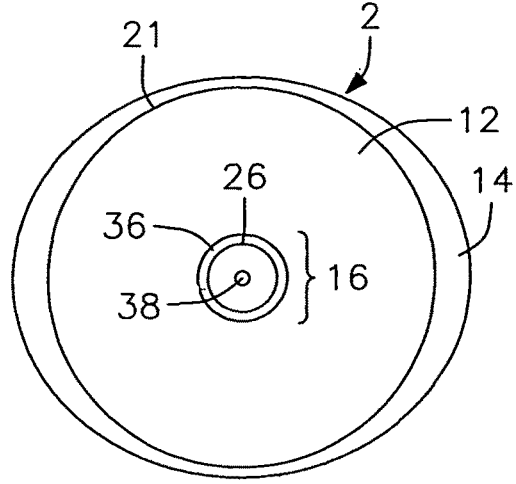
FIGS. 2A-2D schematically illustrate a preferred embodiment of a contact device according the present invention.
Figure 2B:
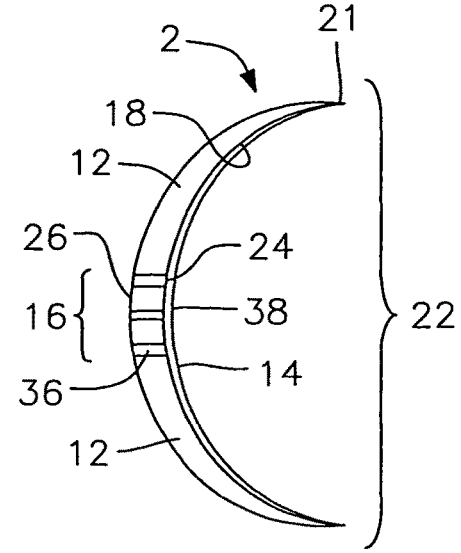
Figure 2C:
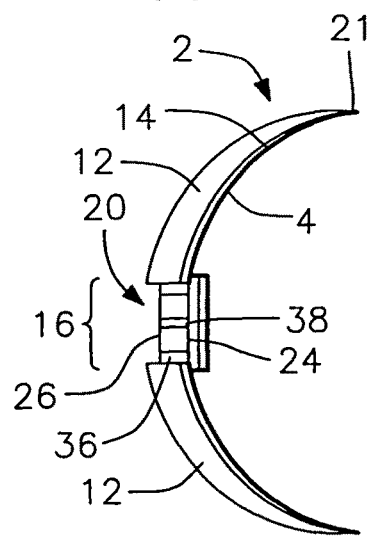
Figure 2D:
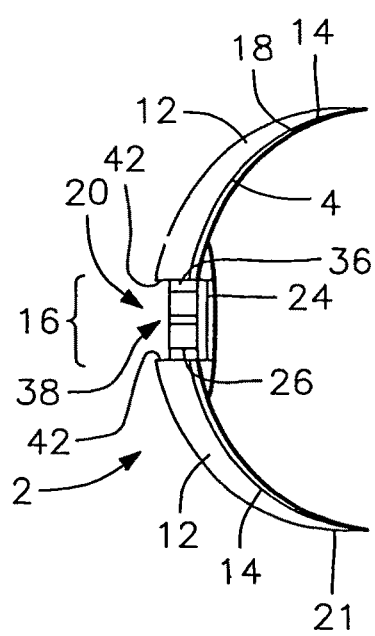

Preferably, the actuation apparatus 6 illustrated in FIG. 1 actuates the movable central piece 16 to cause sliding of the movable central piece 16 in the piston-like manner toward the cornea 4. In doing so, the movable central piece 16 and a central portion of the flexible membrane 14 are caused to project inwardly against the cornea 4. This is shown in FIGS. 2C and 2D. A portion of the cornea 4 is thereby flattened. Actuation continues until a predetermined amount of applanation is achieved.

Preferably, the movable central piece 16 includes a magnetically responsive element 26 arranged so as to slide along with the movable central piece 16 in response to a magnetic field, and the actuation apparatus 6 includes a mechanism 28 for applying a magnetic field thereto. Although it is understood that the mechanism 28 for applying the magnetic field may include a selectively positioned bar magnet, according to a preferred embodiment, the mechanism 28 for applying the magnetic field includes a coil 30 of long wire wound in a closely packed helix and circuitry 32 for producing an electrical current through the coil 30 in a progressively increasing manner. By progressively increasing the current, the magnetic field is progressively increased. The magnetic repulsion between the actuation apparatus 6 and the movable central piece 16 therefore increases progressively, and this, in turn, causes a progressively greater force to be applied against the cornea 4 until the predetermined amount of applanation is achieved.

Using known principles of physics, it is understood that the electrical current passing through the coil 30 will be proportional to the amount of force applied by the movable central piece 16 against the cornea 4 via the flexible membrane 14. Since the amount of force required to achieve the predetermined amount of applanation is proportional to intraocular pressure, the amount of current required to achieve the predetermined amount of applanation will also be proportional to the intraocular pressure. Thus, a conversion factor for converting a value of current to a value of intraocular pressure can easily be determined experimentally upon dimensions of the system, the magnetic responsiveness of the magnetically responsive element 26, number of coil windings, and the like.

Besides using experimentation techniques, the conversion factor may also be determined using known techniques for calibrating a tonometer. Such known techniques are based on a known relationship which exists between the inward displacement of an indentation device and the volume changes and pressure in the indented eye. Examples of such techniques are set forth in Shiotz, Communications: Tonometry, The Brit. J. of Ophthalmology, June 1920, p. 249-266; Friedenwald, Tonometer Calibration, Trans. Amer. Acad. of O. & O., January-February 1957, pp. 108-126; and Moses, Theory and Calibration of the Schiotz Tonometer VII: Experimental Results of Tonometric Measurements: Scale Reading Versus Indentation Volume, Investigative Ophthalmology, September 1971, Vol. 10, No. 9, pp. 716-723.

In light of the relationship between current and intraocular pressure, the calculation unit 10 includes a memory 33 for storing a current value indicative of the amount of current passing through the coil 30 when the predetermined amount of applanation is achieved. The calculation unit 10 also includes a conversion unit 34 for converting the current value into an indication of intraocular pressure.

Preferably, the calculation unit 10 is responsive to the detecting arrangement 8 so that when the predetermined amount of applanation is achieved, the current value (corresponding to the amount of current flowing through the coil 30) is immediately stored in the memory 33. At the same time, the calculation unit 10 produces an output signal directing the current producing circuitry 32 to terminate the flow of current. This, in turn, terminates the force against the cornea 4. In an alternative embodiment, the current producing circuitry 32 could be made directly responsive to the detecting arrangement 8 (i.e., not through the calculation unit 10) so as to automatically terminate the flow of current through the coil 30 upon achieving the predetermined amount of applanation.

The current producing circuitry 32 may constitute any appropriately arranged circuit for achieving the progressively increasing current. However, a preferred current producing circuit 32 includes a switch and a DC power supply, the combination of which is capable of producing a step function. The preferred current producing circuitry 32 further comprises an integrating amplifier which integrates the step function to produce the progressively increasing current.

The magnetically responsive element 26 is circumferentially surrounded by a transparent peripheral portion 36. The transparent peripheral portion 36 is aligned with the transparent area 22 and permits light to pass through the contact device 2 to the cornea 4 and also permits light to reflect from the cornea 4 back out of the contact device 2 through the transparent on peripheral portion 36. Although the transparent peripheral portion 36 may consist entirely of an air gap, for reasons of accuracy and to provide smoother sliding of the movable central piece 16 through the rigid annular member 12, it is preferred that a transparent solid material constitute the transparent peripheral portion 36. Exemplary transparent solid materials include polymethyl methacrylate, glass, hard acrylic, plastic polymers, and the like.

The magnetically responsive element 26 preferably comprises an annular magnet having a central sight hole 38 through which a patient is able to see while the contact device 2 is located on the patient's cornea 4. The central sight hole 38 is aligned with the transparent area 22 of the flexible membrane 14 and is preferably at least 1-2 millimeters in diameter.

Although the preferred embodiment includes an annular magnet as the magnetically responsive element 26, it is understood that various other magnetically responsive elements 26 may be used, including various ferromagnetic materials and/or suspensions of magnetically responsive particles in liquid. The magnetically responsive element 26 may also consist of a plurality of small bar magnets arranged in a circle, to thereby define an opening equivalent to the illustrated central sight hole 38. A transparent magnet may also be used.

A display 40 is preferably provided for numerically displaying the intraocular pressure detected by the system. The display 40 preferably comprises a liquid crystal display (LCD) or light emitting diode (LED) display connected and responsive to the conversion unit 34 of the calculation unit 10.

Alternatively, the display 40 can be arranged so as to give indications, of whether the intraocular pressure is within certain ranges. In this regard, the display 40 may include a green LED 40A, a yellow LED 40B, and a red LED 40C. When the pressure is within a predetermined high range, the red LED 40C is illuminated to indicate that medical attention is needed. When the intraocular pressure is within a normal range, the green LED 40A is illuminated. The yellow LED 40B is illuminated when the pressure is between the normal range and the high range to indicate that the pressure is somewhat elevated and that, although medical attention is not currently needed, careful and frequent monitoring is recommended.

Preferably, since different patients may have different sensitivities or reactions to the same intraocular pressure, the ranges corresponding to each LED 40A,40B,40C are calibrated for each patient by an attending physician. This way, patients who are more susceptible to consequences from increased intraocular pressure may be alerted to seek medical attention at a pressure less than the pressure at which other less-susceptible patients are alerted to take the same action. The range calibrations may be made using any known calibration device 40D including variable gain amplifiers or voltage divider networks with variable resistances.

The detecting arrangement 8 preferably comprises an optical detection system including two primary beam emitters 44,46; two light sensors 48,50; and two converging lenses 52,54. Any of a plurality of commercially available beam emitters may be used as emitters 44,46, including low-power laser beam emitting devices and infra-red (IR) beam emitting devices. Preferably, the device 2 and the primary beam emitters 44,46 are arranged with respect to one another so that each of the primary beam emitters 44,46 emits a primary beam of light toward the cornea through the transparent area 22 of the device and so that the primary beam of light is reflected back through the device 2 by the cornea 4 to thereby produce reflected beams 60,62 of light with a direction of propagation dependent upon the amount of applanation of the cornea. The two light sensors 48,50 and two converging lenses 52,54 are preferably arranged so as to be aligned with the reflected beams 60,62 of light only when the predetermined amount of applanation of the cornea 4 has been achieved. Preferably, the primary beams 56,58 pass through the substantially transparent peripheral portion 36.

Although FIG. 1 shows the reflected beams 60,62 of light diverging away from one another and well away from the two converging lenses 52,54 and light sensors 48,50, it is understood that as the cornea 4 becomes applanated the reflected beams 60,62 will approach the two light sensors 48,50 and the two converging lenses 52,54. When the predetermined amount of applanation is achieved, the reflected beams 60,62 will be directly aligned with the converging lenses 52,54 and the sensors 48,50. The sensors 48,50 are therefore able to detect when the predetermined amount of applanation is achieved by merely detecting the presence of the reflected beams 60,62. Preferably, the predetermined amount of applanation is deemed to exist when all of the sensors 48,50 receive a respective one of the reflected beams 60,62.

Although the illustrated arrangement is generally effective using two primary beam emitters 44,46 and two light sensors 48,50, better accuracy can be achieved in patients with astigmatisms by providing four beam emitters and four light sensors arranged orthogonally with respect to one another about the longitudinal axis of the actuation apparatus 6. As in the case with two beam emitters 44,46 and light sensors 48,50, the predetermined amount of applanation is preferably deemed to exist when all of the sensors receive a respective one of the reflected beams.

A sighting arrangement is preferably provided for indicating when the actuation apparatus 6 and the detecting arrangement 8 are properly aligned with the device 2. Preferably, the sighting arrangement includes the central sight hole 38 in the movable central piece 16 through which a patient is able to see while the device 2 is located on the patient's cornea 4. The central sight hole 38 is aligned with the transparent area 22. In addition, the actuation apparatus 6 includes a tubular housing 64 having a first end 66 for placement over an eye equipped with the device 2 and a second opposite end 68 having at least one mark 70 arranged such that, when the patient looks through the central sight hole 38 at the mark 70, the device 2 is properly aligned with the actuation apparatus 6 and detecting arrangement 8.

Figure 3:
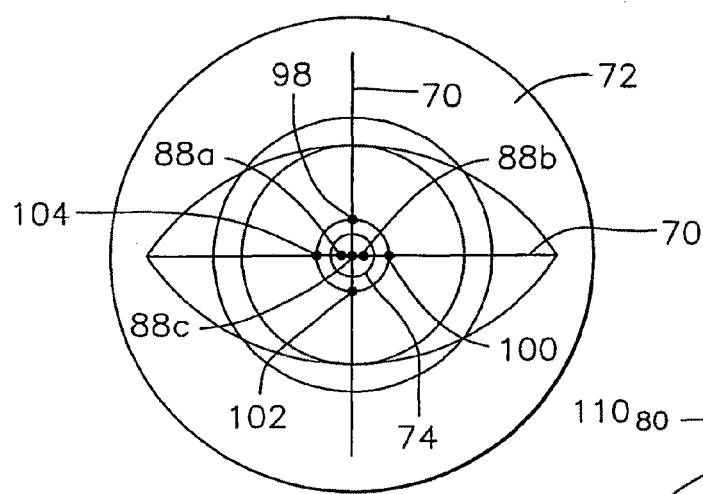
FIG. 3 schematically illustrates a view seen by a patient when utilizing the system illustrated in FIG. 1.

Preferably, the second end 68 includes an internal mirror surface 72 and the mark 70 generally comprises a set of cross-hairs. FIG. 3 illustrates the view seen by a patient through the central sight hole 38 when the device 2 is properly aligned with the actuation apparatus 6 and detecting arrangement 8. When proper alignment is achieved, the reflected image 74 of the central sight hole 38 appears in the mirror surface 72 at the intersection of the two cross-hairs which constitute the mark 70. (The size of the image 74 is exaggerated in FIG. 3 to more clearly distinguish it from other elements in the drawing).

Preferably, at least one light 75 is provided inside the tubular housing 64 to illuminate the inside of the housing 64 and facilitate visualization of the cross-hairs and the reflected image 74. Preferably, the internal mirror surface 72 acts as a mirror only when the light 75 is on, and becomes mostly transparent upon deactivation of the light 75 due to darkness inside the tubular housing 64. To that end, the second end 68 of the tubular housing 68 may be manufactured using "one-way glass" which is often found in security and surveillance equipment.

Alternatively, if the device is to be used primarily by physicians, optometrists, or the like, the second end 68 may be merely transparent. If, on the other hand, the device is to be used by patients for self-monitoring, it is understood that the second end 68 may merely include a mirror.

The system also preferably includes an optical distance measuring mechanism for indicating whether the device 2 is spaced at a proper axial distance from the actuation apparatus 6 and the detecting arrangement 8. The optical distance measurement mechanism is preferably used in conjunction with the sighting arrangement.

Preferably, the optical distance measuring mechanism includes a distance measurement beam emitter 76 for emitting an optical distance measurement beam 78 toward the device 2. The device 2 is capable of reflecting the distance measurement beam 78 to produce a first reflected distance measurement beam 80. Arranged in the path of the first reflected distance measurement beam 80 is a preferably convex mirror 82. The convex mirror 82 reflects the first reflected distance measurement beam 80 to create a second reflected distance measurement beam 84 and serves to amplify any variations in the first reflected beam's direction of propagation. The second reflected distance measurement beam 84 is directed generally toward a distance measurement beam detector 86. The distance measurement beam detector 86 is arranged so that the second reflected distance measurement beam 84 strikes a predetermined portion of the distance measurement beam detector 86 only when the device 2 is located at the proper axial distance from the actuation apparatus 6 and the detecting arrangement 8. When the proper axial distance is lacking, the second reflected distance measurement beam strikes another portion of the beam detector 86.

An indicator 88, such as an LCD or LED display, is preferably connected and responsive to the beam detector 86 for indicating that the proper axial distance has been achieved only when the reflected distance measurement beam strikes the predetermined portion of the distance measurement beam detector.

Preferably, as illustrated in FIG. 1, the distance measurement beam detector 86 includes a multi-filter optical element 90 arranged so as to receive the second reflected distance measurement beam 84. The multi-filter optical element 90 contains a plurality of optical filters 92. Each of the optical filters 92 filters out a different percentage of light, with the predetermined portion of the detector 86 being defined by a particular one of the optical filters 92 and a filtering percentage associated therewith.

The distance measurement beam detector 86 further includes a beam intensity detection sensor 94 for detecting the intensity of the second reflected distance measurement beam 84 after the beam 84 passes through the multi-filter optical element 90. Since the multi-filter optical element causes this intensity to vary with axial distance, the intensity is indicative of whether the device 2 is at the proper distance from the actuation apparatus 6 and the detecting arrangement 8.

A converging lens 96 is preferably located between the multi-filter optical element 90 and the beam intensity detection sensor 94, for focussing the second reflected distance measurement beam 84 on the beam intensity detection sensor 94 after the beam 84 passes through the multi-filter optical element 90.

Preferably, the indicator 88 is responsive to the beam intensity detection sensor 94 so as to indicate what corrective action should be taken, when the device 2 is not at the proper axial distance from the actuation apparatus 6 and the detecting arrangement 8, in order to achieve the proper distance. The indication given by the indicator 88 is based on the intensity and which of the plurality of optical filters 92 achieves the particular intensity by virtue of a filtering percentage associated therewith.

For example, when the device 2 is excessively far from the actuation apparatus 6, the second reflected distance measurement beam 84 passes through a dark one of the filters 92. There is consequently a reduction in beam intensity which causes the beam intensity detection sensor 94 to drive the indicator 88 with a signal indicative of the need to bring the device 2 closer to the actuation apparatus. The indicator 88 responds to this signal by communicating the need to a user of the system.

Alternatively, the signal indicative of the need to bring the device 2 closer to the actuation apparatus can be applied to a computer which performs corrections automatically.

In like manner, when the device 2 is excessively close to the actuation apparatus 6, the second reflected distance measurement beam 84 passes through a lighter one of the filters 92. There is consequently an increase in beam intensity which causes the beam intensity detection sensor 94 to drive the indicator 88 with a signal indicative of the need to move the device 2 farther from the actuation apparatus. The indicator 88 responds to this signal by communicating the need to a user of the system.

In addition, computer-controlled movement of the actuation apparatus farther away from the device 2 may be achieved automatically by providing an appropriate computer-controlled moving mechanism responsive to the signal indicative of the need to move the device 2 farther from the actuation apparatus.

With reference to FIG. 3, the indicator 88 preferably comprises three LEDs arranged in a horizontal line across the second end 68 of the housing 64. When illuminated, the left LED 88a, which is preferably yellow, indicates that the contact device 2 is too far from the actuation apparatus 6 and the detecting arrangement 8. Similarly, when illuminated, the right LED 88b, which is preferably red, indicates that the contact device 2 is too close to the actuation apparatus 6 and the detecting arrangement 8. When the proper distance is achieved, the central LED 88c is illuminated. Preferably, the central LED 88c is green. The LEDs 88a-88c are selectively illuminated by the beam intensity detection sensor 94 in response to the beam's intensity.

Although FIG. 1 illustrates an arrangement of filters 92 wherein a reduction in intensity signifies a need to move the device closer, it is understood that the present invention is not limited to such an arrangement. The multi-filter optical element 90, for example, may be reversed so that the darkest of the filters 92 is positioned adjacent the end 68 of the tubular housing 64. When such an arrangement is used, an increase in beam intensity would signify a need to move the device 2 farther away from the actuation apparatus 6.

Preferably, the actuation apparatus 6 (or at least the coil 30 thereof) is slidably mounted within the housing 64 and a knob and gearing (e.g., rack and pinion) mechanism are provided for selectively moving the actuation apparatus 6 (or coil 30 thereof) axially through the housing 64 in a perfectly linear manner until the appropriate axial distance from the contact device 2 is achieved. When such an arrangement is provided, the first end 66 of the housing 64 serves as a positioning mechanism for the contact device 2 against which the patient presses the facial area surrounding eye to be examined once the facial area rests against the first end 66, the knob and gearing mechanism are manipulated to place the actuation apparatus 6 (or coil 30 thereof) at the proper axial distance from the contact device 2.

Although facial contact with the first end 66 enhances stability, it is understood that facial contact is not an essential step in utilizing the present invention.

The system also preferably includes an optical alignment mechanism for indicating whether the device 2 is properly aligned with the actuation apparatus 6 and the detecting arrangement 8. The optical alignment mechanism includes two alignment beam detectors 48',50' for respectively detecting the reflected beams 60,62 of light prior to any applanation. The alignment beam detectors 48',50' are arranged so that the reflected beams 60,62 of light respectively strike a predetermined portion of the alignment beam detectors 48',50' prior to applanation only when the device 2 is properly aligned with respect to the actuation apparatus 6 and the detecting arrangement 8. When the device 2 is not properly aligned, the reflected beams 60,62 strike another portion of the alignment beam detectors 48',50', as will be described hereinafter.

The optical alignment mechanism further includes an indicator arrangement responsive to the alignment beam detectors 48',50'. The indicator arrangement preferably includes a set of LEDs 98,100,102,104 which indicate that the proper alignment has been achieved only when the reflected beams 60,62 of light respectively strike the predetermined portion of the alignment beam detectors 48',50' prior to applanation.

Figure 4:
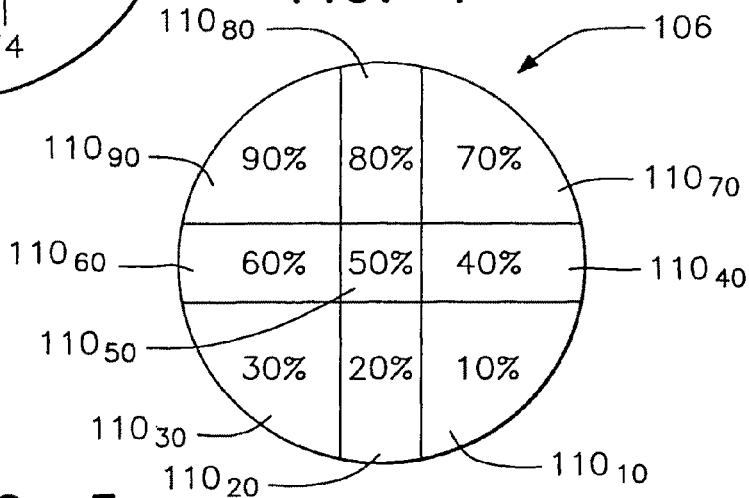
FIGS. 4 and 5 schematically depict multi-filter optical elements in accordance with a preferred embodiment of the present invention.
Figure 5:
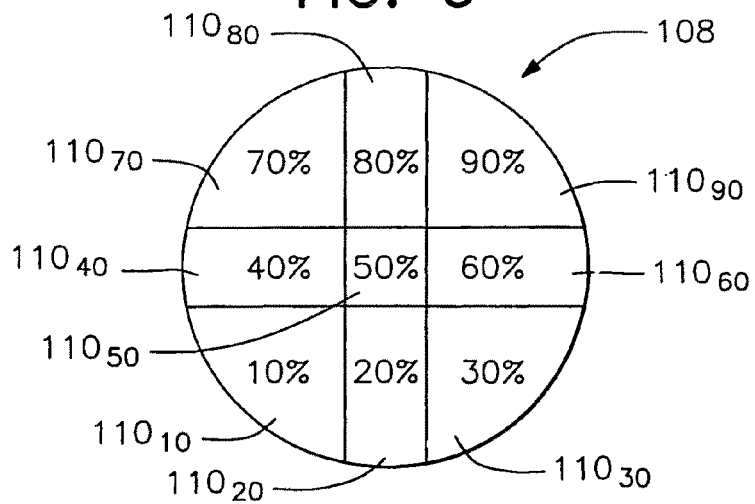
Figure 5A:
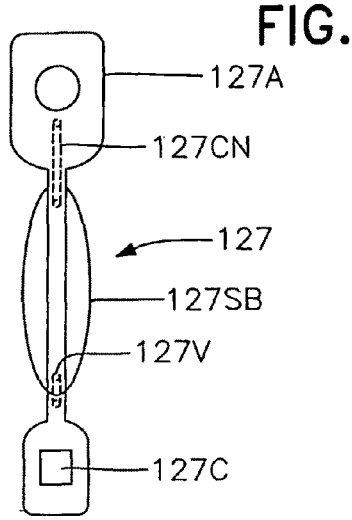
FIGS. 5A-5F illustrate a preferred embodiment of an applicator for gently applying the contact device to the cornea in accordance with the present invention.
Figure 5B:
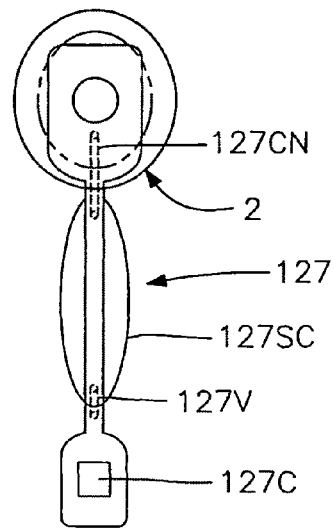
Figure 5C:
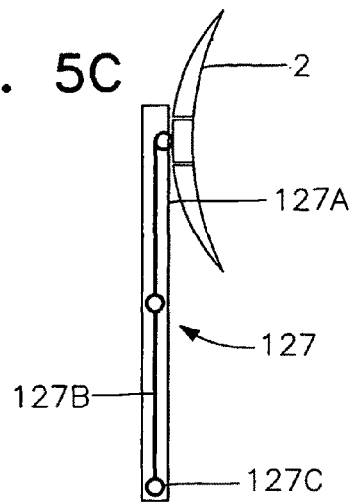
Figure 5D:
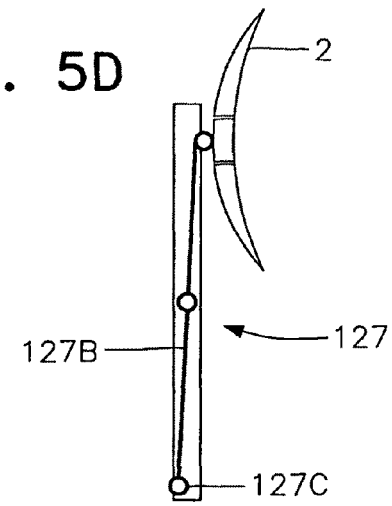
Figure 5E:
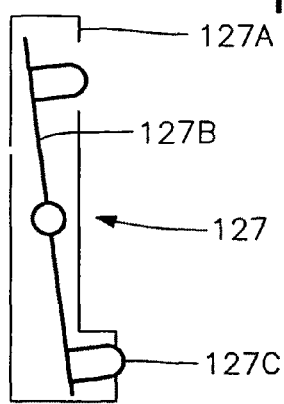
Figure 5F:
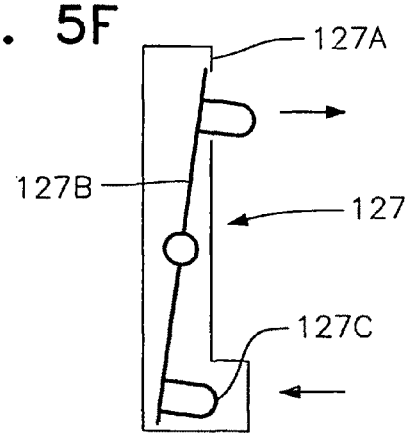

Preferably, each of the alignment beam detectors 48',50' includes a respective multi-filter optical element 106,108. The multi-filter optical elements 106,108 are arranged so as to receive the reflected beams 60,62 of light. Each multi-filter optical element 106,108 contains a plurality of optical filters $110_{10}$-$110_{90}$ (FIGS. 4 and 5), each of which filters out a different percentage of light. In FIGS. 4 and 5, the different percentages are labeled between 10 and 90 percent in increments of ten percent. It is understood, however, that many other arrangements and increments will suffice.

For the illustrated arrangement, it is preferred that the centrally located filters $110_{50}$ which filter out 50% of the light represent the predetermined portion of each alignment beam detector 48',50'. Proper alignment is therefore deemed to exist when the reflected beams 60,62 of light pass through the filters $110_{50}$ and the intensity of the beams 60,62 is reduced by 50%.

Each of the alignment beam detectors 48',50' also preferably includes a beam intensity detector 112,114 for respectively detecting the intensity of the reflected beams 60,62 of light after the reflected beams 60,62 of light pass through the multi-filter optical elements 106,108. The intensity of each beam is indicative of whether the device 2 is properly aligned with respect to the actuation apparatus 6 and the detecting arrangement.

A converging lens 116,118 is preferably located between each multi-filter optical element 106,108 and its respective beam intensity detector 112,114. The converging lens 116, 118 focuses the reflected beams 60,62 of light onto the beam intensity detectors 112,114 after the reflected beams 60,62 pass through the multi-filter optical elements 106,108.

Each of the beam intensity detectors 112,114 has its output connected to an alignment beam detection circuit which, based on the respective outputs from the beam intensity detectors 112,114, determines whether there is proper alignment, and if not, drives the appropriate one or ones of the LEDs 98,100,102,104 to indicate the corrective action which should be taken.

As illustrated in FIG. 3, the LEDs 98,100,102,104 are respectively arranged above, to the right of, below, and to the left of the intersection of the cross-hairs 70. No LEDs 98,100, 102,104 are illuminated unless there is a misalignment. Therefore, a lack of illumination indicates that the device 2 is properly aligned with the actuation apparatus 6 and the detecting arrangement 8.

When the device 2 on the cornea 4 is too high, the beams 56,58 of light strike a lower portion of the cornea 4 and because of the cornea's curvature, are reflected in a more downwardly direction. The reflected beams 60,62 therefore impinge on the lower half of the multi-filter elements 106, 108, and the intensity of each reflected beam 60,62 is reduced by no more than 30%. The respective intensity reductions are then communicated to the alignment detection circuit 120 by the beam intensity detectors 112,114. The alignment detection circuit 120 interprets this reduction of intensity to result from a misalignment wherein the device 2 is too high. The alignment detection circuit 120 therefore causes the upper LED 98 to illuminate. Such illumination indicates to the user that the device 2 is too high and must be lowered with respect to the actuation apparatus 6 and the detecting arrangement 8.

Similarly, when the device 2 on the cornea 4 is too low, the beams 56,58 of light strike an upper portion of the cornea 4 and because of the cornea's curvature, are reflected in a more upwardly direction. The reflected beams 60,62 therefore impinge on the upper half of the multi-filter elements 106, 108, and the intensity of each reflected beam 60,62 is reduced by at least 70%. The respective intensity reductions are then communicated to the alignment detection circuit 120 by the beam intensity detectors 112,114. The alignment detection circuit 120 interprets this particular reduction of intensity to result from a misalignment wherein the device 2 is too low. The alignment detection circuit 120 therefore causes the lower LED 102 to illuminate. Such illumination indicates to the user that the device 2 is too low and must be raised with respect to the actuation apparatus 6 and the detecting arrangement 8.

With reference to FIG. 1, when the device 2 is too far to the right, the beams 56,58 strike a more leftward side of the cornea 4 and because of the cornea's curvature, are reflected in a more leftward direction. The reflected beams 60,62 therefore impinge on the left halves of the multi-filter elements 106,108. Since the filtering percentages decrease from left to right in multi-filter element 106 and increase from left to right in multifilter element 108, there will be a difference in the intensities detected by the beam intensity detectors 112,114. In particular, the beam intensity detector 112 will detect less intensity than the beam intensity detector 114. The different intensities are then communicated to the alignment detection circuit 120 by the beam intensity detectors 112,114. The alignment detection circuit 120 interprets the intensity difference wherein the intensity at the beam intensity detector 114 is higher than that at the beam intensity detector 112, to result from a misalignment wherein the device 2 is too far to the right in FIG. 1 (too far to the left in FIG. 3). The alignment detection circuit 120 therefore causes the left LED 104 to illuminate. Such illumination indicates to the user that the device 2 is too far to the left (in FIG. 3) and must be moved to the right (left in FIG. 1) with respect to the actuation apparatus 6 and the detecting arrangement 8.

Similarly, when the device 2 in FIG. 1 is too far to the left, the beams 56,58 strike a more rightward side of the cornea 4 and because of the cornea's curvature, are reflected in a more rightwardly direction. The reflected beams 60,62 therefore impinge on the right halves of the multi-filter elements 106, 108. Since the filtering percentages decrease from left to right in multi-filter element 106 and increase from left to right in multifilter element 108, there will be a difference in the intensities detected by the beam intensity detectors 112,114. In particular, the beam intensity detector 112 will detect more intensity than the beam intensity detector 114. The different intensities are then communicated to the alignment detection circuit 120 by the beam intensity detectors 112,114. The alignment detection circuit 120 interprets the intensity difference wherein the intensity at the beam intensity detector 114 is lower than that at the beam intensity detector 112, to result from a misalignment wherein the device 2 is too far to the left in FIG. 1 (too far to the right in FIG. 3). The alignment detection circuit 120 therefore causes the right LED 100 to illuminate. Such illumination indicates to the user that the device 2 is too far to the right (in FIG. 3) and must be moved to the left (right in FIG. 1) with respect to the actuation apparatus 6 and the detecting arrangement 8.

The combination of LEDs 98,100,102,104 and the alignment detection circuit 120 therefore constitutes a display arrangement which is responsive to the beam intensity detectors 112,114 and which indicates what corrective action should be taken, when the device 2 is not properly aligned, in order to achieve proper alignment. Preferably, the substantially transparent peripheral portion 36 of the movable central piece 16 is wide enough to permit passage of the beams 56,58 to the cornea 4 even during misalignment.

It is understood that automatic alignment correction may be provided via computer-controlled movement of the actuation apparatus upwardly, downwardly, to the right, and/or to the left, which computer-controlled movement may be generated by an appropriate computer-controlled moving mechanism responsive to the optical alignment mechanism.

The optical alignment mechanism is preferably used in conjunction with the sighting arrangement, so that the optical alignment mechanism merely provides indications of minor alignment corrections while the sighting arrangement provides an indication of major alignment corrections. It is understood, however, that the optical alignment mechanism can be used in lieu of the sighting mechanism if the substantially transparent peripheral portion 36 is made wide enough.

Although the foregoing alignment mechanism uses the same reflected beams 60,62 used by the detecting arrangement 8, it is understood that separate alignment beam emitters may be used in order to provide separate and distinct alignment beams. The foregoing arrangement is preferred because it saves the need to provide additional emitters and thus is less expensive to manufacture.

Nevertheless, optional alignment beam emitters 122,124 are illustrated in FIG. 1. The alignment mechanism using these optional alignment beam emitters 122,124 would operate in essentially the same manner as its counterpart which uses the reflected beams 60,62.

In particular, each of the alignment beam emitters 122,124 emits an optical alignment beam toward the device 2. The alignment beam is reflected by the cornea 4 to produce a reflected alignment beam. The alignment beam detectors 48', 50' are arranged so as to receive, not the reflected beams 60,62 of light, but rather the reflected alignment beams when the alignment beam emitters 122,124 are present. More specifically, the reflected alignment beams strike a predetermined portion of each alignment beam detector 48',50' prior to applanation only when the device 2 is properly aligned with respect to the actuation apparatus 6 and the detecting arrangement 8. The rest of the system preferably includes the same components and operates in the same manner as the system which does not use the optional alignment beam emitters 122, 124.

The system may further include an applicator for gently placing the contact device 2 on the cornea 4. As illustrated in FIGS. 5A-5F, a preferred embodiment of the applicator 127 includes an annular piece 127A at the tip of the applicator 127. The annular piece 127A matches the shape of the movable central piece 16. Preferably, the applicator 127 also includes a conduit 127CN having an open end which opens toward the annular piece 127A. An opposite end of the conduit 127CN is connected to a squeeze bulb 127SB. The squeeze bulb 127SB includes a one-way valve 127V which permits the flow of air into the squeeze bulb 127SB, but prevents the flow of air out of the squeeze bulb 127SB through the valve 127V. When the squeeze bulb 127SB is squeezed and then released, a suction effect is created at the open end of the conduit 127CN as the squeeze bulb 127SB tries to expand to its pre-squeeze shape. This suction effect may be used to retain the contact device 2 at the tip of the applicator 127.

In addition, a pivoted lever system 127B is arranged to detach the movable central piece 16 from the annular piece 127A when a knob 127C at the base of the applicator 127 is pressed, thereby nudging the contact device 2 away from the annular piece 127A.

Alternatively, the tip of the applicator 127 may be selectively magnetized and demagnetized using electric current flowing through the annular piece 127A. This arrangement replaces the pivoted lever system 127B with a magnetization mechanism capable of providing a magnetic field which repels the movable central piece 16, thereby applying the contact device 2 to the cornea 4.

Figure 6:
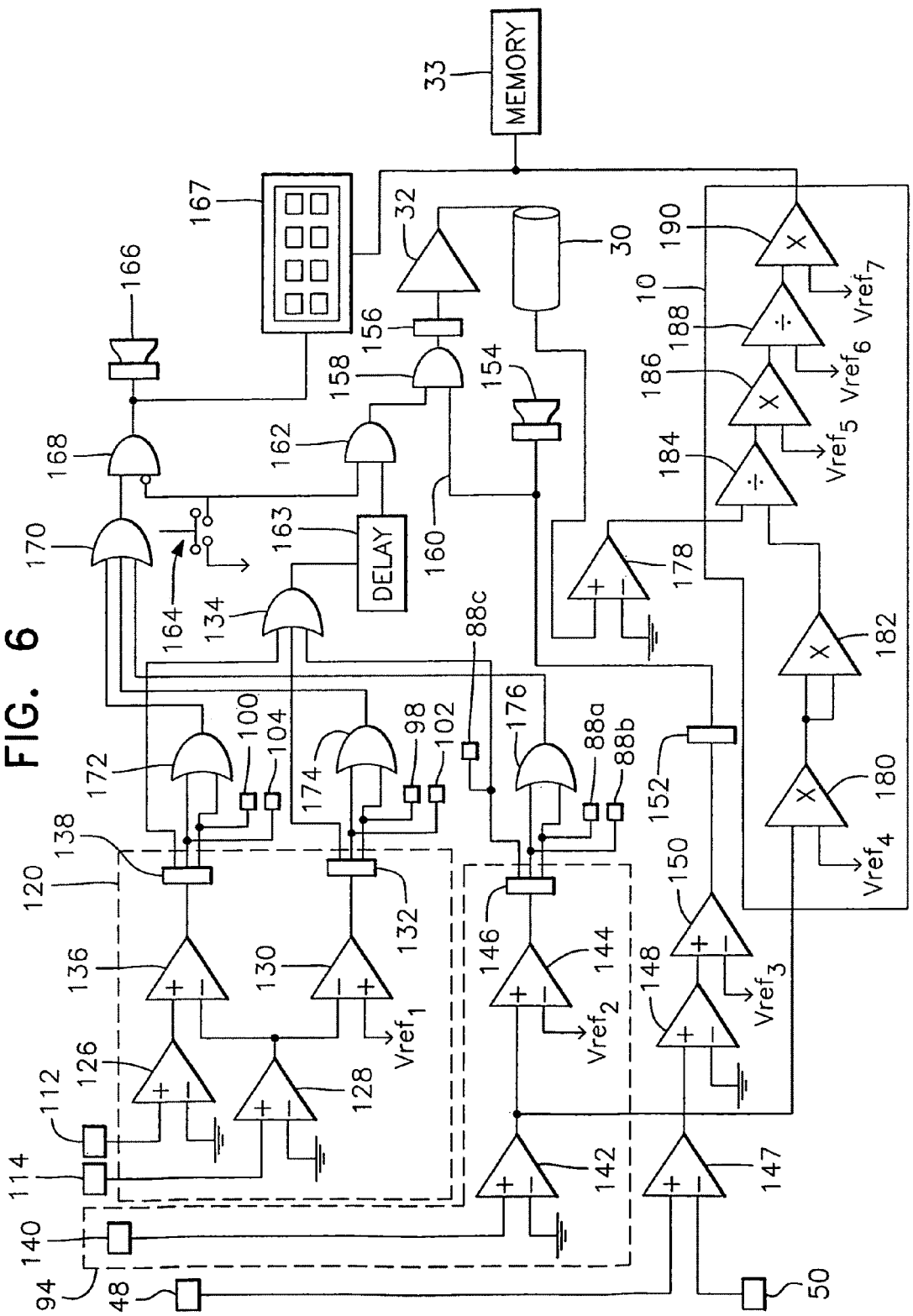
FIG. 6 illustrates an exemplary circuit for carrying out several aspects of the embodiment illustrated in FIG. 1.

A preferred circuit arrangement for implementing the above combination of elements is illustrated schematically in FIG. 6. According to the preferred circuit arrangement, the beam intensity detectors 112,114 comprise a pair of photosensors which provide a voltage output proportional to the detected beam intensity. The output from each beam intensity detector 112,114 is respectively connected to the non-inverting input terminal of a filtering amplifier 126,128. The inverting terminals of the filtering amplifiers 126,128 are connected to ground. The amplifiers 126,128 therefore provide a filtering and amplification effect.

In order to determine whether proper vertical alignment exists, the output from the filtering amplifier 128 is applied to an inverting input terminal of a vertical alignment comparator 130. The vertical alignment comparator 130 has its non-inverting input terminal connected to a reference voltage $Vref_1$. The reference voltage $Vref_1$ is selected so that it approximates the output from the filtering amplifier 128 whenever the light beam 62 strikes the central row of filters $110_{40\text{-}60}$ of the multi-filter optical element 108 (i.e., when the proper vertical alignment is achieved).

Consequently, the output from the comparator 130 is approximately zero when proper vertical alignment is achieved, is significantly negative when the contact device 2 is too high, and is significantly positive when the contact device 2 is too low. This output from the comparator 130 is then applied to a vertical alignment switch 132. The vertical alignment switch 132 is logically arranged to provide a positive voltage to an AND-gate 134 only when the output from the comparator 130 is approximately zero, to provide a positive voltage to the LED 98 only when the output from the comparator 130 is negative, and to provide a positive voltage to the LED 102 only when the output from the comparator 130 is positive. The LEDs 98,102 are thereby illuminated only when there is a vertical misalignment and each illumination clearly indicates what corrective action should to be taken.

In order to determine whether proper horizontal alignment exists, the output from the filtering amplifier 126 is applied to a non-inverting input terminal of a horizontal alignment comparator 136, while the inverting input terminal of the horizontal alignment comparator 136 is connected to the output from the filtering amplifier 128. The comparator 136 therefore produces an output which is proportional to the difference between the intensities detected by the beam intensity detectors 112,114. This difference is zero whenever the light beams 60,62 strike the central column of filters $110_{20}$, $110_{50}$, $110_{80}$ of the multi-filter optical elements 106,108 (i.e., when the proper horizontal alignment is achieved).

The output from the comparator 136 is therefore zero when the proper horizontal alignment is achieved, is negative when the contact device 2 is too far to the right (in FIG. 1), and is positive when the contact device 2 is too far to the left (in FIG. 1). This output from the comparator 130 is then applied to a horizontal alignment switch 138. The horizontal alignment switch 138 is logically arranged to provide a positive voltage to the AND-gate 134 only when the output from the comparator 136 is zero, to provide a positive voltage to the LED 104 only when the output from the comparator 136 is negative, and to provide a positive voltage to the LED 100 only when the output from the comparator 136 is positive. The LEDs 100, 104 are thereby illuminated only when there is a horizontal misalignment and each illumination clearly indicates what corrective action should be taken.

In accordance with the preferred circuit arrangement illustrated in FIG. 6, the beam intensity detection sensor 94 of the distance measurement beam detector 86 includes a photosensor 140 which produces a voltage output proportional to the detected beam intensity. This voltage output is applied to the non-inverting input terminal of a filtering amplifier 142. The inverting terminal of the filtering amplifier 142 is connected to ground. Accordingly, the filtering amplifier 142 filters and amplifies the voltage output from the photosensor 140. The output from the filtering amplifier 142 is applied to the non-inverting input terminal of a distance measurement comparator 144. The comparator 144 has its inverting terminal connected to a reference voltage $V_{ref_2}$. Preferably, the reference voltage $V_{ref_2}$ is selected so as to equal the output of the filtering amplifier 142 only when the proper axial distance separates the contact device 2 from the actuation apparatus 6 and detecting arrangement 8.

Consequently, the output from the comparator 144 is zero whenever the proper axial distance is achieved, is negative whenever the second reflected beam 84 passes through a dark portion of the multi-filter optical element 90 (i.e., whenever the axial distance is too great), and is positive whenever the second reflected beam 84 passes through a light portion of the multifilter optical element 90 (i.e., whenever the axial distance is too short).

The output from the comparator 144 is then applied to a distance measurement switch 146. The distance measurement switch 146 drives the LED 88c with positive voltage whenever the output from the comparator 144 is zero, drives the LED 88b only when the output from the comparator 144 is positive, and drives the LED 88a only when the output from the comparator 144 is negative. The LEDs 88a,88b are thereby illuminated only when the axial distance separating the contact device 2 from the actuation apparatus 6 and the detecting arrangement 8 is improper. Each illumination clearly indicates what corrective action should be taken. Of course, when the LED 88c is illuminated, no corrective action is necessary.

With regard to the detecting arrangement 8, the preferred circuit arrangement illustrated in FIG. 6 includes the two light sensors 48,50. The outputs from the light sensors 48,50 are applied to and added by an adder 147. The output from the adder 147 is then applied to the non-inverting input terminal of a filtering amplifier 148. The inverting input terminal of the same amplifier 148 is connected to ground. As a result, the filtering amplifier 148 filters and amplifies the sum of the output voltages from the light sensor 48,50. The output from the filtering amplifier 148 is then applied to the non-inverting input terminal of an applanation comparator 150. The inverting input terminal of the applanation comparator 150 is connected to a reference voltage $V_{ref_3}$. Preferably, the reference voltage $V_{ref_3}$ is selected so as to equal the output from the filtering amplifier 148 only when the predetermined amount of applanation is achieved (i.e., when the reflected beams 60,62 strike the light sensors 48,50). The output from the applanation comparator 150 therefore remains negative until the predetermined amount of applanation is achieved.

The output from the applanation comparator 150 is connected to an applanation switch 152. The applanation switch 152 provides a positive output voltage when the output from the applanation comparator 150 is negative and terminates its positive output voltage whenever the output from the applanation comparator 150 becomes positive.

Preferably, the output from the applanation switch 152 is connected to an applanation speaker 154 which audibly indicates when the predetermined amount of applanation has been achieved. In particular, the speaker 154 is activated whenever the positive output voltage from the applanation, switch 152 initially disappears.

In the preferred circuit of FIG. 6, the coil 30 is electrically connected to the current producing circuitry 32 which, in turn, includes a signal generator capable of producing the progressively increasing current in the coil 30. The current producing circuitry 32 is controlled by a start/stop switch 156 which is selectively activated and deactivated by an AND-gate 158.

The AND-gate 158 has two inputs, both of which must exhibit positive voltages in order to activate the start/stop switch 156 and current producing circuitry 32. A first input 160 of the two inputs is the output from the applanation switch 152. Since the applanation switch 152 normally has a positive output voltage, the first input 160 remains positive and the AND-gate is enabled at least with respect to the first input 160. However, whenever the predetermined amount of applanation is achieved (i.e. whenever the positive output voltage is no longer present at the output from the applanation switch 152), the AND-gate 158 deactivates the current producing circuitry 32 via the start/stop switch 156.

The second input to the AND-gate 158 is the output from another AND-gate 162. The other AND-gate 162 provides a positive output voltage only when a push-action switch 164 is pressed and only when the contact device 2 is located at the proper axial distance from, and is properly aligned both vertically and horizontally with, the actuation apparatus 6 and the detecting arrangement 8. The current producing circuitry 32 therefore cannot be activated unless there is proper alignment and the proper axial distance has been achieved. In order to achieve such operation, the output from the AND-gate 134 is connected to a first input of the AND-gate 162 and the push-action switch 164 is connected to the second input of the AND-gate 162.

A delay element 163 is located electrically between the AND-gate 134 and the AND-gate 162. The delay element 163 maintains a positive voltage at the first input terminal to the AND-gate 162 for a predetermined period of time after a positive voltage first appears at the output terminal of the AND-gate 134. The primary purpose of the delay element 163 is to prevent deactivation of the current producing circuitry 32 which would otherwise occur in response to changes in the propagation direction of the reflected beams 60,62 during the initial stages of applanation. The predetermined period of time is preferably selected pursuant to the maximum amount of time that it could take to achieve the predetermined amount of applanation.

According to the preferred circuitry illustrated in FIG. 6, misalignment and improper axial separation of the contact device 2 with respect to the actuation apparatus 6 and detecting arrangement 8 is audibly announced by a speaker 166 and causes deactivation of a display 167. The display 167 and speaker 166 are connected and responsive to an AND-gate 168. The AND-gate 168 has an inverting input connected to the push-action switch 164 and another input connected to a three-input OR-gate 170.

Therefore, when the push-action switch 164 is activated, the inverting input terminal of the AND-gate 168 prevents a positive voltage from appearing at the output from the AND-gate 168. Activation of the speaker 166 is thereby precluded. However, when the push-action switch is not activated, any positive voltage at any of the three inputs to the OR-gate 170 will activate the speaker 166. The three inputs to the OR-gate 170 are respectively connected to outputs from three other OR-gates 172,174,176. The OR-gates 172,174,176, in turn, have their inputs respectively connected to the LEDs 100, 104, LEDs 98,102, and LEDs 88a,88b. Therefore, whenever any one of these LEDs 88a, 88b, 98, 100, 102, 104 is activated, the OR-gate 170 produces a positive output voltage. The speaker 166, as a result, will be activated whenever any one of the LEDs 88a,88b,98,100,102,104 is activated while the push-action switch 164 remains deactivated.

Turning now to the current producing circuitry 32, the output from the current producing circuitry 32 is connected to the coil 30. The coil 30, in turn, is connected to a current-to-voltage transducer 178. The output voltage from the current-to-voltage transducer 178 is proportional to the current flowing through the coil 30 and is applied to the calculation unit 10.

The calculation unit 10 receives the output voltage from the transducer 178 and converts this output voltage indicative of current to an output voltage indicative of intraocular pressure. Initially, an output voltage from the filtering amplifier 142 indicative of the axial distance separating the contact device 2 from the actuation apparatus 6 and the detecting arrangement 8, is multiplied by a reference voltage $Vref_4$ using a multiplier 180. The reference voltage $Vref_4$ represents a distance calibration constant. The output from the multiplier 180 is then squared by a multiplier 182 to create an output voltage indicative of distance squared ($d^2$).

The output from the multiplier 182 is then supplied to an input terminal of a divider 184. The other input terminal of the divider 184 receives the output voltage indicative of current from the current-to-voltage transducer 178. The divider 184 therefore produces an output voltage indicative of the current in the coil 30 divided by the distance squared ($I/d^2$).

The output voltage from the divider 184 is applied to a multiplier 186. The multiplier 186 multiplies the output voltage from the divider 184 by a reference voltage $Vref_5$. The reference voltage $Vref_5$ corresponds to a conversion factor for converting the value of ($I/d^2$) to a value indicative of force in Newtons being applied by the movable central piece 16 against the cornea 4. The output voltage from the multiplier 186 is therefore indicative of the force in Newtons being applied by the movable central piece 16 against the cornea.

Next, the output voltage from the multiplier 186 is applied to an input terminal of a divider 188. The other input terminal of the divider 188 receives a reference voltage $Vref_6$. The reference voltage $Vref_6$ corresponds to a calibration constant for converting force (in Newtons) to pressure (in Pascals) depending on the surface area of the movable central piece's substantially flat inner side 24. The output voltage from the divider 188 is therefore indicative of the pressure (in Pascals) being exerted by the cornea 4 against the inner side of the movable central piece 16 in response to displacement of the movable central piece 16.

Since the pressure exerted by the cornea 4 depends upon the surface area of the substantially flat inner side 24, the output voltage from the divider 188 is indicative of intraocular pressure only when the cornea 4 is being applanated by the entire surface area of the inner side 24. This, in turn, corresponds to the predetermined amount of applanation.

Preferably, the output voltage indicative of intraocular pressure is applied to an input terminal of a multiplier 190. The multiplier 190 has another input terminal connected to a reference voltage $Vref_7$. The reference voltage $Vref_7$ corresponds to a conversion factor for converting pressure in Pascals to pressure in millimeters of mercury (mmHg). The voltage output from the multiplier 190 therefore is indicative of intraocular pressure in millimeters of mercury (mmHg) whenever the predetermined amount of applanation is achieved.

The output voltage from the multiplier 190 is then applied to the display 167 which provides a visual display of intraocular pressure based on this output voltage. Preferably, the display 167 or calculation unit 10 includes a memory device 33 which stores a pressure value associated with the output voltage from the multiplier 190 whenever the predetermined amount of applanation is achieved. Since the current producing circuitry 32 is automatically and immediately deactivated upon achieving the predetermined amount of applanation, the intraocular pressure corresponds to the pressure value associated with the peak output voltage from the multiplier 190. The memory therefore can be triggered to store the highest pressure value upon detecting a drop in the output voltage from the multiplier 190. Preferably, the memory is automatically reset prior to any subsequent measurements of intraocular pressure.

Although FIG. 6 shows the display 167 in digital form, it is understood that the display 167 may have any known form. The display 167 may also include the three LEDs 40A,40B, 40C illustrated in FIG. 1 which give a visual indication of pressure ranges which, in turn, are calibrated for each patient.

As indicated above, the illustrated calculation unit 10 includes separate and distinct multipliers 180,182,186,190 and dividers 184,188 for converting the output voltage indicative of current into an output voltage indicative of intraocular pressure in millimeters of mercury (mmHg). The separate and distinct multipliers and dividers are preferably provided so that variations in the system's characteristics can be compensated for by appropriately changing the reference voltages $Vref_4$, $Vref_5$, $Vref_6$ and/or $Vref_7$. It is understood, however, that when all of the system's characteristics remain the same (e.g., the surface area of the inner side 24 and the desired distance separating the contact device 2 from the actuation apparatus 6 and detecting arrangement 8) and the conversion factors do not change, that a single conversion factor derived from the combination of each of the other conversion factors can be used along with a single multiplier or divider to achieve the results provided by the various multipliers and dividers shown in FIG. 6.

Although the above combination of elements is generally effective at accurately measuring intraocular pressure in a substantial majority of patients, some patients have unusually thin or unusually thick corneas. This, in turn, may cause slight deviations in the measured intraocular pressure. In order to compensate for such deviations, the circuitry of FIG. 6 may also include a variable gain amplifier 191 (illustrated in FIG. 7A) connected to the output from the multiplier 190. For the majority of patients, the variable gain amplifier 191 is adjusted to provide a gain (g) of one. The variable gain amplifier 191 therefore would have essentially no effect on the output from the multiplier 190.

However, for patients with unusually thick corneas, the gain (g) is adjusted to a positive gain less than one. A gain (g) of less than one is used because unusually thick corneas are more resistant to applanation and consequently result in a pressure indication that exceeds, albeit by a small amount, the actual intraocular pressure. The adjustable gain amplifier 191 therefore reduces the output voltage from the multiplier 190 by a selected percentage proportional to the cornea's deviation from normal corneal thickness.

For patients with unusually thin corneas, the opposite effect would be observed. Accordingly, for those patients, the gain (g) is adjusted to a positive gain greater than one so that the adjustable gain amplifier 191 increases the output voltage from the multiplier 190 by a selected percentage proportional to the cornea's deviation from normal corneal thickness.

Preferably, the gain (g) is manually selected for each patient using any known means for controlling the gain of a variable gain amplifier, for example, a potentiometer connected to a voltage source. As indicated above, the particular gain (g) used depends on the thickness of each patient's cornea which, in turn, can be determined using known corneal pachymetry techniques. Once the corneal thickness is determined, the deviation from the normal thickness is calculated and the gain (g) is set accordingly.

Figure 7A:
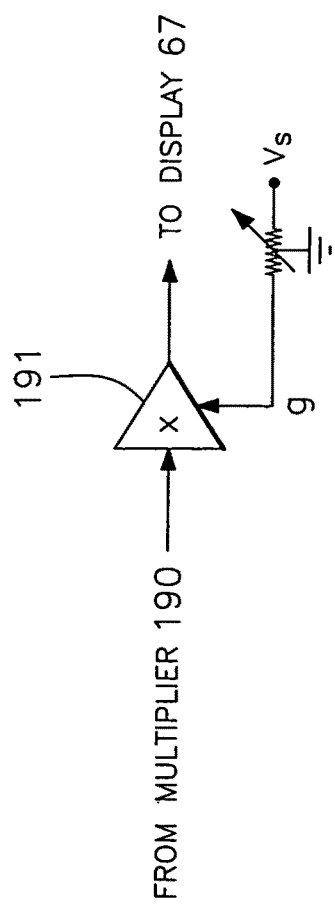
FIGS. 7A and 7B are block diagrams illustrating an arrangement capable compensating for deviations in corneal thickness according to the present invention.
Figure 7B:
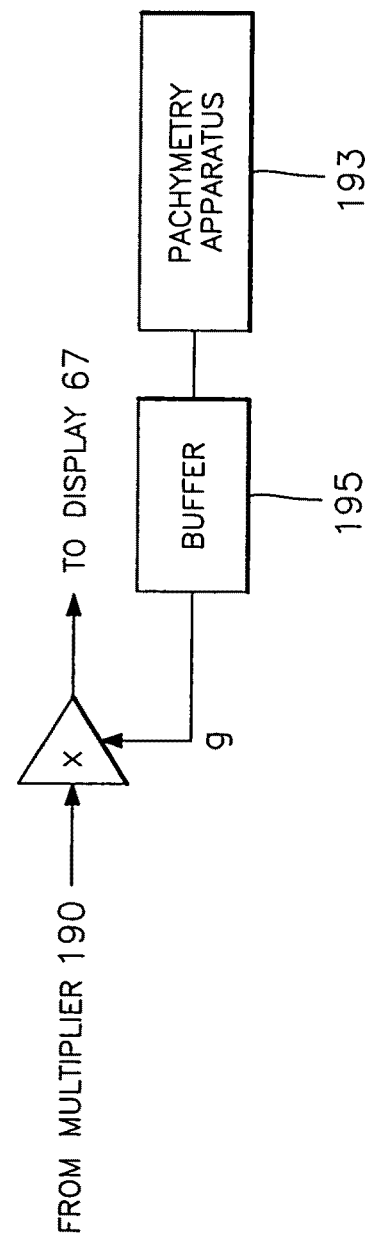

Alternatively, as illustrated in FIG. 7B, the gain (g) may be selected automatically by connecting an output (indicative of corneal thickness) from a known pachymetry apparatus 193 to a buffer circuit 195. The buffer circuit 195 converts the detected corneal thickness to a gain signal associated with the detected thickness' deviation from the normal corneal thickness. In particular, the gain signal produces a gain (g) of one when the deviation is zero, produces a gain (g) greater than one when the detected corneal thickness is less than the normal thickness, and produces a gain (g) less than one when the detected corneal thickness is greater than the normal thickness.

Although FIGS. 7A and 7B illustrate a configuration which compensates only for corneal thickness, it is understood that similar configurations can be used to compensate for corneal curvature, eye size, ocular rigidity, and the like. For levels of corneal curvature which are higher than normal, the gain would be less than one. The gain would be greater than one for levels of corneal curvature which are flatter than normal. Typically, each increase in one diopter of corneal curvature is associated with a 0.34 mm Hg increase in pressure. The intraocular pressure rises 1 mm Hg for very 3 diopters. The gain therefore can be applied in accordance with this general relationship.

In the case of eye size compensation, larger than normal eyes would require a gain which is less than one, while smaller than normal eyes would require a gain which is greater than one.

For patients with "stiffer" than normal ocular rigidities, the gain is less than one, but for patients with softer ocular rigidities, the gain is greater than one.

As when compensating for corneal thickness, the gain may be manually selected for each patient, or alternatively, the gain may be selected automatically by connecting the apparatus of the present invention to a known keratometer when compensating for corneal curvature, and/or a known biometer when compensating for eye size.

Despite not being illustrated, it is understood that the system includes a power supply mechanism for selectively powering the system using either batteries or household AC current.

Operation of the preferred circuitry will now be described. Initially, the contact device 2 is mounted on the corneal surface of a patient and tends to locate itself centrally at the front of the cornea 4 in essentially the same way as conventional contact lenses. The patient then looks through the central sight hole 38 at the intersection of the cross-hairs which define the mark 70, preferably, while the light 75 provided inside the tubular housing 64 is illuminated to facilitate visualization of the cross-hairs and the reflected image 74. A rough alignment is thereby achieved.

Next, the preferred circuitry provides indications of misalignment or improper axial distance should either or both exist. The patient responds to such indications by taking the indicated corrective action.

Once proper alignment is achieved and the proper axial distance exists between the actuation apparatus 6 and the contact device 2, push-action switch 164 is activated and the AND-gate 158 and start/stop switch 156 activate the current producing circuitry 32. In response to activation, the current producing circuitry 32 generates the progressively increasing current in the coil 30. The progressively increasing current creates a progressively increasing magnetic field in the coil 30. The progressively increasing magnetic field, in turn, causes axial displacement of the movable central piece 16 toward the cornea 4 by virtue of the magnetic field's repulsive effect on the magnetically responsive element 26. Since axial displacement of the movable central piece 16 produces a progressively increasing applanation of the cornea 4, the reflected beams 60,62 begin to swing angularly toward the light sensors 48,50. Such axial displacement and increasing applanation continues until both reflected beams 60,62 reach the light sensors 48,50 and the predetermined amount of applanation is thereby deemed to exist. At that instant, the current producing circuit 32 is deactivated by the input 160 to AND-gate 158; the speaker 154 is momentarily activated to give an audible indication that applanation has been achieved; and the intraocular pressure is stored in the memory device 33 and is displayed on display 167.

Although the above-described and illustrated embodiment includes various preferred elements, it is understood that the present invention may be achieved using various other individual elements. For example, the detecting arrangement 8 may utilize various other elements, including elements which are typically utilized in the art of barcode reading.

Figure 8A:
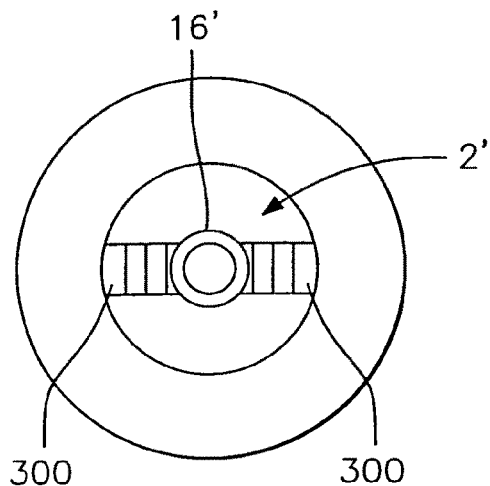
FIGS. 8A and 8B schematically illustrate a contact device utilizing barcode technology in accordance with a preferred embodiment of the present invention.
Figure 8B:
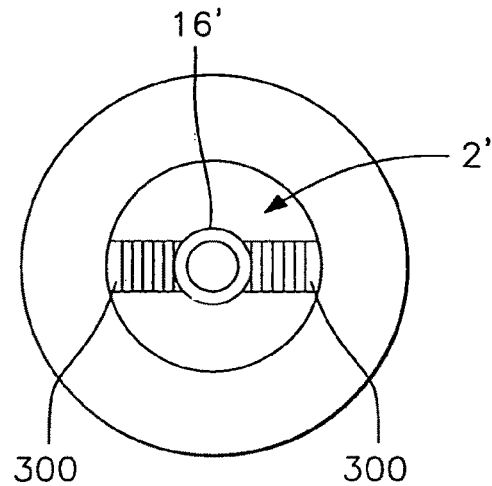

With reference to FIGS. 8A and 8B, a contact device 2' may be provided with a barcode-like pattern 300 which varies in response to displacement of the movable central piece 16'. FIG. 8A illustrates the preferred pattern 300 prior to displacement of the movable central piece 16'; and FIG. 8B shows the preferred pattern 300 when the predetermined amount of applanation is achieved. The detecting arrangement therefore would include a barcode reader directed generally toward the contact device 2' and capable of detecting the differences in the barcode pattern 300.

Figure 9A:
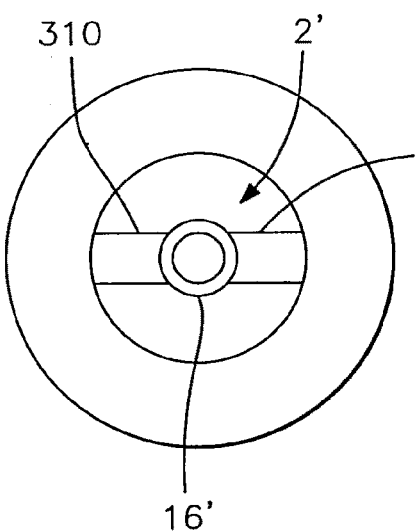
FIGS. 9A and 9B schematically illustrate a contact device utilizing color detection technology in accordance with a preferred embodiment of the present invention.
Figure 9B:
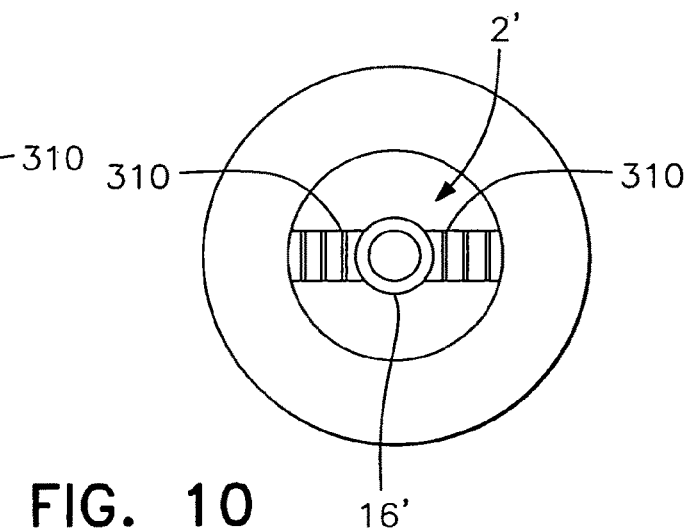

Alternatively, as illustrated in FIGS. 9A and 9E, the contact device 2' may be provided with a multi-color pattern 310 which varies in response to displacement of the movable central piece 16'. FIG. 9A schematically illustrates the preferred color pattern 310 prior to displacement of the movable central piece 16', while FIG. 9B schematically shows the preferred pattern 310 when the predetermined amount of applanation is achieved. The detecting arrangement therefore would include a beam emitter for emitting a beam of light toward the pattern 310 and a detector which receives a reflected beam from the pattern 310 and detects the reflected color to determine whether applanation has been achieved.

Yet another way to detect the displacement of the movable central piece 16 is by using a two dimensional array photosensor that senses the location of a reflected beam of light. Capacitive and electrostatic sensors, as well as changes in magnetic field can then be used to encode the position of the reflected beam and thus the displacement of the movable central piece 16.

Figure 10:
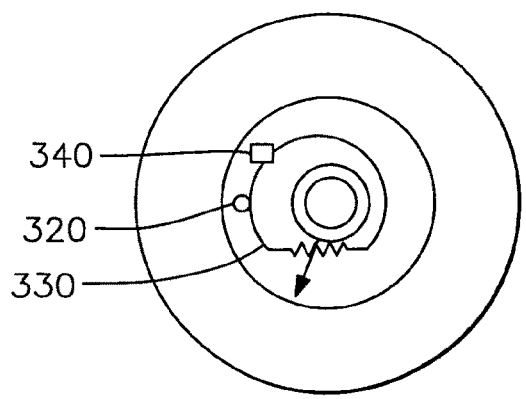
FIG. 10 illustrates an alternative contact device in accordance with yet another preferred embodiment of the present invention.

According to yet another alternative embodiment illustrated in FIG. 10, a miniature LED 320 is inserted into the contact device 2'. The piezoelectric ceramic is driven by ultrasonic waves or is alternatively powered by electromagnetic waves. The brightness of the miniature LED 320 is determined by the current flowing through the miniature LED 320 which, in turn, may be modulated by a variable resistance 330. The motion of the movable central piece 16' varies the variable resistance 330. Accordingly, the intensity of light from the miniature LED 320 indicates the magnitude of the movable central piece's displacement. A miniature, low-voltage primary battery 340 may be inserted into the contact device 2' for powering the miniature LED 320.

With regard to yet another preferred embodiment of the present invention, it is understood that a tear film typically covers the eye and that a surface tension resulting therefrom may cause underestimation of the intraocular pressure. Accordingly, the contact device of the present invention preferably has an inner surface of hydrophobic flexible material in order to decrease or eliminate this potential source of error.

It should be noted that the drawings are merely schematic representations of the preferred embodiments. Therefore, the actual dimensions of the preferred embodiments and physical arrangement of the various elements is not limited to that which is illustrated. Various arrangements and dimensions will become readily apparent to those of ordinary skill in the art. The size of the movable central piece, for example, can be modified for use in animals or experimental techniques. Likewise, the contact device can be made with smaller dimensions for use with infants and patients with eye lid abnormalities.

One preferred arrangement of the present invention includes a handle portion extending out from below the housing 64 and connected distally to a platform. The platform acts as a base for placement on a planar surface (e.g., a table), with the handle projecting up therefrom to support the actuation apparatus 6 above the planar surface.

Indentation

The contact device 2 and associated system illustrated in FIGS. 1-5 may also be used to detect intraocular pressure by indentation. When indentation techniques are used in measuring intraocular pressure, a predetermined force is applied against the cornea using an indentation device. Because of the force, the indentation device travels in toward the cornea, indenting the cornea as it travels. The distance traveled by the indentation device into the cornea in response to the predetermined force is known to be inversely proportional to intraocular pressure. Accordingly, there are various known tables which, for certain standard sizes of indentation devices and standard forces, correlate the distance traveled and intraocular pressure.

In utilizing the illustrated arrangement for indentation, the movable central piece 16 of the contact device 2 functions as the indentation device. In addition, the current producing circuit 32 is switched to operate in an indentation mode. When switched to the indentation mode, the current producing circuit 32 supplies a predetermined amount of current through the coil 30. The predetermined amount of current corresponds to the amount of current needed to produce one of the aforementioned standard forces.

The predetermined amount of current creates a magnetic field in the actuation apparatus 6. This magnetic field, in turn, causes the movable central piece 16 to push inwardly against the cornea 4 via the flexible membrane 14. Once the predetermined amount of current has been applied and a standard force presses against the cornea, it is necessary to determine how far the movable central piece 16 moved into the cornea 4.

Accordingly, when measurement of intraocular pressure by indentation is desired, the system illustrated in FIG. 1 further includes a distance detection arrangement for detecting a distance traveled by the movable central piece 16, and a computation portion 199 in the calculation unit 10 for determining intraocular pressure based on the distance traveled by the movable central piece 16 in applying the predetermined amount of force.

Figure 11A:
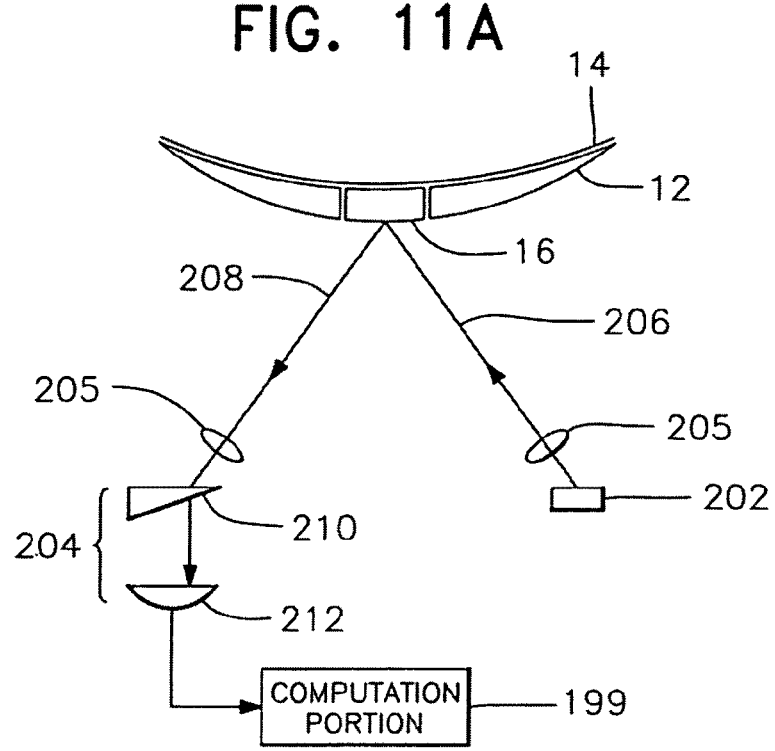
FIGS. 11A and 11B schematically illustrate an indentation distance detection arrangement in accordance with a preferred embodiment of the present invention.
Figure 11B:
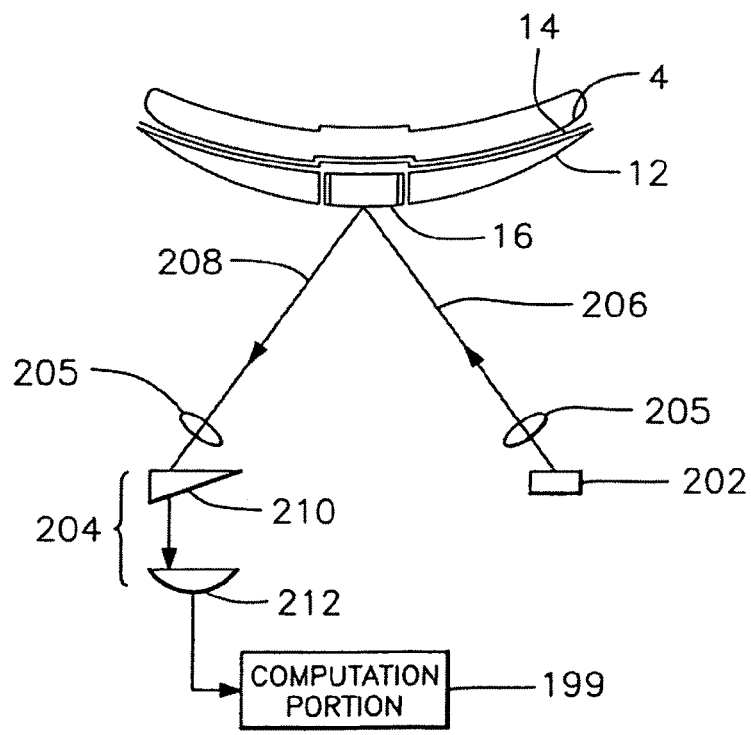

A preferred indentation distance detection arrangement 200 is illustrated in FIGS. 11A and 11B and preferably includes a beam emitter 202 and a beam sensor 204. Preferably, lenses 205 are disposed in the optical path between the beam emitter 202 and beam sensor 204. The beam emitter 202 is arranged so as to emit a beam 206 of light toward the movable central piece 16. The beam 206 of light is reflected back from the movable central piece 16 to create a reflected beam 208. The beam sensor 204 is positioned so as to receive the reflected beam 208 whenever the device 2 is located at the proper axial distance and in proper alignment with the actuation apparatus 6. Preferably, the proper distance and alignment are achieved using all or any combination of the aforementioned sighting mechanism, optical alignment mechanism and optical distance measuring mechanism.

Once proper alignment and the proper axial distance are achieved, the beam 206 strikes a first portion of the movable central piece 16, as illustrated in FIG. 11A. Upon reflection of the beam 206, the reflected beam 208 strikes a first portion of the beam sensor 204. In FIG. 11A, the first portion is located on the beam sensor 204 toward the right side of the drawing.

However, as indentation progresses, the movable central piece 16 becomes more distant from the beam emitter 202. This increase in distance is illustrated in FIG. 11A. Since the movable central piece 16 moves linearly away, the beam 206 strikes progressively more to the left on the movable central piece 16. The reflected beam 206 therefore shifts toward the left and strikes 204 at a second portion which is to the left of the first portion.

The beam sensor 204 is arranged so as to detect the shift in the reflected beam 206, which shift is proportional to the displacement of the movable central piece 16. Preferably, the beam sensor 204 includes an intensity responsive beam detector 212 which produces an output voltage proportional to the detected intensity of the reflected beam 208 and an optical filter element 210 which progressively filters more light as the light's point of incidence moves from one portion of the filter to an opposite portion.

In FIGS. 11A and 11B, the optical filter element 210 comprises a filter with a progressively increasing thickness so that light passing through a thicker portion has a more significantly reduced intensity than light passing through a thinner portion of the filter. Alternatively, the filter can have a constant thickness and progressively increasing filtering density whereby a progressively increasing filtering effect is achieved as the point of incidence moves across a longitudinal length of the filter.

When, as illustrated in FIG. 11A, the reflected beam 208 passes through a thinnest portion of the optical filter element 210 (e.g., prior to indentation), the reflected beam's intensity is reduced by only a small amount. The intensity responsive beam detector 212 therefore provides a relatively high output voltage indicating that no movement of the movable central piece 16 toward the cornea 4 has occurred.

However, as indentation progresses, the reflected beam 208 progressively shifts toward thicker portions of the optical filter element 210 which filter more light. The intensity of the reflected beam 208 therefore decreases proportionally to the displacement of the movable central piece 16 toward the cornea 4. Since the intensity responsive beam detector 212 produces an output voltage proportional to the reflected beam's intensity, this output voltage decreases progressively as the displacement of the movable central piece 16 increases. The output voltage from the intensity responsive beam detector 212 is therefore indicative of the movable central piece's displacement.

Preferably, the computation portion 199 is responsive to the current producing circuitry 32 so that, once the predetermined amount of force is applied, the output voltage from the beam detectors 212 is received by the computation portion 199. The computation portion then, based on the displacement associated with the particular output voltage, determines intraocular pressure. Preferably, the memory 33 includes, a memory location for storing a value indicative of the intraocular pressure.

Also, the computation portion 199 preferably has access to an electronically or magnetically stored one of the aforementioned known tables. Since the tables indicate which intraocular pressure corresponds with certain distances traveled by the movable central piece 16, the computation portion 199 is able to determine intraocular pressure by merely determining which pressure corresponds with the distance traveled by the movable central piece 16.

The system of the present invention may also be used to calculate the rigidity of the sclera. In particular, the system is first used to determine intraocular pressure by applanation and then is used to determine intraocular pressure by indentation. The differences between the intraocular pressures detected by the two methods would then be indicative of the sclera's rigidity.

Although the foregoing description of the preferred systems generally refers to a combined system capable of detecting intraocular pressure by both applanation and indentation, it is understood that a combined system need not be created. That is, the system capable of determining intraocular pressure by applanation may be constructed independently from a separate system for determining intraocular pressure by indentation and vice versa.

Measuring Hydrodynamics of the Eye

The indentation device of the present invention may also be utilized to non-invasively measure hydrodynamics of an eye including outflow facility. The method of the present invention preferably comprises several steps including the following:

According to a first step, an indentation device is placed in contact with the cornea. Preferably, the indentation device comprises the contact device 2 illustrated in FIGS. 1 and 2A-2D.

Next, at least one movable portion of the indentation device is moved in toward the cornea using a first predetermined amount of force to achieve indentation of the cornea. When the indentation device is the contact device 2, the movable portion consists of the movable central piece 16.

An intraocular pressure is then determined based on a first distance traveled toward the cornea by the movable portion of the indentation device during application of the first predetermined amount of force. Preferably, the intraocular pressure is determined using the aforementioned system for determining intraocular pressure by indentation.

Next, the movable portion of the indentation device is rapidly reciprocated in toward the cornea and away from the cornea at a first predetermined frequency and using a second predetermined amount of force during movement toward the cornea to thereby force intraocular fluid out from the eye. The second predetermined amount of force is preferably equal to or greater than the first predetermined amount of force. It is understood, however, that the second predetermined amount of force may be less than the first predetermined amount of force. The reciprocation, which preferably continues for 5 seconds, should generally not exceed 10 seconds induration.

The movable portion is then moved in toward the cornea using a third predetermined amount of force to again achieve indentation of the cornea.

A second intraocular pressure is then determined based on a second distance traveled toward the cornea by the movable portion of the indentation device during application of the third predetermined amount of force. This second intraocular pressure is also preferably determined using the aforementioned system for determining intraocular pressure by indentation. Since intraocular pressure decreases as a result of forcing intraocular fluid out of the eye during the rapid reciprocation of the movable portion, it is generally understood that, unless the eye is so defective that no fluid flows out therefrom, the second intraocular pressure will be less than the first intraocular pressure. This reduction in intraocular pressure is indicative of outflow facility.

Next, the movable portion of the indentation device is again rapidly reciprocated in toward the cornea and away from the cornea, but at a second predetermined frequency and using a fourth predetermined amount of force during movement toward the cornea. The fourth predetermined amount of force is preferably equal or greater than the second predetermined amount of force. It is understood, however, that the fourth predetermined amount of force may be less than the second predetermined amount of force. Additional intraocular fluid is thereby forced out from the eye. This reciprocation, which also preferably continues for 5 seconds, should generally not exceed 10 seconds in duration.

The movable portion is subsequently moved in toward the cornea using a fifth predetermined amount of force to again achieve indentation of the cornea.

Thereafter, a third intraocular pressure is determined based on a third distance traveled toward the cornea by the movable portion of the indentation device during application of the fifth predetermined amount of force.

The differences are then preferably calculated between the first, second, and third distances, which differences are indicative of the volume of intraocular fluid which left the eye and therefore are also indicative of the outflow facility. It is understood that the difference between the first and last distances may be used, and in this regard, it is not necessary to use the differences between all three distances. In fact, the difference between any two of the distances will suffice.

Although the relationship between the outflow facility and the detected differences varies when the various parameters of the method and the dimensions of the indentation device change, the relationship for given parameters and dimensions can be easily determined by known experimental techniques and/or using known Friedenwald Tables.

The method of the present invention is preferably carried out using an indenting surface which is three millimeters in diameter and a computer equipped with a data acquisition board. In particular, the computer generates the predetermined forces via a digital-to-analog (D/A) converter connected to the current generating circuitry 32. The computer then receives signals indicative of the first, second, and third predetermined distances via an analog-to-digital (A/D) converter. These signals are analyzed by the computer using the aforementioned relationship between the differences in distance and the outflow facility. Based on this analysis, the computer creates an output signal indicative of outflow facility. The output signal is preferably applied to a display screen which, in turn, provides a visual indication of outflow facility.

Preferably, the method further comprises the steps of plotting the differences between the first, second, and third distances to a create a graph of the differences and comparing the resulting graph of differences to that of a normal eye to determine if any irregularities in outflow facility are present. As indicated above, however, it is understood that the difference between the first and last distances may be used, and in this regard, it is not necessary to use the differences between all three distances. In fact, the difference between any two of the distances will suffice.

Preferably, the first predetermined frequency and second predetermined frequency are substantially equal and are approximately 20 Hertz. Generally, any frequencies up to 35 Hertz can be used, though frequencies below 1 Hertz are generally less desirable because the stress relaxation of the eye's outer coats would contribute to changes in pressure and volume.

The fourth predetermined amount of force is preferably at least twice the second predetermined amount of force, and the third predetermined amount of force is preferably approximately half of the first predetermined amount of force. It is understood, however, that other relationships will suffice and that the present method is not limited to the foregoing preferred relationships.

According to a preferred use of the method, the first predetermined amount of force is between 0.01 Newton and 0.015 Newton; the second predetermined amount of force is between 0.005 Newton and 0.0075 Newton; the third predetermined amount of force is between 0.005 Newton and 0.0075 Newton; the fourth predetermined amount of force is between 0.0075 Newton and 0.0125 Newton; the fifth predetermined amount of force is between 0.0125 Newton and 0.025, Newton; the first predetermined frequency is between 1 Hertz and 35 Hertz; and the second predetermined frequency is also between 1 Hertz and 35 Hertz. The present method, however, is not limited to the foregoing preferred ranges.

Although the method of the present invention is preferably carried out using the aforementioned device, it is understood that various other tonometers may be used. The method of the present invention therefore is not limited in scope to its use in conjunction with the claimed system and illustrated contact device.

Alternative Embodiments of the Contact Device

Although the foregoing description utilizes an embodiment of the contact device 2 which includes a flexible membrane 14 on the inside surface of the contact device 2, it is readily understood that the present invention is not limited to such an arrangement. Indeed, there are many variations of the contact device which fall well within the scope of the present invention.

The contact device 2, for example, may be manufactured with no flexible membrane, with the flexible membrane on the outside surface of the contact device 2 (i.e., the side away from the cornea), with the flexible membrane on the inside surface of the contact device 2, or with the flexible membrane on both sides of the contact device 2.

Also, the flexible membrane (s) 14 can be made to have an annular shape, thus permitting light to pass undistorted directly to the movable central piece 16 and the cornea for reflection thereby.

Figure 12:
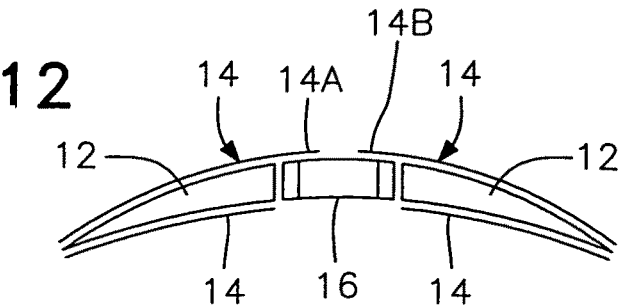
FIG. 12 is a cross-sectional view of an alternative contact device in accordance with another preferred embodiment of the present invention.

In addition, as illustrated in FIG. 12, the movable central piece 16 may be formed with a similar annular shape so that a transparent central portion thereof merely contains air. This way, light passing through the entire contact device 2 impinges directly on the cornea without undergoing any distortion due to the contact device 2.

Alternatively, the transparent central portion can be filled with a transparent solid material. Examples of such transparent solid materials include polymethyl methacrylate, glass, hard acrylic, plastic polymers, and the like. According to a preferred arrangement, glass having an index of refraction substantially greater than that of the cornea is utilized to enhance reflection of light by the cornea when the light passes through the contact device 2. Preferably, the index of refraction for the glass is greater than 1.7, compared to the typical index of refraction of 1.37 associated with the cornea.

It is understood that the outer surface of the movable central piece 16 may be coated with an anti-reflection layer in order to eliminate extraneous reflections from that surface which might otherwise interfere with operation of the alignment mechanism and the applanation detecting arrangement.

The interconnections of the various components of the contact device 2 are also subject to modification without departing from the scope and spirit of the present invention. It is understood therefore that many ways exist for interconnecting or otherwise maintaining the working relationship between the movable central piece 16, the rigid annular member 12, and the membranes 14.

When one or two flexible membranes 14 are used, for example, the substantially rigid annular member 12 can be attached to any one or both of the flexible membrane(s) 14 using any known attachment techniques, such as gluing, heat-bonding, and the like. Alternatively, when two flexible membranes 14 are used, the components may be interconnected or otherwise maintained in a working relationship, without having to directly attach the flexible membrane 14 to the substantially rigid annular member 12. Instead, the substantially rigid annular member 12 may be retained between the two flexible membranes 14 by bonding the membranes to one another about their peripheries while the rigid annular member 12 is sandwiched between the membranes 14.

Although the movable central piece 16 may be attached to the flexible membrane(s) 14 by gluing, heat-bonding, and the like, it is understood that such attachment is not necessary.

Instead, one or both of the flexible membranes 14 can be arranged so as to completely or partially block the movable central piece 16 and prevent it from falling out of the hole in the substantially rigid annular member 12. When the aforementioned annular version of the flexible membranes 14 is used, as illustrated by way of example in FIG. 12, the diameter of the hole in at least one of the annular flexible membranes 14 is preferably smaller than that of the hole in the substantially rigid annular member 12 so that a radially inner portion 14A of the annular flexible membrane 14 overlaps with the movable central piece 16 and thereby prevents the movable central piece 16 from falling out of the hole in the substantially rigid annular member 12.

Figure 13A:
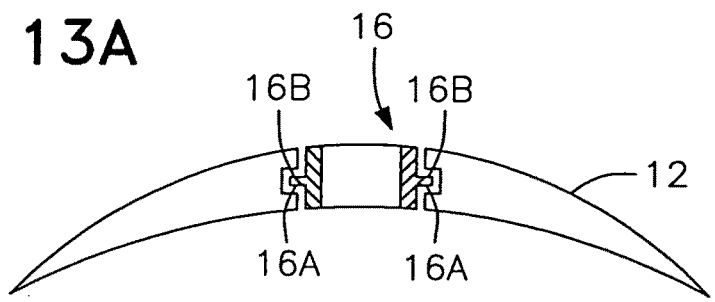
FIGS. 13A-15 are cross-sectional views of alternative contact devices in accordance with other embodiments of the present invention.

As illustrated in FIG. 13A, another way of keeping the movable central piece 16 from falling out of the hole in the substantially rigid annular member 12 is to provide arms 16A which extend radially out from the movable central piece 16 and are slidably received in respective grooves 16B. The grooves 16B are formed in the rigid annular member 12. Each groove 16B has a longitudinal dimension (vertical in FIG. 13) which is selectively chosen to restrict the range of movement of the movable central piece 16 to within predetermined limits. Although FIG. 13 shows an embodiment wherein the grooves are in the substantially rigid annular member 12 and the arms extend out from the movable central piece 16, it is understood that an equally effective arrangement can be created by reversing the configuration such that the grooves are located in the movable central piece 16 and the arms extend radially in from the substantially rigid annular member 12.

Preferably, the grooves 16B include resilient elements, such as miniature springs, which bias the position of the movable central piece 16 toward a desired starting position. In addition, the arms 16A may include distally located miniature wheels which significantly reduce the friction between the arms 16A and the walls of the grooves 16B.

Figure 13B:
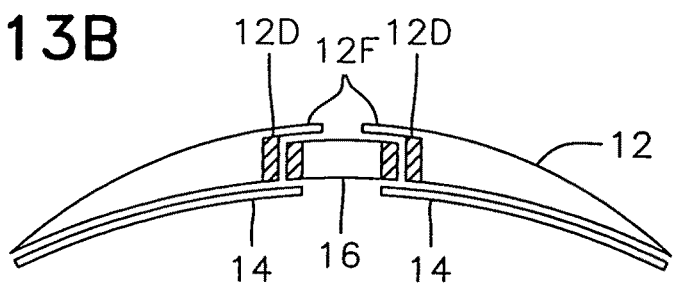

FIG. 13B illustrates another way of keeping the movable central piece 16 from falling out of the hole in the substantially rigid annular member 12. In FIG. 13B, the substantially rigid annular member 12 is provided with radially inwardly extending flaps 12F at the outer surface of the annular member 12. One of the aforementioned annular membranes 14 is preferably disposed on the inner side of the substantially rigid annular member 12. Preferably, a portion of the membrane 14 extends radially inwardly past the walls of the rigid annular member's hole. The combination of the annular membrane 14 and the flaps 12F keeps the movable central piece 16 from falling out of the hole in the substantially rigid annular member 12.

The flaps 12F may also be used to achieve or facilitate actuation of the movable central piece 16. In a magnetically actuated embodiment, for example, the flaps 12F may be magnetized so that the flaps 12F move inwardly in response to an externally applied magnetic field.

Figure 14:
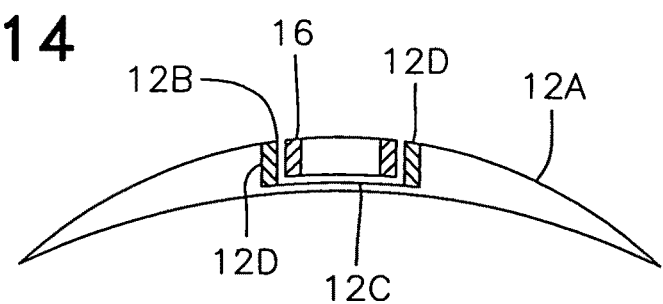

With reference to FIG. 14, an alternative embodiment of the contact device 2 is made using a soft contact lens material 12A having a progressively decreasing thickness toward its outer circumference. A cylindrical hole 12B is formed in the soft contact lens material 12A. The hole 12B, however, does not extend entirely through the soft contact lens material 12A. Instead, the hole has a closed bottom defined by a thin portion 12C of the soft contact lens material 12A. The movable central piece 16 is disposed slidably within the hole 12B, and preferably, the thin portion 12C is no more than 0.2 millimeters thick, thereby allowing the movable central piece 16 to achieve applanation or indentation when moved against the closed bottom of the hole toward the cornea with very little interference from the thin portion 12C.

Preferably, a substantially rigid annular member 12D is inserted and secured to the soft contact material 12A to define a more stable wall structure circumferentially around the hole 12B. This, in turn, provides more stability when the movable central piece 16 moves in the hole 12B.

Although the soft lens material 12A preferably comprises Hydrogel, silicone, flexible acrylic, or the like, it is understood that any other suitable materials may be used. In addition, as indicated above, any combination of flexible membranes may be added to the embodiment of FIG. 14. Although the movable central piece 16 in FIG. 14 is illustrated as being annular, it is understood that any other shape may be utilized. For example, any of the previously described movable central pieces 16 would suffice.

Similarly, the annular version of the movable central piece 16 may be modified by adding a transparent bottom plate (not illustrated) which defines a flat transparent bottom surface of the movable central piece 16. When modified in this manner, the movable central piece 16 would have a generally cup-shaped appearance. Preferably, the flat transparent bottom surface is positioned toward the cornea to enhance the flattening effect of the movable central piece 16; however, it is understood that the transparent plate can be located on the outside surface of the movable central piece 16 if desired.

Although the movable central piece 16 and the hole in the substantially rigid annular member 12 (or the hole in the soft contact lens material 12A) are illustrated as having complementary cylindrical shapes, it is understood that the complementary shapes are not limited to a cylinder, but rather can include any shape which permits sliding of the movable central piece 16 with respect to its surrounding structure.

It is also understood that the movable central piece 16 may be mounted directly onto the surface of a flexible membrane 14 without using a substantially rigid annular member 12. Although such an arrangement defines a working embodiment of the contact device 2, its stability, accuracy, and level of comfort are significantly reduced compared to that of a similar embodiment utilizing the substantially rigid annular member 12 with a progressively tapering periphery.

Although the illustrated embodiments of the movable central piece 16 include generally flat outside surfaces with well defined lateral edges, it is understood that the present invention is not limited to such arrangements. The present invention, for example, can include a movable central piece 16 with a rounded outer surface to enhance comfort and/or to coincide with the curvature of the outer surface of the substantially rigid annular member 12. The movable central piece can also be made to have any combination of curved and flat surfaces defined at its inner and outer surfaces, the inner surface being the surface at the cornea and the outer surface being the surface directed generally away from the cornea.

Figure 15:
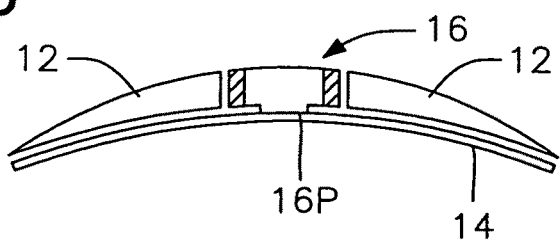

With reference to FIG. 15, the movable central piece 16 may also include a centrally disposed projection 16P directed toward the cornea. The projection 16P is preferably created by extending the transparent solid material in toward the cornea at the center of the movable central piece 16.

Alternative Embodiment for Measuring Intraocular Pressure by Applanation

Figure 16:
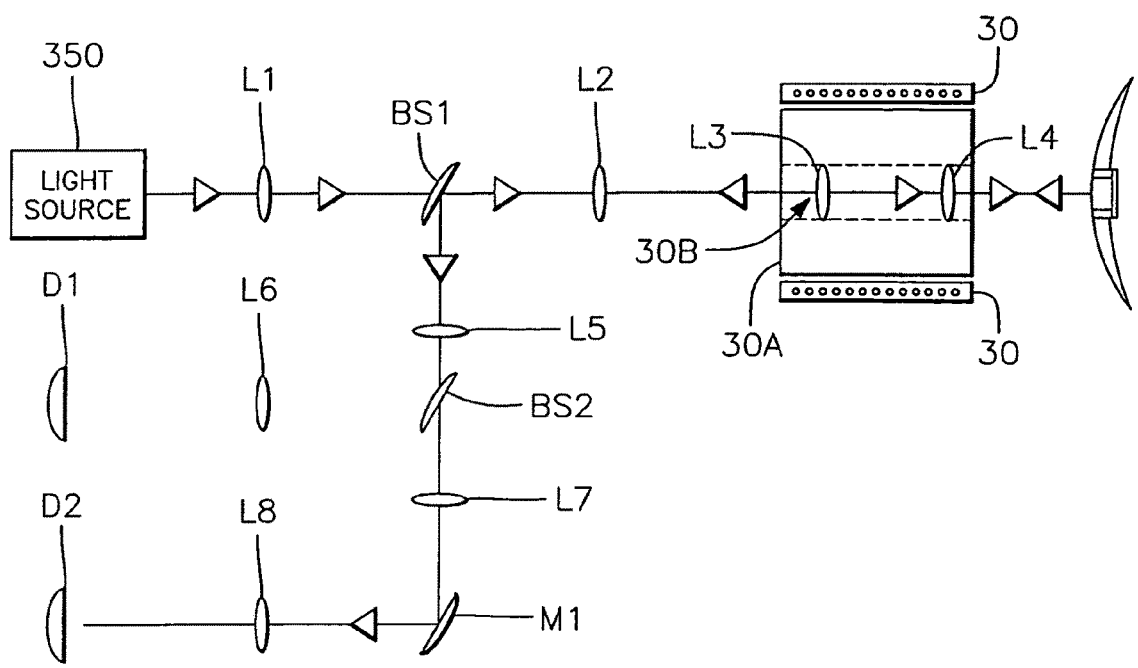
FIG. 16 schematically illustrates an alternative embodiment of the system for measuring intraocular pressure by applanation, according to the present invention.

With reference to FIG. 16, an alternative embodiment of the system for measuring intraocular pressure by applanation will now be described. The alternative embodiment preferably utilizes the version of the contact device 2 which includes a transparent central portion.

According to the alternative embodiment, the schematically illustrated coil 30 of the actuation apparatus includes an iron core 30A for enhancing the magnetic field produced by the coil 30. The iron core 30A preferably has an axially extending bore hole 30B (approximately 6 millimeters in diameter) which permits the passage of light through the iron core 30A and also permits mounting of two lenses L3 and L4 therein.

In order for the system to operate successfully, the strength of the magnetic force applied by the coil 30 on the movable central piece 16 should be sufficient to applanate patients' corneas over at least the full range of intraocular pressures encountered clinically (i.e. 5-50 mm Hg). According to the illustrated alternative embodiment, intraocular pressures ranging from 1 to over 100 mm of mercury can be evaluated using the present invention. The forces necessary to applanate against such intraocular pressures may be obtained with reasonably straightforward designs and inexpensive materials as will be demonstrated by the following calculations:

It is known that the force F exerted by an external magnetic field on a small magnet equals the magnet's magnetic dipole moment m multiplied by the gradient of the external field's magnetic induction vector "grad B" acting in the direction of the magnet's dipole moment.

$$F = m * \text{grad } B \tag{1}$$

The magnetic dipole moment m for the magnetic version of the movable central piece 16 can be determined using the following formula:

$$m = (B*V)/u_0 \tag{2}$$

where B is the magnetic induction vector just at the surface of one of the poles of the movable central piece 16, V is its volume, and $u_0$ is the magnetic permeability of free space which has a value of $12.57*10^{-7}$ Henry/meter.

A typical value of B for magnetized Alnico movable central pieces 16 is 0.5 Tesla. If the movable central piece 16 has a thickness of 1 mm, a diameter of 5 mm, and 50% of its initial volume is machined away, its volume V=9.8 cubic millimeters ($9.8*10^{-9}$ cubic meters). Substituting these values into Equation 2 yields the value for the movable central piece's magnetic dipole moment, namely, m=0.00390 Amp*(Meter)$^2$.

Using the foregoing calculations, the specifications of the actuation apparatus can be determined. The magnetic field gradient "grad B" is a function of the distance x measured from the front face of the actuation apparatus and may be calculated as follows:

$$gradB = \frac{u_0 * X * N * I * (RAD)^2 * \left\{ \frac{[(x+L)^2 + RAD^2]^{-3/2} -}{[x^2 + RAD^2]^{3/2}} \right\}}{2*L} \tag{3}$$

where X is the magnetic susceptibility of the iron core, N is the number of turns in the coil's wire, I is the electric current carried by the wire, L is the length of the coil 30, and RAD is the radius of the coil 30.

The preferred values for these parameters in the alternative embodiment are: X=500, N=200, I=1.0 Amp, L=0.05 meters, and RAD=0.025 meters. It is understood, however, that the present invention is not limited to these preferred parameters. As usual, $u_0 = 12.57*10^{-7}$ Henry/meter.

The force F exerted by the magnetic actuation apparatus on the movable central piece 16 is found from Equation 1 using the aforementioned preferred values as parameters in Equation 3, and the above result for m=0.00390 Amp*(Meter)$_2$. A plot of F as a function of the distance x separating the movable central piece 16 from the pole of the magnetic actuation apparatus appears as FIG. 16A.

Figure 16A:
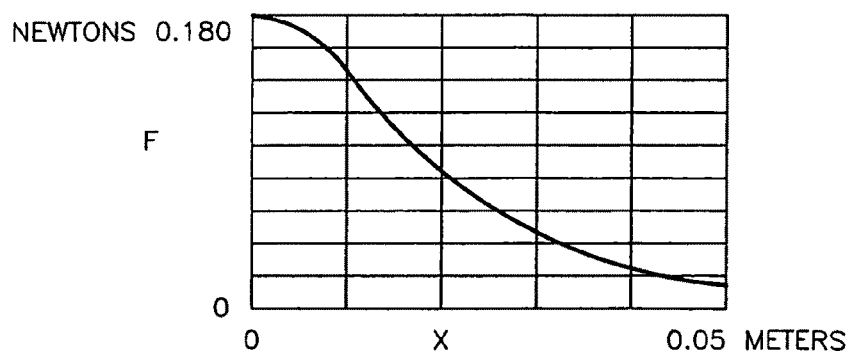
FIG. 16A is a graph depicting force (F) as a function of the distance (x) separating a movable central piece from the pole of a magnetic actuation apparatus in accordance with the present invention.

Since a patient's cornea 4, when covered by the contact device 2 which holds the movable central piece 16, can be placed conveniently at a distance x=2.5 cm (0.025 m) from the actuation apparatus, it is noted from FIG. 16A that the magnetic actuation force is approximately F=0.063 Newtons.

This force is then compared to $F_{required}$ which is the force actually needed to applanate a cornea 4 over a typical applanation area when the intraocular pressure is as high as 50 mm Hg. In Goldman tonometry, the diameter of the applanated area is approximately 3.1 mm and therefore the typical applanated AREA will equal 7.55 mm$^2$. The typical maximum pressure of 50 mm Hg can be converted to metric form, yielding a pressure of 0.00666 Newtons/mm$^2$. The value Of $F_{required}$ then can be determined using the following equation:

$$F_{required} = \text{PRESSURE} * \text{AREA} \tag{4}$$

After mathematical substitution, $F_{required}$=0.050 Newtons. Comparing the calculated magnetic actuation force F to the force required $F_{required}$, it becomes clear that $F_{required}$ is less than the available magnetic driving force F. Therefore, the maximum force needed to applanate the cornea 4 for intraocular pressure determinations is easily achieved using the actuation apparatus and movable central piece 16 of the present invention.

It is understood that, if a greater force becomes necessary for whatever reason (e.g, to provide more distance between the contact device 2 and the actuation apparatus), the various parameters can be manipulated and/or the current in the coil 30 can be increased to achieve a satisfactory arrangement.

In order for the actuation apparatus to properly actuate the movable central piece 16 in a practical way, the magnetic actuation force (and the associated magnetic field) should increase from zero, reach a maximum in about 0.01 sec., and then return back to zero in approximately another 0.01 sec. The power supply to the actuation apparatus therefore preferably includes circuitry and a power source capable of driving a "current pulse" of peak magnitude in the 1 ampere range through a fairly large inductor (i.e. the coil 30).

For Asingle-pulse@ operation, a DC-voltage power supply can be used to charge a capacitor C through a charging resistor. One side of the capacitor is grounded while the other side ("high" side) may be at a 50 volt DC potential. The "high" side of the capacitor can be connected via a high current-carrying switch to a "discharge circuit" consisting of the coil 30 and a damping resistor R. This arrangement yields an R-L-C series circuit similar to that which is conventionally used to generate large pulses of electrical current for such applications as obtaining large pulsed magnetic fields and operating pulsed laser power systems. By appropriately choosing the values of the electrical components and the initial voltage of the capacitor, a Acurrent pulse@ of the kind described above can be generated and supplied to the coil 30 to thereby operate the actuation apparatus.

It is understood, however, that the mere application of a current pulse of the kind described above to a large inductor, such as the coil 30, will not necessarily yield a zero magnetic field after the current pulse has ended. Instead, there is usually an undesirable residual magnetic field from the iron-core 30A even though no current is flowing in the coil 30. This residual field is caused by magnetic hysteresis and would tend to produce a magnetic force on the movable central piece 16 when such a force is not wanted.

Therefore, the alternative embodiment preferably includes means for zeroing the magnetic field outside the actuation apparatus after operation thereof. Such zeroing can be provided by a demagnetizing circuit connected to the iron-core 30A.

Methods for demagnetizing an iron-core are generally known and are easy to implement. It can be done, for example, by reversing the current in the coil repeatedly while decreasing its magnitude. The easiest way to do this is by using a step-down transformer where the input is a sinusoidal voltage at 60 Hz which starts at a "line voltage" of 110 VAC and is gradually dampened to zero volts, and where the output of the transformer is connected to the coil 30.

The actuation apparatus therefore may include two power circuits, namely, a "single pulse" current source used for conducting applanation measurements and a "demagnetization circuit" for zeroing the magnetic field of the coil 30 immediately after each applanation measurement.

Figure 17:
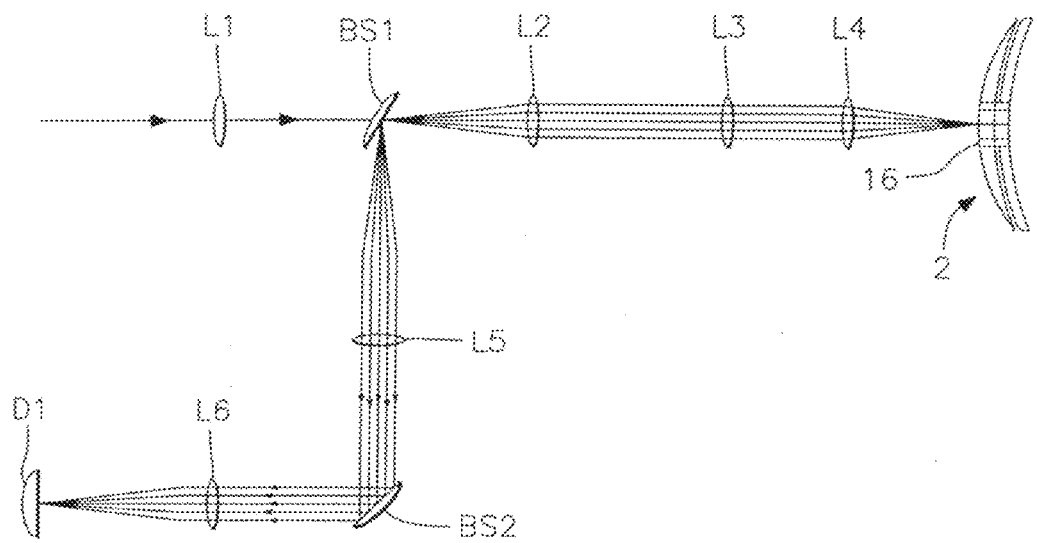
FIG. 17 schematically illustrates an alternative optical alignment system in accordance with the present invention.

As illustrated in FIG. 16 and more specifically in FIG. 17, the alternative embodiment used for applanation also includes an alternative optical alignment system. Alignment is very important because, as indicated by the graph of FIG. 16A, the force exerted by the actuation apparatus on the movable central piece 16 depends very much on their relative positions. In addition to the movable central piece's axial location with respect to the actuation apparatus (x-direction), the magnetic force exerted on the movable central piece 16 also depends on its lateral (y-direction) and vertical (z-direction) positions, as well as on its orientation (tip and tilt) with respect to the central axis of the actuation apparatus.

Considering the variation of force F with axial distance x shown in FIG. 16A, it is clear that the movable central piece 16 should be positioned in the x-direction with an accuracy of about +/−1 mm for reliable measurements. Similarly, since the diameter of the coil 30 is preferably 50 mm, the location of the movable central piece 16 with respect to the y and z directions (i.e. perpendicular to the longitudinal axis of the coil 30) should be maintained to within +/−2 mm (a region where the magnetic field is fairly constant) of the coil's longitudinal axis.

Finally, since the force on the movable central piece 16 depends on the cosine of the angle between the coil's longitudinal axis and the tip or tilt angle of the movable central piece 16, it is important that the range of the patient's gaze with respect to the coil's longitudinal axis be maintained within about +/−2 degrees for reliable measurements.

In order to satisfy the foregoing criteria, the alternative optical alignment system facilitates precise alignment of the patient's corneal vertex (situated centrally behind the movable central piece 16) with the coil's longitudinal axis, which precise alignment can be achieved independently by a patient without the assistance of a trained medical technician or health care professional.

The alternative optical alignment system functions according to how light reflects and refracts at the corneal surface. For the sake of simplicity, the following description of the alternative optical alignment system and FIGS. 16 and 17 does not refer specifically to the effects of the movable central piece's transparent central portion on the operation of the optical system, primarily because the transparent central portion of the movable central piece 16 is preferably arranged so as not to affect the behavior of optical rays passing through the movable central piece 16.

Also, for the sake of simplicity, FIG. 17 does not show the iron core 30A and its associated bore 30B, though it is understood that the alignment beam (described hereinafter) passes through the bored hole 30B and that the lenses L3 and L4 are mounted within the bored hole 30B.

As illustrated in FIG. 16, a point-like source 350 of light such as an LED is located at the focal plane of a positive (i.e., convergent) lens L1. The positive lens L1 is arranged so as to collimate a beam of light from the source 350. The collimated beam passes through a beam splitter BS1 and a transmitted beam of the collimated beam continues through the beam splitter BS1 to a positive lens L2. The positive lens L2 focuses the transmitted beam to a point within lens L3 located at the focal plane of a lens L4. The light rays passing through L4 are collimated once again and enter the patient's eye where they are focused on the retina 5. The transmitted beam is therefore perceived by the patient as a point-like light.

Figure 18:
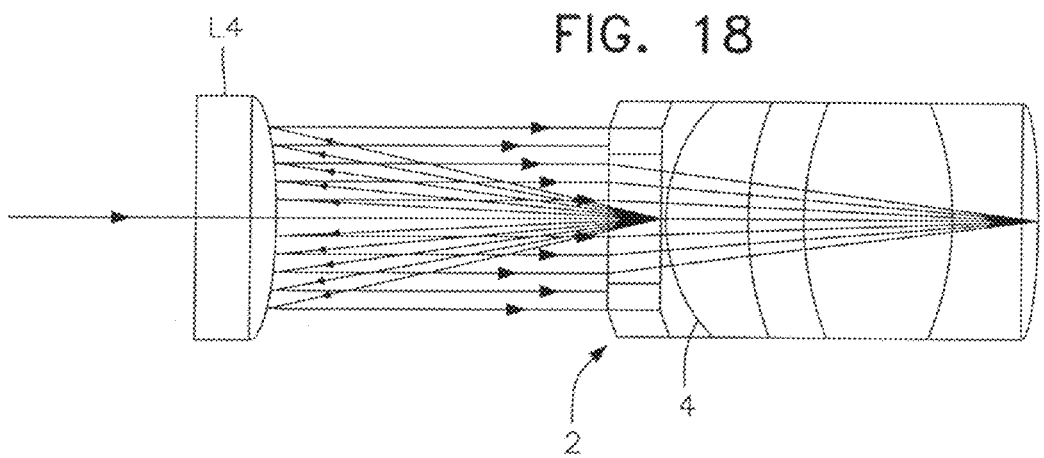
FIGS. 18 and 19 schematically illustrate arrangements for guiding the patient during alignment of his/her eye in the apparatus of the present invention.

Some of the rays which reach the eye are reflected from the corneal surface in a divergent manner due to the cornea's preapplanation curvature, as shown in FIG. 18, and are returned back to the patient's eye by a partially mirrored planar surface of the lens L4. These rays are perceived by the patient as an image of the corneal reflection which guides the patient during alignment of his/her eye in the instrument as will be described hereinafter.

Those rays which are reflected by the convex cornea 4 and pass from right-to-left through the lens L4 are made somewhat more convergent by the lens L4. From the perspective of lens L3, these rays appear to come from a virtual point object located at the focal point. Therefore, after passing through L3, the rays are once again collimated and enter the lens L2 which focuses the rays to a point on the surface of the beam splitter BS1. The beam splitter BS1 is tilted at 45 degrees and consequently deflects the rays toward a lens L5 which, in turn, collimates the rays. These rays then strike the surface of a tilted reflecting beam splitter BS2. The collimated rays reflected from the beam splitter BS2 enter lens L6 which focuses them onto the small aperture of a silicon photodiode which functions as an alignment sensor D1.

Therefore, when the curved cornea 4 is properly aligned, an electric current is produced by the alignment sensor D1. The alignment system is very sensitive because it is a confocal arrangement (i.e., the point image of the alignment light due to the corneal reflection—Purkinje image—in its fiducial position is conjugate to the small light-sensitive aperture of the silicon photodiode). In this manner, an electrical current is obtained from the alignment sensor only when the cornea 4 is properly aligned with respect to the lens L4 which, in turn, is preferably mounted at the end of the magnetic actuation apparatus. The focal lengths of all the lenses shown in FIG. 17 are preferably 50 mm except for the lens L3 which preferably has a focal length of 100 MM.

An electrical circuit capable of operating the alignment sensor D1 is straight-forward to design and build. The silicon photodiode operates without any bias voltage ("photovoltaic mode@) thus minimizing inherent detector noise. In this mode, a voltage signal, which corresponds to the light level on the silicon surface, appears across a small resistor spanning the diode's terminals. Ordinarily this voltage signal is too small for display or subsequent processing; however, it can be amplified many orders of magnitude using a simple transimpedance amplifier circuit. Preferably, the alignment sensor D1 is utilized in conjunction with such an amplified photodiode circuit.

Preferably, the circuitry connected to the alignment sensor D1 is arranged so as to automatically activate the actuation apparatus immediately upon detecting via the sensor D1 the existence of proper alignment. If, however, the output from the alignment sensor D1 indicates that the eye is not properly aligned, the circuitry preferably prevents activation of the actuation apparatus. In this way, the alignment sensor D1, not the patient, determines when the actuation apparatus will be operated.

As indicated above, the optical alignment system preferably includes an arrangement for guiding the patient during alignment of his/her eye in the instrument. Such arrangements are illustrated, by way of example, in FIGS. 18 and 19.

The arrangement illustrated in FIG. 18 allows a patient to precisely position his/her eye translationally in all x-y-z directions. In particular, the lens L4 is made to include a plano surface, the piano surface being made partially reflective so that a patient is able to see a magnified image of his/her pupil with a bright point source of light located somewhere near the center of the iris. This point source image is due to the reflection of the incoming alignment beam from the curved corneal surface (called the first Purkinje image) and its subsequent reflection from the mirrored or partially reflecting plano surface of the lens L4. Preferably, the lens L4 makes the reflected rays parallel as they return to the eye which focuses them onto the retina 5.

Although FIG. 18 shows the eye well aligned so that the rays are focused at a central location on the surface of the retina 5, it is understood that movements of the eye toward or away (x—direction) from the lens L4 will blur the image of the corneal reflection, and that movements of the eye in either the y or z direction will tend to displace the corneal reflection image either to the right/left or up/down.

The patient therefore performs an alignment operation by gazing directly at the alignment light and moving his/her eye slowly in three dimensions until the point image of the corneal reflection is as sharp as possible (x-positioning) and merges with the point image of the alignment light (y & z positioning) which passes straight through the cornea 4.

Figure 19:
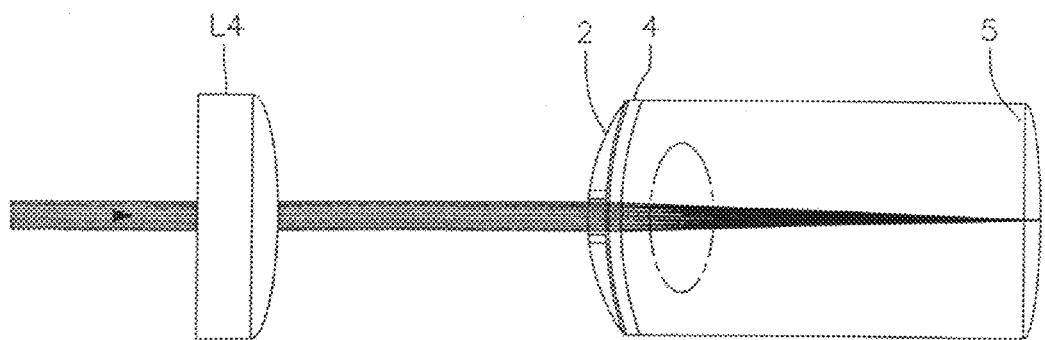

As illustrated in FIG. 19, the lens L4 need not have a partially reflective portion if the act of merely establishing a proper direction of gaze provides sufficient alignment.

Once alignment is achieved, a logic signal from the optical alignment system activates the "pulse circuit" which, in turn, powers the actuation apparatus. After the actuation apparatus is activated, the magnetic field at the patient's cornea increases steadily for a time period of about 0.01 sec. The effect of this increasing field is to apply a steadily increasing force to the movable central piece 16 resting on the cornea which, in turn, causes the cornea 4 to flatten increasingly over time. Since the size of the applanation area is proportional to the force on the movable central piece 16 (and Pressure=Force/Area), the intraocular pressure (IOP) is found by determining the ratio of the force to the area applanated by the force.

In order to detect the applanated area and provide an electrical signal indicative of the size of the applanated area, the alternative embodiment includes an applanation sensor D2. The rays that are reflected from the applanated corneal surface are reflected in a generally parallel manner by virtue of the flat surface presented by the applanated cornea 4. As the rays pass from right-to-left through the lens L4, they are focused within the lens L3 which, in turn, is in the focal plane of the lens L2. Consequently, after passing through the lens L2, the rays are once again collimated and impinge on the surface of beam splitter BS1. Since the beam splitter BS1 is tilted at 45 degrees, the beam splitter BS1 deflects these collimated rays toward the lens L5 which focuses the rays to a point at the center of beam splitter BS2. The beam splitter BS2 has a small transparent portion or hole in its center which allows the direct passage of the rays on to the lens L7 (focal length of preferably 50 mm). The lens L7 pertains to an applanation sensing arm of the alternative embodiment.

The focal spot on the beam splitter BS2 is in the focal plane of the lens L7. Consequently, the rays emerging from the lens L7 are once again collimated. These collimated rays impinge on the mirror M1, preferably at a 45 degree angle, and are deflected toward a positive lens L8 (focal length of 50 mm) which focuses the rays onto the small aperture of a silicon photodiode which defines the applanation sensor D2.

It is understood that rays which impinge upon the cornea 4 slightly off center tend to be reflected away from the lens L4 when the cornea's curvature remains undisturbed. However, as applanation progresses and the cornea becomes increasingly flat, more of these rays are reflected back into the lens L4. The intensity of light on the applanation sensor D2 therefore increases, and as a result, an electric current is generated by the applanation sensor D2, which electric current is proportional to the degree of applanation.

Preferably, the electrical circuit utilized by the applanation sensor D2 is identical or similar to that used by the alignment sensor D1.

The electric signal indicative of the area of applanation can then be combined with signals indicative of the time it takes to achieve such applanation and/or the amount of current (which, in turn, corresponds to the applied force) used to achieve the applanation, and this combination of information can be used to determine the intraocular pressure using the equation Pressure=Force/Area.

The following are preferred operational steps for the actuation apparatus during a measurement cycle:

1) While the actuation apparatus is OFF, there is no magnetic field being directed toward the contact device 2.

2) When the actuation apparatus is turned ON, the magnetic field initially remains at zero.

3) Once the patient is in position, the patient starts to align his/her eye with the actuation apparatus. Until the eye is properly aligned, the magnetic field remains zero.

4) When the eye is properly aligned (as automatically sensed by the optical alignment Sensor), the magnetic field (driven by a steadily increasing electric current) starts to increase from zero.

5) During the time period of the current increase (approximately 0.01 sec.), the force on the movable central piece also increases steadily.

6) In response to the increasing force on the movable central piece, the surface area of the cornea adjacent to the movable central piece is increasingly flattened.

7) Light from the flattened surface area of the cornea is reflected toward the detecting arrangement which detects when a predetermined amount of applanation has been achieved. Since the amount of light reflected straight back from the cornea is proportional to the size of the flattened surface area, it is possible to determine exactly when the predetermined amount of applanation has been achieved, preferably a circular area of diameter 3.1 mm, of the cornea. It is understood, however, that any diameter ranging from 0.10 mm to 10 mm can be utilized.

8) The time required to achieve applanation of the particular surface area (i.e, the predetermined amount of applanation) is detected by a timing circuit which is part of the applanation detecting arrangement. Based on prior calibration and a resulting conversion table, this time is converted to an indication of intraocular pressure. The longer the time required to applanate a specific area, the higher the intraocular pressure, and vice versa.

9) After the predetermined amount of applanation is achieved, the magnetic field is turned OFF.

10) The intraocular pressure is then displayed by a readout meter, and all circuits are preferably turned completely OFF for a period of 15 seconds so that the automatic measurement cycle will not be immediately repeated if the patient's eye remains aligned. It is understood, however, that the circuits may remain ON and that a continuous measurement of intraocular pressure may be achieved by creating an automatic measurement cycle. The data provided by this automatic measurement cycle then may be used to calculate blood flow.

11) If the main power supply has not been turned OFF, all circuits are turned back ON after 15 seconds and thus become ready for the next measurement.

Although there are several methods for calibrating the various elements of the system for measuring intraocular pressure by applanation, the following are illustrative examples of how such calibration can be achieved:

Initially, after manufacturing the various components, each component is tested to ensure the component operates properly. This preferably includes verifying that there is free piston-like movement (no twisting) of the movable central piece in the contact device; verifying the structural integrity of the contact device during routine handling; evaluating the magnetic field at the surface of the movable central piece in order to determine its magnetic dipole moment (when magnetic actuation is utilized); verifying that the electrical current pulse which creates the magnetic field that actuates the magnetically responsive element of the movable central piece, has an appropriate peak magnitude and duration, and ensuring that there is no "ringing"; verifying the efficacy of the "demagnetization circuit" at removing any residual magnetization in the iron-core of the actuation apparatus after it has been pulsed; measuring the magnetic field as a function of time along and near the longitudinal axis of the coil where the movable central piece will eventually be placed; determining and plotting grad B as a function of time at several x-locations (i.e., at several distances from the coil); and positioning the magnetic central piece (contact device) at several x-locations along the coil's longitudinal axis and determining the force F acting on it as a function of time during pulsed-operation of the actuation apparatus.

Next, the optical alignment system is tested for proper operation. When the optical alignment system comprises the arrangement illustrated in FIGS. 16 and 17, for example, the following testing and calibration procedure may be used:

a) First, a convex glass surface (one face of a lens) having a radius of curvature approximately the same as that of the cornea is used to simulate the cornea and its surface reflection. Preferably, this glass surface is placed in a micrometer-adjusted mounting arrangement along the longitudinal axis of the coil. The micrometer-adjusted mounting arrangement permits rotation about two axes (tip & tilt) and translation in three-dimensional x-y-z space.

b) With the detector D1 connected to a voltage or current meter, the convex glass surface located at its design distance of 25 mm from lens L4 will be perfectly aligned (tip/tilt/x/y/z) by maximizing the output signal at the read-out meter.

c) After perfect alignment is achieved, the alignment detection arrangement is "detuned" for each of the positional degrees of freedom (tip/tilt/x/y/z) and curves are plotted for each degree of freedom to thereby define the system's sensitivity to alignment.

d) The sensitivity to alignment will be compared to the desired tolerances in the reproducibility of measurements and also can be based on the variance of the magnetic force on the movable central piece as a function of position.

e) Thereafter, the sensitivity of the alignment system can be changed as needed by such procedures as changing the size of the aperture in the silicon photodiode which functions as the alignment sensor D1, and/or changing an aperture stop at lens L4.

Next, the detection arrangement is tested for proper operation. When the detection arrangement comprises the optical detection arrangement illustrated in FIG. 16, for example, the following testing and calibration procedure may be used:

a) A flat glass surface (e.g., one face of a short polished rod) with a diameter of preferably 4-5 mm is used to simulate the applanated cornea and its surface reflection.

b) A black, opaque aperture defining mechanism (which defines clear inner apertures with diameters ranging from 0.5 to 4 mm and which has an outer diameter the same as that of the rod) is arranged so as to partially cover the face of the rod, thus simulating various stages of applanation.

c) The flat surfaced rod is placed in a mount along the longitudinal axis of the coil in a micrometer-adjusted mounting arrangement that can rotate about two axes (tip & tilt) and translate in three-dimensional x-y-z space.

d) The applanation sensor D2 is then connected to a voltage or current meter, while the rod remains located at its design distance of 25 mm from the lens L4 where it is perfectly aligned (tip/tilt/x/y/z) by maximizing the output signal from the applanation sensor D2. Alignment, in this case, is not sensitive to x-axis positioning.

e) After perfect alignment is achieved, the alignment is "detuned" for each of the positional degrees of freedom (tip/tilt/x/y/z) and curves are plotted for each degree of freedom thus defining the system's sensitivity to alignment. Data of this kind is obtained for the variously sized apertures (i.e. different degrees of applanation) at the face of the rod.

f) The sensitivity to alignment is then compared to the tolerances required for reproducing applanation measurements which depends, in part, on the results obtained in the aforementioned testing and calibration method associated with the alignment apparatus.

g) The sensitivity of the applanation detecting arrangement is then changed as needed by such procedures as changing the size of the aperture in front of the applanation sensor D2 and/or changing the aperture stop (small hole) at the beam splitter BS2.

Further calibration and in-vitro measurements can be carried out as follows: After the aforementioned calibration and testing procedures have been carried out on the individual subassemblies, all parts can be combined and the system tested as an integrated unit. For this purpose, ten enucleated animal eyes and ten enucleated human eyes are measured in two separate series. The procedures for both eye types are the same. The eyes are mounted in non-magnetic holders, each having a central opening which exposes the cornea and part of the sclera. A 23 gauge needle attached to a short piece of polyethylene tubing is then inserted behind the limbus through the sclera and ciliary body and advanced so that the tip passes between the lens and iris. Side ports are drilled in the cannulas about 2 mm from the tip to help avoid blockage of the cannula by the iris or lens. This cannula is attached to a pressure transducer with an appropriate display element. A normal saline reservoir of adjustable height is also connected to the pressure transducer tubing system. The hydrostatic pressure applied to the eye by this reservoir is adjustable between 0 and 50 mm Hg, and intraocular pressure over this range can be measured directly with the pressure transducer.

In order to verify that the foregoing equipment is properly set up for each new eye, a standard Goldman applanation tonometer can be used to independently measure the eye's intraocular pressure at a single height of the reservoir. The intraocular value measured using the Goldman system is then compared to a simultaneously determined intraocular pressure measured by the pressure transducer. Any problems encountered with the equipment can be corrected if the two measurements are significantly different.

The reservoir is used to change in 5 mm Hg sequential steps the intraocular pressure of each eye over a range of pressures from 5 to 50 mm Hg. At each of the pressures, a measurement is taken using the system of the present invention. Each measurement taken by the present invention consists of recording three separate time-varying signals over the time duration of the pulsed magnetic field.

The three signals are: 1) the current flowing in the coil of the actuation apparatus as a function of time, labelled I (t), 2) the voltage signal as a function of time from the applanation detector D2, labelled APPLN (t), and 3) the voltage signal as a function of time from the alignment sensor D1, labelled ALIGN (t). The three signals, associated with each measurement, are then acquired and stored in a computer equipped with a multi-input "data acquisition and processing" board and related software.

The computer, allows many things to be done with the data including: 1) recording and storing many signals for subsequent retrieval, 2) displaying graphs of the signals versus time, 3) numerical processing and analyses in any way that is desired, 4) plotting final results, 5) applying statistical analyses to groups of data, and 6) labeling the data (e.g. tagging a measurement set with its associated intraocular pressure).

The relationship between the three time-varying signals and intraocular pressure are as follows:

1. I(t) is an independent input signal which is consistently applied as current pulse from the power supply which activates the actuation apparatus. This signal I (t) is essentially constant from one measurement to another except for minor shot-to-shot variations. I(t) is a "reference" waveform against which the other waveforms, APPLN (t) and ALIGN (t) are compared as discussed further below.

2. APPLN(t) is a dependent output signal. APPLN(t) has a value of zero when I(t) is zero (i.e. at the very beginning of the current pulse in the coil of the actuation apparatus. The reason for this is that when I=0, there is no magnetic field and, consequently, no applanation force on the movable central piece. As I(t) increases, so does the extent of applanation and, correspondingly, so does APPLN(t). It is important to note that the rate at which APPLN(t) increases with increasing I(t) depends on the eye's intraocular pressure. Since eyes with low intraocular pressures applanate more easily than eyes with high intraocular pressures in response to an applanation force, it is understood that APPLN(t) increases more rapidly for an eye having a low intraocular pressure than it does for an eye having a high intraocular pressure. Thus, APPLN (t) increases from zero at a rate that is inversely proportional to the intraocular pressure until it reaches a maximum value when full applanation is achieved.

3. ALIGN(t) is also a dependent output signal. Assuming an eye is aligned in the setup, the signal ALIGN(t) starts at some maximum value when I(t) is zero (i.e. at the very beginning of the current pulse to the coil of the actuation apparatus). The reason for this is that when I=0, there is no magnetic field and, consequently, no force on the movable central piece which would otherwise tend to alter the cornea's curvature. Since corneal reflection is what gives rise to the alignment signal, as I(t) increases causing applanation (and, correspondingly, a decrease in the extent of corneal curvature), the signal ALIGN (t) decreases until it reaches zero at full applanation. It is important to note that the rate at which ALIGN (t) decreases with increasing I(t) depends on the eye's intraocular pressure. Since extraocular pressure applanate more easily than eyes with high intraocular pressure, it is understood that ALIGN (t) decreases more rapidly for an eye having a low intraocular pressure than for an eye having a high intraocular pressure. Thus, ALIGN(t) decreases from some maximum value at a rate that is inversely proportional to the intraocular pressure until it reaches zero when full applanation is achieved.

From the foregoing, it is clear that the rate of change of both output signals, APPLN and ALIGN, in relation to the input signal I is inversely proportional to the intraocular pressure. Therefore, the measurement of intraocular pressure using the present invention may depend on determining the SLOPE of the AAPPLN versus I@ measurement data (also, although probably with less certainty, the slope of the "ALIGN versus I" measurement data).

For the sake of brevity, the following description is limited to the "APPLN versus I" data; however, it is understood that the "ALIGN versus I" data can be processed in a similar manner.

Plots of AAPPLN versus I@ can be displayed on the computer monitor for the various measurements (all the different intraocular pressures for each and every eye) and regression analysis (and other data reduction algorithms) can be employed in order to obtain the "best fit" SLOPE for each measurement. Time can be spent in order to optimize this data reduction procedure. The end result of a series of pressure measurements at different intraocular pressures on an eye (determined by the aforementioned pressure transducer) will be a corresponding series of SLOPE's (determined by the system of the present invention).

Next, a single plot is prepared for each eye showing SLOPE versus intraocular pressure data points as well as a best fitting curve through the data. Ideally, all curves for the 10 pig eyes are perfectly coincident—with the same being true for the curves obtained for the 10 human eyes. If the ideal is realized, any of the curves can be utilized (since they all are the same) as a CALIBRATION for the present invention. In practice, however, the ideal is probably not realized.

Therefore, all of the SLOPE versus intraocular pressure data for the 10 pig eyes is superimposed on a single plot (likewise for the SLOPE versus intraocular pressure data for the 10 human eyes). Such superimposing generally yields an "averaged" CALIBRATION curve, and also indication of the reliability associated with the CALIBRATION.

Next, the data in the single plots can be analyzed statistically (one for pig eyes and one for human eyes) which, in turn, shows a composite of all the SLOPE versus intraocular pressure data. From the statistical analysis, it is possible to obtain: 1) an averaged CALIBRATION curve for the present invention from which one can obtain the Amost likely intraocular pressure" associated with a measured SLOPE value, 2) the Standard Deviation (or Variance) associated with any intraocular pressure determination made using the present invention, essentially the present invention's expected "ability" to replicate measurements, and 3) the "reliability" or "accuracy" of the present invention's CALIBRATION curve which is found from a "standard-error-of-the mean" analysis of the data.

In addition to data obtained with the eyes aligned, it is also possible to investigate the sensitivity of intraocular pressure measurements made using the present invention, to translational and rotational misalignment.

Alternative Embodiment for Measuring Intraocular Pressure by Indentation

With reference to FIGS. 20A and 20B, an alternative embodiment for measuring intraocular pressure by indentation will now be described.

The alternative embodiment includes an indentation distance detection arrangement and contact device. The contact device has a movable central piece 16 of which only the outside surface is illustrated in FIGS. 20A and 20B. The outside surface of the movable central piece 16 is at least partially reflective.

The indentation distance detection arrangement includes two converging lenses L1 and L2; a beam splitter BS1; a light source LS for emitting a beam of light having a width w; and a light detector LD responsive to the diameter of a reflected beam impinging on a surface thereof.

FIG. 20A illustrates the alternative embodiment prior to actuation of the movable central piece 16. Prior to actuation, the patient is aligned with the indentation distance detection arrangement so that the outer surface of the movable central piece 16 is located at the focal point of the converging lens L2. When the movable central piece 16 is so located, the beam of light from the light source LS strikes the beam splitter BS and is deflected through the converging lens L1 to impinge as a point on the reflective outer surface of the movable central piece 16. The reflective outer surface of the movable central piece 16 then reflects this beam of light back through the converging lens L1, through the beam splitter BS, and then through the converging lens L2 to strike a surface of the light detector LD. Preferably, the light detector LD is located at the focal point of the converging lens L2 so that the reflected beam impinges on a surface of the light detector LD as a point of virtually zero diameter when the outer surface of the movable central piece remains at the focal point of the converging lens L1.

Preferably, the indentation distance detection arrangement is connected to a display device so as to generate an indication of zero displacement when the outer surface of the movable central piece 16 has yet to be displaced, as shown in FIG. 20A.

By subsequently actuating the movable central piece 16 using an actuating device (preferably, similar to the actuating devices described above), the outer surface of the movable central piece 16 moves progressively away from the focal point of the converging lens L1, as illustrated in FIG. 20B. As a result, the light beam impinging on the reflective outer surface of the movable central piece 16 has a progressively increasing diameter. This progressive increase in diameter is proportional to the displacement from the focal point of the converging lens L1. The resulting reflected beam therefore has a diameter proportional to the displacement and passes back through the converging lens L1, through the beam splitter BS, through the converging lens C2 and then strikes the surface of the light detector LD with a diameter proportional to the displacement of the movable central piece 16. Since the light detector LD is responsive, as indicated above, to the diameter of the reflected light beam, any displacement of the movable central piece 16 causes a proportional change in output from the light detector LD.

Preferably, the light detector LD is a photoelectric converter connected to the aforementioned display device and capable of providing an output voltage proportional to the diameter of the reflected light beam impinging upon the light detector LD. The display device therefore provides a visual indication of displacement based on the output voltage from the light detector LD.

Alternatively, the output from the light detector LD may be connected to an arrangement, as described above, for providing an indication of intraocular pressure based on the displacement of the movable central piece 16.

Additional Capabilities

Generally, the present apparatus and method makes it possible to evaluate intraocular pressure, as indicated above, as well as ocular rigidity, eye hydrodynamics such as outflow facility and inflow rate of eye fluid, eye hemodynamics such as the pressure in the episcleral veins and the pulsatile ocular blood flow, and has also the ability to artificially increase intraocular pressure, as well as the continuous recording of intraocular pressure.

With regard to the measurement of intraocular pressure by applanation, the foregoing description sets forth several techniques for accomplishing such measurement, including a variable force technique wherein the force applied against the cornea varies with time. It is understood, however, that a variable area method can also be implemented.

The apparatus can evaluate the amount of area applanated by a known force. The pressure is calculated by dividing the force by the amount of area that is applanated. The amount of area applanated is determined using the optical means and/or filters previously described.

A force equivalent to placing 5 gram of weight on the cornea, for example, will applanate a first area if the pressure is 30 mmHg, a second area if the pressure is 20 mmHg, a third area if the pressure is 15 mmHg and so on. The area applanated is therefore indicative of intraocular pressure.

Alternatively, intraocular pressure can be measured using a non-rigid interface and general applanation techniques. In this embodiment, a flexible central piece enclosed by the magnet of the movable central piece is used and the transparent part of the movable central piece acts like a micro-balloon. This method is based on the principle that the interface between two spherical balloons of unequal radius will be flat if the pressures in the two balloons are equal. The central piece with the balloon is pressed against the eye until the eye/central piece interface is planar as determined by the aforementioned optical means.

Also, with regard to the previously described arrangement which measures intraocular pressure by indentation, an alternative method can be implemented with such an embodiment wherein the apparatus measures the force required to indent the cornea by a predetermined amount. This amount of indentation is determined by optical means as previously described. The movable central piece is pressed against the cornea to indent the cornea, for example, 0.5 mm (though it is understood that virtually any other depth can be used). Achievement of the predetermined depth is detected by the previously described optical means and filters. According to tables, the intraocular pressure can be determined thereafter from the force.

Yet another technique which the present invention facilitates use of is the ballistic principle. According to the ballistic principle, a parameter of a collision between the known mass of the movable central piece and the cornea is measured. This measured parameter is then related theoretically or experimentally to the intraocular pressure. The following are exemplary parameters:

Impact Acceleration

The movable central piece is directed at the cornea at a well defined velocity. It collides with the cornea and, after a certain time of contact, bounces back. The time-velocity relationships during and after impact can be studied. The applanating central piece may have a spring connecting to the rigid annular member of the contact device. If the corneal surface-is-hard, the impact time will be short. Likewise, if the corneal surface is soft the impact time will be longer. Optical sensors can detect optically the duration of impact and how long it takes for the movable central piece to return to its original position.

Impact Duration

Intraocular pressure may also be estimated by measuring the duration of contact of a spring driven movable central piece with the eye. The amount of time that the cornea remains flattened can be evaluated by the previously described optical means.

Rebound Velocity

The distance traveled per unit of time after bouncing is also indicative of the rebound energy and this energy is proportional to intraocular pressure.

Vibration Principle

The intraocular pressure also can be estimated by measuring the frequency of a vibrating element in contact with the contact device and the resulting changes in light reflection are related to the pressure in the eye.

Time

The apparatus of the present invention can also be used, as indicated above, to measure the time that it takes to applanate the cornea. The harder the cornea, the higher the intraocular pressure and thus the longer it takes to deform the cornea. On the other hand, the softer the cornea, the lower the intraocular pressure and thus the shorter it takes to deform the cornea. Thus, the amount of time that it takes to deform the cornea is proportional to the intraocular pressure.

Additional uses and capabilities of the present invention relate to alternative methods of measuring outflow facility (tonography). These alternative methods include the use of conventional indentation techniques, constant depth indentation techniques, constant pressure indentation techniques, constant pressure applanation techniques, constant area applanation techniques, and constant force applanation techniques.

1. Conventional Indentation

When conventional indentation techniques are utilized, the movable central piece of the present invention is used to indent the cornea and thereby artificially increase the intraocular pressure. This artificial increase in intraocular pressure forces fluid out of the eye more rapidly than normal. As fluid leaves the eye, the pressure gradually returns to its original level. The rate at which the intraocular pressure falls depends on how well the eye's drainage system is functioning. The drop in pressure as a function of time is used to calculated the C value or coefficient of outflow facility. The C value is indicative of the degree to which a change in intraocular pressure will cause a change in the rate of fluid outflow. This, in turn, is indicative of the resistance to outflow provided by the eye's drainage system. The various procedures for determining outflow facility are generally known as tonography and the C value is typically expressed in terms of microliters per minute per millimeter of mercury. The C value is determined by raising the intraocular pressure using the movable central piece of the contact device and observing the subsequent decay in intraocular pressure with respect to time. The elevated intraocular pressure increases the rate of aqueous outflow which, in turn, provides a change in volume. This change in volume can be calculated from the Friedenwald tables which correlate volume change to pressure changes. The rate of volume decrease equals the rate of outflow. The change in intraocular pressure during the tonographic procedure can be computed as an arithmetical average of pressure increments for successive 2 minute intervals. The C value is derived then from the following equation: $C=\Delta V/t*(Pave-Po)$, in which t is the duration of the procedure, Pave is the average pressure elevation during the test and can be measured, Po is the initial pressure and it is also measured, and $\Delta V$ is difference between the initial and final volumes and can be obtained from known tables. The Flow (AF@) of fluid is then calculated using the formula: $F=C*(Po-Pv)$, in which Pv is the pressure in the episcleral veins which can be measured and generally has a constant value of 10.

2. Constant Depth Indentation

When constant depth indentation techniques are utilized, the method involves the use of a variable force which is necessary to cause a certain predetermined amount of indentation in the eye. The apparatus of the present invention is therefore configured so as to measure the force required to indent the cornea by a predetermined amount. This amount of indentation may be detected using optical means as previously described. The movable central piece is pressed against the cornea to indent the eye, for example, by approximately 0.5 mm. The amount of indentation is detected by the optical means and filters previously described. With the central piece indenting the cornea using a force equivalent to a weight of 10 grams, a 0.5 mm indentation will be achieved under normal pressure conditions (e.g., intraocular pressure of 15 mm Hg) and assuming there is an average corneal curvature. With that amount of indentation and using standard dimensions for the central piece, 2.5 mm$^3$ of fluid will be displaced. The force recorded by the present invention undergoes a slow decline and it levels off at a more or less steady state value after 2 to 4 minutes. The decay in pressure is measured based on the difference between the value of the first indentation of the central piece and the final level achieved after a certain amount of time. The pressure drop is due to the return of pressure to its normal value, after it has been artificially raised by the indentation caused by the movable central piece. A known normal value of decay is used as a reference and is compared to the values obtained. Since the foregoing provides a continuous recording of pressure overtime, this method can be an important tool for physiological research by showing, for example, an increase in pressure during forced expiration. The pulse wave and pulse amplitude can also be evaluated and the pulsatile blood flow calculated.

3. Constant Pressure Indentation

When constant pressure indentation techniques are utilized, the intraocular pressure is kept constant by increasing the magnetic field and thereby increasing the force against the cornea as fluid leaks out of the eye. At any constant pressure, the force and rate of outflow are linearly related according to the Friedenwald tonometry tables. The intraocular pressure is calculated using the same method as described for conventional indentation tonometry. The volume displacement is calculated using the tonometry tables. The facility of outflow (C) may be computed using two different techniques. According to the first technique, C can be calculated from two constant pressure tonograms at different pressures according to the equation, $C=\{[(\Delta V_1/t_1)-(\Delta V_2/t_2)]/(P_1-P_2)\}$, in which 1 corresponds to a measurement at a first pressure and 2 corresponds to a measurement at a second pressure (which is higher than the first pressure). The second way to calculate C is from one constant pressure tonogram and an independent measure of intraocular pressure using applanation tonometry ($P_a$), in $C=[(\Delta V/t)/(P-P_a-\Delta P_e)]$, where $\Delta P_e$ is a correction factor for rise in episcleral venous pressure with indentation tonometry and P is the intraocular pressure obtained using indentation tonometry.

4. Constant Pressure Applanation

When constant pressure applanation techniques are utilized, the intraocular pressure is kept constant by increasing the magnetic field and thus the force as fluid leaks out of the eye. If the cornea is considered to be a portion of a sphere, a mathematical formula relates the volume of a spherical segment to the radius of curvature of the sphere and the radius of the base of the segment. The volume displaced is calculated based on the formula $V=A^2/(4*\pi*R)$, in which V is volume, A is the area of the segment base, and R is the radius of curvature of the sphere (this is the radius of curvature of the cornea). Since A=weight/pressure, then $V=W^2/(4*\pi*R*P^2)$. The weight is constituted by the force in the electromagnetic field, R is the curvature of the cornea and can be measured with a keratometer, P is the pressure in the eye and can be measured using the same method as described for conventional applanation tonometry. It is therefore possible to calculate the volume displaced and the C value or outflow facility. The volume displaced, for example, can be calculated at 15 second intervals and is plotted as a function of time.

5. Constant Area Applanation

When constant area applanation techniques are utilized, the method consists primarily of evaluating the pressure decay curve while the flattened area remains constant. The aforementioned optical applanation detecting arrangements can be used in order to keep constant the area flattened by the movable central piece. The amount of force necessary to keep the flattened area constant decreases and this decrease is registered. The amount of volume displaced according to the different areas of applanation is known. For instance, a 5 mm applanating central piece displaces 4.07 mm$^3$ of volume for the average corneal radius of 7.8 mm. Using the formula $\Delta V/\Delta t=1/(R*\Delta P)$, it is possible to calculate R which is the reciprocal of C. Since a continuous recording of pressure over time is provided, this method can be an important-tool for research and evaluation of blood flow.

6. Constant Force Applanation

When constant force applanation techniques are utilized, the same force is constantly applied and the applanated area is measured using any of the aforementioned optical applanation detection arrangements. Once the area flattened by a known force is measured, the pressure can be calculated by dividing the force by the amount of area that is applanated. As fluid leaves the eye the amount of area applanated increases with time. This method consists primarily of evaluating a resulting area augmentation curve while the constant force is applied. The amount of volume displaced according to the different areas of applanation is known. Using the formula $\Delta V/\Delta t=1/(R*\Delta P)$, it is possible to calculate R which is the reciprocal of C.

Still additional uses of the present invention relate to detecting the frequency response of the eye, using indentation tonometry. In particular, if an oscillating force is applied using the movable central piece 16, the velocity of the movable central piece 16 is indicative of the eye's frequency response. The system oscillates at the resonant frequency determined primarily by the mass of the movable central piece 16. By varying the frequency of the force and by measuring the response, the intraocular pressure can be evaluated. The evaluation can be made by measuring the resonant frequency and a significant variation in resonant frequency can be obtained as a function of the intraocular pressure.

The present invention may also be used with the foregoing conventional indentation techniques, but where the intraocular pressure used for calculation is measured using applanation principles. Since applanation virtually does not disturb the hydrodynamic equilibrium because it displaces a very small volume, this method can be considered more accurate than intraocular pressure measurements-made using traditional indentation techniques.

Another use of the present invention involves a time related way of measuring the resistance to outflow. In particular, the resistance to outflow is detected by measuring the amount of time necessary to transfigure the cornea with either applanation or indentation. The time necessary to displace, for example, 5 microliters of eye fluid would be 1 second for normal patients and above 2 seconds for glaucoma-stricken individuals.

Yet another use of the present invention involves measuring the inflow of eye fluid. In particular, this measurement is made by applying the formula $F=\Delta P/R$, in which $\Delta P$ is $P-P_v$, and P is the steady state intraocular pressure and $P_v$ is the episcleral venous pressure which, for purposes of calculation, is considered constant at 10. R is the resistance to outflow, which is the reciprocal of C that can be calculated. F, in units of volume/min, can then be calculated.

The present invention is also useful at measuring ocular rigidity, or the distensibility of the eye in response to an increased intraocular pressure. The coefficient of ocular rigidity can be calculated using a nomogram which is based on two tonometric readings with different weights. A series of conversion tables to calculate the coefficient of ocular rigidity was developed by Friedenwald. The technique for determining ocular rigidity is based on the concept of differential tonometry, using two indentation tonometric readings with different weights or more accurately, using one indentation reading and one applanation reading and plotting these readings on the nomogram. Since the present invention can be used to measure intraocular pressure using both applanation and indentation techniques, a more accurate evaluation of the ocular rigidity can be achieved.

Measurements of intraocular pressure using the apparatus of the present invention can also be used to evaluate hemodynamics, in particular, eye hemodynamics and pulsatile ocular blood flow. The pulsatile ocular blood flow is the component of the total ocular arterial inflow that causes a rhythmic fluctuation of the intraocular pressure. The intraocular pressure varies with each pulse due to the pulsatile influx of a bolus of arterial blood into the eye with each heartbeat. This bolus of blood enters the intraocular arteries with each heartbeat causing a temporary increase in the intraocular pressure. The period of inflow causes a stretching of the eye walls with a concomitant increase in pressure followed by a relaxation to the previous volume and a return to the previous pressure as the blood drains from the eye. If this process of expansion during systole (contraction of the heart) and contraction during diastole (relaxation of the heart) occurs at a certain pulse rate, then the blood flow rate would be the incremental change in eye volume times the pulse rate.

The fact that intraocular pressure varies with time according to the cardiac cycle is the basis for measuring pulsatile ocular blood flow. The cardiac cycle is approximately in the order of 0.8 Hz. The present invention can measure the time variations of intraocular pressure with a frequency that is above the fundamental human heart beat frequency allowing the evaluation and recording of intraocular pulse. In the normal human eye, the intraocular pulse has a magnitude of approximately 3 mm Hg and is practically synchronous with the cardiac cycle.

As described, measurements of intraocular pressure show a time variation that is associated with the pulsatile component of arterial pressure. Experimental results provide means of transforming ocular pressure changes into eye volume changes. Each bolus of blood entering the eye increases the ocular volume and the intraocular pressure. The observed changes in pressure reflect the fact that the eye volume must change to accommodate changes in the intraocular blood volume induced by the arterial blood pulse. This pulse volume is small relative to the ocular volume, but because the walls of the eye are stiff, the pressure increase required to accommodate the pulse volume is significant and can be measured. Therefore, provided that the relationship between the increased intraocular pressure and increased ocular volume is known, the volume of the bolus of fluid can be determined. Since this relationship between pressure change and volume change has been well established (Friedenwald 1937, McBain 1957, Ytteborg 1960, Eisenlohr 1962, McEwen 1965), the pressure measurements can be used to obtain the volume of a bolus of blood and thereby determine the blood flow.

The output of the tonometer for the instantaneous pressure can be converted into instantaneous change in eye volume as a function of time. The time derivative of the change in ocular volume is the net instantaneous pulsatile component of the ocular blood flow. Under these conditions, the rate of pulsatile blood flow through the eye can be evaluated from the instantaneous measurement of intraocular pressure. In order to rapidly quantify and analyze the intraocular pulse, the signal from the tonometer may be digitalized and fed into a computer.

Moreover, measurements of intraocular pressure can be used to obtain the intraocular volume through the use of an independently determined pressure-volume relationship such as with the Friedenwald equation (Friedenwald, 1937). A mathematical model based on experimental data from the pressure volume relationship (Friedenwald 1937, McBain 1957, Eisenlohr 1962, McEwen 1965) can also be used to convert a change in ocular pressure into a change in ocular volume.

In addition, a model can also be constructed to estimate the ocular blood flow from the appearance of the intraocular pressure waveform. The flow curve is related to parameters that come from the volume change curve. This curve is indirectly measured since the intraocular pressure is the actual measured quantity which is transformed into volume change through the use of the measured pressure-volume relation. The flow is then computed by taking the change in volume Vmax−Vmin multiplied by a constant that is related to the length of the time interval of the inflow and the total pulse length. Known mathematical calculations can be used to evaluate the pulsatile component of the ocular blood flow. Since the present invention can also be used to measure the ocular rigidity, this parameter of coefficient of ocular rigidity can be used in order to more precisely calculate individual differences in pulsatile blood flow.

Moreover, since the actuation apparatus 6 and contact device 2 of the present invention preferably include transparent portions, the pulsatile blood flow can be directly evaluated optically to quantify the change in size of the vessels with each heart beat. A more precise evaluation of blood flow therefore can be achieved by combining the changes in intraocular pulse with changes in vessel diameter which can be automatically measured optically.

A vast amount of data about the vascular system of the eye and central nervous system can be obtained after knowing the changes in intraocular pressure over time and the amount of pulsatile ocular blood flow. The intraocular pressure and intraocular pulse are normally symmetrical in pairs of eyes. Consequently, a loss of symmetry may serve as an early sign of ocular or cerebrovascular disease. Patients afflicted with diabetes, macular degeneration, and other vascular disorders may also have a decreased ocular blood flow and benefit from evaluation of eye hemodynamics using the apparatus of the present invention.

The present invention may also be used to artificially elevate intraocular pressure. The artificial elevation of intraocular pressure is an important tool in the diagnosis and prognosis of eye and brain disorders as well as an important tool for research.

Figure 21:
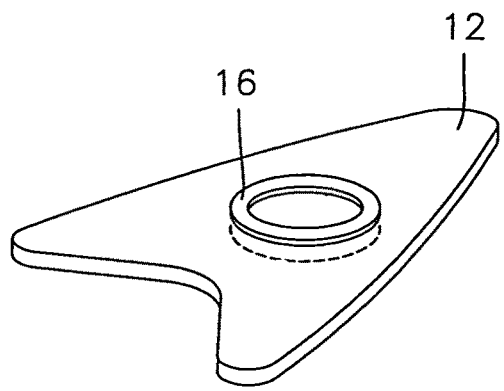
FIGS. 21 and 22 schematically illustrate embodiments of the present invention which facilitate placement of the contact device on the sclera of the eye.
Figure 22:
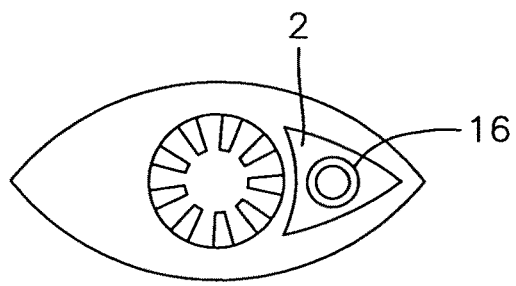

Artificial elevation of intraocular pressure using the present invention can be accomplished in different ways. According to one way, the contact device of the present invention is modified in shape for placement on the sclera (white of the eye). This arrangement, which will be described hereinafter, is illustrated in FIGS. 21-22, wherein the movable central piece 16 may be larger in size and is preferably actuated against the sclera in order to elevate the intraocular pressure. The amount of indentation can be detected by the optical detection system previously described.

Another way of artificially increasing the intraocular pressure is by placing the contact device of the present invention on the cornea in the same way as previously described, but using the movable central piece to apply a greater amount of force to achieve deeper indentation. This technique advantageously allows visualization of the eye while exerting the force, since the movable central portion of the contact device is preferably transparent. According to this technique, the size of the movable central piece can also be increased to indent a larger area and thus create a higher artificial increase of intraocular pressure. Preferably, the actuation apparatus also has a transparent central portion, as indicated above, to facilitate direct visualization of the eye and retina while the intraocular pressure is being increased. When the intraocular pressure exceeds the ophthalmic arterial diastolic pressure, the pulse amplitude and blood flow decreases rapidly. Blood flow becomes zero when the intraocular pressure is equal or higher than the ophthalmic systolic pressure. Thus, by allowing direct visualization of the retinal vessels, one is able to determine the exact moment that the pulse disappears and measure the pressure necessary to promote the cessation of the pulse which, in turn, is the equivalent of the pulse pressure in the ophthalmic artery. The present invention thus allows the measurement of the pressure in the arteries of the eye.

Also, by placing a fixation light in a back portion of the actuation apparatus and asking the patient to indicate when he/she can no longer see the light, one can also record the pressure at which a patient's vision ceases. This also would correspond to the cessation of the pulse in the artery of the eye. The pressure in which vessels open can also be determined by increasing intraocular pressure until the pulse disappears and then gradually decreasing the intraocular pressure until the pulse reappears. Thus, the intraocular pressure necessary for vessels to open can be evaluated.

It is important to note that the foregoing measurements can be performed automatically using an optical detection system, for example, by aiming a light beam at the pulsating blood vessel. The cessation of pulsation can be optically recognized and the pressure recorded. An attenuation of pulsations can also be used as the end point and can be optically detected. The apparatus also allows direct visualization of the papilla of the optic nerve while an increased intraocular pressure is produced. Thus, physical and chemical changes occurring inside the eye due to the artificial increase in intraocular pressure may be evaluated at the same time that pressure is measured.

Advantageously, the foregoing, test can be performed on patients with media opacities that prevent visualization of the back of the eye. In particular, the aforementioned procedure wherein the patient indicates when vision ceases is particular useful in patients with media opacities. The fading of the peripheral vision corresponds to the diastolic pressure and fading of the central vision corresponds to the systolic pressure.

The present invention, by elevating the intraocular pressure, as indicated above and by allowing direct visualization of blood vessels in the back of the eye, may be used for tamponade (blockade of bleeding by indirect application of pressure) of hemorrhagic processes such as those which occur, for example, in diabetes and macular degeneration. The elevation of intraocular pressure may also be beneficial in the treatment of retinal detachments.

As yet another use of the present invention, the aforementioned apparatus also can be used to measure outflow pressure of the eye-fluid. In order to measure outflow pressure in the eye fluid, the contact device is placed on the cornea and a measurable pressure is applied to the cornea. The pressure causes the aqueous vein to increase in diameter when the pressure in the cornea equals the outflow pressure. The pressure on the cornea is proportional to the outflow pressure. The flow of eye fluid out of the eye is regulated according to Poiseuille's Law for laminar currents. If resistance is inserted into the formula, the result is a formula similar to Ohm's Law. Using these known formulas, the rate of flow (volume per time) can be determined. The change in the diameter of the vessel which is the reference point can be detected manually by direct observation and visualization of the change in diameter or can be done automatically using an optical detection system capable of detecting a change in reflectivity due to the amount of fluid in the vein and the change in the surface area. The actual cross-section of the vein can be detected using an optical detection system.

The eye and the brain are hemodynamically linked by the carotid artery and the autonomic nervous system. Pathological changes in the carotid, brain, heart, and the sympathetic nervous system can secondarily affect the blood flow to the eye. The eye and the brain are low vascular resistance systems with high reactivity. The arterial flow to the brain is provided by the carotid artery. The ophthalmic artery branches off of the carotid at a 90 degree angle and measures approximately 0.5 mm in diameter in comparison to the carotid which measures 5 mm in diameter. Thus, most processes that affect the flow to the brain will have a profound effect on the eye. Moreover, the pulsation of the central retinal artery may be used to determine the systolic pressure in the ophthalmic artery, and due to its anatomic relationship with the cerebral circulatory system, the pressure in the brain's vessels can be estimated. Total or partial occlusion of the vascular system to the brain can be determined by evaluating the ocular blood flow. There are numerous vascular and nervous system lesions that alter the ocular pulse amplitude and/or the intraocular pressure curve of the eye. These pathological situations may produce asymmetry of measurements between the two eyes and/or a decrease of the central retinal artery pressure, decrease of pulsatile blood flow and alter the pulse amplitude.

An obstruction in the flow in the carotid (cerebral circulation) can be evaluated by analyzing the ocular pulse amplitude and area, pulse delay and pulse width, form of the wave and by harmonic analysis of the ocular pulse.

The eye pulsation can be recorded optically according to the change in reflection of the light beam projected to the cornea. The same system used to record distance traveled by the movable central piece during indentation can be used on the bare cornea to detect the changes in volume that occurs with each pulsation. The optical detection system records the variations in distance from the surface of the cornea that occurs with each heart beat. These changes in the position of the cornea are induced by the volume changes in the eye. From the pulsatile character of these changes, the blood flow to the eye can be calculated.

With the aforementioned technique of artificial elevation of pressure, it is possible to measure the time necessary for the eye to recover to its baseline and this recovery time is an indicator of the presence of glaucoma and of the coefficient of outflow facility.

Figure 23:
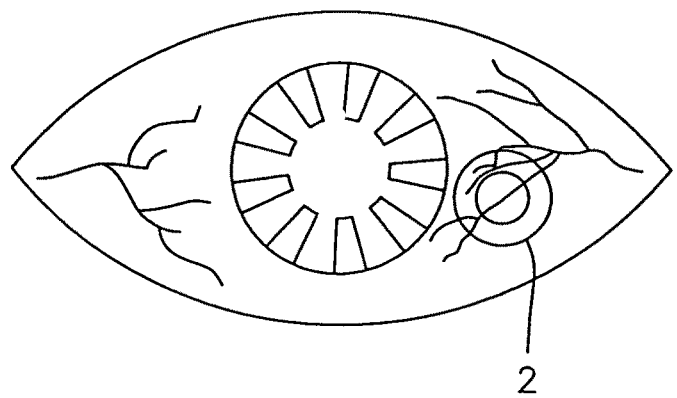
FIG. 23 is a plan view of an alternative contact device which may be used to measure episcleral venous pressure in accordance with the present invention.

The present invention may also be used to measure pressure in the vessels on the surface of the eye, in particular the pressure in the episcleral veins. The external pressure necessary to collapse a vein is utilized in this measurement. The method involves applying a variable force over a constant area of conjunctive overlying the episcleral vein until a desired end point is obtained. The pressure is applied directly onto the vessel itself and the preferred end point is when the vessel collapses. However, different end points may be used, such as blanching of the vessel which occurs prior to the collapse. The pressure of the end point is determined by dividing the force applied by the area of the applanating central piece in a similar way as is used for tonometry. The vessel may be observed through a transparent applanating movable central piece using a slit-lamp biomicroscope. The embodiment for this technique preferably includes a modified contact device which fits on the sclera (FIG. 23). The preferred size of the tip ranges from 250 micrometers to 500 micrometers. Detection of the end point can be achieved either manually or automatically.

According to the manual arrangement, the actuation apparatus is configured for direct visualization of the vessel through a transparent back window of the actuation apparatus, and the time of collapse is manually controlled and recorded. According to an automatic arrangement, an optical detection system is configured so that, when the blood stream is no longer visible, there is a change in a reflected light beam in the same way as described above for tonometry, and consequently, the pressure for collapse is identifiable automatically. The end point marking in both situations is the disappearance of the blood stream, one detected by the operator's vision and the other detected by an optical detection system. Preferably, in both cases, the contact device is designed in a way to fit the average curvature of the sclera and the movable central piece, which can be a rigid or flexible material, is used to compress the vessel.

The present invention may also be used to provide real-time recording of intraocular pressure. A built-in single chip microprocessor can be made responsive to the intraocular pressure measurements over time and can be programmed to create and display a curve relating pressure to time. The relative position of the movable central piece can be detected, as indicated above, using an optical detection system and the detected position in combination with information regarding the amount of current flowing through the coil of the actuation apparatus can be rapidly collected and analyzed by the microprocessor to create the aforementioned curve.

It is understood that the use of a microprocessor is not limited to the arrangement wherein curves are created. In fact, microprocessor technology may be used to create at least the aforementioned calculation unit 10 of the present invention. A microprocessor preferably evaluates the signals and the force that is applied. The resulting measurements can be recorded or stored electronically in a number of ways. The changes in current over time, for example, can be recorded on a strip-chart recorder. Other methods of recording and storing the data can be employed. Logic microprocessor control technology can also be used in order to better evaluate the data.

Still other uses of the present invention relate to evaluation of pressure in deformable materials in industry and medicine. One such example is the use of the present invention to evaluate soft tissue, such as organs removed from cadavers.

Cadaver dissection is a fundamental method of learning and studying the human body. The deformability of tissues such as the brain, liver, spleen, and the like, can be measured using the present invention and the depth of indentation can be evaluated. In this regard, the contact device of the present invention can be modified to fit over the curvature of an organ. When the movable central piece rests upon a surface, it can be actuated to project into the surface a distance which is inversely proportional to the tension of the surface and rigidity of the surface to deformation.

The present invention can also be used to evaluate and quantify the amount of cicatrization, especially in burn scar therapy. The present, invention can be used to evaluate the firmness of the scar in comparison to normal skin areas. The scar skin tension is compared to the value of normal skin tension. This technique can be used to monitor the therapy of patients with burn scars allowing a numerical quantification of the course of cicatrization. This technique can also be used as an early indicator for the development of hypertrophic (thick and elevated) scarring. The evaluation of the tissue pressure and deformability in a variety of conditions such as: a) lymphoedema b) post-surgical effects, such as with breast surgery, and c) endoluminal pressures of hollow organs, is also possible with the apparatus. In the above cases, the piston-like arrangement provided by the contact device does not have to be placed in an element that is shaped like a contact lens. To the contrary, any shape and size can be used, with the bottom surface preferably being flat and not curved like a contact lens.

Yet another use of the present invention relates to providing a bandage lens which can be used for extended periods of time. Glaucoma and increased intraocular pressure are leading causes for rejection of corneal transplants. Many conventional tonometers in the market are unable to accurately measure intraocular pressure in patients with corneal disease. For patients with corneal disease and who have recently undergone corneal transplant, a thinner and larger contact device is utilized and this contact device can be used for a longer period of time. The device also facilitates measurement of intraocular pressure in patients with corneal disease which require wearing of contact lenses as part of their treatment.

The present invention may also be modified to non-invasively measure infant intracranial pressure, or to provide instantaneous and continuous monitoring of blood pressure through an intact wall of a blood vessel. The present invention may also be used in conjunction with a digital pulse meter to provide synchronization with the cardiac cycle. Also, by providing a contact microphone, arterial pressure can be measured. The present invention may also be used to create a dual tonometer arrangement in one eye. A first tonometer can be defined by the contact device of the present invention applied over the cornea, as described above. The second tonometer can be defined by the previously mentioned contact device which is modified for placement on the temporal sclera. In using the dual tonometer arrangement, it is desirable to permit looking into the eye at the fundus while the contact devices are being actuated. Accordingly, at least the movable central piece of the contact device placed over the cornea is preferably transparent so that the fundus can be observed with a microscope.

Although the foregoing illustrated embodiments of the contact device generally show only one movable central piece 16 in each contact device 2, it is understood that more than one movable central piece 16 can be provided without departing from the scope and spirit of the present invention. Preferably, the multiple movable central pieces 16 would be concentrically arranged in the contact device 2, with at least one of the flexible membranes 14 interconnecting the concentrically arranged movable central pieces 16. This arrangement of multiple movable central pieces 16 can be combined with any of the aforementioned features to achieve a desired overall combination.

Although the foregoing preferred embodiments include at least one magnetically actuated movable central piece 16, it is understood that there are many other techniques for actuating the movable central piece 16. Sound or ultrasound generation techniques, for example, can be used to actuate the movable central piece. In particular, the sonic or ultrasonic energy can be directed to a completely transparent version of the movable central piece which, in turn, moves in toward the cornea in response to the application of such energy.

Similarly, the movable central piece may be provided with means for retaining a static electrical charge. In order to actuate such a movable central piece, an actuation mechanism associated therewith would create an electric field of like polarity, thereby causing repulsion of the movable central piece away from the source of the electric field.

Other actuation techniques, for example, include the discharge of fluid or gas toward the movable central piece, and according to a less desirable arrangement, physically connecting the movable central piece to a mechanical actuation device which, for example, may be motor driven and may utilize a strain gauge.

Alternatively, the contact device may be eliminated in favor of a movable central piece in an actuation apparatus. According to this arrangement, the movable central piece of the actuation apparatus may be connected to a slidable shaft in the actuation apparatus, which shaft is actuated by a magnetic field or other actuation means. Preferably, a physician applies the movable central piece of the actuation apparatus to the eye and presses a button which generates the magnetic field. This, in turn, actuates the shaft and the movable central piece against the eye. Preferably, the actuation apparatus, the shaft, and the movable central piece of the actuation apparatus are appropriately arranged with transparent portions so that the inside of the patient's eye remains visible during actuation.

Any of the above described detection techniques, including the optical detection technique, can be used with the alternative actuation techniques.

Also, the movable central piece 16 may be replaced by an inflatable bladder (not shown) disposed of the substantially rigid annular member 12. When inflated, the bladder extends out of the hole in the substantially rigid annular member 12 and toward the cornea.

Similarly, although some of the foregoing preferred embodiments utilize an optical arrangement for determining when the predetermined amount of applanation has been achieved, it is understood that there are many other techniques for determining when applanation occurs. The contact device, for example, may include an electrical contact arranged so as to make or break an electrical circuit when the movable central piece moves a distance corresponding to that which is necessary to produce applanation. The making or breaking of the electrical circuit is then used to signify the occurrence of applanation.

It is also understood that, after applanation has occurred, the time which it takes for the movable central piece 16 to return to the starting position after termination of the actuating force will be indicative of the intraocular pressure when the intraocular pressure is high, the movable central piece 16 returns more quickly to the starting position. Similarly, for lower intraocular pressures, it takes longer for the movable central piece 16 to return to its starting position. Therefore, the present invention can be configured to also consider the return time of the movable central piece 16 in determining the measured intraocular pressure.

As indicated above, the present invention may be formed with a transparent central portion in the contact device. This transparent central portion advantageously permits visualization of the inside of the eye (for example, the optic nerve) while the intraocular pressure is artificially increased using the movable central piece. Some of the effects of increased intraocular pressure on the optic nerve, retina, and vitreous are therefore readily observable through the present invention, while intraocular pressure is measured simultaneously.

With reference to FIGS. 21 and 22, although the foregoing examples describe placement of the contact device 2 on the cornea, it is understood that the contact device 2 of the present invention may be configured with a quasi-triangular shape (defined by the substantially rigid annular member) to facilitate placement of the contact device 2 on the sclera of the eye.

Figure 24:
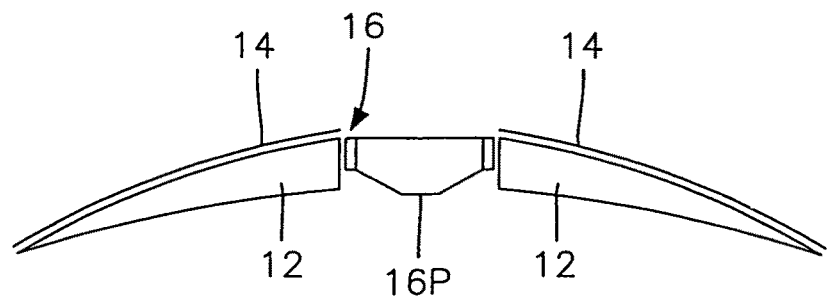
FIG. 24 is a cross-sectional view of the alternative contact device which may be used to measure episcleral venous pressure in accordance with the present invention.
Figure 27:
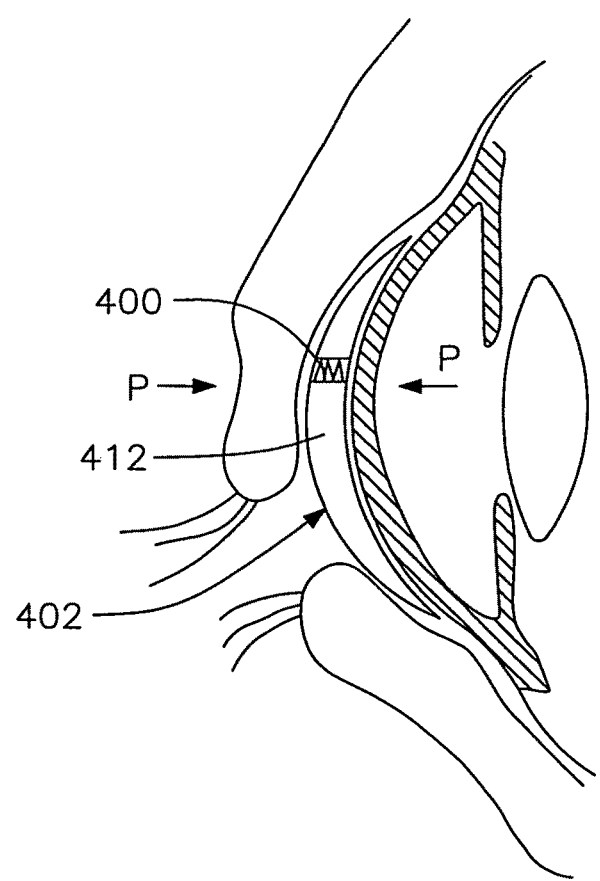
FIG. 27 schematically illustrates the alternative embodiment of FIG. 25 when located in a patient's eye.
Figure 25A:
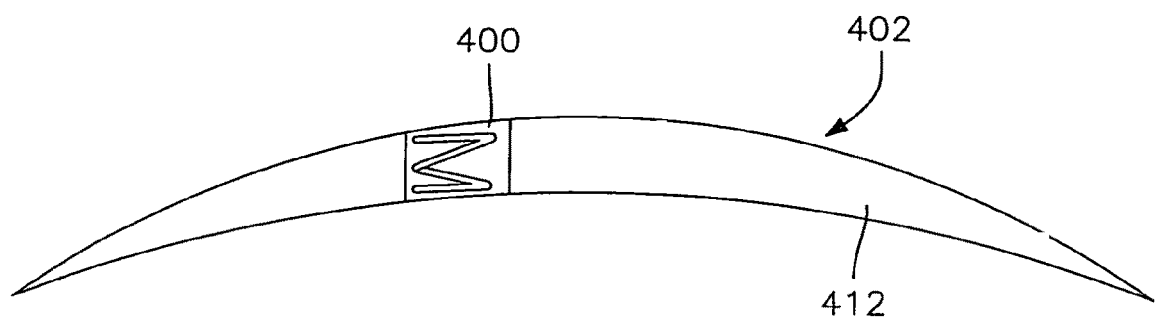
FIG. 25A is a cross-sectional view of the alternative embodiment illustrated in FIG. 25.
Figure 25:
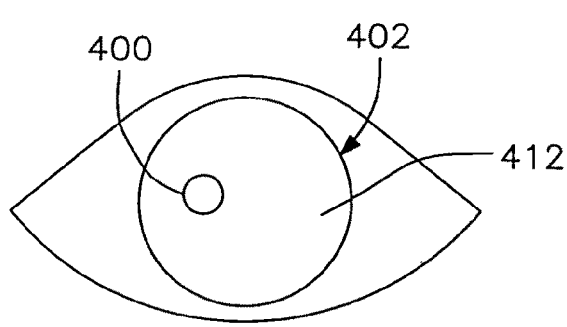
FIG. 25 schematically illustrates an alternative embodiment of the present invention, which includes a contact device with a pressure transducer mounted therein.

With reference to FIGS. 23 and 24, the contact device 2 of the present invention may be used to measure episcleral venous pressure. Preferably, when episcleral venous pressure is to be measured, the movable central piece 6 has a transparent centrally disposed frustoconical projection 16P. The embodiment illustrated FIG. 24 advantageously permits visualization of the subject in through at least the transparent central portion of the movable central piece 16.

Furthermore, as indicated above, the present invention may also be used to measure pressure in other parts of the body (for example, scar pressure in the context of plastic surgery) or on surfaces of various objects. The contact device of the present invention, therefore, is not limited to the corneal-conforming curved shape illustrated in connection with the exemplary embodiments, but rather may have various other shapes including a generally flat configuration.

Alternative Embodiment Actuated by Closure of the Eye Lid

With reference to FIGS. 25-31, an alternative embodiment of the system will now be described. The alternative apparatus and method uses the force and motion generated by the eye lid during blinking and/or closure of the eyes to act as the actuation apparatus and activate at least one transducer 400 mounted in the contact device 402 when the contact device 402 is on the cornea. The method and device facilitate the remote monitoring of pressure and other physiological events by transmitting the information through the eye lid tissue, preferably via electromagnetic waves. The information transmitted is recovered at a receiver 404 remotely placed with respect to the contact device 402, which receiver 404 is preferably mounted in the frame 408 of a pair of eye glasses. This alternative embodiment also facilitates utilization of forceful eye lid closure to measure outflow facility. The transducer is preferably a microminiature pressure-sensitive transducer 400 that alters a radio frequency signal in a manner indicative of physical pressure exerted on the transducer 400.

Although the signal response from the transducer 400 can be communicated by cable, it is preferably actively or passively transmitted in a wireless manner to the receiver 404 which is remotely located with respect to the contact device 402. The data represented by the signal response of the transducer 400 can then be stored and analyzed. Information derived from this data can also be communicated by telephone using conventional means.

According to the alternative embodiment, the apparatus comprises at least one pressure-sensitive transducer 400 which is preferably activated by eye lid closure and is mounted in the contact device 402. The contact device 402, in turn, is located on the eye. In order to calibrate the system, the amount of motion and squeezing of the contact device 402 during eye lid motion/closure is evaluated and calculated. As the upper eyelid descends during blinking, it pushes down and squeezes the contact device 402, thereby forcing the contact device 402 to undergo a combined sliding and squeezing motion.

Since normal individuals involuntarily blink approximately every 2 to 10 seconds, this alternative embodiment of the present invention provides frequent actuation of the transducer 400. In fact, normal individuals wearing a contact device 402 of this type will experience an increase in the number of involuntary blinks, and this, in turn, tends to provide quasi-continuous measurements. During sleep or with eyes closed, since there is uninterrupted pressure by the eye lid, the measurements can be taken continuously.

As indicated above, during closure of the eye, the contact device 402 undergoes a combined squeezing and sliding motion caused by the eye lid during its closing phase. Initially the upper eye lid descends from the open position until it meets the upper edge of the contact device 402, which is then pushed downward by approximately 0.5 mm to 2 mm. This distance depends on the type of material used to make the structure 412 of the contact device 402 and also depends on the diameter thereof.

When a rigid structure 412 is used, there is little initial overlap between the lid and the contact device 402. When a soft structure 412 is used, there is a significant overlap even during this initial phase of eye lid motion. After making this initial small excursion the contact device 402 comes to rest, and the eye lid then slides over the outer surface of the contact device 402 squeezing and covering it. It is important to note that if the diameter of the structure 412 is greater than the lid aperture or greater than the corneal diameter, the upper lid may not strike the upper edge of the contact device 402 at the beginning of a blink.

The movement of the contact device 402 terminates approximately at the corneo-scleral junction due to a slope change of about 13 degrees in the area of intersection between cornea (radius of 9 mm) and sclera (radius of 11.5 mm). At this point the contact device 402, either with a rigid or soft structure 412, remains immobile and steady while the eye lid proceeds to cover it entirely.

When a rigid structure 412 is used, the contact device 402 is usually pushed down 0.5 mm to 2 mm before it comes to rest. When a soft structure 412 is used, the contact device 402 is typically pushed down 0.5 mm or less before it comes to rest. The larger the diameter of the contact device 402, the smaller the motion, and when the diameter is large enough there may be zero vertical motion. Despite these differences in motion, the squeezing effect is always present, thereby allowing accurate measurements to be taken regardless of the size of the structure 412. Use of a thicker structure 412 or one with a flatter surface results in an increased squeezing force on the contact device 402.

The eye lid margin makes a re-entrant angle of about 35 degrees with respect to the cornea. A combination of forces, possibly caused by the contraction of the muscle of Riolan near the rim of the eye lid and of the orbicularis muscle, are applied to the contact device 402 by the eye lid. A horizontal force (normal force component) of approximately 20,000 to 25,000 dynes and a vertical force (tangential force component) of about 40 to 50 dynes is applied on the contact device 402 by the upper eye lid. In response to these forces, the contact device 402 moves both toward the eye and tangentially with respect thereto. At the moment of maximum closure of the eye, the tangential motion and force are zero and the normal force and motion are at a maximum.

The horizontal lid force of 20,000 to 25,000 dynes pressing the contact device 402 against the eye generates enough motion to activate the transducer 400 mounted in the contact device 402 and to permit measurements to be performed. This eye lid force and motion toward the surface of the eye are also capable of sufficiently deforming many types of transducers or electrodes which can be mounted in the contact device 402. During blinking, the eye lids are in full contact with the contact device 402 and the surface of each transducer 400 is in contact with the cornea/tear film and/or inner surface of the eye lid.

The microminiature pressure-sensitive radio frequency transducer 400 preferably consists of an endoradiosonde mounted in the contact device 402 which, in turn, is preferably placed on the cornea and is activated by eye lid motion and/or closure. The force exerted by the eye lid on the contact device 402, as indicated above, presses it against the cornea.

Figure 26:
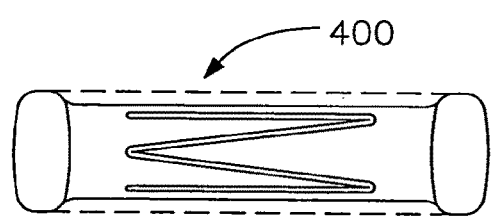
FIG. 26 is a cross-sectional view illustrating the pressure transducer of FIG. 25.

According to a preferred alternative embodiment illustrated in FIG. 26, the endoradiosonde includes two opposed matched coils which are placed within a small pellet. The flat walls of the pellet act as diaphragms and are attached one to each coil such that compression of the diaphragm by the eye lid brings the coils closer to one another. Since the coils are very close to each other, minimal changes in their separation affect their resonant frequency.

A remote grid-dip oscillator 414 may be mounted at any convenient location near the contact device 402, for example, on a hat or cap worn by the patient. The remote grid-dip oscillator 414 is used to induce oscillations in the transducer 400. The resonant frequency of these oscillations is indicative of intraocular pressure.

Briefly, the contact of the eye lid with the diaphragms forces a pair of parallel coaxial archimedean-spiral coils in the transducer 400 to move closer together. The coils constitute a high-capacitance distributed resonant circuit having a resonant frequency that varies according to relative coil spacing. When the coils approach one another, there is an increase in the capacitance and mutual inductance, thereby lowering the resonant frequency of the configuration. By repeatedly scanning the frequency of an external inductively coupled oscillating detector of the grid-dip type, the electromagnetic energy which is absorbed by the transducer 400 at its resonance is sensed through the intervening eye lid tissue.

Pressure information from the transducer 400 is preferably transmitted by radio link telemetry. Telemetry is a preferred method since it can reduce electrical noise pickup and eliminates electric shock hazards. FM (frequency modulation) methods of transmission are preferred since FM transmission is less noisy and requires less gain in the modulation amplifier, thus requiring less power for a given transmission strength. FM is also less sensitive to variations in amplitude of the transmitted signal.

Several other means and transducers can be used to acquire a signal indicative of intraocular pressure from the contact device 402. For example, active telemetry using transducers which are energized by batteries or using cells that can be recharged in the eye by an external oscillator, and active transmitters which can be powered from a biologic source can also be used.

The preferred method to acquire the signal, however, involves at least one of the aforementioned passive pressure sensitive transducers 400 which contain no internal power source and operate using energy supplied from an external source to modify the frequency emitted by the external source. Signals indicative of intraocular ocular pressure are based on the frequency modification and are transmitted to remote extra-ocular radio frequency monitors. The resonant frequency of the circuit can be remotely sensed, for example, by a grid-dip meter.

In particular, the grip-dip meter includes the aforementioned receiver 404 in which the resonant frequency of the transducer 400 can be measured after being detected by external induction coils 415 mounted near the eye, for example, in the eyeglass frames near the receiver or in the portion of the eyeglass frames which surround the eye. The use of eyeglass frames is especially practical in that the distance between the external induction coils 415 and the radiosonde is within the typical working limits thereof. It is understood, however, that the external induction coils 415, which essentially serve as a receiving antenna for the receiver 404 can be located any place that minimizes signal attenuation. The signal from the external induction coils 415 (or receiving antenna) is then received by the receiver 404 for amplification and analysis.

When under water, the signal may be transmitted using modulated sound signals because sound is less attenuated by water than are radio waves. The sonic resonators can be made responsive to changes in temperature and voltage.

Although the foregoing description includes some preferred methods and devices in accordance with the alternative embodiment of the present invention, it is understood that the invention is not limited to these preferred devices and methods. For example, many other types of miniature pressure sensitive radio transmitters can be used and mounted in the contact device, and any microminiature pressure sensor that modulates a signal from a radio transmitter and sends the modulated signal to a nearby radio receiver can be used.

Other devices such as strain gauges, preferably piezoelectric pressure transducers, can also be used on the cornea and are preferably activated by eye lid closure and blinking. Any displacement transducer contained in a distensible case also can be mounted in the contact device. In fact, many types of pressure transducers can be mounted in and used by the contact device. Naturally, virtually any transducer that can translate the mechanical deformation into electric signals is usable.

Since the eye changes its temperature in response to changes in pressure, a pressure-sensitive transducer which does not require motion of the parts can also be used, such as a thermistor. Alternatively, the dielectric constant of the eye, which also changes in response to pressure changes, can be evaluated to determine intraocular pressure. In this case, a pressure-sensitive capacitor can be used. Piezoelectric and piezo-resistive transducers, silicon strain gauges, semiconductor devices and the like can also be mounted and activated by blinking and/or closure of the eyes.

In addition to providing a novel method for performing single measurements, continuous measurements, and self-measurement of intraocular pressure during blinking or with the eyes closed, the apparatus can also be used to measure outflow facility and other physiological parameters. The inventive method and device offer a unique approach to measuring outflow facility in a physiological manner and undisturbed by the placement of an external weight on the eye.

In order to determine outflow facility in this fashion, it is necessary for the eye lid to create the excess force necessary to squeeze fluid out of the eye. Because the present invention permits measurement of pressure with the patient's eyes closed, the eye lids can remain closed throughout the procedure and measurements can be taken concomitantly. In particular, this is accomplished by forcefully squeezing the eye lids shut. Pressures of about 60 mm Hg will occur, which is enough to squeeze fluid out of the eye and thus evaluate outflow facility. The intraocular pressure will decrease over time and the decay in pressure with respect to time correlates to the outflow facility. In normal individuals, the intraocular fluid is forced out of the eye with the forceful closure of the eye lid and the pressure will decrease accordingly; however, in patients with glaucoma, the outflow is compromised and the eye pressure therefore does not decrease at the same rate in response to the forceful closure of the eye lids. The present system allows real time and continuous measurement of eye pressure and, since the signal can be transmitted through the eye lid to an external receiver, the eyes can remain closed throughout the procedure.

Telemetry systems for measuring pressure, electrical changes, dimensions, acceleration, flow, temperature, bioelectric activity, chemical reactions, and other important physiological parameters and power switches to externally control the system can be used in the apparatus of the invention. The use of integrated circuits and technical advances occurring in transducer, power source, and signal processing technology allow for extreme miniaturization of the components which, in turn, permits several sensors to be mounted in one contact device, as illustrated for example in FIG. 28.

Figure 31:
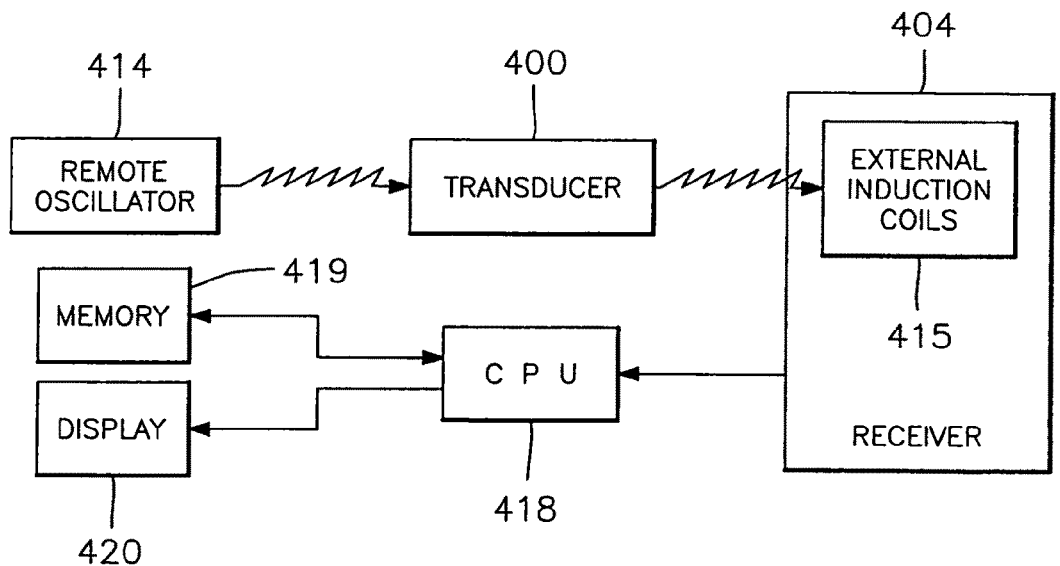
FIG. 31 is a block diagram of a preferred circuit defined by the alternative embodiment illustrated in FIG. 25.

Modern resolutions of integrated circuits are in the order of a few microns and facilitate the creation of very high density circuit arrangements. Preferably, the modern techniques of manufacturing integrated circuits are exploited in order to make electronic components small enough for placement on the eyeglass frame 408. The receiver 404, for example, may be connected to various miniature electronic components 418, 419, 420, as schematically illustrated in FIG. 31, capable of processing, storing, and even displaying the information derived from the transducer 400.

Radio frequency and ultrasonic micro-circuits are available and can be mounted in the contact device for use thereby. A number of different ultrasonic and pressure transducers are also available and can be used and mounted in the contact device. It is understood that further technological advances will occur which will permit further applications of the apparatus of the invention.

The system may further comprise a contact device for placement on the cornea and having a transducer capable of detecting chemical changes in the tear film. The system may further include a contact device for placement on the cornea and having a microminiature gas-sensitive radio frequency transducer (e.g., oxygen-sensitive). A contact device having a microminiature blood velocity-sensitive radio frequency transducer may also be used for mounting on the conjunctiva and is preferably activated by eye lid motion and/or closure of the eye lid.

The system also may comprise a contact device in which a radio frequency transducer capable or measuring the negative resistance of nerve fibers is mounted in the contact device which, in turn, is placed on the cornea and is preferably activated by eye lid motion and/or closure of the eye lid. By measuring the electrical resistance, the effects of microorganisms, drugs, poisons and anesthetics can be evaluated.

The system of the present invention may also include a contact device in which a microminiature radiation-sensitive radio frequency transducer is mounted in the contact device which, in turn, is placed on the cornea and is preferably activated by eye lid motion and/or closure of the eye lid.

In any of the foregoing embodiments having a transducer mounted in the contact device, a grid-dip meter can be used to measure the frequency characteristics of the tuned circuit defined by the transducer.

Besides using passive telemetry techniques as illustrated by the use of the above transducers, active telemetry with active transmitters and a microminiature battery mounted in the contact device can also be used.

The contact device preferably includes a rigid or flexible transparent structure 412 in which at least one of the transducers 400 is mounted in hole(s) formed in the transparent structure 412. Preferably, the transducers 400 is/are positioned so as to allow the passage of light through the visual axis. The structure 412 preferably includes an inner concave surface shaped to match an outer surface of the cornea.

Figure 29:
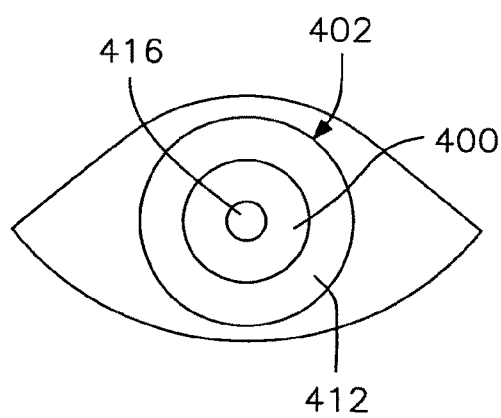
FIG. 29 illustrates an alternative embodiment utilizing a centrally disposed pressure transducer.
Figure 30:
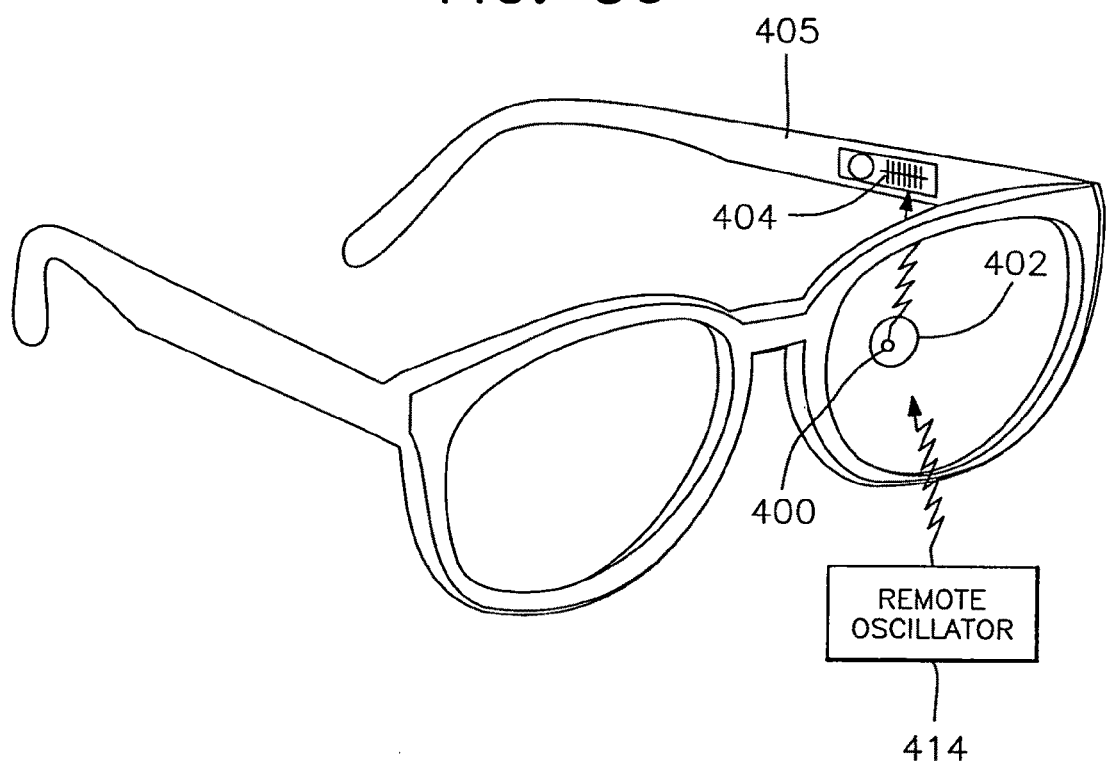
FIG. 30 illustrates a preferred mounting of the alternative embodiment to eye glass frames.

As illustrated in FIG. 29, a larger transducer 400 can be centrally arranged in the contact device 402, with a transparent portion 416 therein preserving the visual axis of the contact device 402.

The structure 412 preferably has a maximum thickness at the center and a progressively decreasing thickness toward a periphery of the structure 412. The transducers is/are preferably secured to the structure 412 so that the anterior side of each transducer 400 is in contact with the inner surface of the eye lid during blinking and so that the posterior side of each transducer 400 is in contact with the cornea, thus allowing eye lid motion to squeeze the contact device 402 and its associated transducers 400 against the cornea.

Preferably, each transducer 400 is fixed to the structure 412 in such a way that only the diaphragms of the transducers experience motion in response to pressure changes. The transducers 400 may also have any suitable thickness, including matching or going beyond the surface of the structure 412.

The transducers 400 may also be positioned so as to bear against only the cornea or alternatively only against the inner surface of the eye lid. The transducers 400 may also be positioned in a protruding way toward the cornea in such a way that the posterior part flattens a portion of the cornea upon eye lid closure. Similarly, the transducers 400 may also be positioned in a protruding way toward the inner surface of the eye lid so that the anterior part of the transducer 400 is pressed by the eye lid, with the posterior part being covered by a flexible membrane allowing interaction with the cornea upon eye lid closure.

Figure 28:
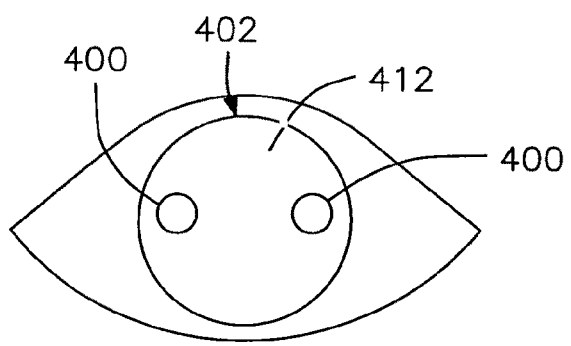
FIG. 28 illustrates an alternative embodiment wherein two pressure transducers are utilized.

A flexible membrane of the type used in flexible or hydrogel lenses may encase the contact device 402 for comfort as long as it does not interfere with signal acquisition and transmission. Although the transducers 400 can be positioned in a manner to counterbalance each other, as illustrated in FIG. 28, it is understood that a counter weight can be used to maintain proper balance.

Figure 32:
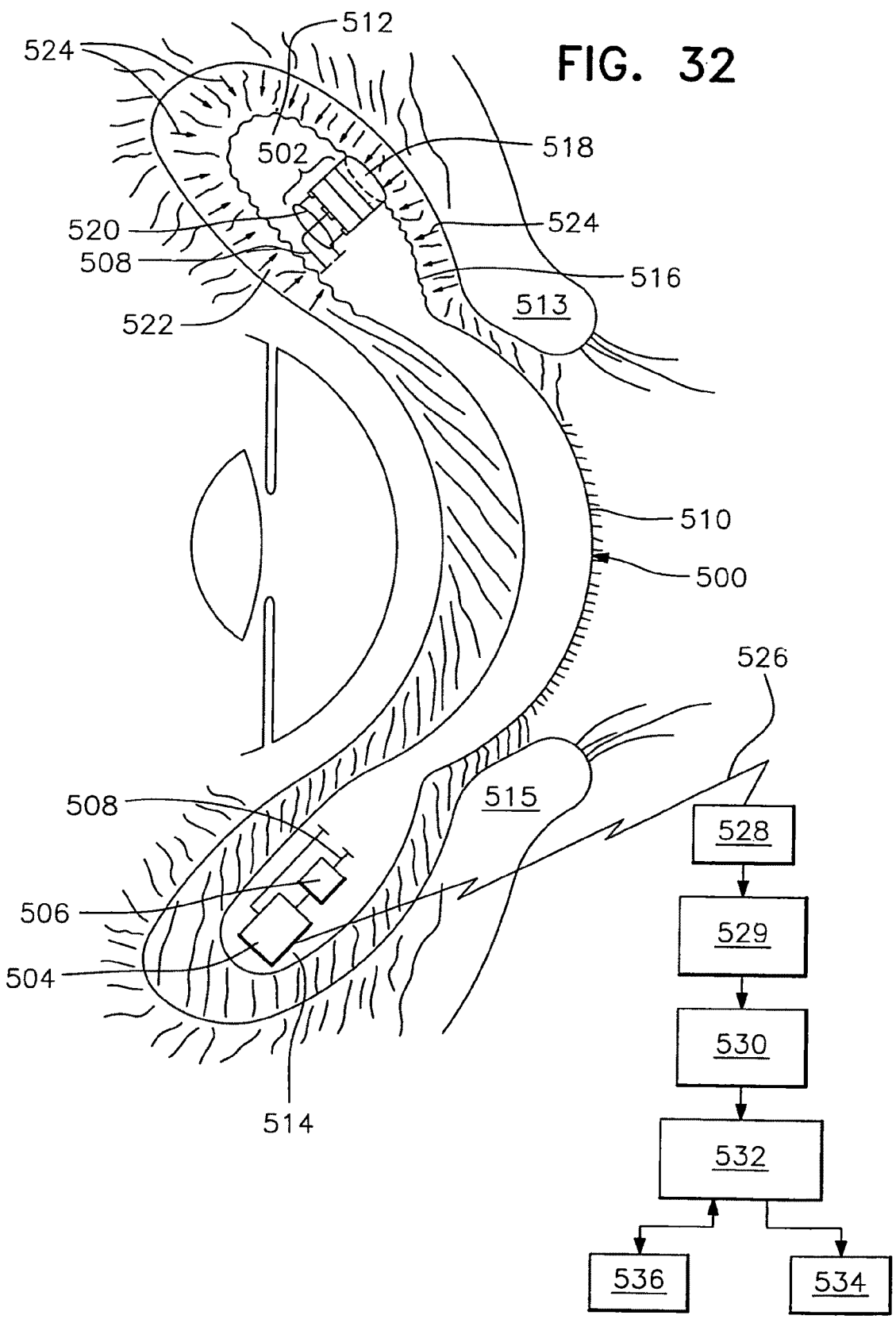
FIG. 32 is a schematic representation of a contact device situated on the cornea of an eye with lateral extensions of the contact device extending into the sclera sack below the upper and lower eye lids and illustrating schematically the reception of a signal transmitted from a transmitter to a receiver and the processes performed on the transmitted signal.

FIG. 32 illustrates the contact device 500 placed on the surface of the eye with mounted sensor 502, transmitter 504, and power source 506 which are connected by fine wire 508 (shown only partially extending from sensor 502 and from transmitter 504), encased in the contact device. The contact device shown measures approximately 24 mm in its largest diameter with its corneal portion 510 measuring approximately 11 mm in diameter with the remaining 13 mm subdivided between 8 mm of a portion 512 under the upper eyelid 513 and 5 mm of a portion 514 under the lower eyelid 515. The contact device in FIG. 32 has microprotuberances 516 in its surface which increases friction and adhesion to the conjunctiva allowing diffusion of tissue fluid from the blood vessels into the sensor selective membrane surface 518. The tissue fluid goes through membranes in the sensor and reaches an electrode 520 with generation of current proportional to the amount of analyte found in the tear fluid 522 moving in the direction of arrows 524. A transmitter 504 transmitting a modulated signal 526 to a receiver 528 with the signal 526 being amplified and filtered in amplifier and filter 529, decoded in demultiplexes 530, processed in CPU 532, displayed at monitor 534, and stored in memory 536.

Figure 33A:
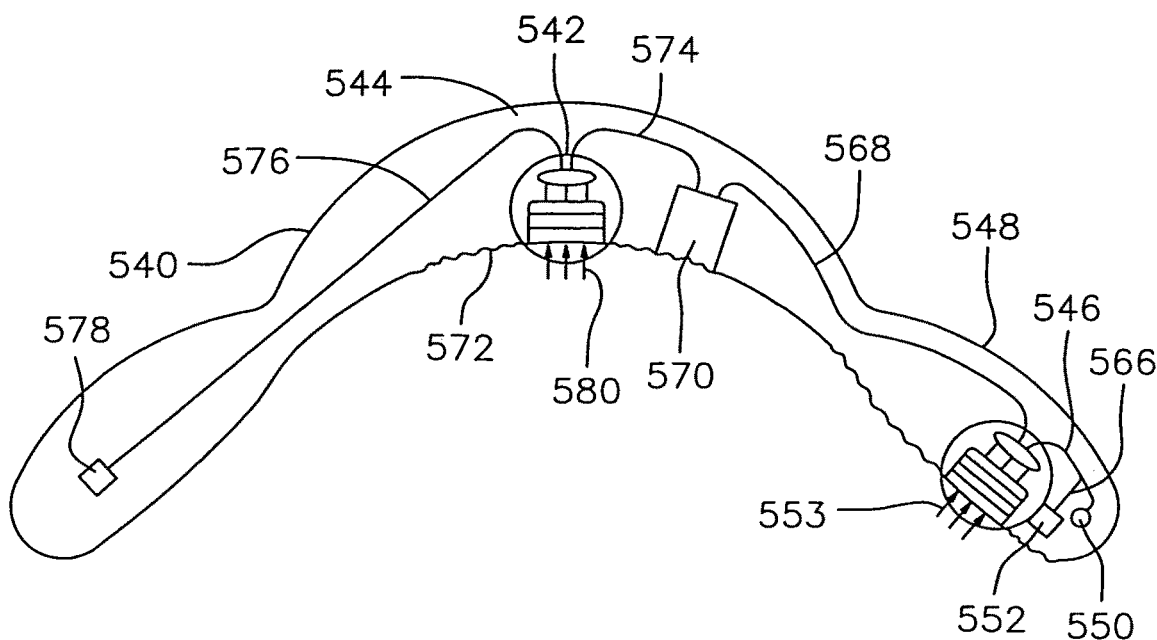
FIG. 33A is an enlarged view of the contact device shown in FIG. 32 with further enlarged portions of the contact device encircled in FIG. 33A being shown in further detail in FIGS. 33B and 33C.

The contact device 540 shown in FIG. 33A includes two sensors, one sensor 542 for detection of glucose located in the main body 544 of the contact device and a cholesterol sensor 546 located on a myoflange 548 of the contact device 540. Forming part of the contact device is a heating electrode 550 and a power source 552 next to the cholesterol sensor 546 with the heating electrode 550 increasing the local temperature with subsequent transudation of fluid in the direction of arrows 553 toward the cholesterol sensor 546.

Figure 33B:
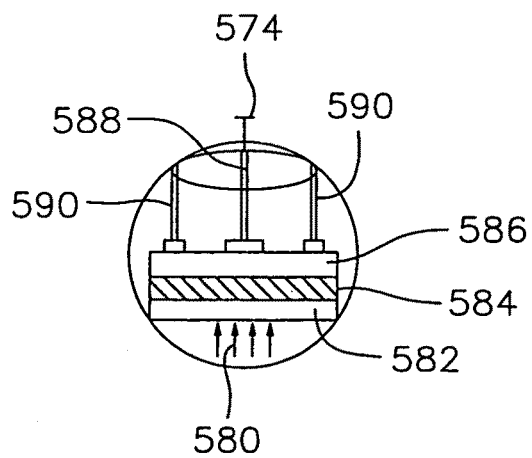
Figure 33C:
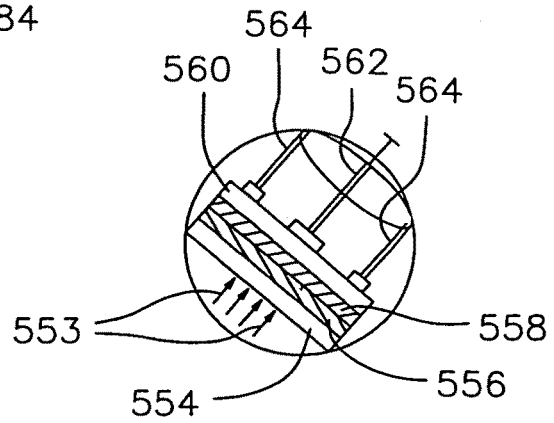

In one embodiment the cholesterol sensor shown in FIG. 33C includes an outer selectively permeable membrane 554, and mid-membranes 556, 558 with immobilized cholesterol esterase and cholesterol oxidase enzymes and an inner membrane 560 permeable to hydrogen peroxide. The external membrane 554 surface has an area preferably no greater than 300 square micrometers and an overall thickness of the multiple membrane layers is in the order of 30-40 micrometers. Covered by the inner membrane are a platinum electrode 562 and two silver electrodes 564 measuring 0.4 mm (platinum wire) and 0.15 mm (silver wire). Fine wires 566, 568 connect the cholesterol sensor 546 to the power source 552 and transmitter 570. The glucose sensor 542 includes a surrounding irregular external surface 572 to increase friction with the sensor connected by fine wires 574, 576 to the power source 578 and transmitter 570. The power source 578 is connected to the sensor in order to power the sensor 542 for operation.

The transmitter includes integrated circuits for receiving and transmitting the data with the transmitters being of ultra dense integrated hybrid circuits measuring approximately 500 microns in its largest dimension. The corneal tissue fluid diffuses in the direction of arrows 580 toward the glucose sensor 542 and reaches an outer membrane 582 permeable to glucose and oxygen followed by an immobilized glucose oxidase membrane 584 and an inner membrane 586 permeable to hydrogen peroxide. The tissue fluid then reaches the one platinum 588 and two silver 590 electrodes generating a current proportional to the concentration of glucose. The dimensions of the glucose sensor are similar to the dimensions of the cholesterol sensor.

FIG. 34 illustrates by, a block diagram, examples of signals obtained for measuring various biological variables such as glucose 600, cholesterol 602 and oxygen 604 in the manner as exemplified in FIGS. 33A-33C. A glucose signal 606, a cholesterol signal 608 and an oxygen signal 610 are generated by transducers or sensors as shown in FIGS. 33B and 33C. The signals are transmitted to a multiplexer 612 which transmits the signals as a coded signal by wire 614 to a transmitter 616. A coded and modulated signal is transmitted, as represented by line 618, by radio, light, sound, wire telephone or the like with noise suppression to a receiver 620. The signal is then amplified and filtered at amplifier and filter 622. The signal passes through a demultiplexer 624 and the separated signals are amplified at 626, 628, 630, respectively and transmitted and displayed at display 632 of a CPU and recorded for transmission by modem 634 to an intensive care unit, for example.

FIGS. 35A-35C illustrate an intelligent contact lens being activated by closure of the eyelids with subsequent increased diffusion of blood components to the sensor. During movement of the eye lids from the position shown in FIG. 35C to the position shown in FIG. 35A by blinking and/or closure of the eye, a combination of forces are applied to the contact device 636 by the eyelid with a horizontal force (normal force component) of approximately 25,000 dynes which causes an intimate interaction between the contact device and the surface of the eye with a disruption of the lipid layer of the tear film allowing direct interaction of the outer with the palpebral conjunctiva as well as a direct interaction of the inner surface of the contact device with the aqueous layer of the tear film and the epithelial surface of the cornea and bulbar conjunctiva. Blinking promotes a pump system which extracts fluid from the supero-temporal corner of the eye and delivery of fluid to the puncta in the infero-medial corner of the eye creating a continuous flow which bathes the contact device. During blinking, the close interaction with the palpebral conjunctiva, bulbar conjunctiva, and cornea, the slightly rugged surface of the contact device creates microdisruption of the blood barrier and of the epithelial surface with transudation and increased flow of tissue fluid toward the surface of the contact device. The tear fluid then diffuses through the selectively permeable membranes located on the surface of the contact device 636 and subsequently reaching the electrodes of the sensor 638 mounted in the contact device. In the preferred embodiment for glucose measurement, glucose and oxygen flow from the capillary vessels 640 toward a selectively permeable outer membrane and subsequently reach a mid-membrane with immobilized glucose oxidase enzyme. At this layer of immobilized glucose oxidase enzyme, a enzymatic oxidation of glucose in the presence of the enzyme oxidase and oxygen takes place with the formation of hydrogen peroxide and gluconic acid. The hydrogen peroxide then diffuses through an inner membrane and reaches the surface of a platinum electrode and it is oxidized on the surface of the working electrode creating a measurable electrical current. The intensity of the current generated is proportional to the concentration of hydrogen peroxide which is proportional to the concentration of glucose. The electrical current is subsequently converted to a frequency audio signal by a transmitter mounted in the contact device with signals being transmitted to a remote receiver using preferably electromagnetic energy for subsequent amplification, decoding, processing, analysis, and display.

In FIGS. 36A through 36J, various shapes of contact devices are shown for use in different situations. In FIG. 36A, a contact device 642 is shown of an elliptical, banana or half moon shape for placement under the upper or lower eye lid. FIGS. 36B and 36C show a contact device 644 having, in side view a wide base portion 646 as compared to an upper portion 648. FIG. 36D shows a contact device 650 having a truncated lens portion 652.

In FIGS. 36E and 36F, the contact device 654 is shown in side view in FIG. 36E and includes a widened base portion 656 which as shown in FIG. 36F is of a semi-truncated configuration.

FIG. 36G shows a contact device 658, having a corneal portion 650 and a scleral portion 652. In FIG. 36H, an oversized contact device 664, includes a corneal portion 666 and a scleral portion 668.

A more circular shaped contact device 670 is shown in FIG. 36I having a corneal-scleral lens 672.

The contact device 674 shown in FIG. 36J is similar to the ones shown in FIGS. 32, 33A, 35A and 35C. The contact device includes a main body portion 676 with upper myoflange or minus carrier 678 and lower myoflange or minus carrier 680.

Figure 37B:
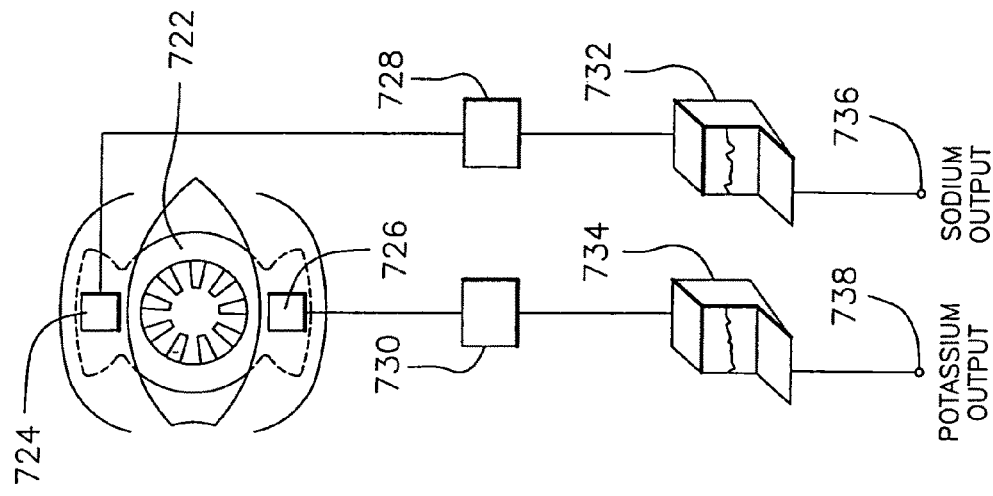
FIGS. 37A and 37B schematically illustrate interpretation of signals generated from the contact device of the present invention and the analysis of the signals to provide different test measurements and transmission of this data to remote locations, such as an intensive care unit setting.
Figure 37A:
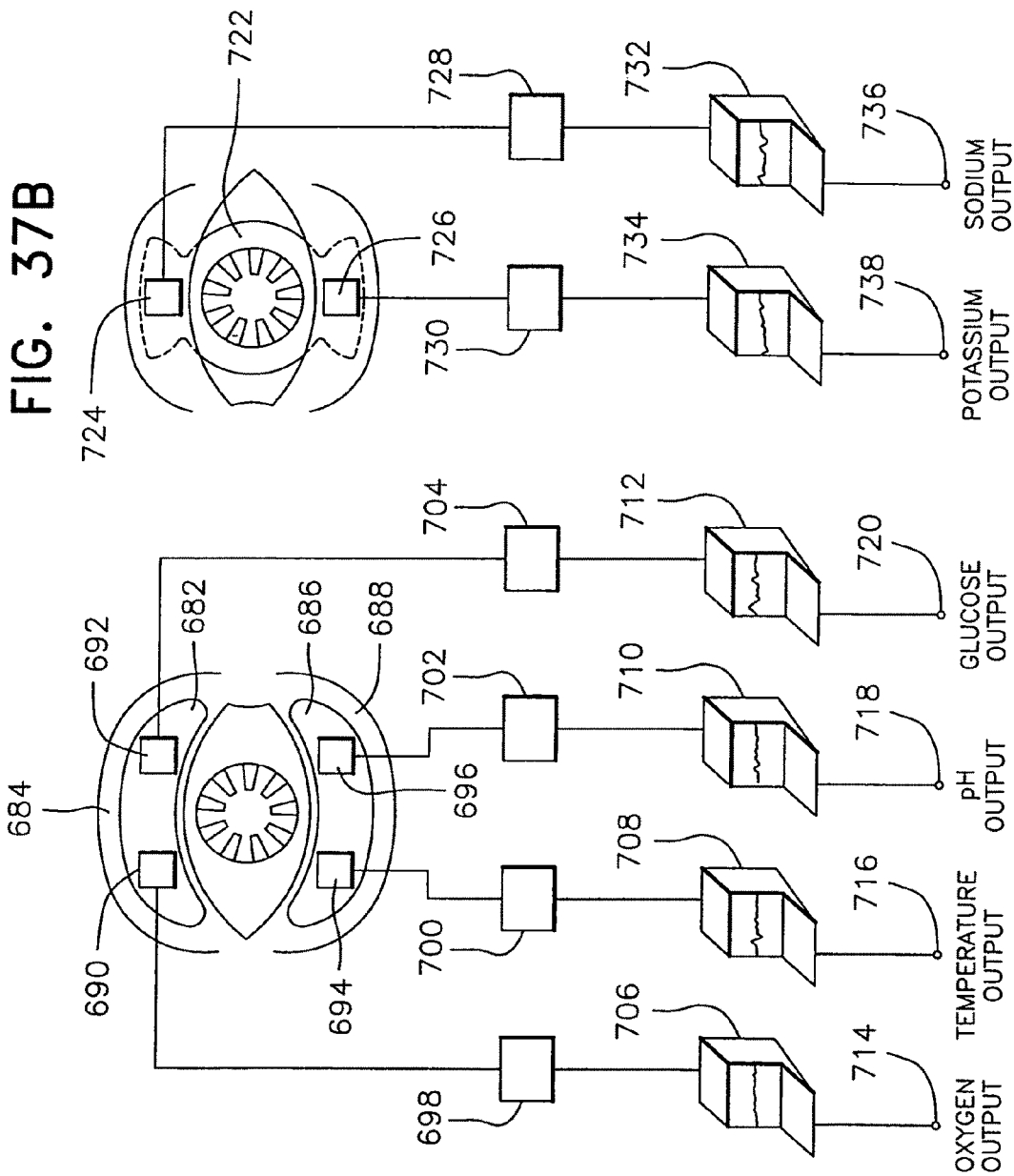

In FIG. 37A, an upper contact device 682 is placed under an upper eye lid 684. Similarly, a lower contact device 686 is placed underneath a lower eye lid 688. Upper contact device 682 includes an oxygen sensor/transmitter 690 and a glucose transmitter 692. Similarly, the lower contact device includes a temperature sensor transmitter 694 and a pH sensor/transmitter 696.

Each of these four sensors outputs a signal to respective receivers 698, 700, 702 and 704, for subsequent display in CPU displays 706, 708, 710, 712, respectively. The CPUs display an indication of a sensed oxygen output 714, temperature output 716, pH output 718 and glucose output 720.

In FIG. 37B, a single contact device 722, in an hour glass shape, includes an upper sodium sensor/transmitter 724 and a lower potassium sensor/transmitter 726. The two sensors send respective signals to receivers 728 and 730 for display in CPUs 732, 734 for providing a sodium output indicator 736 and a potassium output indicator 738.

Figure 38A:
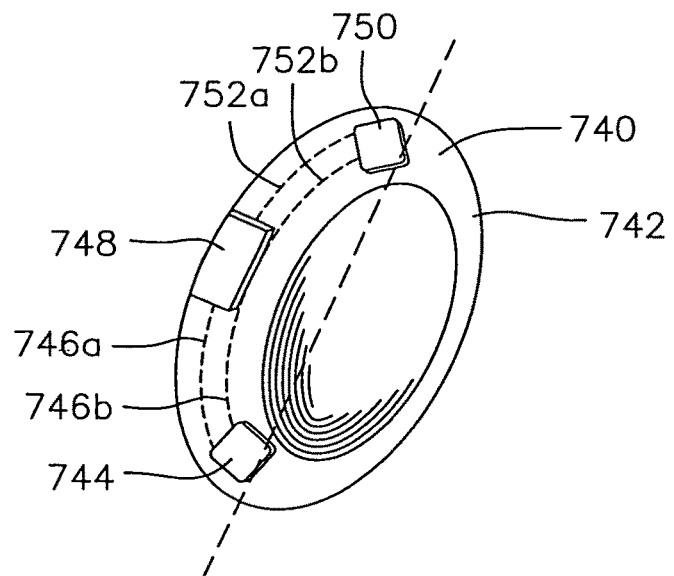
FIG. 38A schematically illustrates a contact device of the present invention with FIG. 38B being a sectional view taken along the section line shown in FIG. 38A.

In FIG. 38A, a contact device 740 is shown which may be formed of an annular band 742 so as to have a central opening with the opening overlying a corneal portion or if the contact device includes a corneal portion, the corneal portion lays on the surface of the cornea.

Figure 38B:
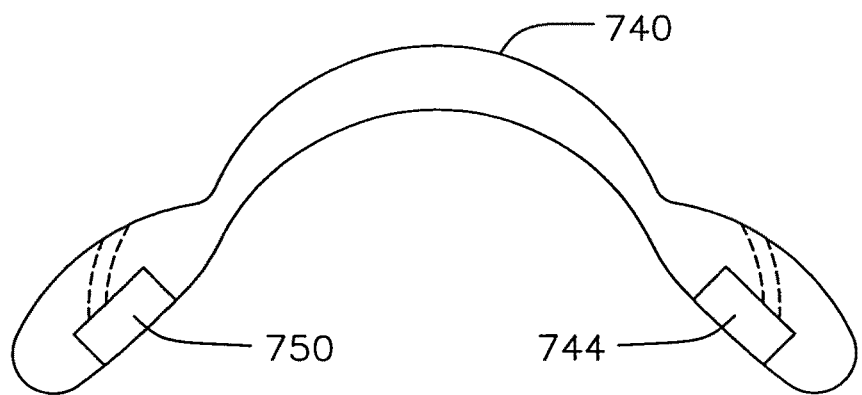

Limited to annular band 742 is a sensor 744 positioned on the scleral portion of the contact device so as to be positioned under an eye lid. The sensor is connected by wires 746a, 746b to transmitter 748 which is in communication with the power source 750 by wires 752a, 752b. The intelligent contact lens device 740 is shown in section in FIG. 38B with the power source 750 and sensor 744 located on opposite ends of the contact device on the scleral portion of the contact device.

FIG. 39A schematically illustrates the flow of tear fluid as illustrated by arrows 754 from the right lacrimal gland 756 across the eye to the lacrimal punctum 758a and 758. Taking advantage of the flow of tear fluid, in FIG. 39B, a contact device 760 is positioned in the lower cul-de-sac 762 beneath the lower eye lid 764 so that a plurality of sensors 764a, 764b and 764c in wire communication with a power source 766 and transducer 768 can be connected by a wire 770 to an external device. The flow of tear fluid from the left lacrimal gland 762 to the lacrimal punctum 764a and 764b is taken advantage of to produce a reading indicative of the properties to be detected by the sensors.

Figure 40A:
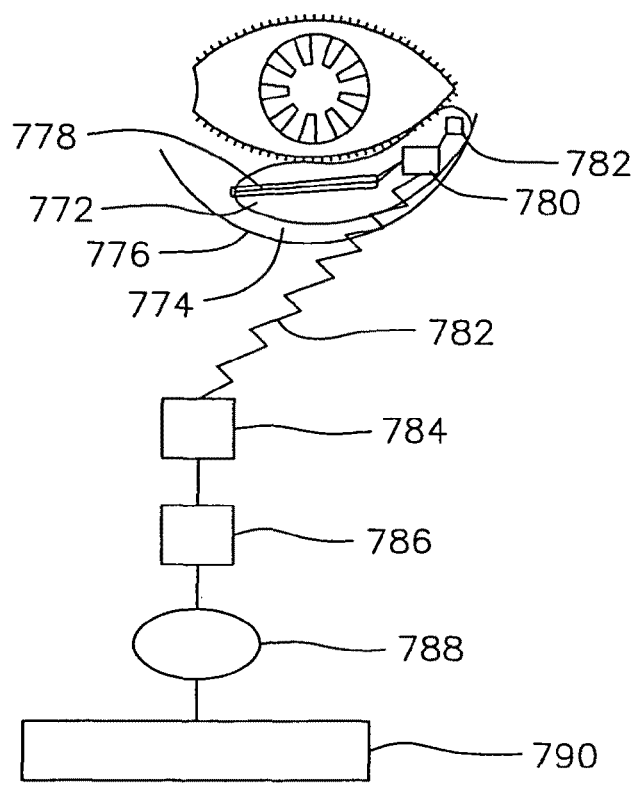
FIG. 40A schematically illustrates an alternative embodiment of the present invention, used under the eye lid to produce signals indicative of sensed glucose levels which are radio transmitted to a remote station followed by communication through a publically available network.

In FIG. 40A, a contact device 772 is positioned in the cul-de-sac 774 of the lower eye lid 776. The contact device includes a needle-type glucose sensor 778 in communication with a transmitter 780 and a power source 782. A signal 782 is transmitted to a receiver, demultiplexer and amplifier 784 for transmission to a CPU and modem 786 and subsequent transmission over a public communication network 788 for receipt and appropriate action at an interface 790 of a hospital network.

Figure 40B:
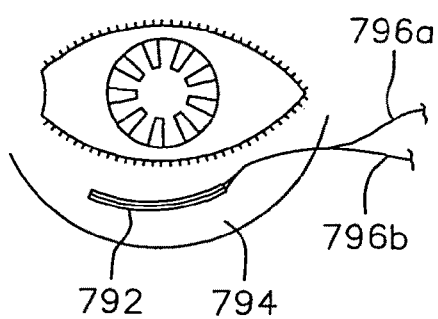
FIG. 40B schematically illustrates an alternative embodiment of the glucose sensor to be used under the eyelid with signals transmitted through wires.

In FIG. 40B, a similar arrangement to that shown in FIG. 40A is used except the glucose sensor 792 is a needle type sensor with a curved shape so as to be placed directly against the eye lid. The sensor 792 is silicone coated or encased by coating with silicone for comfortable wear under the eye lid 794. Wires 796a and 796b extend from under the eye lid and are connected to an external device. The sensor 792 is placed in direct contact with the conjunctiva with signals and power source connected by wires to external devices.

Figure 41:
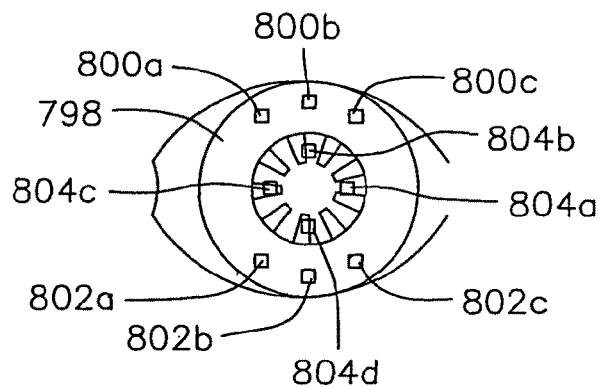
FIG. 41 illustrates an oversized contact device including a plurality of sensors.

FIG. 41 shows an oversized contact device 798 including sensors 800a, 800b, 800c and the scleral portion of the contact device to be positioned under the upper eye lid. In addition, sensors 802a, 802b, 802c are to be positioned under the lower eye lid in contact with the bulbar and/or palpebral conjunctiva. In addition, sensors 804a-d are located in the corneal portion in contact with the tear film over the cornea.

FIG. 42A shows a contact device 806 having a sensor 808 and a transmitter 810 in position, at rest, with the eye lids open. However, in FIG. 42B, when the eye lids move towards a closed position, and the individual is approaching a state of sleep, the Bell phenomenon will move the eye and therefore the contact device upward in the direction of arrows 812. The pressure produced from the eye lid as the contact device moves up, will produce a signal 814 from the sensor 808 which is transmitted to a receive 816. The signal passes through an amplifier and filter 818 to a demultiplexer 820 for activation of an alarm circuit 822 and display of data at 824. The alarm should be sufficient to wake a dozing driver or operator of other machinery to alert the user of signs of somnolence.

In FIG. 43, a heat stimulation transmission device 825 for external placement on the surface of the eye is shown for placement on the scleral and corneal portions of the eye. The device 825 includes a plurality of sensors 826 spaced across the device 825. With reference to FIG. 44, the device 825 includes heating elements 828a-c, a thermistor 830, an oxygen sensor 832, and a power source 834. Signals generated by the sensors are transmitted by transmitter 836 to hardware 838 which provides an output representative of a condition detected by the sensors.

In FIG. 46, an annular band 840 includes a plurality of devices 842a-e. The annular band shaped heat stimulation transmission device 840 can be used externally or internally by surgical implication in any part of the body. Another surgically implantable device 844 is shown in FIG. 46. In this example, the heat stimulation transmission device 844 is implanted between eye muscles 846, 848. Another example of a surgically implantable heat stimulation transmission device 850 is shown in FIG. 47, having four heating elements 852, a temperature sensor 854 and an oxygen sensor 856, with a power source 858 and a transmitter 860 for transmitting signal 852.

FIGS. 48, 49 and 51 through 53 illustrate the use of an overheating transmission device, as shown in FIG. 50, for the destruction of tumor cells after the implantation of the overheating transmission device by surgery. As shown in FIG. 50, the overheating transmission device 864 includes a plurality of heating elements 866a, 866b, 866c, a temperature sensor 868, a power source 870 which is inductively activated and a transmitter 872 for transmitting a signal 874. By activation of the device 864, an increase in temperature results in the immediately adjacent area. This can cause the destruction of tumor cells from a remote location.

In FIG. 48, the device 864 is located adjacent to a brain tumor 876. In FIG. 49, the device 864 is located adjacent to a kidney tumor 878.

In FIG. 51, the device 864 is located adjacent to an intraocular tumor 880. In FIG. 52, a plurality of devices 864 are located adjacent to a lung tumor 882. In FIG. 53, a device 864 is located externally on the breast, adjacent to a breast tumor 884.

Figure 54A:
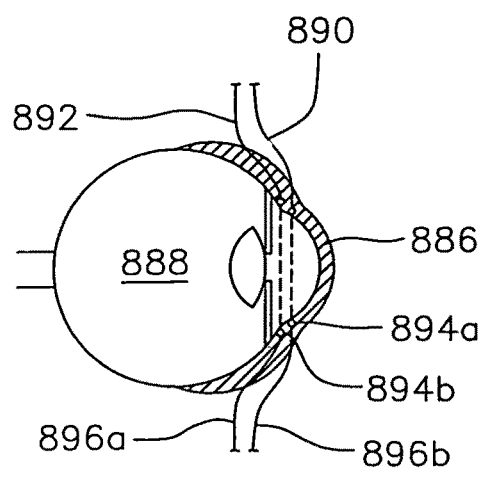
FIG. 54A is a side sectional view and FIG. 54B is a front view of a contact device used to detect chemical compounds in the aqueous humor located on the eye, with FIG. 54C being a side view thereof.
Figure 54B:
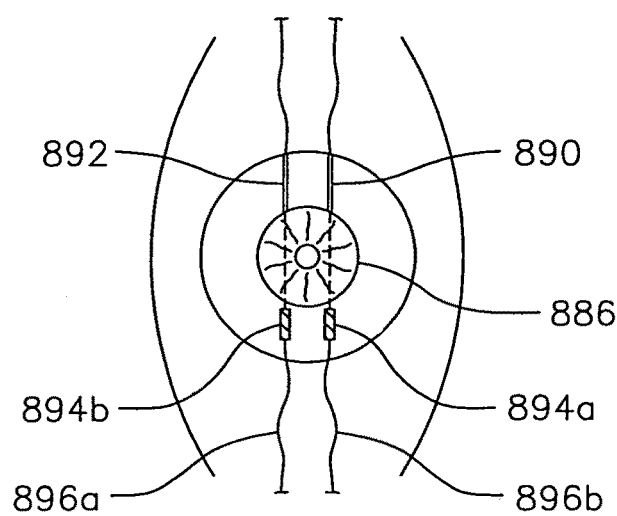

In FIGS. 54A and 54B, a contact device 886 is located on the eye 888. The contact device is used to detect glucose in the aqueous humor by emitting light from light emitting optical fiber 890, which is sensitive to glucose, as compared to a reference optical fiber light source 892, which is not sensitive to glucose. Two photo detectors 894a, 894b measure the amount of light passing from the reference optical fiber 892 and the emitting optical fiber 890 sensitive to glucose and transmit the received signals by wires 896a, 896b for analysis.

Figure 54C:
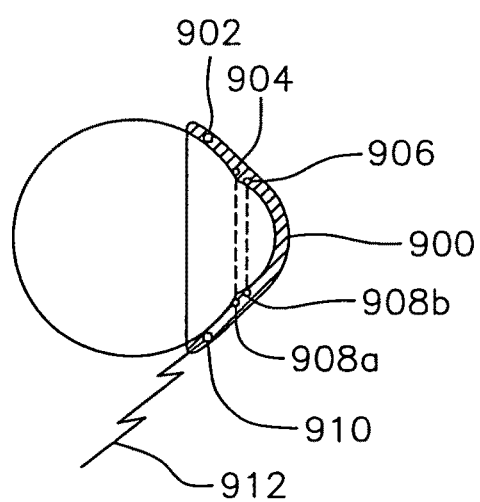

In FIG. 54C, a glucose detecting contact device 900 is used having a power source 902, an emitting light source 904 sensitive to glucose and a reference light source 906, non-sensitive to glucose. Two photo detectors 908a and 908b, provide a signal to a transmitter 910 for transmission of a signal 912 to a remote location for analysis and storage.

Figure 55A:
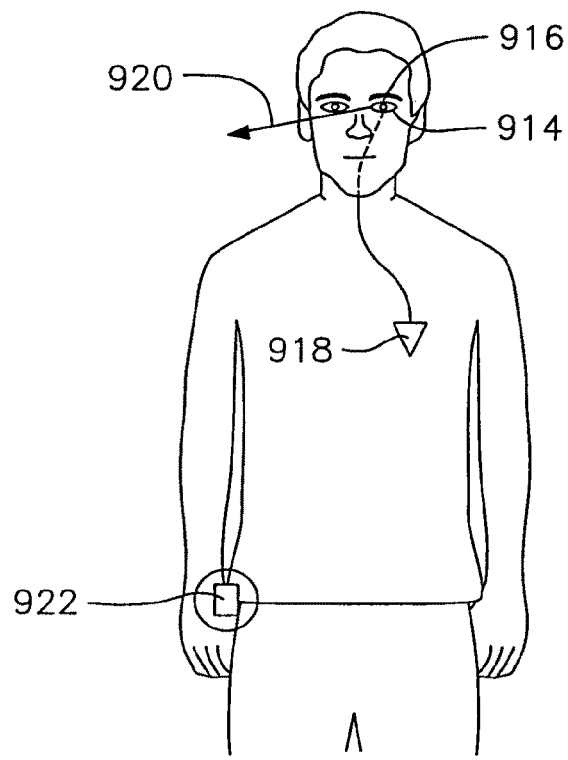
FIG. 55A schematically illustrates a microphone or motion sensor mounted on a contact device sensor positioned over the eye for detection of heart pulsations or sound and transmission of a signal representative of heart pulsations or sound to a remote alarm device with FIG. 55B being an enlarged view of the alarm device encircled in FIG. 55A.
Figure 55B:
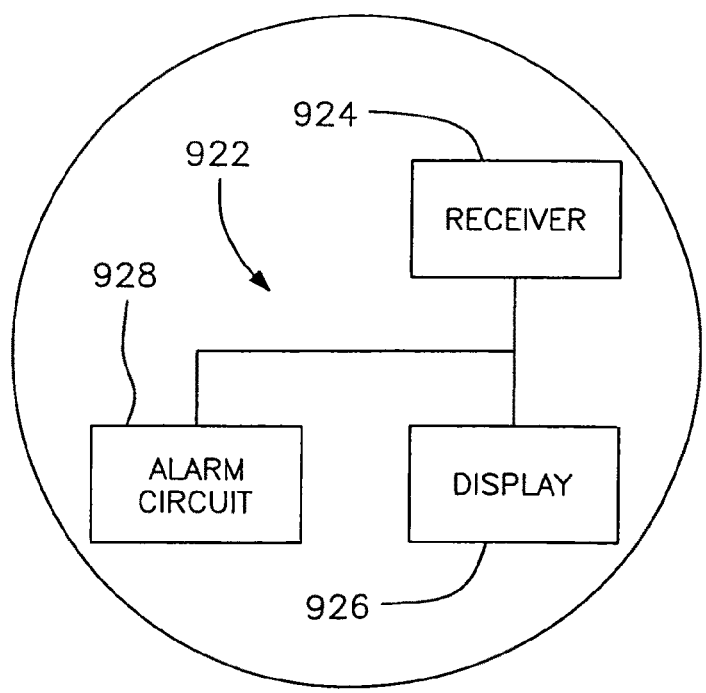

In FIG. 55A, a contact device 914 is positioned on an eye 916 for detection of heart pulsations or heart sounds as transmitted to eye 916 by the heart 918 as a normal bodily function. A transmitter provides a signal 920 indicative of the results of the heart pulsations or heart sound. A remote alarm device 922 may be worn by the individual. The details of the alarm device are shown in FIG. 55B where the receiver 924 receives the transmitted signal 920 and conveys the signal to a display device 926 as well as to an alarm circuit 928 for activation of an alarm if predetermined parameters are exceeded.

Figure 56:
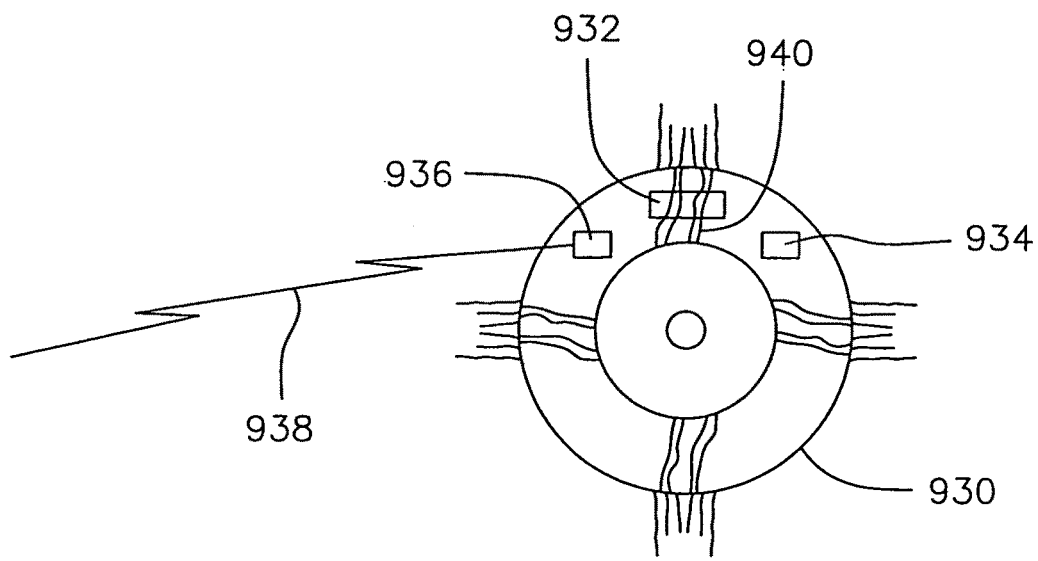
FIG. 56 illustrates a contact device with an ultrasonic dipolar sensor, power source and transmitter with the sensor located on the blood vessels of the eye.

In FIG. 56, a contact device 930 is shown. The contact device includes an ultra sound sensor 932, a power source 934 and a transmitter 936 for conveying a signal 938. The ultra sound sensor 932 is placed on a blood vessel 940 for measurement of blood flow and blood velocity. The result of this analysis is transmitted by signal 938 to a remote receiver for analysis and storage.

Figure 57:
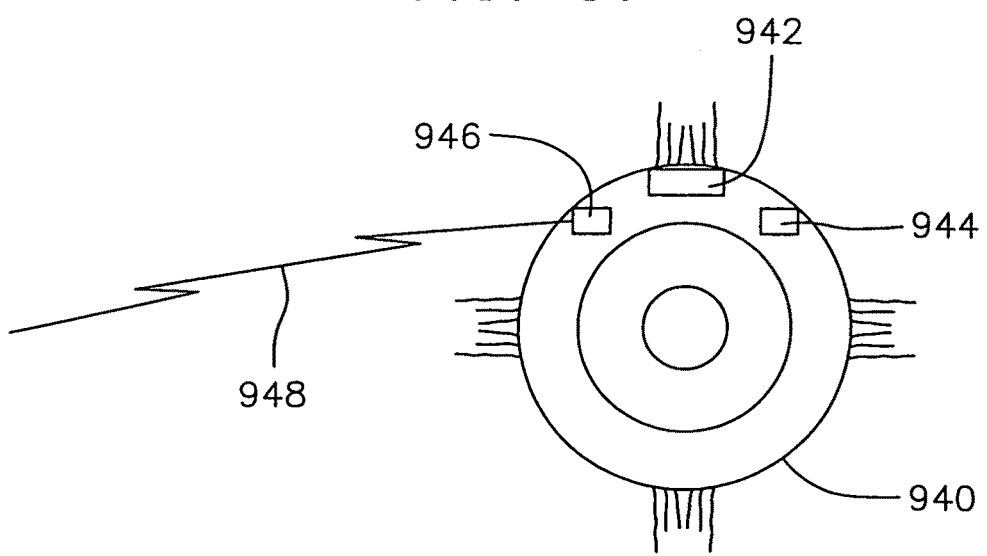
FIG. 57 schematically illustrates the location of a contact device with a sensor placed near an extraocular muscle.

In FIG. 57, an oversized contact device 940 includes a sensor 942, a power source 944 and a transmitter 946 for transmitting a signal 948. The sensor 942 is positioned on the superior rectus muscle for measurement of eye muscle potential. The measured potential is transmitted by signal 948 to a remote receiver for analysis and storage.

Figure 58A:
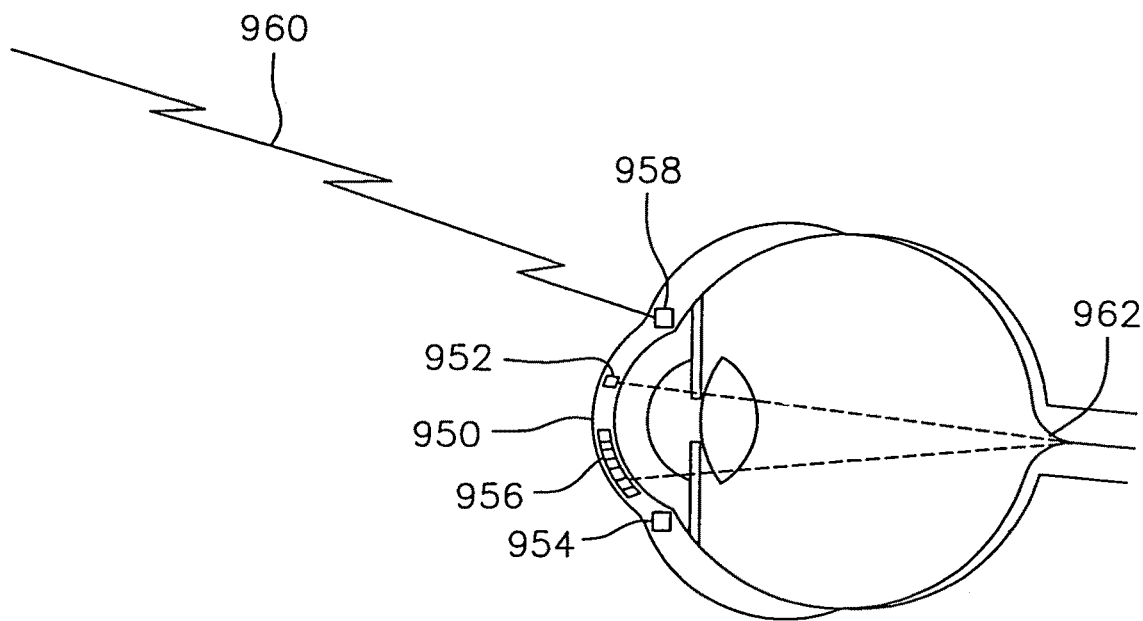
FIG. 58A is a side sectional view illustrating a contact device having a light source for illumination of the back of the eye.

In FIG. 58A, a contact device 950 includes a light source 952, a power source 954, multioptical filter system 956 and a transmitter 958 for transmission of a signal 960. The light source 952 emits a beam of light to the optic nerve head 962. The beam of light is reflected on to the multioptical filter system 956 for determination of the angle of reflection.

Figure 58B:
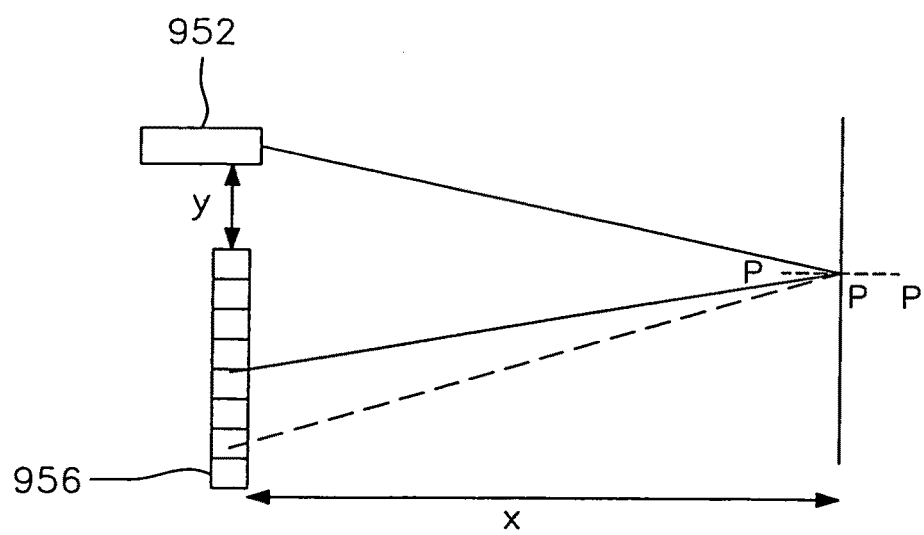
FIG. 58B illustrates schematically the transmission of light from a light source for reflection off a blood vessel at the cup of the optic nerve and for receipt of the reflected light by a multioptical filter system separated from the reflecting surface by a predetermined distance and separated from the light source by a predetermined distance for interpretation of the measurement of the reflected light.

As shown in FIG. 58B, since the distance X of separation between the multioptical filter system and the head of the optic nerve 962 remains constant as does the separation distance Y between the light source 952 and the multoptical filter system 956, a change in the point P which is representative of the head of the optic nerve will cause a consequent change in the angle of reflection so that the reflected light will reach a different point on the multioptical filter system 956. The change of the reflection point on multioptical filter system 956 will create a corresponding voltage change based on the reflection angle. The voltage signal is transmitted as an audio frequency signal 960 to a remote location for analysis and storage.

Figure 59A:
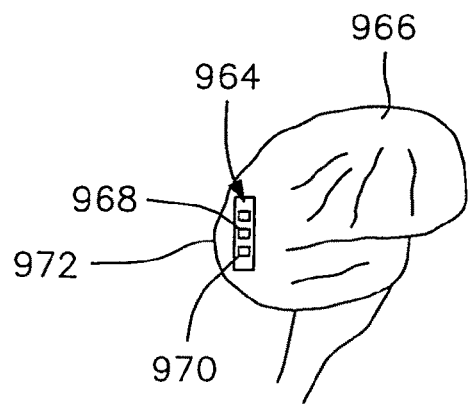
FIGS. 59A through 59C illustrate positioning of contact devices for neurostimulation of tissues in the eye and brain.
Figure 59B:
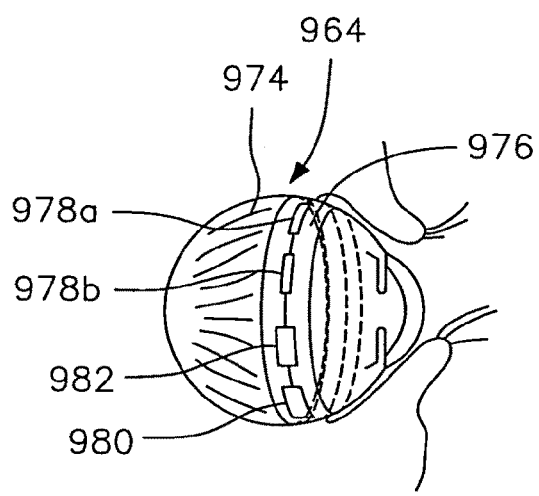
Figure 59C:
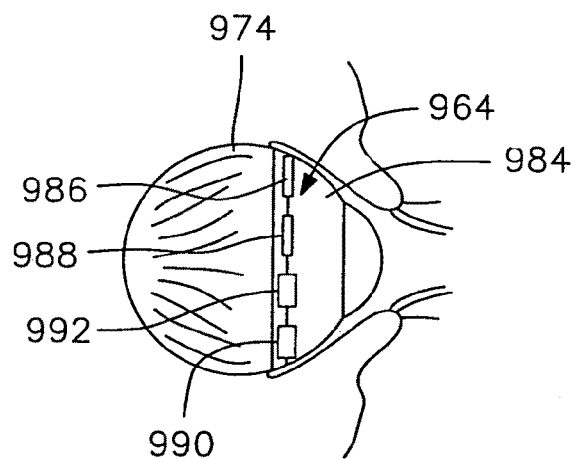

In FIGS. 59A through 59C, a neuro stimulation transmission device 964 is shown. In FIG. 59A, the device 964 is surgically implanted in the brain 966. The device 964 includes microphotodiodes or electrodes 968 and a power source/transmitter 970. The device is implanted adjacent to the occipital cortex 972.

In FIG. 59B, the device 964 is surgically implanted in the eye 974 on a band 976 including microphotodiodes 978a, 978b with a power source 980 and a transmitter 982.

In FIG. 59C, the device 964 is externally placed on the eye 974 using an oversized contact device 984 as a corneal scleral lens. The device includes an electrode 986 producing a microcurrent, a microphotodiode or electrode 988, a power source 990 and a transmitter 992 for transmission of a signal to a remote location for analysis and storage.

Figure 60:
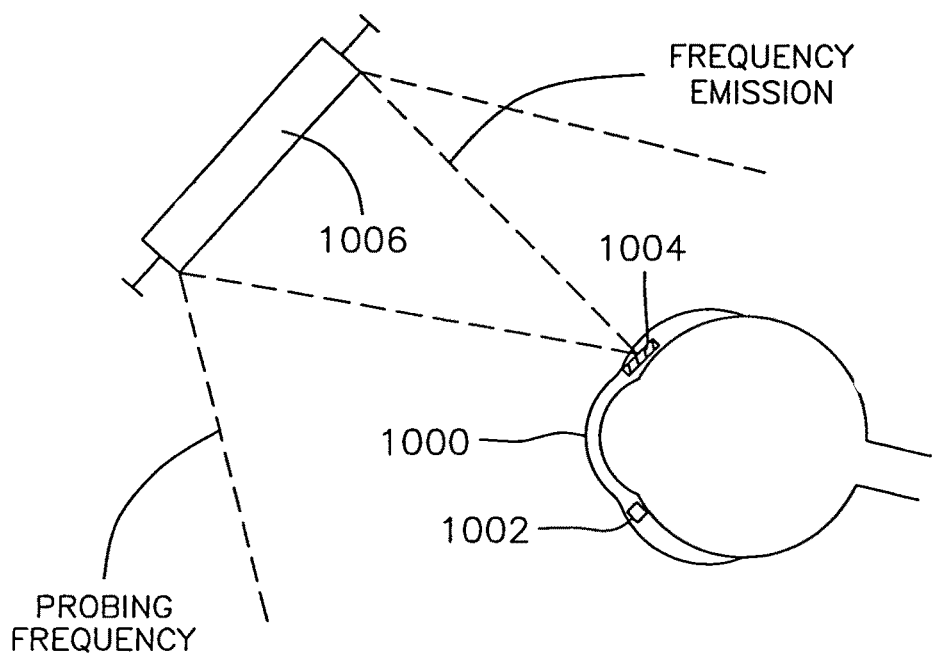
FIG. 60 is a schematic illustration of a contact device having a fixed frequency transmitter and power source for being tracked by an orbiting satellite.

In FIG. 60, a contact device 1000 includes a power source 1002 and a fixed frequency transmitter 1004. The transmitter 1004 emits a frequency which is received by an orbiting satellite 1006. Upon detection of the frequency of the signal transmitted by the transmitter 1004, the satellite can transmit a signal for remote reception indicative of the location of the transmitter 1004 and accordingly the exact location of the individual wearing the contact device 1000. This would be useful in military operations to constantly monitor the location of all personal.

Figure 61:
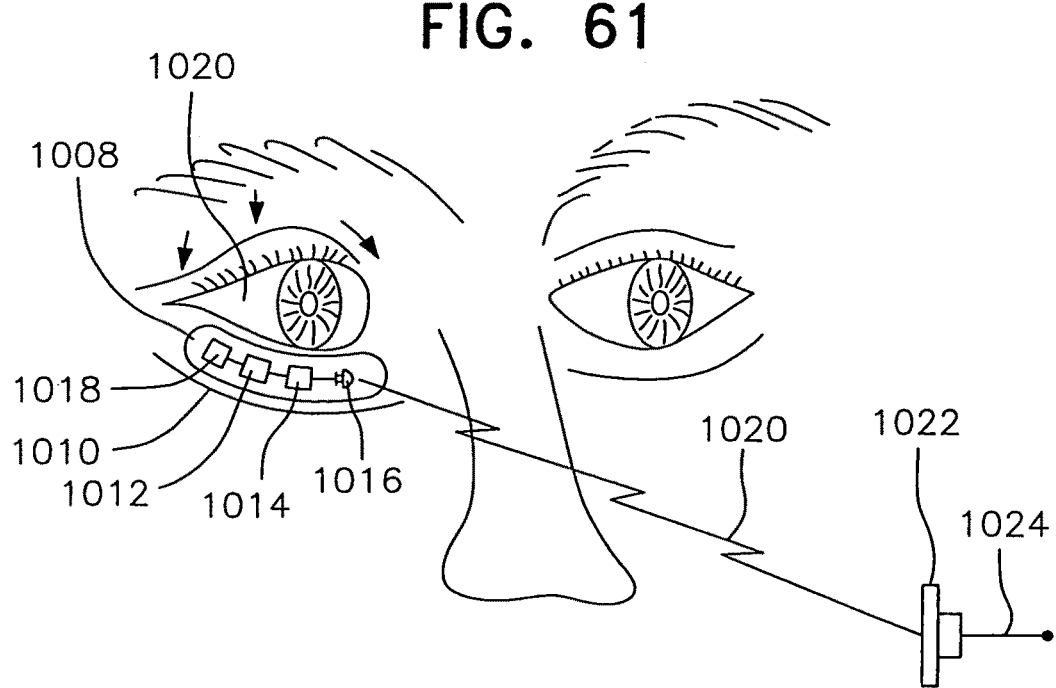
FIG. 61 illustrates a contact device under an eyelid including a pressure sensor incorporated in a circuit having a power source, an LED drive and an LED for production of an LED signal for remote activation of a device having a photodiode or optical receiver on a receptor screen.

In FIG. 61, a contact device 1008 is located below the lower eye lid 1010. The contact device includes a pressure sensor, an integrated circuit 1012, connected to an LED drive 1014 and an LED 1016. A power source 1018 is associated with the device located in the contact device 1008.

By closure of the eye 1020 by the eye lids, the pressure sensor 1012 would be activated to energize the LED drive and therefore the LED for transmission of a signal 1020 to a remote photodiode or optical receiver 1022 located on a receptor system. The photodiode or optical receiver 1022, upon receipt of the signal 1020, can transmit a signal 1024 for turning on or off a circuit. This application has may uses for those individuals limited in their body movement to only their eyes.

Figure 62:
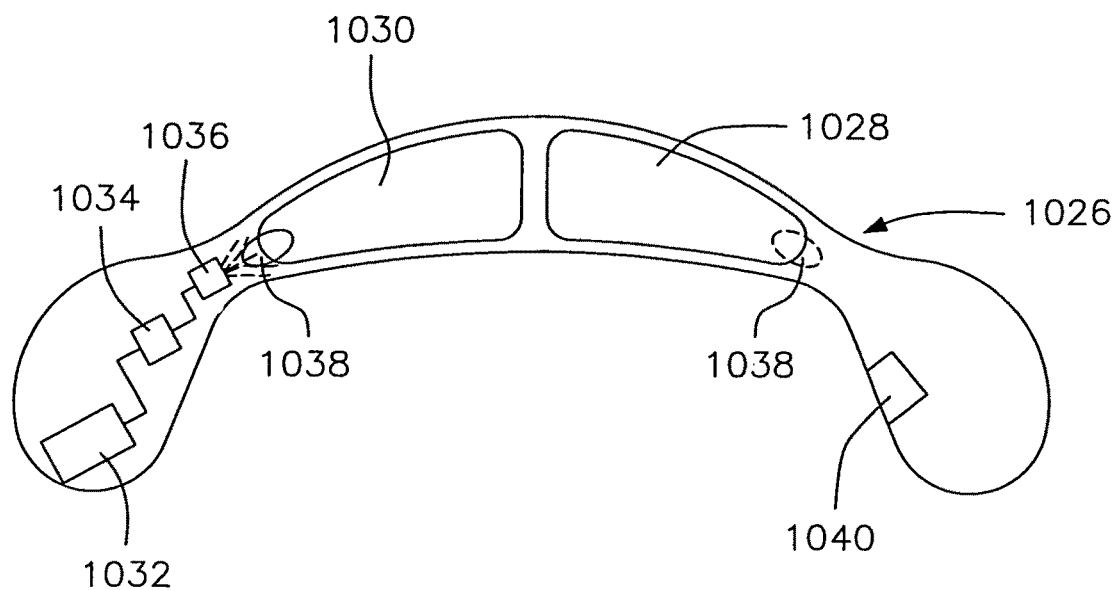
FIG. 62 is a cross-sectional view of a contact device having a drug delivery system incorporated therein.

In FIG. 62, a contact device 1026 includes compartments 1028, 1030 which include a chemical or drug which can be dispensed at the location of the contact device 1026. The sensor 1032 provides an signal indicative of a specific condition or parameter to be measured. Based upon the results of the analysis of this signal, when warranted, by logic circuit 1034, a heater device 1036 can be activated to melt a thread or other closure member 1038 sealing the compartments 1028, 1030 so as to allow release of the chemical or drug contained in the compartments 1028, 1030. The system is powered by power source 1040 based upon the biological variable signal generated as a result of measurement by sensor 1032.

Figure 63:
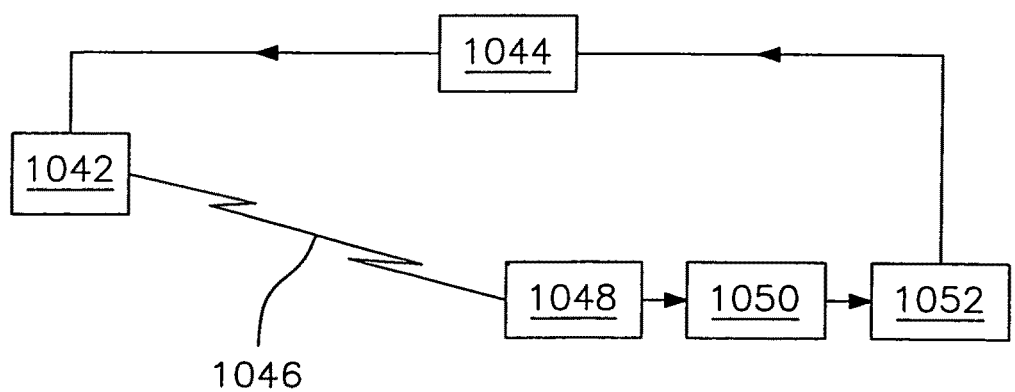
FIG. 63 schematically illustrates a block diagram of an artificial pancreas system.

According to the system shown in FIG. 63, a glucose sensor 1042, positioned on the eye 1044, can generate a glucose level signal 1046 to a receiver 1048 associated with an insulin pump 1050 for release of insulin into the blood stream 1052. The associated increase in insulin will again be measured on the eye 1044 by the sensor 1042 so as to control the amount of insulin released by the insulin pump 1050. A constant monitoring system is thereby established.

In reference to FIG. 64A through 64D there is shown the steps for the experimental in-vitro testing according to the biological principles of the invention. The biological principles of the current invention include the presence of superficially located fenestrated blood vessels in the conjunctiva allowing tissue fluid to freely flow from the vessels of the eye for analysis.

Figure 64A:
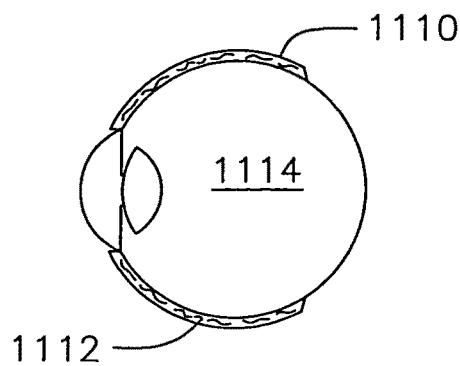
FIG. 64A through 64D are schematic sectional illustrations of experiments performed on an eye.
Figure 64B:
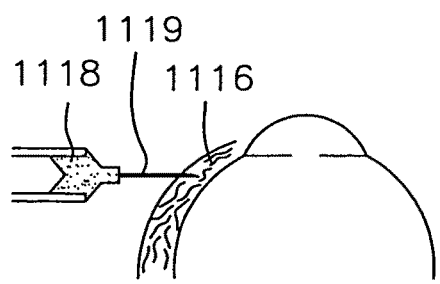
Figure 64C:
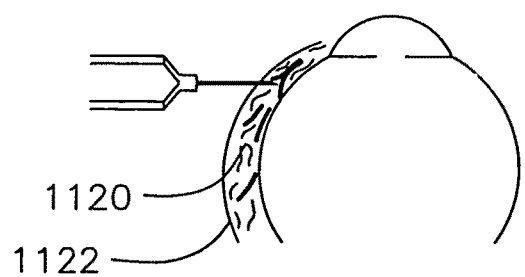
Figure 64D:
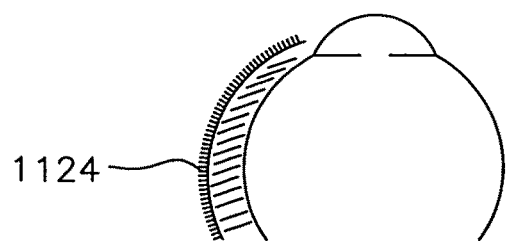

FIGS. 64A-64D shows the schematic illustration of the testing of an eye to confirm the location of fenestated vessels. A side view of the eye ball in FIG. 64A shows the conjunctiva 1110 with its vessels 1112 covering both the eye ball 1114 and the eye lid (not shown). A main conjunctival vessel 1116 in the limbal area shown in FIG. 64B is then cannulated and fluorescein dye 1118 injected through syringe 1119 into the vessel 1116. The dye starts to leak from the fenestrated vessels into the conjunctival space 1120 and surface of the eye 1122 in mid-phase in FIG. 64C. In the late phase (FIG. 64D) there is a massive leakage 1124 of fluid (fluorescein dye) completely covering the surface of the eye due to the presence of superficially located fenestrated vessels.

Another experiment consisted of attaching a glucose oxidase strip to a variety of contact lens materials which were subsequently placed in the eye lid pocket. Blood samples were acquired from non-diabetic subjects using whole blood from the tip of the finger. The glucose oxidase enzyme detects the oxidable species present in the eye, in this example, the amount of glucose. The enzymes are coupled to a chromogen which created a color change based on the amount of the analyte (glucose). A combination of the forces caused by the physiologic muscular activity of the orbicularis muscle and muscle of Riolam in the eye lid generating a normal force component of 25,000 dynes acts on the contact device which promotes a fluid flux of analyte toward the strip with the subsequent development of color changes according to the amount of glucose. Fasting plasma concentration of glucose as identified by the contact lens system of the current invention was 15% higher than whole blood which corresponds to the physiologic difference between whole blood glucose and plasma glucose.

In reference to FIGS. 65A-65F there are shown a series of pictures related to in-vivo testing in humans related to the biological principles of the invention. FIG. 65A through 65F show an angiogram of conjunctival blood vessels present on the surface of the eye in a normal healthy living human subject. The fluorescein dye is injected into the vein of the subject and serial photographs with special illumination and filters are taken from the surface of the eye. The fluorescein angiogram allows evaluation of the anatomic structure and integrity of blood vessels as well as their physiologic behavior. Vessels which do not leak keep the fluorescein dye (seen as white) inside the vessel and appear as straight lines. Vessels in which there is leakage appear as white lines surrounded by white areas. The white areas represent the fluorescein (white) which left the vessels and is spreading around said blood vessels. Since there is continuous leakage as the dye reaches the conjunctiva, as time progresses the whole area turns white due to the widespread and continuous leakage.

Figure 65A:
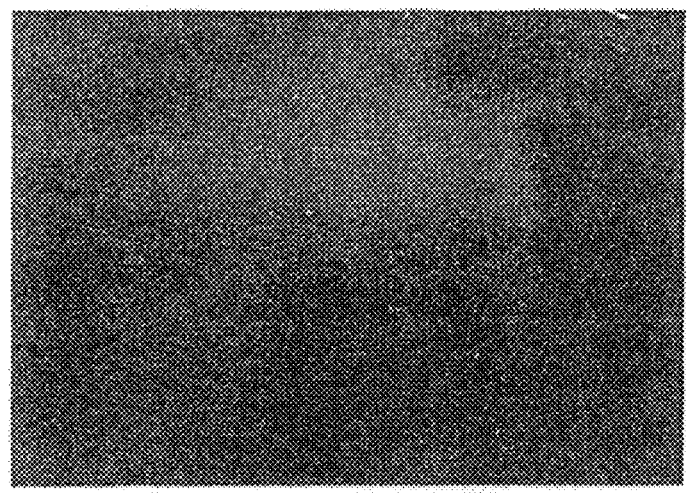
FIG. 65A through 65F shows a series of pictures related to in-vivo testing using fluorescein angiogram
Figure 65B:
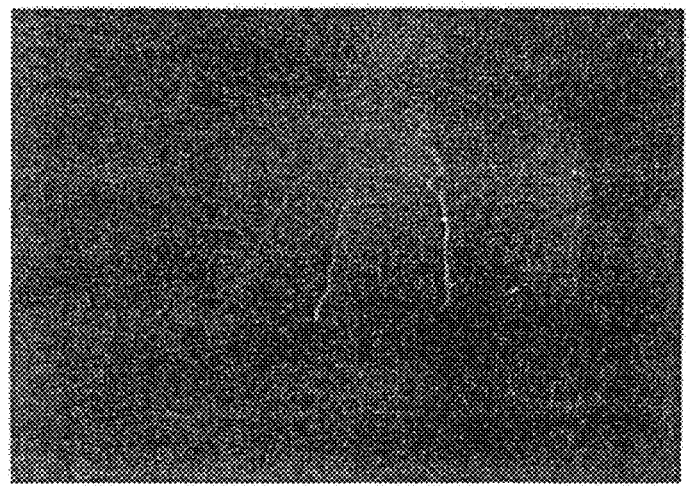
Figure 65C:
Figure 65D:
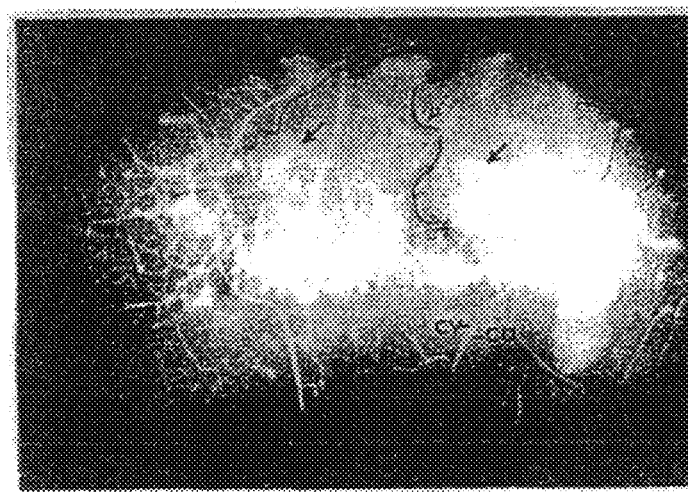

FIG. 65A shows a special photograph of the conjunctiva before dye is injected and the area appears as black. About 15 seconds after the dye is injected into a vein of a patient, the dye appears in the conjunctiva and starts to fill the conjunctival blood vessels (FIG. 65B). The initial filling of few conjunctival vessels is followed by filling of other vessels after 22 seconds from injection into the vein (FIG. 65C) with progressive leakage of the dye from the conjunctival vessels forming the fluffy white images around the vessels as filling of vessels progresses. After about 30 seconds from the time of injection most of the conjunctival vessels begin to leak due to fenestration which is observed as large white spots. In the late phase, leakage from conjunctival vessels has increased markedly and reaches the surface engulfing the whole conjunctival area as shown in FIG. 65D. Note the intense hyper-fluorescence (white areas) due to leakage that is present in the conjunctiva.

Figure 65E:
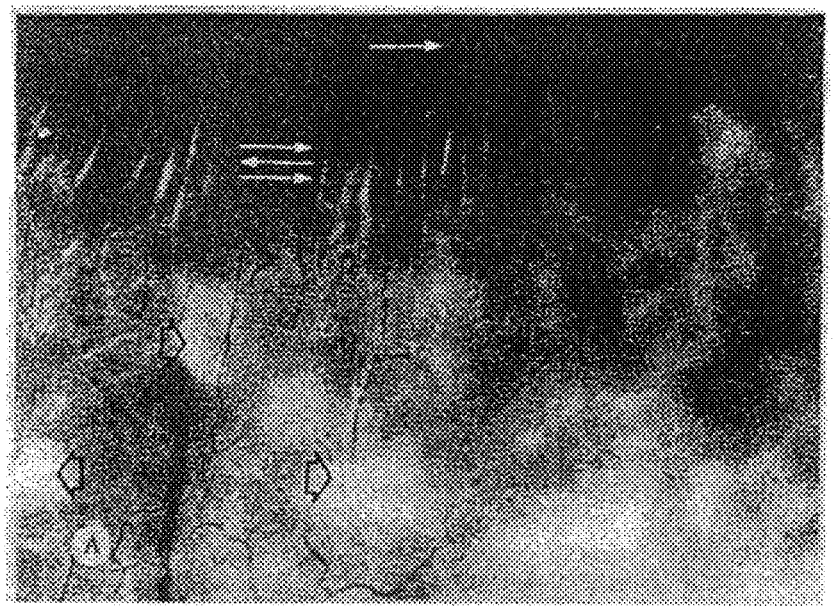

As with FIG. 68 which shows junction of conjunctiva and skin, FIG. 65E shows the junction of conjunctiva and cornea. According to the biological principles of the invention one can easily see the difference between vessels with holes (conjunctiva) and vessels without holes (limbal area which is the transition zone between conjunctiva and cornea).

FIG. 65E (photo A) shows an enlarged view of late phase with leakage by conjunctival vessels pointed by the large arrow heads with the conjunctival vessels surrounded by fluffy white areas (=leakage). Contrary to that; when one leaves the conjunctiva the vessels are non-fenestrated (=no holes) and thus the vessels are observed as straight white lines without surrounding fluffy white areas. Note that no leakage is seen from vessels next to the cornea (triple arrows) which are seen as straight white lines without surrounding white infiltrates which means no leakage. Only the conjunctival vessels have fenestration (pores) and leakage of plasma to the surface allowing any analytes and cells present in the eye to be measured.

Figure 65F:
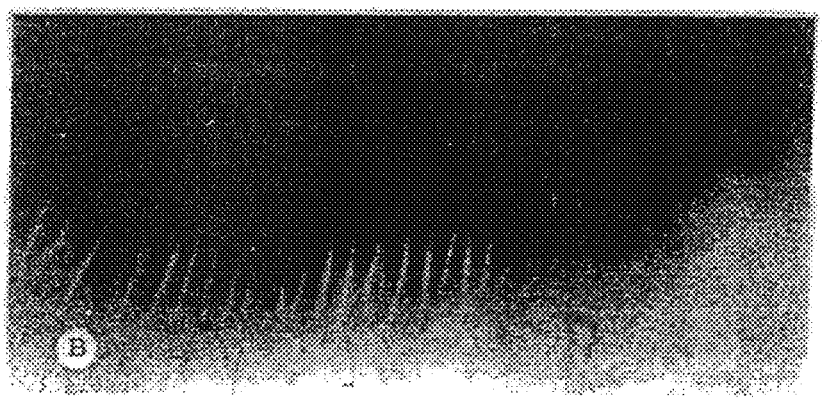

FIG. 65F (photo B) is an enlarged view showing the complete lack of leakage by the non-conjunctival blood vessels in the transition between cornea and conjunctiva which are seen as white straight lines.

Note that these conjunctival vessels leaking fluid (see FIG. 65C-65E, for example) are part the lining of the eye lid pockets in which to insert the ICL according to the principles of the present invention. It takes about 10 seconds from the time the dye is injected in the vein until it reaches the eye. The time correlates with the pumping action of the heart. As long as the heart is pumping blood, the conjunctival vessels will continue to leak allowing the continuous non-invasive measurement of blood elements according to the principles of the invention.

Please note that the conjunctiva is the only superficial organ with such fenestrated blood vessels. There are areas inside the body such as liver and kidney with fenestrated vessels but for obvious reasons such organs are not accessible for direct non-invasive collection and analysis of plasma. As previously described the conjunctiva posses all of the characteristics needed for non-invasive and broad diagnostics including fluid and cells for analysis.

Figure 66A:
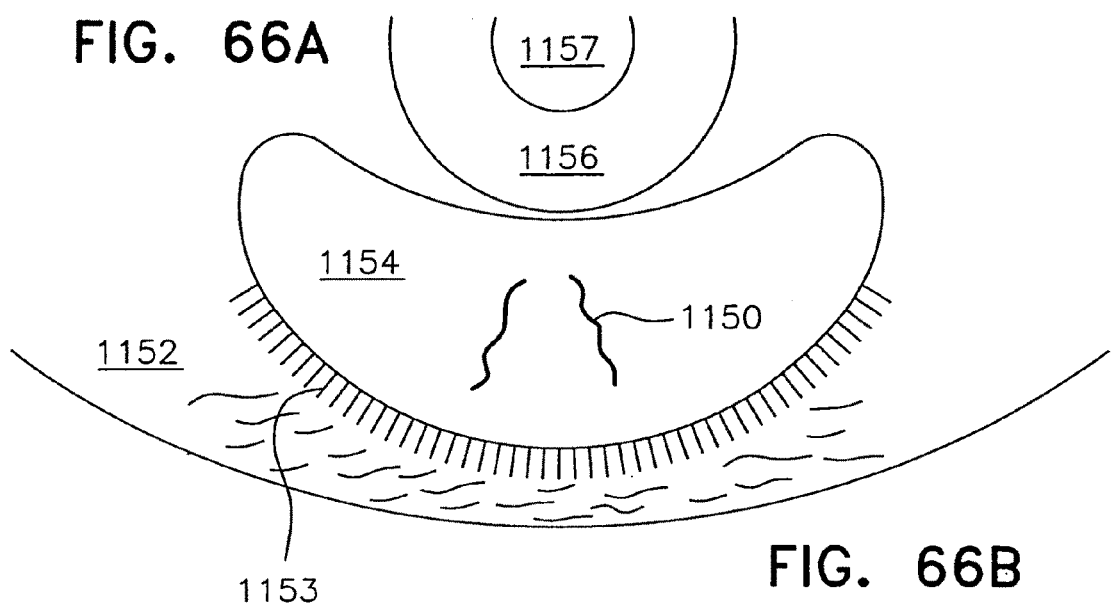
FIG. 66A through 66C are schematic illustrations of an in-vivo angiogram according to the biological principles of the invention.
Figure 66B:
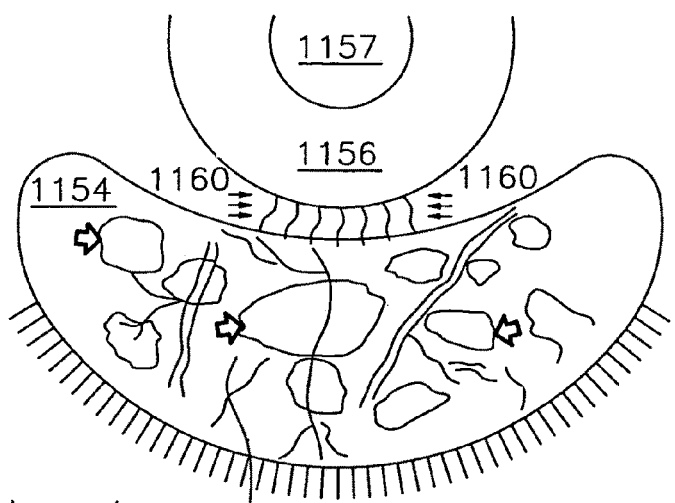
Figure 66C:
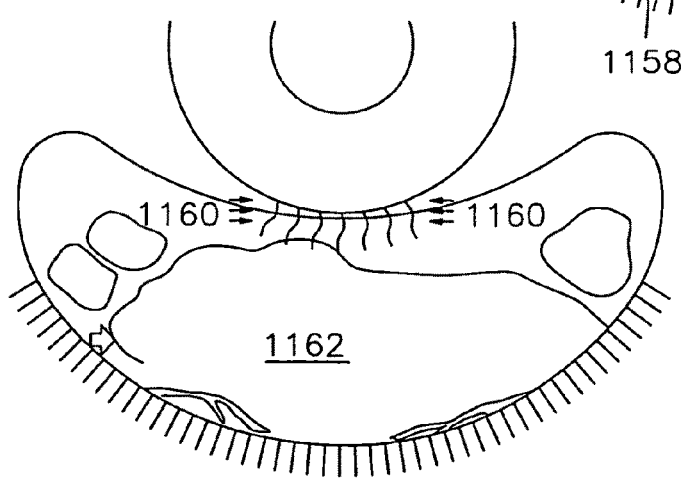

FIG. 66A through 66C are schematic illustrations of an angiogram. FIG. 66A shows initial filling of conjunctival vessels 1150 with fluorescein dye. The lower eye lid 1152 with eye lashes 1153 was pulled down to expose the conjunctival vessels 1150 present in the eye lid pocket 1154. FIG. 66A through 66C also show the cornea 1156 and pupil 1157 of the eye located above the conjunctival area 1154. FIG. 66B shows mid-phase filling of conjunctival vessels with leakage represented by large arrow heads 1158. The same figure also shows the lack of leakage in the vessels next to the cornea represented by triple arrows 1160 indicating the presence of fenestrated vessels only in the conjunctival area 1154. FIG. 66C shows a late phase of the angiogram of the conjunctival vessels with almost complete filling of the conjunctival space and surface 1162 of the eye in the eyelid pocket 1154. Note that the limbal vessels (not fenestrated, no holes) remain as straight, white lines without leakage.

Figure 67A:
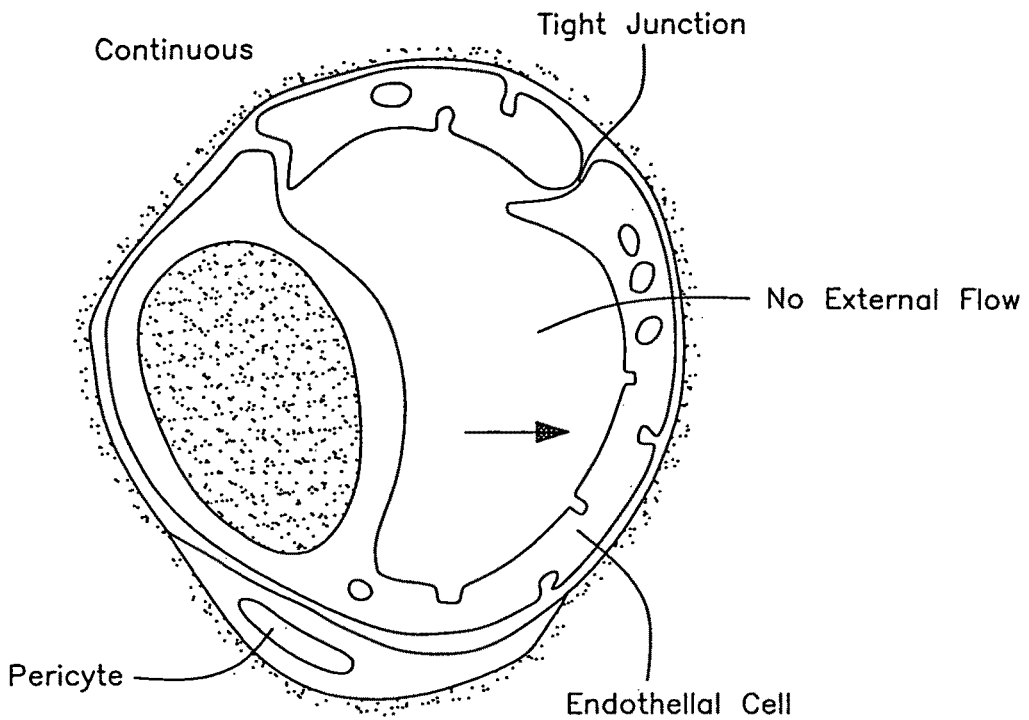
FIG. 67A is an exemplary schematic of the blood vessels in the skin, non-fenestrated.
Figure 67B:
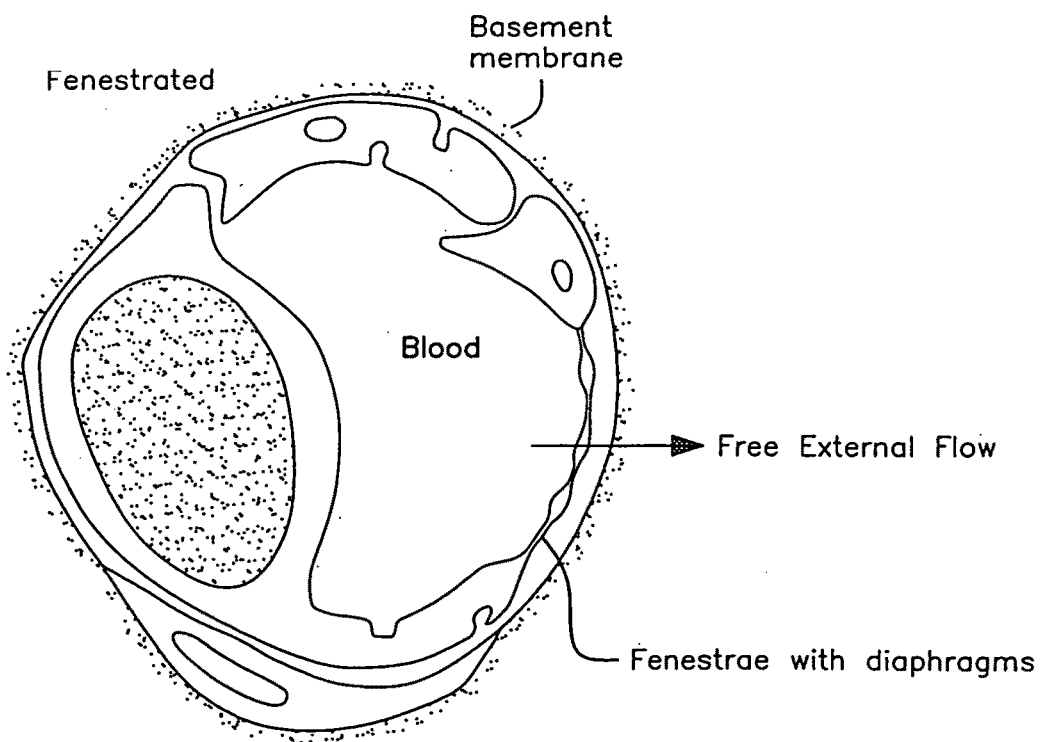
FIG. 67B is an exemplary schematic of the blood vessels in the conjunctiva, fenestrated.

FIGS. 67A and 67B show a schematic representation of the blood vessels found in the conjunctiva with fenestrations (holes) in FIG. 67B compared to continuous blood vessels (no holes) in FIG. 67A. The fenestrated vessels in the conjunctiva have a discontinuous flat membrane as thin as 40 angstroms in thickness and perforated by pores measuring about 600 to 700 angstroms. This structural arrangement is of prime importance in the permeability functions of the vessel, allowing plasma to freely leave the vessel, and thus any substance and/or cell present in the plasma can be evaluated according to the principles of the current invention. Contrary to FIG. 67B, FIG. 67A shows continuous walled vessels with complete lining of endothelial cells and continuous basement membrane which does not allow leakage or external flow of blood components. Those non-fenestrated vessels are commonly found in the subcutaneous layer deep under the skin, muscle tissue and connective tissues.

Figure 68A:
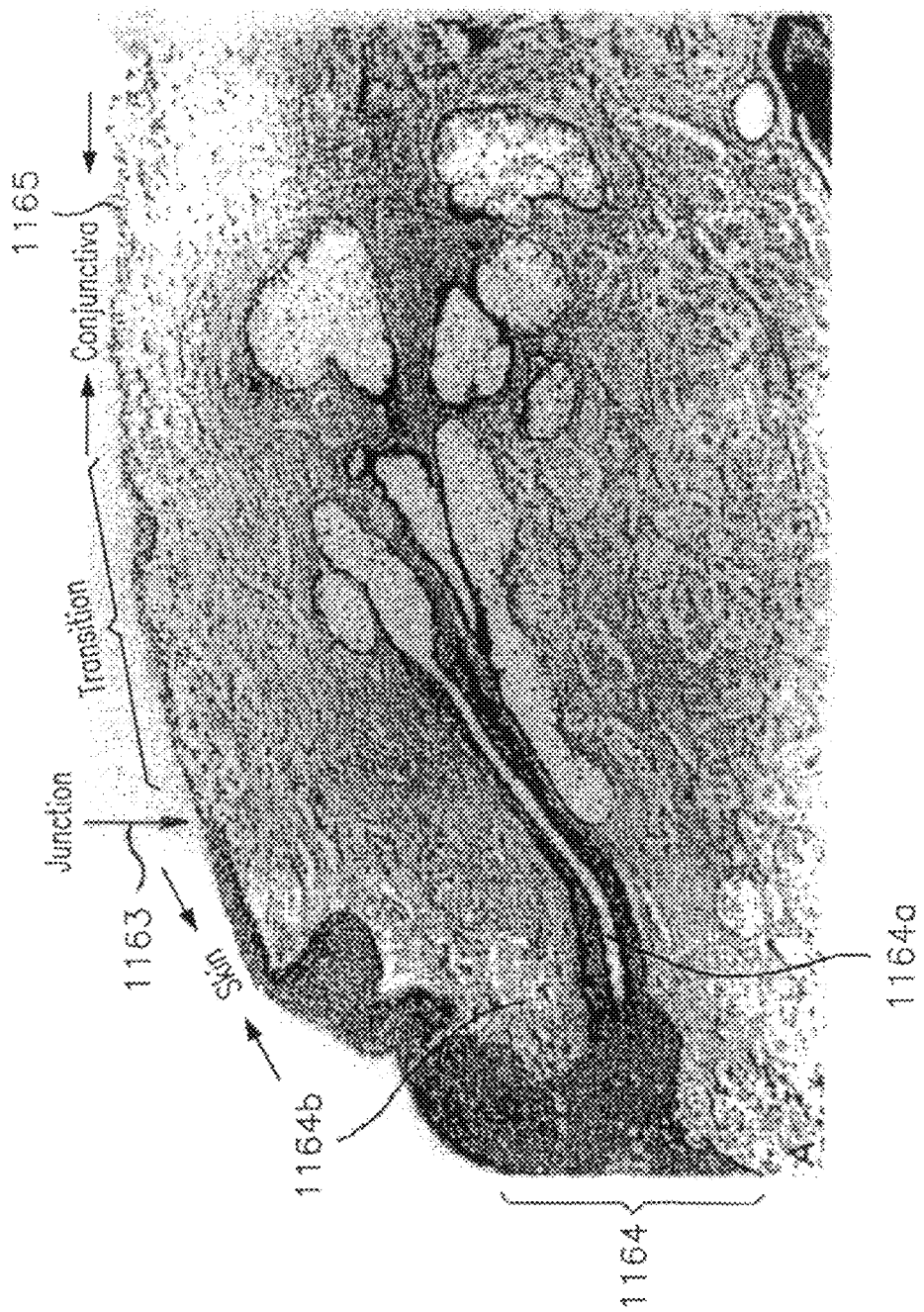
FIG. 68A shows a photomicrograph of the junction between skin and conjunctiva.

Besides demonstrating that functionally and physiologically the conjunctiva and the eye provides the ideal characteristics for diagnostics with superficial vessels that leak fluid, the inventor also demonstrated from a morphologic standpoint that the conjunctival area and the eye have the ideal anatomic characteristics for the measurements according to the principles of the present invention. Thus, FIG. 68A shows a microphotograph depicting the microscopic structure of the junction (arrow) 1163 between conjunctiva and skin present in the eye lid of a normal adult individual.

This junction 1163 which lies next to the eye lash line is called the lid margin mucosal-cutaneous junction and provides a great illustration for comparison between the skin and conjunctiva of the current invention. The skin has previously been used for acquiring blood invasively as with needles and lasers or minimally invasively as with electroporation, electroosmosis, and the like. However besides not having the superficial fenestrated blood vessels, one can clearly see by this photograph that the skin is not suitable for such evaluations. The arrow points to the junction 1163 of skin and conjunctiva. To the left of the junction arrow 1163 the epithelium of the skin 1164 is seen as this dark layer of varying thickness in a wave-like shape. The epithelium of the skin consists of densely organized multiple non-homogeneous cell layers overlying a thick and continuous tight base cell layer. The dark band is very thick and associated with large appendages such as a duct of a sebaceous gland 1164*a*. The tissue 1164*b* under the black thick superficial band is also thick (dark gray color) because it is composed of dense tissue. The blood vessels 1167 are located deep in the subcutaneous area.

Figure 68B:
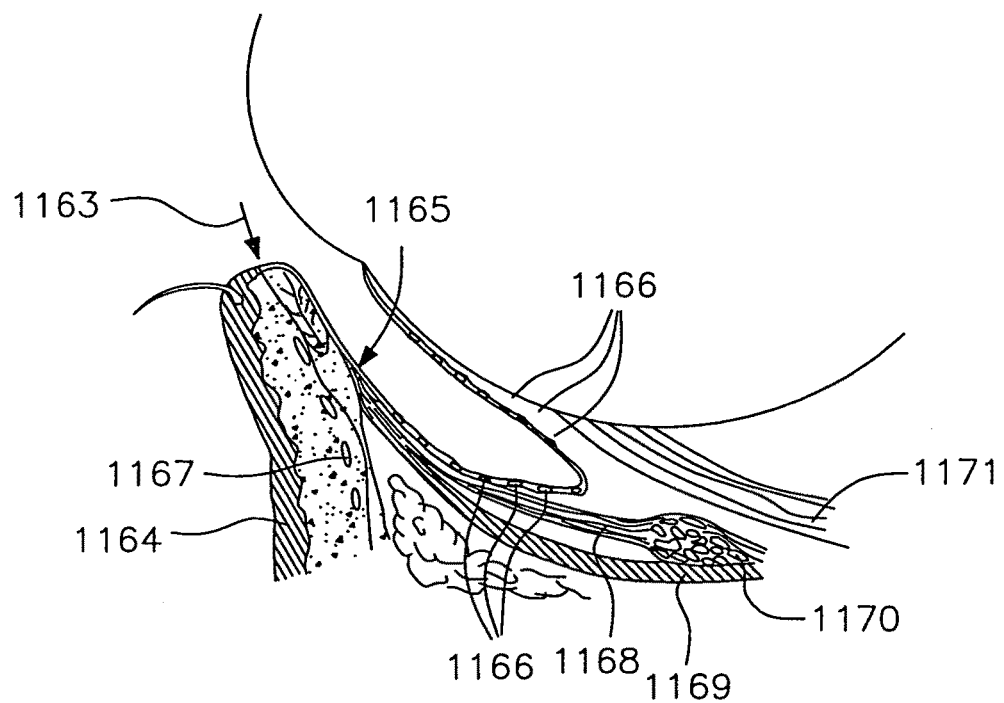
FIG. 68B shows a schematic illustration of a cross section of the eye showing the location of the microscopic structure depicted in FIG. 68A and associated structure in the eye.

Compare now to the conjunctiva on the right of the junction arrow 1163. The epithelium 1165 is so thin that one can barely identify a darker band superficially located in the photomicrograph. The conjunctiva is transparent and can be illustrated as a very thin cellophane-like material with blood vessels 1166. The epithelium of the conjunctiva 1165 besides being thin, as shown in FIGS. 68A and 68C is also quite homogeneous in thickness and becomes even thinner as one moves away from the skin (far right). The epithelium of the conjunctiva 1165 consists of a few loosely organized cell layers overlying a thin, discontinuous basement membrane with few hemidesmossomes and very wide intercellular spaces. The tissue underneath the thin epithelium of the conjunctiva 1165 is whitish (much lighter than the tissue under the thick dark skin epithelium). The reason for the whitish appearance is that the conjunctiva has a very loose substantia propria and loose connective tissue allowing easy permeation of fluid through those layers. The skin which is thick and dense does not provide the same easy passage of fluid. The conjunctiva has a voluminous blood supply and the vessels 1166 in the conjunctiva are right underneath the surface allowing immediate reach and permeation to the surface with the adjunct pump function of the eye lid tone. FIG. 68B shows the junction (arrow) 1163 in accordance with FIG. 68A. The illustration includes the epithelium 1164, and blood vessels 1167 of the skin of the eye lid and blood vessels 1166 and epithelium 1165 (shown as a single top line) of the conjunctiva. FIG. 68B also includes muscles and ligaments in proximity to the conjunctiva and eye lid pocket such as the inferior tarsal muscle 1168, the lower lid retractors 1169, the inferior suspensory ligament of Lockwood 1170, and the inferior rectus muscle 1171. Although, the eye lid has the thinnest skin in the body, the blood vessels are still incredibly deeply located when compared to the conjunctival vessels. These muscles 1168, 1169, 1170, 1171 which are in proximity to the conjunctiva can be used as a electromechanical source of energy for the Implantable ICLs.

Figure 69A:
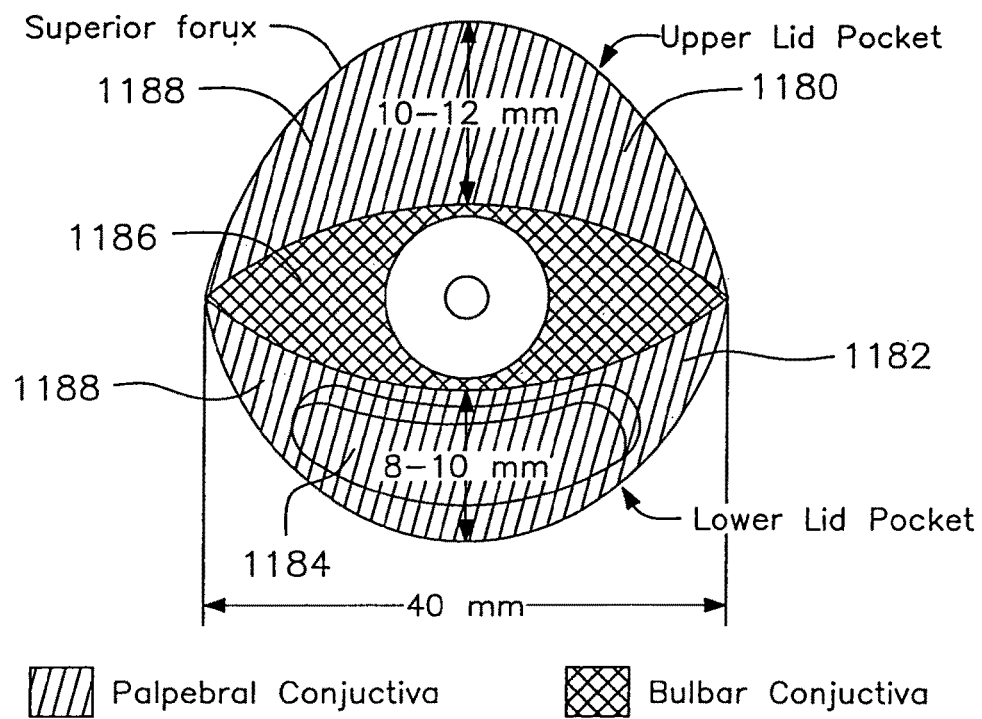
FIG. 69A and 69B show schematic illustrations of the dimensions and location of the conjunctiva.
Figure 69B:
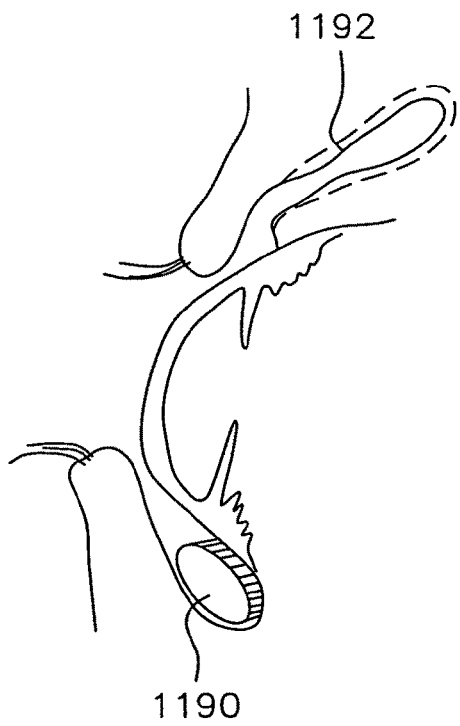

FIGS. 69A and 69B show the surprising large conjunctival area for diagnostics in accordance with the present invention. There are two large pockets, one superior 1180 and one inferiorly 1182. These eye lids pockets are lined by the vascularized conjunctiva. The pocket formed by the upper eye lid measures in height about 10 to 12 mm in a half moon shape by 40 mm in length. The lower eye lid pocket measures about 8 to 10 mm in height by 40 mm in length and can easily accommodate an ICL 1184 according to the principles of the invention. FIG. 69A also shows the different locations for the conjunctiva, the bulbar conjunctiva 1186 lining the eye ball and the palpebral conjunctiva 1188 lining the eye lid internally covering the whole eye lid pocket.

FIG. 69B shows a cross-sectional side view of the eye lid pockets inferiorly with an ICL 1190. Superiorly the figure shows the lid pocket in a resting state and a distensible state. The eye lid pocket is quite distensible and can accommodate a substantially thick device.

Figure 69C:
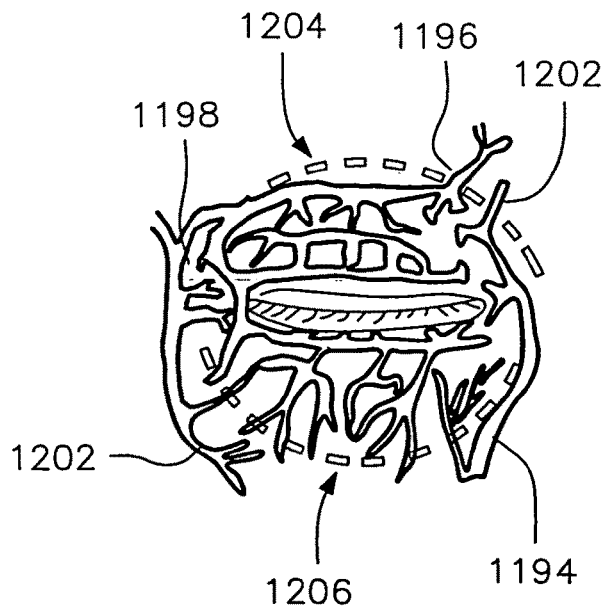
FIG. 69C shows a schematic illustration of the vascularization of the conjunctiva and eye.

FIG. 69C shows the vascular supply of the lids and conjunctiva including facial vessel 1194, supraorbital vessel 1196, lacrimal vessel 1198, frontal vessel 1200 and transverse facial vessel 1202. The eye is the organ with highest amount of blood flow per gram of tissue in the whole human body. This high vascularization and blood supply provides the fluid flow and volume for measurement in accordance with the current invention. Dashed lines in FIG. 69C mark the eye lid pockets, superiorly 1204 and inferiorly 1206.

Figure 69D:
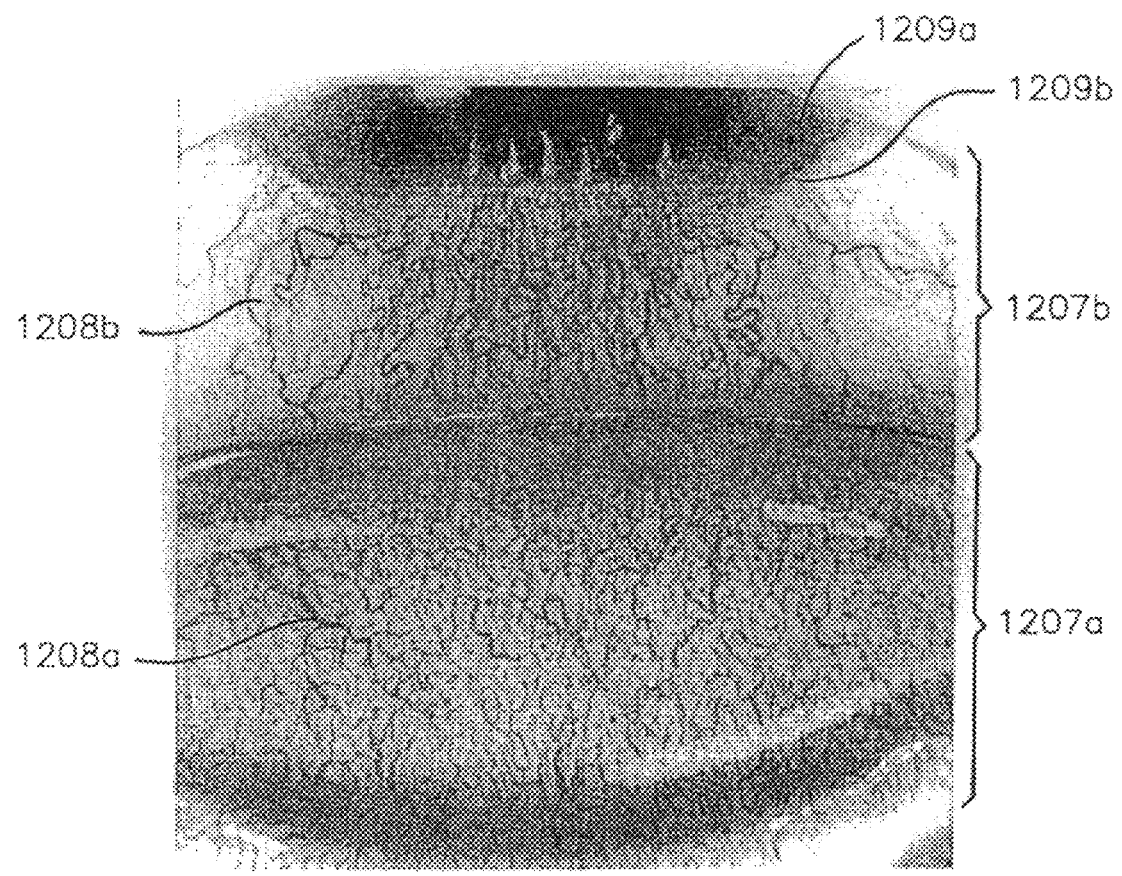
FIG. 69D is a photographic illustration of the palpebral and bulbar conjunctiva and blood vessels.

FIG. 69D shows a photograph of the palpebral conjunctiva 1207*a* and bulbar conjunctiva 1207*b* with its blood vessels 1208*a*, 1208*b*. The conjunctival vessels 1208*a*, 1208*b* consists of a multilayered vascular network pattern easily visible through the thin conjunctival epithelium. The structural vascular organization of the conjunctiva creates a favorable arrangement for measurement according to the principles of the invention since the capillaries lie more superficially, the veins more deeply and the arteries in between. However considering that the conjunctiva is extremely thin, the distance from the surface is virtually the same for all three types of vessels. The photograph is being used with the sole purpose to clearly illustrate the conjunctival blood vessels. The bottom part of the figure shows the palpebral conjunctiva 1207*a* with the eye lid everted to show the blood vessels 1208*a* which lines the eye lids internally. Above that one can see the bulbar conjunctiva 1207*b* and its blood vessels 1208*b* covering the eye ball (white part of the eye). On top of the figure, the cornea 1209*a* is partially shown and the limbal area 1209*b*, which is the transition between cornea and conjunctiva.

Figure 70A:
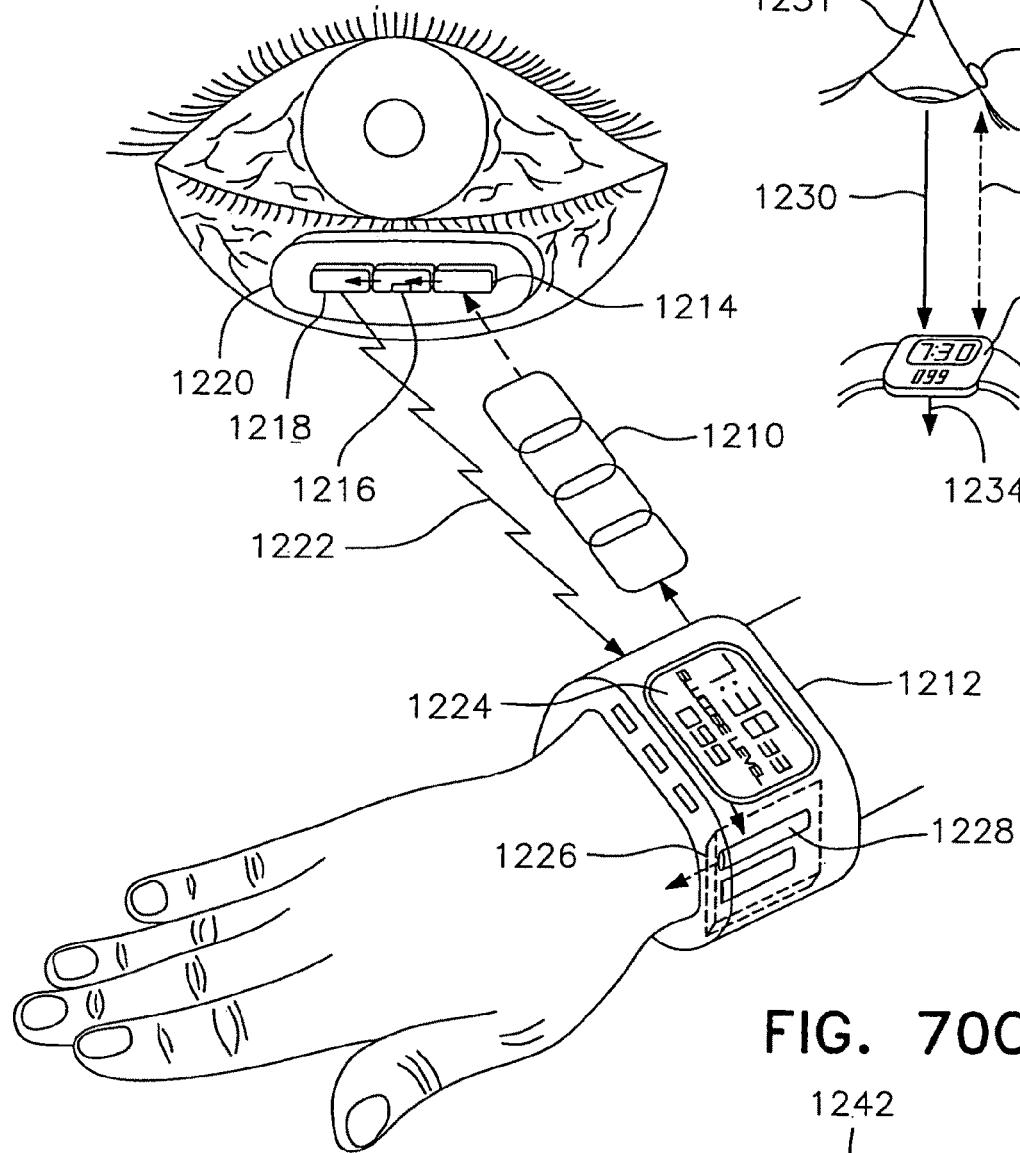
FIG. 70A through 70C exemplary embodiments illustrating a continuous feed-back system for non-invasive blood glucose monitoring.

FIG. 70A shows an exemplary embodiment of a non-invasive glucose detection system with the ICL 1220 in accordance with the principles of the invention with the ICL being powered by electromagnetic induction coupling means 1210 produced at a remotely placed source such as a wrist-band 1212 or alternatively the frame of eye glasses. Electromagnetic energy from the wrist-device is transferred to an ultracapacitor 1214 in the ICL 1220 which acts as the power source for the ICL working on a power-on-demand fashion supplying power in turn to the sensor 1216 which is then activated.

Subsequent to that, the glucose level is measured by the sensor 1216 as an electrical current proportional to the concentration of glucose in the eye fluid which is then converted into an audiofrequency signal by the integrated circuit radio frequency transceiver 1218. The audiofrequency signal 1222 is then transmitted to the wrist-band receiver 1212, with said audiofrequency signal 1222 being demodulated and converted to an electrical signal corresponding to the glucose concentration which is displayed in the LED display 1224 according to the principles of the invention. Subsequent to that, with the use of a microprocessor controlled feed-back arrangement, the wrist-band device 1212 transdermally 1226 delivers substances from reservoir 1228 by means such as iontophoresis, sonophoresis, electrocompression, electroporation, chemical or physical permeation enhancers, hydrostatic pressure or passively with the amount of substance delivered done according to the levels measured and transmitted by the ICL. The wrist-band device 1212 besides displaying the glucose level acts as a reservoir 1228 for a variety of substances.

Figure 70B:
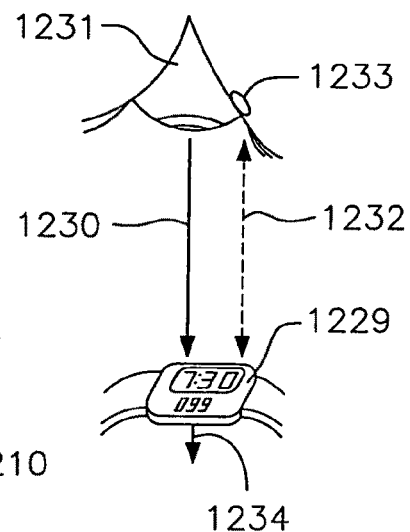

FIG. 70B shows a summary of the system which includes the natural motion of looking at a wrist-watch 1229 by eye 1231 to check time 1230 which automatically activate the ICL 1233 to transmit the signal 1232 and deliver the substance into the user=s skin 1234.

Figure 70C:
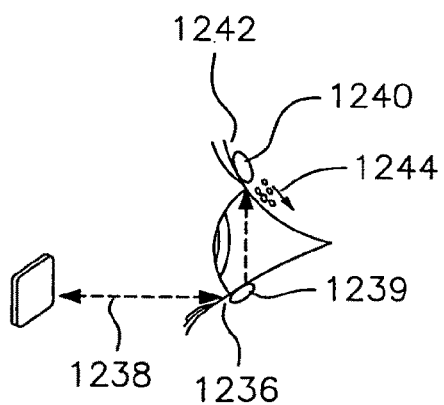

FIG. 70C shows an exemplary embodiment in which the same steps are taken as described above with the ICL 1239 located in the lower eye lid pocket 1236 which is remotely activated by signal 1238, but now the delivery of substances 1244 is done by an ICL 1240 located in the upper eyelid pocket 1242 that acts as a drug reservoir using the same principles as iontophoresis, sonophoresis, electroporation, electrocompression, chemical or other physical enhancers, hydrostatic pressure or passively according to the levels measured. The characteristics of the conjunctiva allows a Therapeutic ICL to deliver chemical compounds in a variety of ways both conventionally (invasive or simple absorption as with eye drops) and non-conventionally as described above.

The fact that the conjunctiva does not have a high electrical resistance, since the conjunctiva does not have stratum corneum and high lipid content, makes the conjunctiva an ideal place for using ICL drug delivery system associated with stimulus by electrical energy. Therapeutic ICLs can also contain sensors that detect the chemical signature of diseases and cancers before they turn into life-threatening conditions. Once the disease is identified, therapeutic solutions are released, for instance smart bombs, which kill, for instance cancer cells, according to the chemical signature of the cancer cell. The Therapeutic ICLs can deliver a plurality of drugs contained in microchips according to information provided by the sensor. Although the Therapeutic ICL system is preferably used in conjunction with chemical detection, it is understood that the Therapeutic ICLs can work as a drug delivery system as an isolated unit in accordance with the principles described in the current invention. Therapeutic is referred to herein as a means to deliver substances into the body using an ICL placed in the eye.

Figure 71:
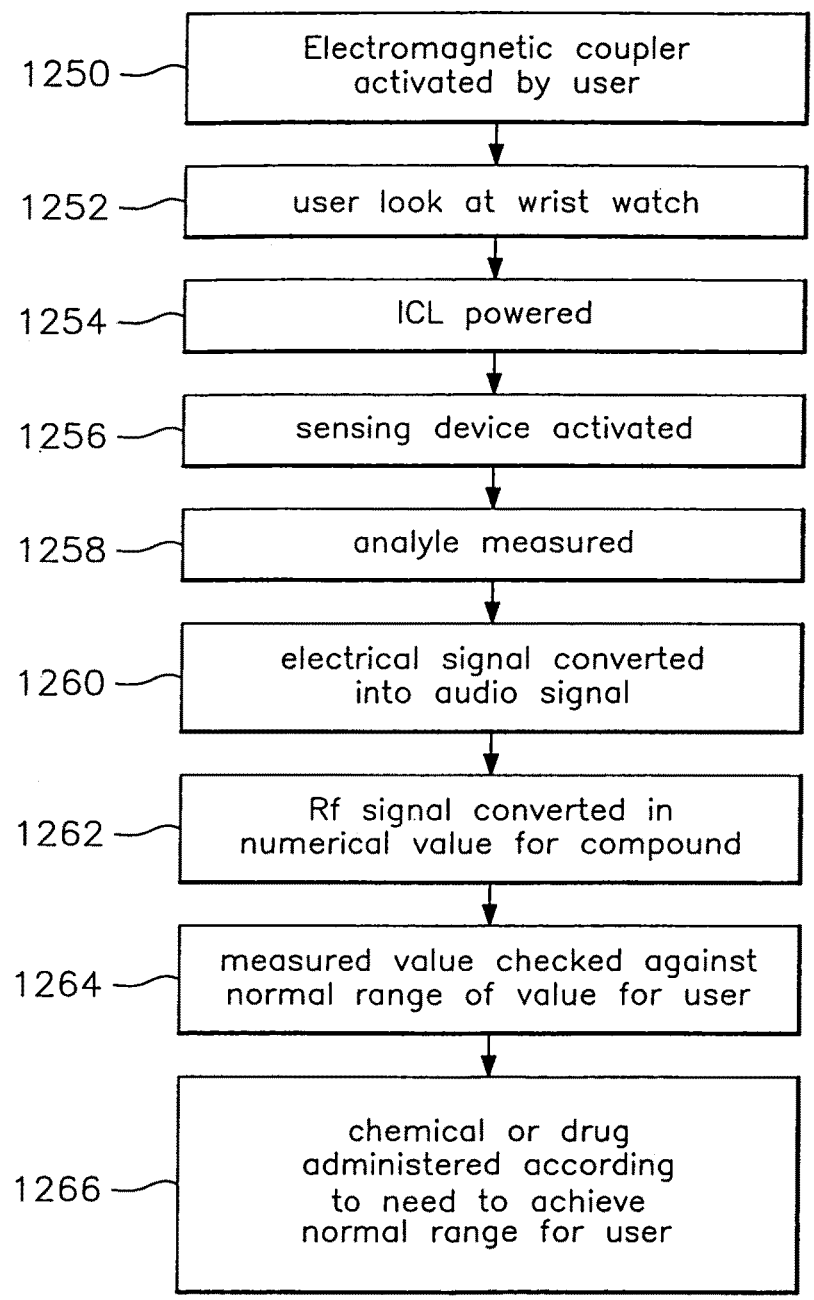
FIG. 71 is a flow diagram showing the operational steps of the system depicted in FIG. 70A-70C.

FIG. 71 shows the flow diagram with steps of the function using the system in FIG. 70. The ICL is remotely powered in order to decrease cost and the amount of hardware in the body of the ICL, creating extra space for a multisensor system. Furthermore, the power-on-demand system allow the user to have control on how many times to check the glucose level according to the prescription by their doctor. Sometimes patients need to check only at certain times of the day, this design allows a more cost-effective device for each patient individually. Using an active system, the ICL can be set to periodically and automatically check the glucose level. Patients who need continuous monitoring can have a power source in the lens or alternatively with a continuous electromagnetic coupling derived from a source placed in the frame of eye glasses. In accordance with the current description at step 1250, the user activates the wrist-watch. Then at step 1252 the user looks at his wrist-watch in the conventional manner to check time. At step 1254 the ICL sensor is powered and at step 1256 the sensor is activated with the analyte measured at step 1258. At Step 1260 the integrated circuit radio frequency transceiver converts the electrical signal into an audio signal. At step 1262 the wrist-watch converts the audio signal into a numerical value. Step 1264 checks the numerical value acquired against normal numerical value stored for the user. At step 1266 substance is delivered to the user in order to achieve normal range for the user.

Figure 72A:
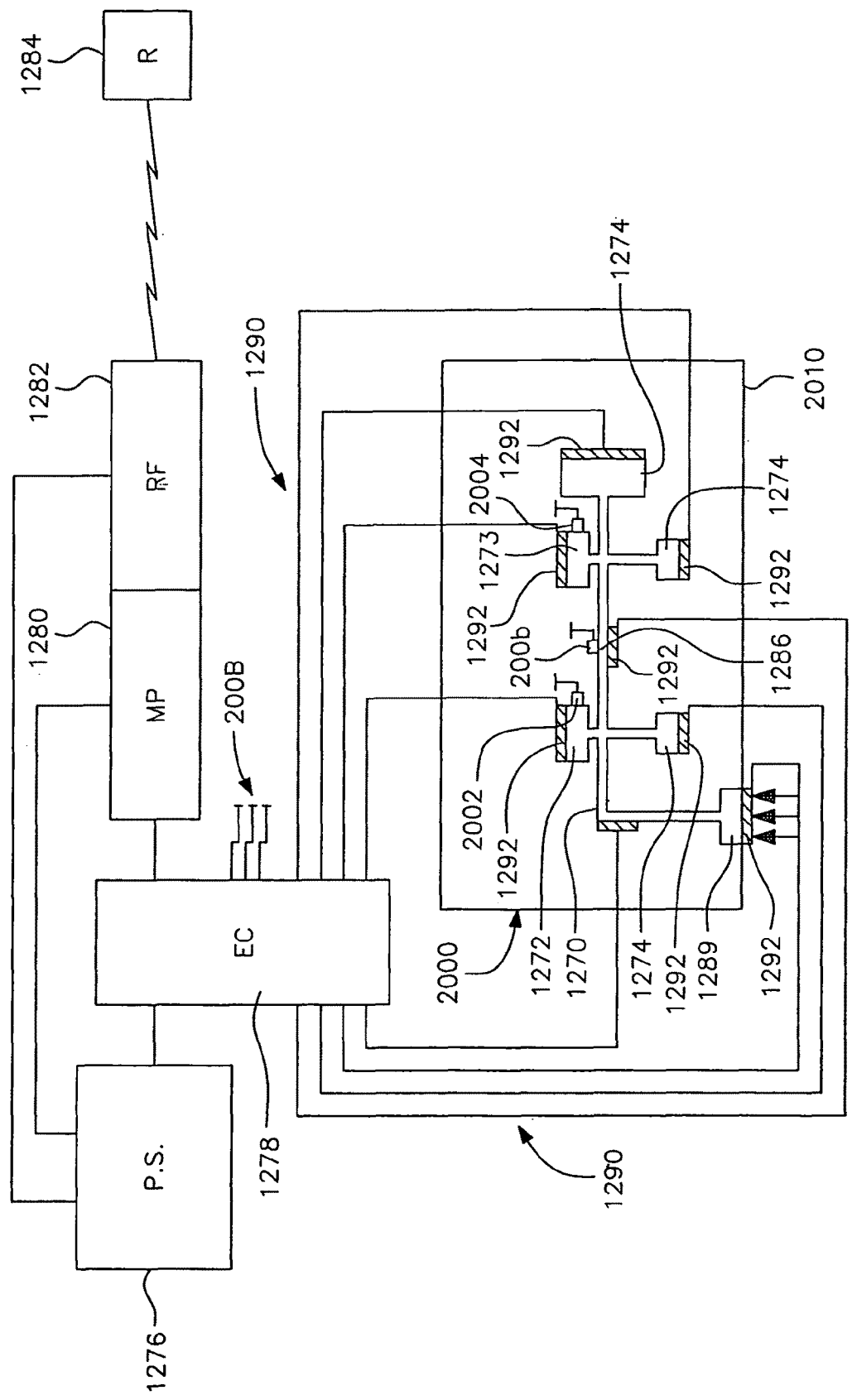
FIG. 72A and 72B are exemplary embodiments of the intelligent contact lens illustrating a complete microlaboratory of the current invention using microfluidics technology including power, control, processing and transmission systems.

FIG. 72A shows an exemplary embodiment of a microfluidic ICL 2000 comprised of a network of microchannels 1270 in communication with each other and with reaction chambers 1272 and reservoirs 1274. The system includes a combination of a microfluidic analysis system and a biosensing system, power source 1276, electrical controller 1278, microprocessor 1280 with an integrated circuit radio frequency transceiver 1282 and a remotely placed receiver system 1284. The central electrical controller 1278 applies electrical energy to any of the channels 1286, reservoirs 1274 or/and reaction chambers 1272 in which evaluation occurs according to the application used. With the appropriate electrical stimulus, mechanical stimulus, diffusion or/and capillary action or a combination thereof, either naturally by the eye or artificially created, eye fluid and/or cells moves through a selectively permeable membrane into the primary chamber 1288 which is in apposition with the conjunctival surface.

FIG. 72A also shows wires 1290 and electrodes 1292 which are placed in contact with the fluid channel 1270, chambers 1272, 1273 and/or reservoirs 1274 for applying electrical energy in order to move and direct the transport of fluid in the network of microchannels 1270 with the consequent electrokinetic motion of the substances within the ICL microchannel network 2000 according to the application used. The ICL microfluidic system includes a control and monitoring arrangement for controlling the performance of the processes carried out within the device such as controlling the flow and direction of fluid, controlling internal fluid transport and direction, and monitoring outcome of the processes done and signal detection. The dimensions of the microchannels are in the microscale range on average from 1 µm to 300 µm with the membrane surface in the primary chamber with dimensions around 300 µm in diameter and with the microchannels and chambers containing positive and/or negative surface charges and/or electrodes in its surface such as for example thin film electrodes. Electrokinetics are preferably used to move fluids in the network of microchannels and chambers creating a uniform flow velocity across the entire channel diameter.

Although a pressure-driven system can be used, in this pressure driven in the system the friction that occurs when the fluid encounters the walls of the channels results in laminar or parabolic flow profiles. A good example of such flow profile is present in the blood vessels which is a laminar flow in a pressure-driven system powered by the pumping function of the heart. These pressure-driven system generates non-uniform flow velocities with the highest velocity in the middle of the microchannel or blood vessel and close to zero as it moves towards the walls.

As previously described, the microfabrication techniques and materials used in the semiconductor industry can be used in the manufacturing of the ICL microfluidic system allowing etching of microscopic laboratories onto the surface of chips made of silicon, glass or plastic with the creation of microchannels which allow uniform flow. The power supply 1276 in combination with the electrical controller 1278 according to the application needed delivers electrical energy to the various electrodes 1292 in the channel network which are in electrical contact with the fluid and/or cells acquired from the eye. In the exemplary embodiment a couple of reaction chambers 1272, 1273 are depicted.

Reaction chamber 1272 has a temperature sensor 2002 and reaction chamber 1273 has a pressure sensor 2004, while a pH sensor 2006 is placed in the wall of the channel in order to detect pH changes as the fluid flows through the microchannel 1270. The signals from the sensors are coupled to the controller 1278 and microprocessor 1280 by wires 2008 (partially shown and extending from electrodes 2202, 2204 and 2006) and radio frequency transceiver 1282 for further processing and transmission of signal to a remote receiver 1284. The outer ICL structure 2010 works as an insulating coating and shields the eye environment from the chemical and physical processing occurring in the ICL microfluidic system 2000.

Figure 72B:
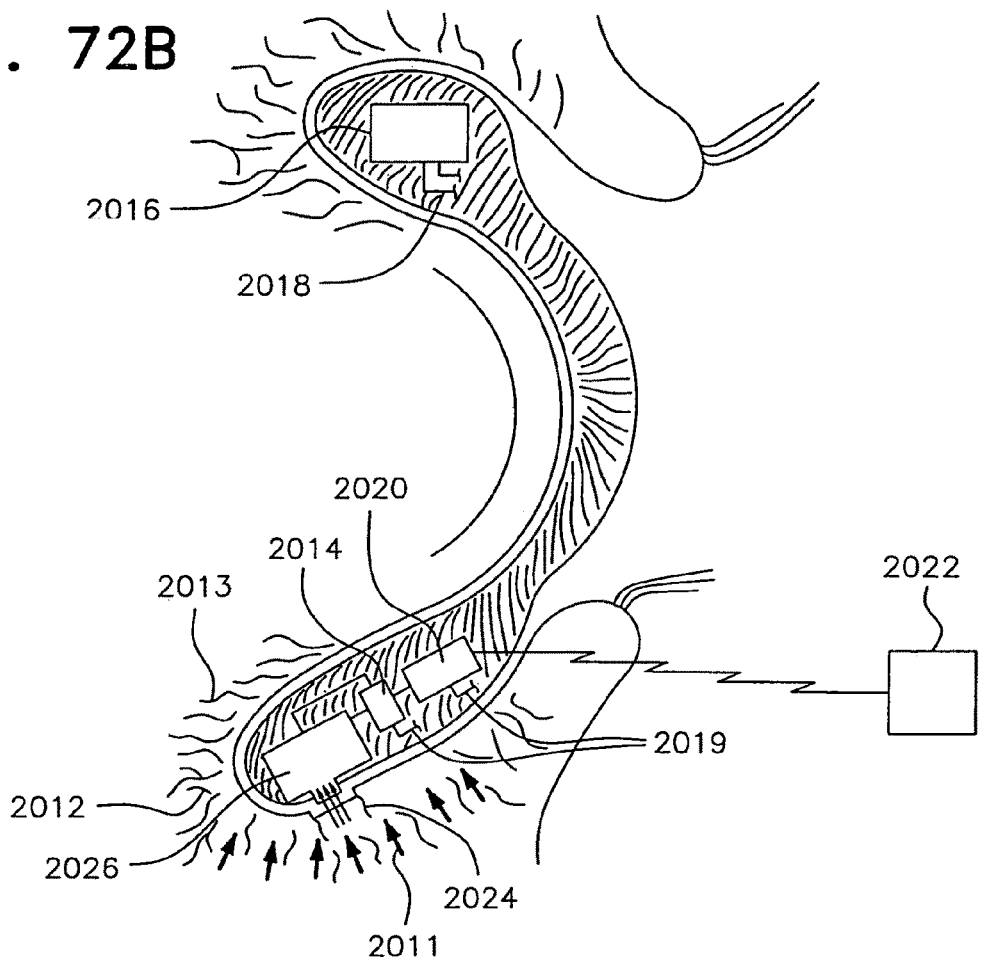

FIG. 72B illustrates the microfluidic ICL placed on the surface of the eye laying against the conjunctival blood-vessels-2013 with mounted microfluidic system 2012, controller 2014, power source 2016 and transmitter 2020 which are connected by fine wires 2018 (showing only partially extending from power source 2016 to the integrated circuit processor transmitter 2020 and controller 2014 via wires 2019, also partially shown). The signals acquired from the analysis of eye fluid and cells is then transmitted to a remote receiver 2022. The sensing unit 2026 is placed in complete apposition with the conjunctival surface and its blood vessels 2024. Although in the schematic illustration there is shown a small space between the surface of the ICL and the conjunctival surface, in its natural state the surface of the ICL is in complete apposition with the surface of the conjunctiva due to the natural tension and force of the eye lid (large arrows 2011). Thus allowing the ICL to easily acquire cells (surface of the eye is composed of loosely arranged living tissue) and/or fluid from the surface of the eye with the cells and/or fluid moving into the ICL microfluidic system as the small arrows indicate.

Figure 73A:
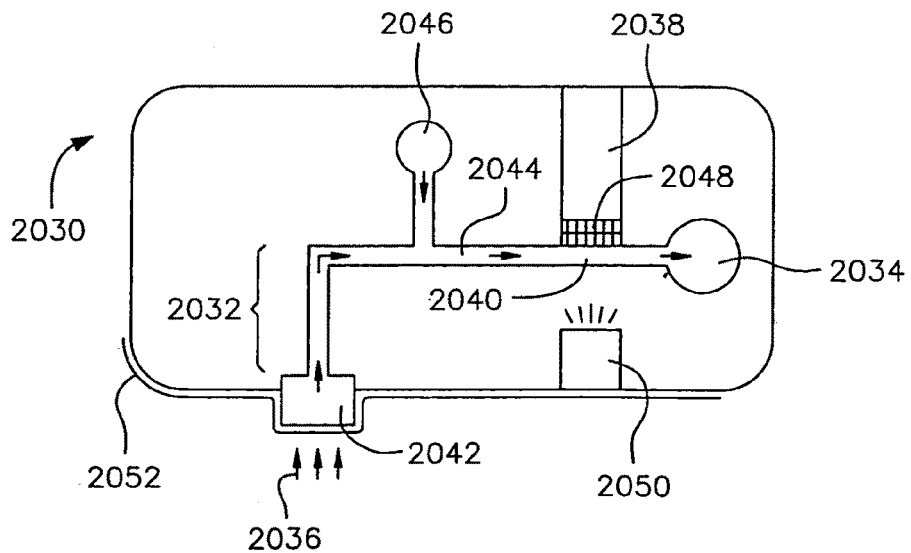
FIG. 73A through 73C are schematic illustrations of examples of microfluidics systems according to the current invention.

FIG. 73A illustrates an exemplary embodiment of the microfluidic ICL 2030 with a network of interconnected microchannels 2032 and reservoirs with reagents with each microcavity preferably containing a separate testing substance with the microfluidic ICL 2030 in apposition with the conjunctiva 2052. This exemplary embodiment also includes disposal reservoir 2034, detection system and ports for electrodes (not shown) as previously described.

The ICL electrical system applies selectable energy levels simultaneously or individually to any of the microcavities or channels by electrodes positioned in connection with each of the reservoirs. The substances present in the reservoirs are transported through the channel system with the precise delivery of the appropriate amount of substance to a certain area or reaction chamber in order to carry out the application.

In accordance with the invention, the fluid and/or cells from the eye are introduced at 2036 into the ICL microfluidic system with materials being transported using electrokinetic forces through the channels 2032 of the ICL microfluidic system 2030. After the eye fluid is introduced in the ICL microchannel network 2032, the fluid is manipulated to create an interaction between at least two elements creating a detectable signal. In accordance with the invention, if a continuous steady flow of eye fluid occurs in the microchannels but no detectable element is present, then no detectable optical signal is generated by optical detection system 2038, thus no signal is acquired and transmitted. If for instance the immunointeraction creates a change in the optical property of the reaction medium, then the detectable signal indicates the presence of the substance being evaluated and an optical signal is generated by optical detection system 2038. Thus a detectable optical signal is created and transmitted. This embodiment includes a detection zone 2040 for optical detection of for example chemiluminescent material or the amount of light absorbed using a variety of optical detection systems and laser systems. Exemplary optical techniques include immunosensors based on optical detection of a particular immunointeraction including optical detection of a product of an enzymatic reaction formed as a result of a transformation catalyzed by an enzyme label as well as direct optical detection of the immunointeraction and optical detection of a fluorescent labeled immunocomplex.

An exemplary embodiment in accordance with the invention shows the eye fluid 2036 flowing through the microchannel network 2032 from the primary chamber 2042 with a certain heart marker (antigen) present in the eye fluid. Measurement of the heart markers such as for example PAI-1 (plasminogen activator inhibitor) indicates the risk of cardiovascular disease and risk of a life-threatening heart attack. Other markers such as troponin T can help identify silent heart damage. Many patients sustain heart attacks, but because of the lack of symptoms, the heart damage goes undetected.

When a second heart attack then occurs with or without symptoms there is already too much damage to the heart leading then to the demise of the patient, sometimes described as sudden cardiac death. However, in reality the deterioration of the heart was not sudden, but simply further damage that occurred associated with an undetected initial heart damage. If silent heart damage was identified, the patient could have been treated on a timely manner. If a marker that shows risk for heart damage before the damage occurs is identified, then the patient can be timely treated and could have normal life. However, a patient at risk of a heart attack in order to identify a marker for damage has to have daily monitoring which is now possible with the present invention.

In accordance with the invention, the eye fluid is transported to the main channel 2044 and then periodically a certain amount of antibody to the PAI-1 (antibody) flows from reservoir 2046 into the main channel 2044 with the consequent mixing of antigen and antibody and the formation of an antigen-antibody complex considering that the heart marker PAI-1 (antigen) is present in the eye fluid. The formation of the antigen-antibody complex in the surface of the optical transducer 2048 creates a detectable signal indicating the presence of the marker.

A low-cost exemplary embodiment comprises of simultaneous activation of a light source 2050 and flow of antibody to the main channel 2044. This light source 2050 is coupled to a photodetector 2038 and lens. If the marker is present, then the creation of the antigen-antibody complex leads to a change in the amount of light reaching the photodetector 2038 indicating the presence of the marker. The surface of the optical system 2048 can also be coated with antibody against the antigen-antibody complex which would create a coating of the optical system 2048 creating a shield with the consequent significant decrease of light reaching the photodetector 2038 coming form the light source 2050. The signal is then transmitted to the user informing them that the heart marker was detected since there Was a signal coming from optical detector 2038 and in view of that, the optical system surface is covered with a specific antibody. Then, the signal generated refers to the presence of the antigen. Although only one detection system is described, a multiple system can be achieved with detection of multiple substances and/or markers simultaneously. Any other fluid or material can then subsequently be transported to the disposal reservoir 2034. Although only one exemplary optical detection was described in more detail it is understood that any optical detection system can be used for carrying out the present invention including other optical immunosensing systems.

Figure 73B:
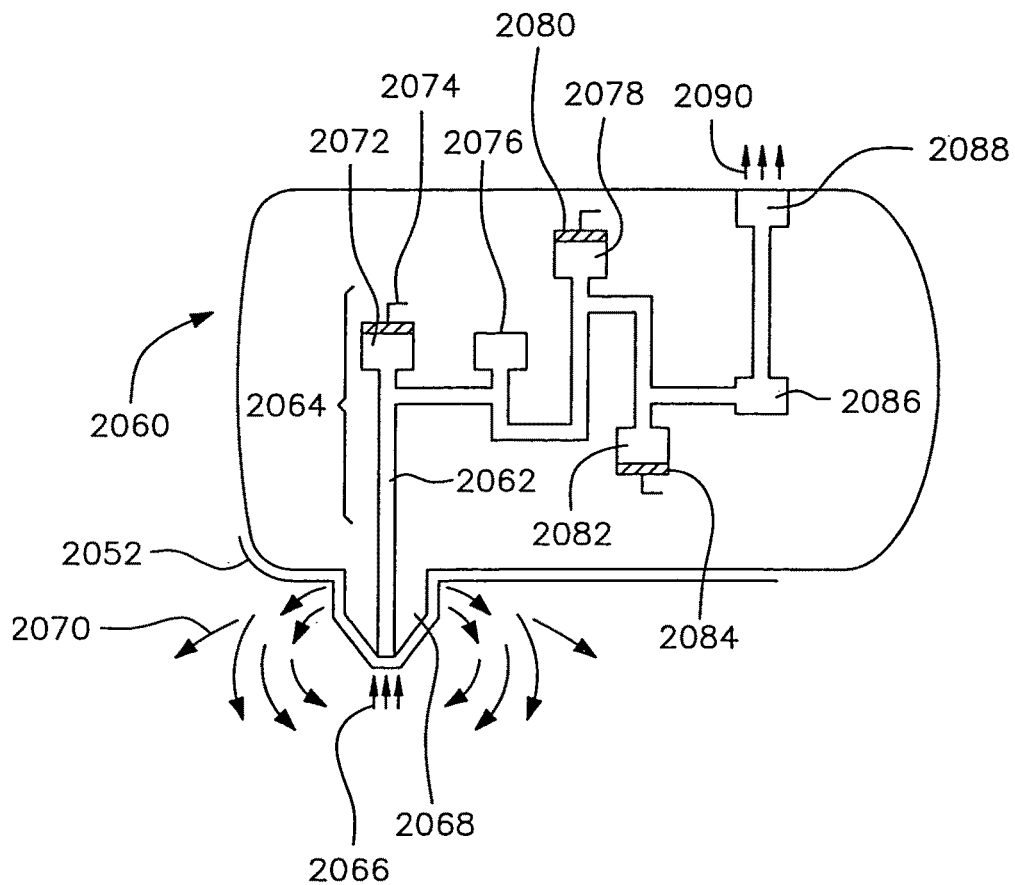

FIG. 73B shows an ICL microfluidic system 2060 in apposition with the conjunctiva 2052 with various capabilities in accordance with electrokinetic principles, microfluidics and other principles of the invention. The fluid from the eye 2066 is moved into the primary microchannel 2062 of the ICL microchannel network 2064 by capillary action associated with the mechanical displacement 2070 of fluid by the protruding element 2068 with further pushing of fluid and/or cells into the ICL microchannel 2062. The design of this ICL creates an enhancement of flow that may be needed according to certain applications.

This design with protrusion element 2068 creates a strong apposition of the ICL 2060 against the conjunctival surface 2052. An interesting analogy relates to a person laying on a bed of nails in which the nails do not penetrate the skin because the force is evenly distributed along the body surface. If only one nail is displaced upwards the nail will penetrate the skin. The same physical principle of equal distribution of forces apply to this design.

The conjunctiva 2052 is a moldable tissue and thin, and the even distribution of pressure by a smooth ICL surface leads to a certain permeation rate. However if a protrusion 2068 on the surface of the ICL is created there is an increase in the rate of permeation and capillary action due to the surrounding pressure and uneven distribution of pressure forcing more fluid and cells into the ICL microchannel 2062. This ultra rapid passive flow may be important when multiple substances, fluid and cells are analyzed in a continuous manner such as multiple gene analysis. Most important is that the conjunctival area proves again to be the ideal place for diagnostics with the ICL system since the conjunctiva, contrary to other parts of the body, does not have pressure sensing nerve fibers and thus a patient does not feel the protrusion 2068 present in the surface of the ICL, although the protrusion is still very small.

In accordance with the invention, the fluid moves into microcavity 2072 which consists of a glucose oxidase amperometric biosensor. The glucose level present in the eye fluid is then quantified as previously described and the glucose level of the sample eye fluid 2066 being then identified and transmitted to a remote receiver via micro lead 2074 (partially shown). Processing then can activate electrical energy to move the eye fluid 2066 to microcavity 2076 which contains an antibody for a certain drug. A reaction antigen-antibody then occurs in response thereto if the drug being evaluated is present in the eye fluid collected forming an antigen-antibody complex. The eye fluid with the antigen-antibody complex actively or passively moves to microcavity 2078 which contains a catalytic antibody to the antigen-antibody complex. The catalytic antibody is immobilized in a membrane with associated pH sensitive electrodes 2080. The antigen-antibody complex when interacting with the catalytic antibody present in the microcavity promotes the formation of acetic acid with a consequent change in pH and formation of a current proportional to the concentration of antigens—in this illustration, a certain drug allowing thus therapeutic drug monitoring.

The exemplary embodiment also includes microcavity 2082 which contains immobilized electrocatalytic enzyme and associated electrode 2084, which in the presence of a substrate, for instance a certain hormone, produce an electrocatalytic reaction resulting in a current proportional to the amount of the substrate. Fluid is then moved to microcavity 2086 in which a neutralization of chemicals can be achieved before leaving the system through cavity 2088 into the surface of the conjunctiva 2090 with the neutralization for instance including neutralization of pH regarding the potential presence of chemicals produced such as remaining acetic acid from cavity 2078.

The ICL system then can repeat the same process, for example, every hour for continuous monitoring, including during sleeping. Although the amount of acid formed and reagents is minute and the tear film washes much more noxious elements, a variety of safety systems can be created such as selectively permeable membranes, valves, neutralization cavities, and the like. A variety of elements can be detected with the tests performed by the ICL such as microorganisms, viruses, chemicals, markers, hormones, therapeutic drugs, drugs of abuse, detection of pregnancy complications such as preterm labor (such as detecting Fetal Fibronectin), and the like.

Figure 73C:
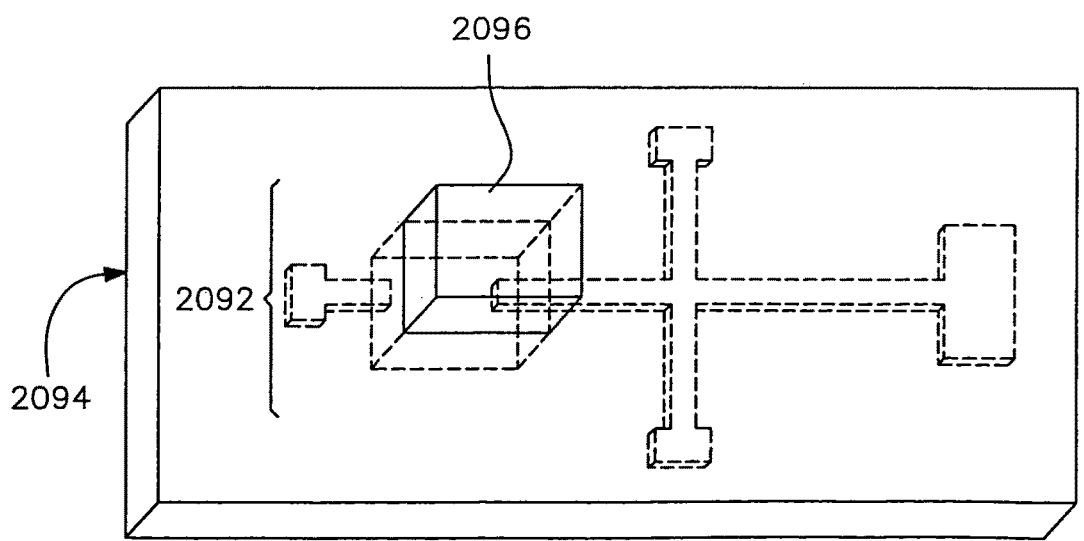

FIG. 73C shows a schematic view of the microfluidic ICL with the network of microchannels 2092 located in the body of the ICL microfluidic substrate 2094 and the primary chamber 2096 comprising a protruding element configuration. It is noted that the microfluidic system consists of an ultrathin substrate plate as with a silicon chip but with a larger dimension in length which fits ideally with the anatomy of the eye lid pockets.

Figure 74A:
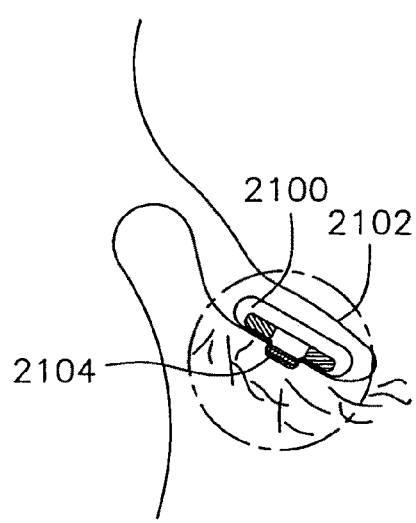
FIG. 74A through 74E are schematic illustrations of an exemplary biosensor according to the principles of the current invention with the encircled area in FIG. 74A being shown on an enlarged scale in FIG. 74B.

FIG. 74A shows an ICL 2100 for glucose monitoring placed in the lower eyelid pocket 2102 in apposition to the conjunctival surface and blood vessels 2104 present in the surface of the eye. The exemplary ICL shown in FIG. 74B on an enlarged scale includes in more detail the sensor 2106 for detection of glucose located in the main body of the ICL 2100 with its associated power source 2108 and transmitter system 2110. The sensor surface 2106 extends beyond the surface of the remaining ICL surface in order to increase flow rate of fluid to the sensor and associated membrane.

Figure 74B:
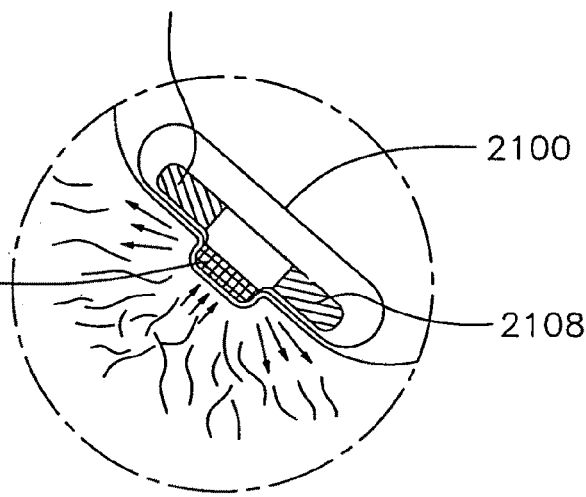
Figure 74C:
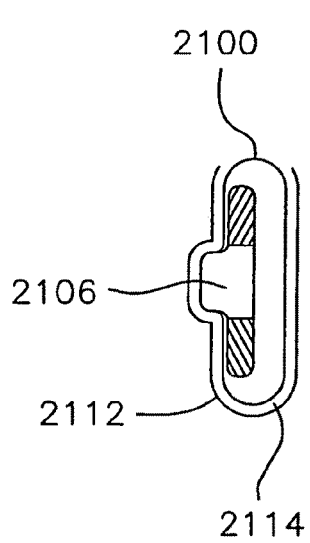
Figure 74E:
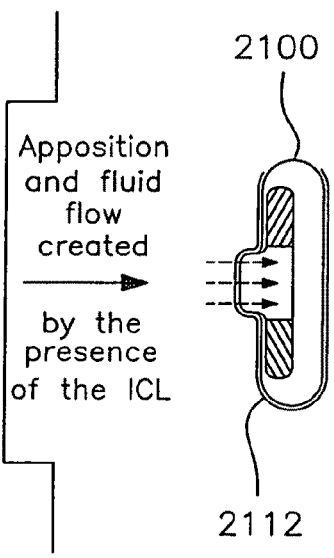

FIGS. 74C and 74E show the eye lid pumping action in more detail moving fluid toward the sensor 2106 and creating complete apposition of the ICL 2100 with the conjunctiva 2112. The presence of the ICL 2100 in the eye lid pocket 2114 in FIG. 74E stimulates the increase in tension of the eye lid creating an instantaneous natural pumping action due to the presence of the ICL 2100 in the eye lid pocket 2114.

Figure 74D:
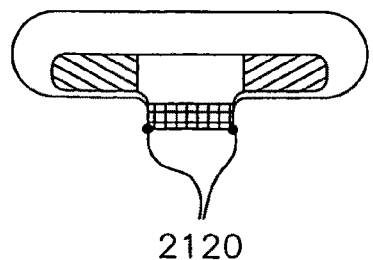

FIG. 74D shows the same ICL 2100 as in FIG. 74B but with an associated ring of silicone 2120 surrounding the protruding membrane area to better isolate the area from contaminants and surrounding eye fluid.

Figure 75A:
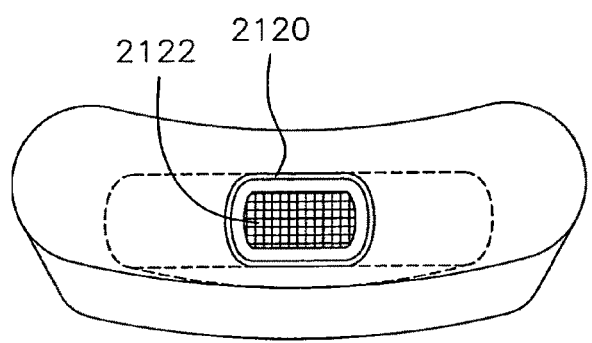
FIG. 75A through 75D are schematic illustrations of various designs for chemical membrane biosensors according to the principles of the current invention.
Figure 75B:
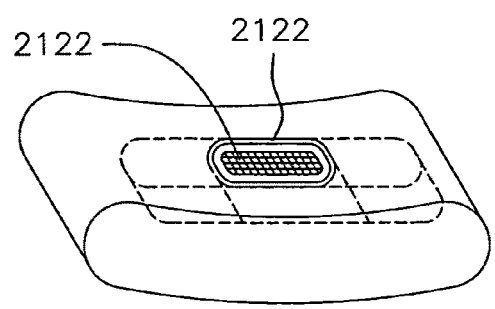
Figure 75C:
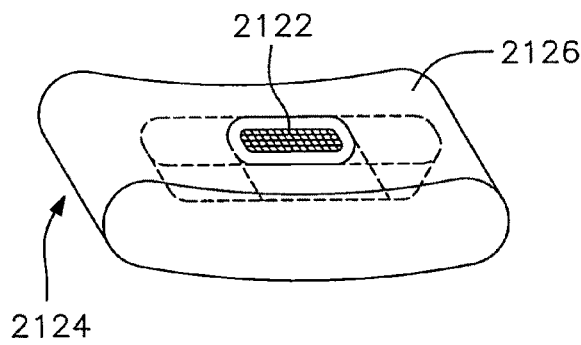
Figure 75D:
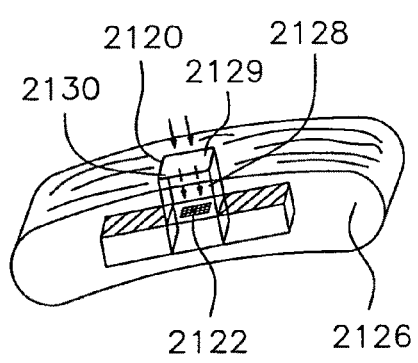

The ICL shown in FIG. 75A includes the exposed membrane 2122 surrounded by a silicone ring 2120. Although silicone is described, a variety of other adherent polymers and substances can be used to better isolate the membrane surface from the surrounding eye environment. FIG. 75A shows a planar view and FIG. 75B shows a side view. FIG. 75C shows an exemplary embodiment with the whole sensor and membrane being encased by the ICL 2124. In this case polymers which are permeable to glucose can be used and the whole sensor and hardware (transmitter and power supply) is encased by a polymer. The membrane sensor area 2122 encased in the lens body 2126 can be completely isolated from the rest of the hardware and lens matrix in the body of the lens 2126. In this embodiment a channel 2128 within the body of the lens 2126 which can have an irregular surface 2129 to increase flow, is created thus isolating and directing the eye fluid for precise quantification of the amount of glucose entering a known surface of the lens 2130 and reaching the surface of the membrane sensor 2122 as shown in FIG. 75D. A silicone ring 2120 is placed on the outer part of the channel 2128 to isolate the channel 2128 from the surrounding environment of the eye. By completely encasing the sensor system, the surface of the ICL covering the membrane can be made with various shapes and surface irregularities in order to increase flow, create suction effect, and the like.

Figure 76:
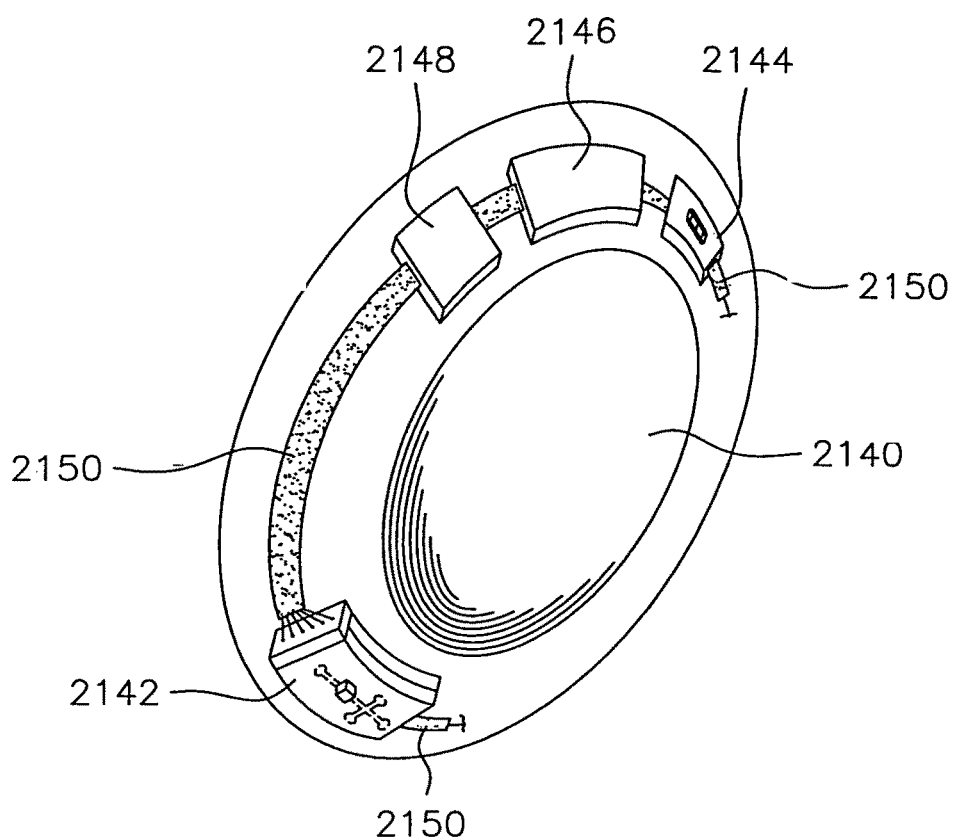
FIG. 76 is a schematic illustration of an exemplary embodiment with a dual system in one single piece lens using both upper and lower eyelid pockets.

FIG. 76 shows an ICL with optical properties in the center 2140 as in conventional contact lenses, with sensing devices and other hardware encased in a ring fashioned around the optical center 2140. This ICL includes a microfluidic system 2142, a biosensor 2144, power supply with controller 2146 and transceiver 2148 connected by various wires 2150.

Figure 77:
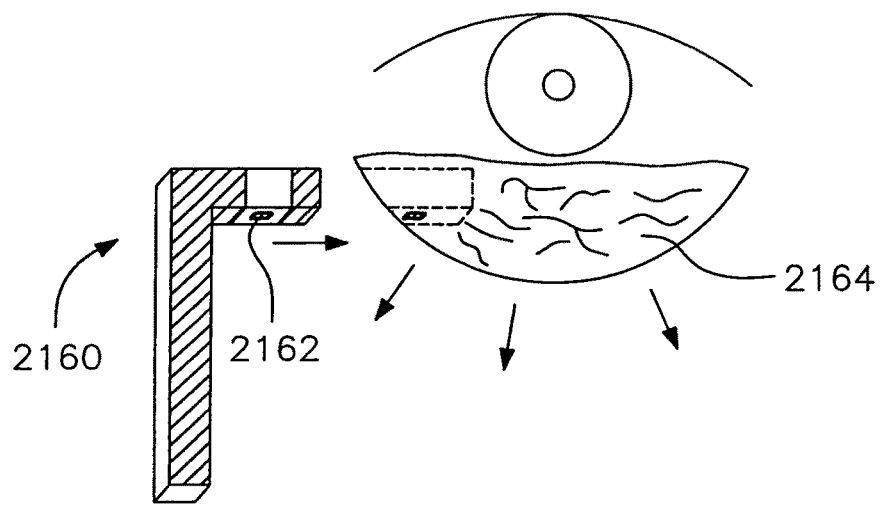
FIG. 77 is an exemplary embodiment in accordance with the principles of the invention.

FIG. 77 shows an exemplary embodiment in which, in contrast to a lens system, a manual rod-like system 2160 is used in which the user holds an intelligent rod 2160 which contains the hardware and sensing units according to the principles of the present invention. The user then places the sensor surface 2162 against the eye, preferably by holding down the lower eye lid. The sensor surface 2162 then rests against the conjunctival surface 2164 and the measurement is done. Since with this embodiment the user looses the pump action, friction, and natural pumping action of the eye lid, the user can, before placing the sensor surface against the eye, rub the opposite side of the sensor which in this case would have an irregular surface, in order to create the flow as naturally produced by the eye lid physiologic action. This embodiment can be used by a user who only wants one measurement, let=s say for instance to check-cholesterol levels once a month. The embodiment also would be useful for holding an enormous amount of hardware and sensing devices since the rod 2160 can be made in any dimension needed while the lens has to fit within the eye anatomy. The other advantage of this other embodiment is that there is no need for wireless transmission as the handle itself can display the results. One must keep in mind though that this embodiment is not well suited for continuous measurement and also would demand an action by the user contrary to the lens embodiment which measurement takes place while the user performs his/her daily routines.

Alternatively, the tip of the rod can be coated with antigen. The tip is then rubbed or placed against the conjunctiva and/or surface of the eye. If antibodies to the antigen are present a detectable signal is produced, with for instance a variety of electrical signals as previously described. The tip of the rod can contain a variety of antigens and when any one of those is identified by the corresponding antibody a specific signal related to the antigen is produced. Alternatively, the tip can have antibodies and detect the presence of antigens. Naturally the simpler systems described above can be used in any embodiment such as a rod, contact lens, and the like.

Figure 78A:
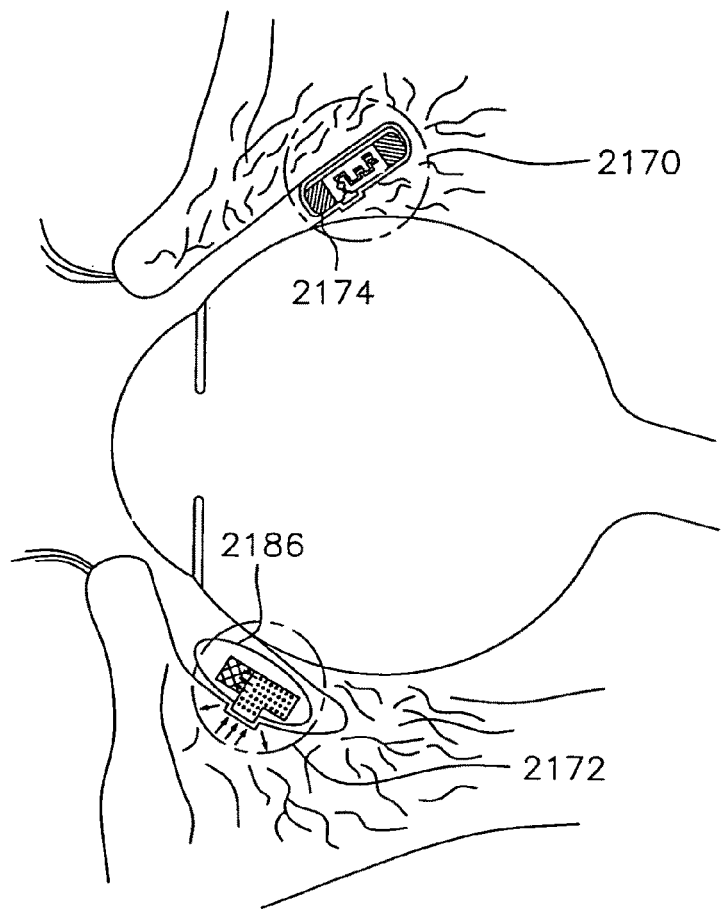
FIG. 78A through 78C are schematic illustrations of an exemplary embodiment of dual system with two lenses using both upper and lower eyelid pockets with FIG. 78B being an enlarged view of the upper area encircled in FIG. 78A and FIG. 78C being an enlarged view of the lower area encircled in FIG. 78A.
Figure 78B:
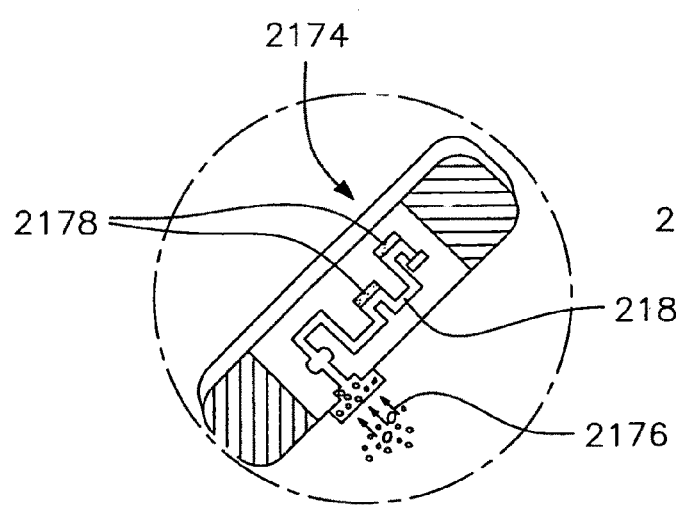

FIG. 78A shows a two piece ICL in both conjunctival pockets, superiorly 2170 and inferiorly 2172. The ICL placed superiorly includes a microfluidic ICL 2174 positioned against the conjunctival surface with the eye fluid 2176 moving from the conjunctiva as shown in more detail in FIG. 78B. The fluid and cells 2176 move into the ICL microchannel network in accordance with the eye lid pumping effect and the other principles of the present invention. This exemplary ICL also includes a couple of reaction chambers 2178 and microvalves and membranes 2180 within the microchannels.

Figure 78C:
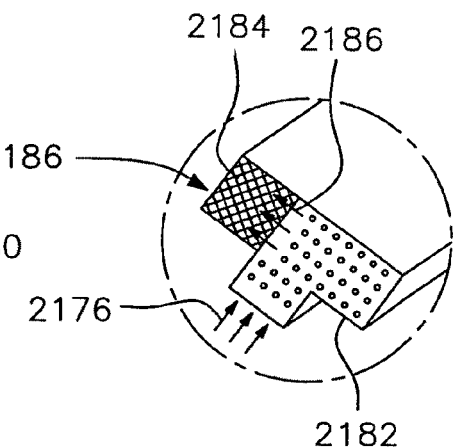

FIG. 78C shows in more detail the ICL 2186 placed in the lower eye lid pocket 2172. This exemplary ICL includes a reservoir 2182 which is filled over time with eye fluid and/or cells 2176 for further processing after removal from the eye. This embodiment also includes a biosensor 2184. Thus said ICL 2186 has a dual function of immediate analysis of fluid as well as storage of eye fluid with part of the fluid being analyzed in the ICL body with the part of fluid permeating a-selective permeable membrane 2186 in the surface of the biosensor 2184.

The ICL in FIG. 79A includes an electroporation system and other means to transfer a variety of substances, molecules and ions across tissue with increase in permeability of tissues associated with an electrical stimulus for transport of the substances, molecules and ions. Electrodes in contact with the conjunctival surface 2192 minimally invasively remove fluid and/or penetrate surface 2192 with minimal sensation. A variety of fine wires (not shown) can also be used and penetrate the surface 2192 with minimal sensation. Those systems can be more ideally used with ICLs and in contact with the conjunctiva 2192 than with skin due to the more appropriate anatomy of the conjunctiva 2192 as described, compared to the skin since the conjunctiva 2192 is a very thin layer of tissue with abundant plasma underneath. The ICL in FIG. 79B include a physical transport enhancement system 2194 such as application of electrical energy and/or creation of an electrical field to increase flow of fluid and/or substances into the ICL sensing systems. The ICL in FIG. 79C includes a chemical transport enhancement system 2196 such as an increase of permeation of a variety of substances, such as for example increased flow of glucose with the use of alkali salts.

Although not depicted, a variety of combinations of ICLs can be accomplished such as total, partial or no encasement of the sensor surface and with or without isolation rings, with or without transport enhancers, with or without protruding areas, with or without surface changes, and the like.

FIG. 80 shows a microfluidic chip ICL 2200 which includes a couple of silicon chips 2202, 2204 in a 5-by-5 array electrode arrangement, a reaction chamber 2206 and a disposal chamber 2208. Cells and fluid 2212 from the surface of the eye are pumped into the main microchannel 2210 with the first chip 2202 electrically separating cells and fluid with subsequent analysis of substances according to the principles of the invention. The cellular elements are then moved into the reaction chamber 2206 in which electric current is applied and break the cell walls with extrusion of its contents. Specific enzymes for organelles present in the reaction chamber 2206 degrade the proteins and organelles present but without affecting nucleic acids such as DNA and RNA. The released DNA and RNA can then be further analyzed in the second chip 2204 or in a microchannel fluidic system as previously described. A variety of oligonucleotide probes can be attached to reaction chambers 2206 or microcavities in chips 2204 or in chambers in microfluidics network in order to capture specific nucleic acid with the creation of a detectable signal such as an electrical signal in which an electrode is coupled with said probe. The ICL technology, by providing a continuous or quasi-continuous evaluation, can identify a mutant gene, for instance related to cancer or disease, among a large number of normal genes and be used for screening high risk populations or monitoring high risk patients undergoing treatment as well as identifying occult allergies and occult diseases and risk for certain diseases and reactions to drugs allowing preventive measures to be taken before injury or illness occur or timely treating the illness before significant damage occurs.

The Human Genome Project will bring valuable information for patients but this information could be underutilized because patients do not want to be tested with fear of rejection by insurance companies. People with genetic predisposition to certain disorders could have a difficult time to find health insurance and/or life insurance coverage.

With the prior practices for genetic testing done in laboratories, patients could be vulnerable to disclosure of their genetic profile. Unfortunately, then life-saving genetic information that allows early detection and early treatment is not going to be fully used to the benefit of patients and society in general.

The ICL system by providing the PIL (Personal Invisible Laboratory) allows the user to do self-testing and identify genetic abnormalities that can cause diseases in a complete private manner. The genetic ICL PIL can, in a bloodless and painless fashion, identify the genetic predisposition to diseases, and sometimes just a change in diet can significantly decrease the development of these diseases.

With the current invention the patient can privately, individually and confidentially identify any disease the patient is at risk of, and then take the necessary measures for treatment. For example, if a patient has genes which are predisposed to glaucoma, a blinding but treatable disease, then the patient can check his/her eye pressure more often and visit eye doctors on a more frequent basis.

Some cancers are virtually 100% fatal and unfortunately not because there is no cure or treatment available but because the cancer was not timely identified. A devastating example concerns a cancer in the genitals or cancer of the ovary. This cancer kills virtually 100% of the women who are diagnosed with this cancer. It is the highest fatality rate for all cancers in women and not because there is no cure or treatment, but because there are no symptoms or signs that would alert those women to seek medical attention, and even sometimes routine examination by the doctor does not identify the occult malignancies.

If a woman knows she has a genetic predisposition for ovarian cancer, being privately and confidentiality identified with the ICL PIL systems, the patient can take the necessary preventive steps, be treated on a timely fashion, and have normal life. A simple small surgery of just removing the affected tissue can be curative, compared to the catastrophic many months of surgeries, chemotherapy and other aggressive therapies, previously used as a course of treatment still only to delay the inevitable demise.

There are many medical situations affecting both men and women, adults and children alike concerning similar situations and diseases as the described ovarian cancer. In general, the most devastating and fatal disorders are the silent ones, which sometimes are very easy to treat. The current invention thus allows full and secure use of information provided by the Human Genome Project in which only the user alone, and nobody else will know about a particular genetic predisposition. The user acquires the ICL of interest and places it in the eye and receives the signal using a personal device receiver.

FIG. 81 shows a complete integrated ICL 2220 with a three-layer configuration. The top layer 2222 which rests against the conjunctiva contains microchannels, reservoirs, and reaction chambers where the chemical reactions take place. The middle layer 2224 has the electrical connections and controller that controls the voltage in the reservoirs and microchannels and the bottom layer 2226 contains the integrated circuit and transmission system.

FIG. 82A through 82D shows an exemplary embodiment of an implantable ICL. As mentioned the conjunctiva is an ideal place since it is easily accessible and the implantation can be accomplished easily using only eye drops to anesthetize the eye. There is no need to inject anesthetic for this procedure which is a great advantage compared to other areas of the body. It is interesting to note that amazingly the conjunctiva heals without scarring which makes the area an even more ideal location for placement of implantable ICLs.

Figure 82A:
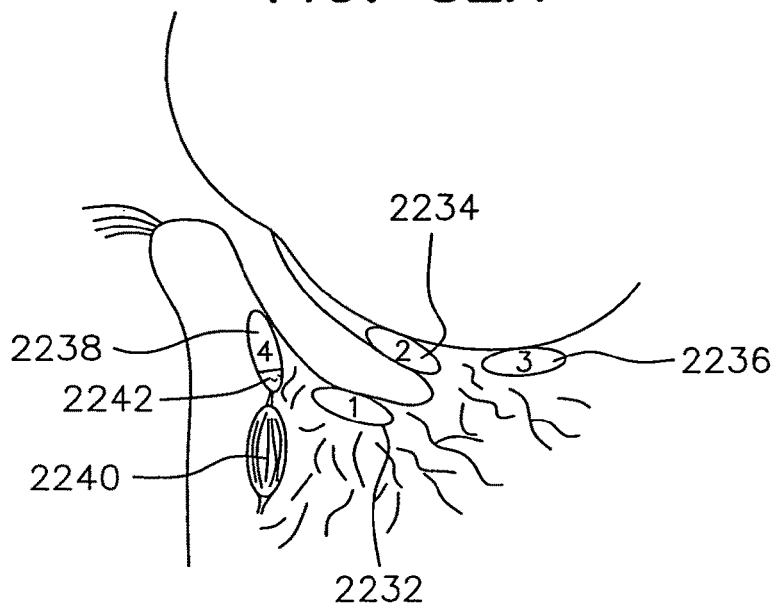
FIG. 82A through 82D are schematic illustrations of an exemplary embodiment for surgical implantation in the eye according to the principles of the current invention with FIG. 82C being an enlarged illustration of a portion of FIG. 82B.

FIG. 82A shows exemplary areas for placement of the ICL under the conjunctiva 2232 (area 1), 2234 (area 2) and/or anchored to the surface of the eye (area 3) 2236. Implantable ICL 2238 (area 4) uses a biological source such as muscular contraction of the eye muscles to generate energy. The eye muscles are very active metabolic and can continuously generate energy by electromechanical means. In this embodiment the eye lid-muscles or extra-ocular muscles 2240 which lie underneath the conjunctiva is connected to a power transducer 2242 housed in the ICL 2238 which converts the muscular work into electrical energy which can be subsequently stored in a standard energy storage medium.

Figure 82B:
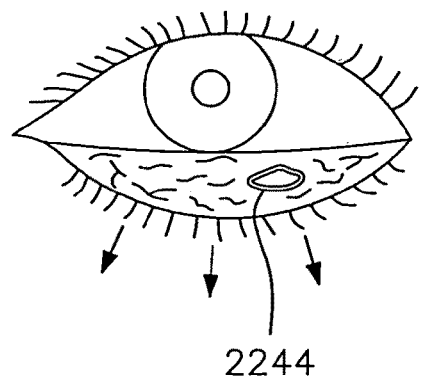
Figure 82C:
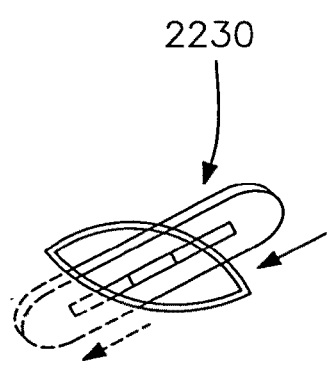
Figure 82D:
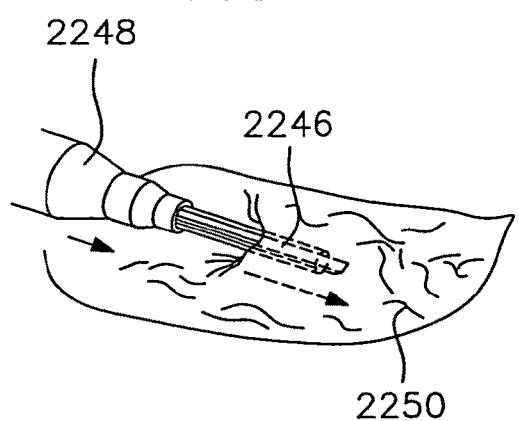

FIG. 82B shows in more detail the steps taken for surgical implantation. After one drop of anesthetic is placed on the eye, a small incision 2244 (exaggerated in size for the purpose of better illustration) is made in the conjunctiva. As shown in FIG. 82C, one simply slides the ICL 2230 under the conjunctiva which by gravity and anatomy of the eye sits in the eye lid pocket, preferably without any fixation stitches. FIG. 82D shows insertion of the ICL 2246 by injecting the ICL 2246 with a syringe and needle 2248 under the conjunctiva 2250. The conjunctiva will heal without scaring.

The location identified in the invention as a source for diagnostics and blood analysis can be used less desirably in a variety of ways besides the ones described. Alternatively a cannula can be placed under or in the conjunctiva and plasma aspirated and analyzed in the conventional manner. Furthermore a suction cup device can be placed on the surface of the conjunctiva and by aspiration acquire the elements to be measured. These elements can be transferred to conventional equipment or the suction cup has a cannule directly connected to conventional analyzing machinery.

Figure 83:
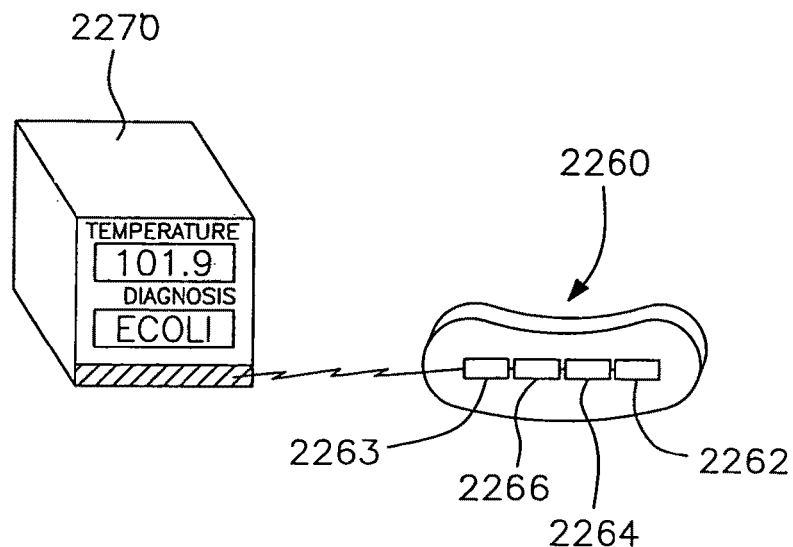
FIG. 83 is a schematic illustration of an exemplary embodiment for measurement of temperature and infectious agents according to the principles of the current invention.

The ICL 2260 in FIG. 83 includes a temperature sensor 2262 coupled to a bioelectronic chip 2264 for identifying microorganisms, a power source 2266, a transmitter 2268 and a receiving unit 2270. When bacteria reach the blood stream there is usually an associated temperature spike. At that point there is maximum flow of bacteria in the blood. The temperature spike detected by temperature sensor 2262 activates bioelectronic chip 2264 which then starts to analyze the eye fluid and/or cells for the presence of bacteria, with for example probes for *E. coli* and other gram negatives and gram positives organisms associated with common infections. The information on the organisms identified is then transmitted to a receiver allowing immediate life-saving therapy to be instituted on a timely fashion.

Previously, nurses had to check the patient=s temperature on a very frequent basis in order to detect temperature changes. Naturally this is a labor intensive and costly procedure. Then if the nurse identifies the temperature change, blood is removed from the patient, usually three times in a row which is a quite painful procedure. Then the blood has to be taken for analysis, including cultures to detect the organism and may take weeks for the results to come back. Sometimes because of a lack of timely identification of the infectious agents the patients dies even though curative treatment was available. The ICL thus can provide life-saving information for the patients. Naturally the ICL temperature can be used alone as for instance monitoring infants during the night with an alarm going off to alert the parents that the child has a fever.

Figure 84:
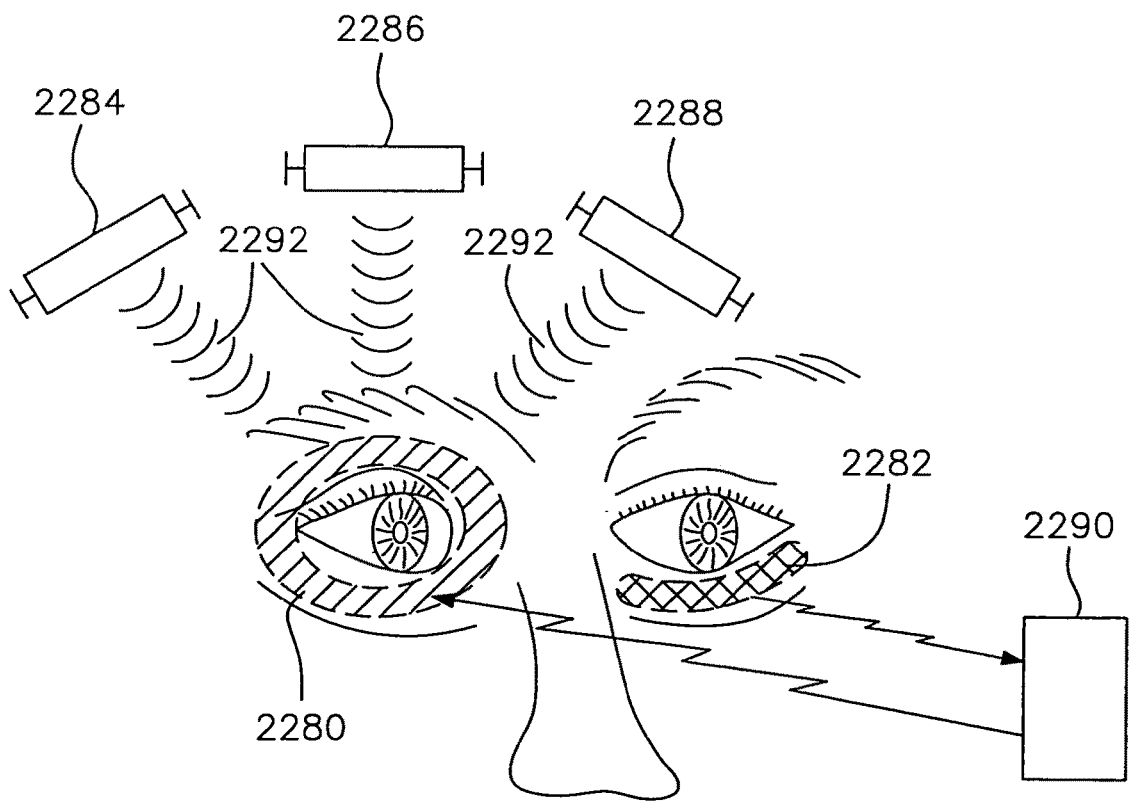
FIG. 84 shows a schematic illustration of a dual system ICL with a chemical sensing and a tracking device using global positioning system technology.

FIG. 84 shows a dual system ICL used in both eyes primarily for use in the battlefield with the ICL 2280 for tracking placed in the right eye and ICL 2282 for chemical sensing placed in the left eye with the ICL 2280 and/or 2282 placed externally on the eye or surgically temporarily implanted in the conjunctiva which allows easy surgical insertion and removal of the ICLs as described in FIGS. 82A through 82D. The tracking-chemical ICL system also includes a receiver 2290. Radio pulses 2292 based on GPS technology are emitted from satellites 2284, 2286, 2288 in orbit as spheres of position with alternative decoding by ground units (not shown) which gives the position of the transceiver ICL 2280 placed in the right eye. ICL 2280 can be periodically automatically activated for providing position. If a biological or chemical weapon is detected by chemical sensing ICL 2282, the receiver 2290 displays the information (not shown) and activates the tracking ICL 2280 to immediately locate the troops exposed. Alternatively, as soon as receiver 2290 receives a signal concerning chemical weapons, the users can then manually activate the tracking ICL 2280 to provide their exact position.

It is understood that as miniaturization of systems progress a variety of new separation and analysis technologies will be created and can be used in the present invention as well as a combination of other separation systems such as nanotechnology, molecular chromatography, nanoelectrophoresis, capillary electrochromatography, and the like. It is also understood that a variety of chips, nanoscale sensing devices, bioelectronic chips, microfluidic devices, and other technological areas will advance rapidly in the coming years and such advances can be used in the ICL system in accordance with the principles of the invention.

The ICL PIL systems allow any assay to be performed and any substance, analyte or molecule, biological, chemical or pharmacological and physical parameters to be evaluated allowing preventive and timely testing using low-cost systems while eliminating human operators involved in hazardous activities including the accidental transmission of fatal diseases such as AIDS, hepatitis, other virus and prions, and the like.

Contrary to the prior art that has used non-physiologic and non-natural means to perform diagnostics and blood analysis with means such as tearing and cutting the skin with blades and needles, shocking, destroying tissue electrically or with lasers, placing devices in the mouth that can be swallowed and have no means for natural apposition, and so forth, the present invention uses placement of an ICL in an disturbed fashion in order to acquire the signal, with the signal being physiologically and naturally acquired as the analytes are naturally and freely delivered by the body.

If one thinks about the conjunctival area and sensors according to the principles of the invention, and consider that the area not only has superficial blood vessels, but also has fenestrated blood vessels with plasma pouring from the lumen through the holes in the vessel wall, one would appreciate the ideal situation of the present invention. However, further, the blood vessels are easily accessible, no keratin is present and also living tissue is present on the surface allowing complete fluid and cell analysis. Moreover a very thin and permeable epithelium associated with a very homogeneous thickness throughout its whole surface is available with the direct view of the blood vessels. Also, natural eye lid force acts as a natural pump for fluid.

Furthermore, sensors are placed in natural pockets, and there is not just one small pocket, but four large pockets with over 16 square centimeters of area that can be used as a laboratory. In this pocket a sensor can be left completely undisturbed without affecting the function of the eye and due to high oxygen content in the surface of the conjunctiva the ICL can be left in place for long periods of time, even a month based upon material currently available for long-term use in the eye. In addition, the area is highly vascularized, and the eye has the highest amount of blood per gram of tissue among all organs in the human body. Furthermore, it provides not only chemical parameters, but also the ideal location for physical parameters such as measurement of temperature since it gives core temperature, pressure and evaluation of the brain and heart due to the direct connection of the eye with the brain and the heart vasculature and innervation. In addition, the area is poorly innervated which means that the patient will not feel the ICL device that is placed in the pocket, and the lid supports the device naturally with an absolutely cosmetically acceptable design in which the ICLs are hidden in place while non-invasively providing life-saving information.

The ICL PIL offers all of that plus time-savings and effort-savings allowing users to take care of their health while doing their daily activities in a painless fashion and without the user spending money, time and effort to get to a laboratory and without the need to manipulate blood associated with benefits of decreasing harm by illnesses, preventing life-threatening complications by various diseases, timely identifying cancers and other diseases, monitoring glucose, metabolic function, drugs and hormones, calcium, oxygen and other chemicals and gases, and virtually any element present in the blood or tissues, detecting antigen and antibodies, locating troops exposed to biological warfare, allowing timely detection and treatment, temperature detection with simultaneous detection of microorganisms, creation of artificial organs and drug delivery systems, and providing means to allow full and secure use of information by the Human Genome Project, ultimately improving quality of life and increasing life-expectancy while dramatically reducing health care costs. The ICL PIL thus accomplishes the rare feat in medical sciences of innovation associated with dramatic reduction of health care costs.

Figure 85:
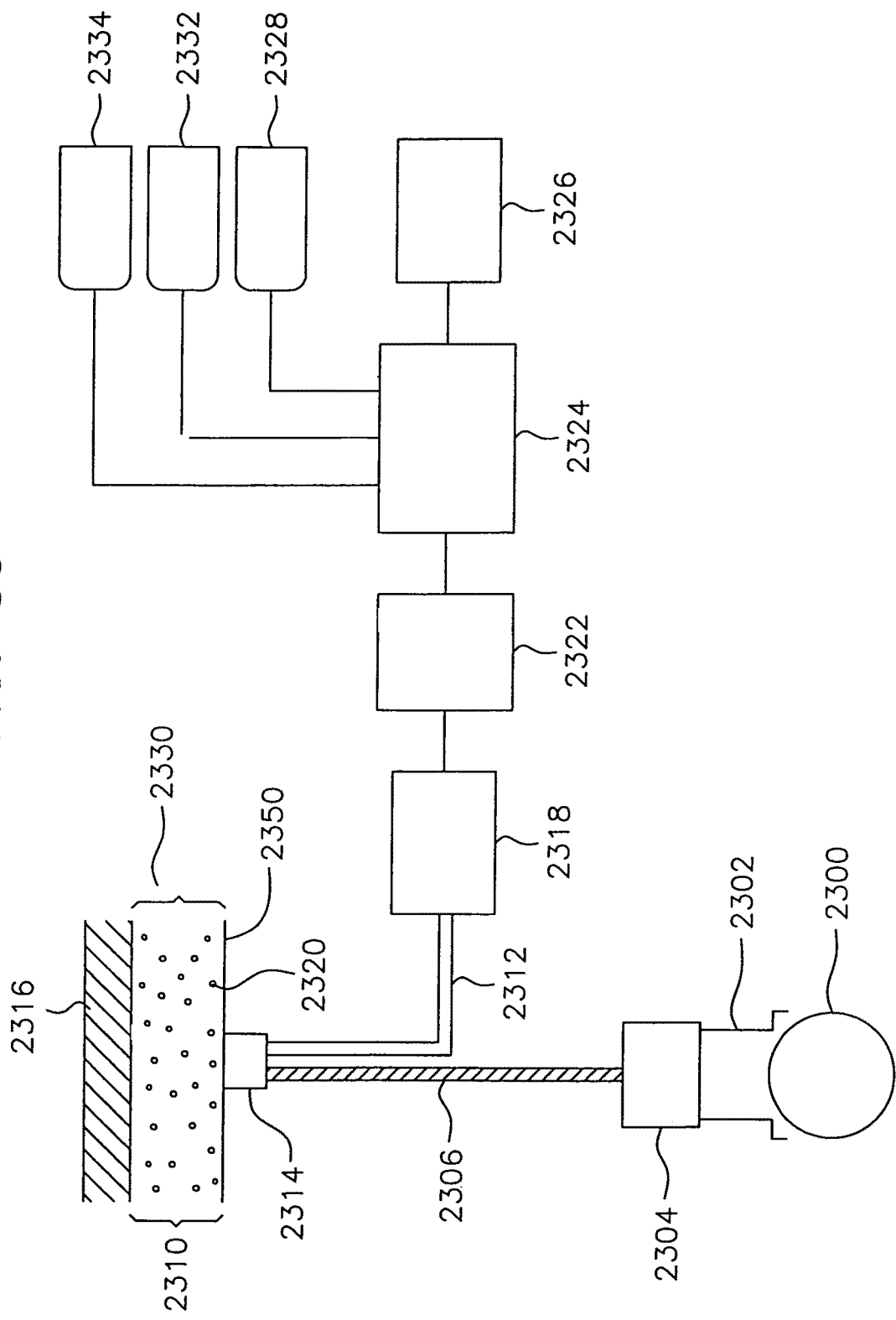
FIG. 85 is a schematic block diagram of an apparatus according to one preferred embodiment of the present invention.

FIG. 85 shows a schematic block diagram of one preferred reflectance measuring apparatus of the present invention. The system includes a radiation source 2300 emitting preferably at least one near-infrared wavelength, but alternatively a plurality of different wavelengths can be used. The light source emits radiation 2302, preferably between 750 and 3000 nm, including a wavelength typical of the absorption spectrum for the substance of interest. The radiation is then filtered and focused by the optical interface system 2304 onto fiber optic cable 2306 which transmits the radiation to the plasma/conjunctiva interface 2310. The plasma/conjunctiva interface 2310 is comprised of the thin conjunctiva lining 2320 with plasma interface 2330 and a substance of interest 2350 underneath said conjunctiva 2320. Optic fiber cable 2306 is part of a dual optic fiber cable system preferably with fiber cable 2306 and collecting fiber cable 2312 located side-by-side. The diameter of the optic fiber is 300 µm, although a variety of diameters can be used.

The radiation is directed at the plasma interface 2330 and delivered via sensor head 2314 in apposition to conjunctival lining 2320. The plasma 2330 is present between the thin conjunctival lining 2320 and the sclera 2316, a white and water free structure which is the external layer of the eyeball. In addition, it is understood that there are areas in the eye which the plasma is interposed between the conjunctiva and ligaments or other tissues but not the sclera, as it occur in areas in the cul-de-sac (not shown).

The optic fiber 2306 delivers the radiation 2302 provided by the source 2300 to the plasma interface 2330. The radiation 2302 directed at the plasma 2330 is partially absorbed and scattered according to the interaction with the conjunctival lining 2320 and the substance of interest 2350 present in the plasma 2330. Conjunctiva 2320 is the only tissue interposed between radiation 2302 and the substance of interest 2350. The conjunctiva 2320 does not absorb near-infrared light and scattering is insignificant as the conjunctiva is an extremely thin membrane. Part of the radiation 2302 is then absorbed by the substance of interest 2350 and the resulting radiation emitted from the eye corresponds to said substance of interest 2350.

The resulting radiation from the eye is reflected back and collected by collecting optical fibers 2312 via sensor head 2314 and delivered to the detector 2318. The system includes a spectrum analyzer/detector 2318 for detecting and analyzing radiation 2302 emitted by the radiation source 2300 and which has interacted with the plasma interface 2330 with said resulting radiation containing spectral information for the substance of interest 2350. The resulting radiation is converted into a signal by the spectrum/analyzer/detector 2318 which can be amplified and converted to digital information by the A/D converter 2322. The information in then fed into a processor 2324 and memory 2326 for analyzing the spectral information contained therein and calculating the concentration of at least one chemical substance in the eye fluid derived from the resulting spectral information.

The concentration of the substance of interest 2350 is accomplished by detecting the magnitude of light attenuation collected which is caused by the absorption signature of the substance of interest. Models, calibration procedures, and mathematical/statistical analysis such as multivariate analysis and PLS can be used to determine the concentration of the substance of interest 2350 from the measured absorption spectrum.

Data analysis by empirical or physical methods previously mentioned can be used for analysis of the resulting spectra associated with signal processing and which are performed by the processor 2324 including Fourier Transformation, digital filtering, and the like. Algorithm or other analyses are employed to compensate for the background response, noise, source of errors, and variability. Since the spectral information according to the principles of the invention has very few interfering factors, statistical extraction of the spectra of interest is facilitated allowing accurate determination of the concentration of the substance of interest 2350.

Processor 2324 can contain or be connected to a memory unit 2326 which can store data related to calibration, patient's measurement data, reference data, suitable algorithms, and the like. Display part 2328 is adapted to output results of the concentration of the substance of interest by the processor. The processor 2324 can also be connected to an audio transmitter 2334, such as a speaker, which can audibly communicate abnormal levels, and to a device 2332 for delivery of medications according to the concentration of the substance of interest 2350.

Since the present invention reduces or eliminates the interfering elements and background interference such as fat, melanin, skin texture, and the like as previously described, the value indicative of the resulting spectra and data analysis accurately and precisely determine the concentration of the substance of interest 2350.

A variety of radiation sources 2300 can be used in the present invention including LEDs with or without a spectral filter, a variety of lasers including diode lasers, halogen lights and white light sources, having maximum output power in the near infrared region with or without a filter, and the like. The radiation sources 2300 have preferably enough power and wavelengths required for the measurements and a high spectral correlation with the substance of interest 2350. The range of wavelengths chosen preferably corresponds to a known range and includes the band of absorption for the substance of interest 2350.

Light source 2300 can provide the bandwidth of interest with said light 2302 being directed at the substance of interest 2350. A variety of filters can be used to selectively pass one or more wavelengths which highly correlate with the substance of interest 2350. The light radiation 2302 can be directly emitted from a light source 2300 and directly collected by a photodetector 2318, or the light radiation 2302 can be delivered and collected using optic fiber cables. An interface lens system can be used to convert the rays to spatial parallel rays, such as from an incident divergent beam to a spatially parallel beam.

When a laser light or a continuous wavelength source is employed an optical interface may not be necessary as one single optical path is derived from the source 2300. The output of a white light source, some lasers, and the like can be coupled directly into the receiving end of optical fibers which can be used as a light pipe. Due to the sample characteristics of the conjunctiva/plasma interface 2310 as previously described, the system can use a variety of diodes and detectors beyond 2500 nm allowing more spectrum regions to be used which in turn facilitate the accurate measurement of the substance of interest 2350.

Wavelength selection means can include bandpass filters, interference filters, a grating monochromator, a prism monochromator, acousto-optic tunable filter, or any wavelength dispersing device. Although dual optical fibers were used in the illustration, it is understood that direct light sources and direct collection detectors can be used as well as a single fiber optic bundle that transmits radiation to the conjunctiva 2320 and collects resulting radiation from said conjunctiva 2320. A variety of amplifiers, pre-amplifiers, and filters and the like can be used for reducing noise, amplifying signals, filtering, smoothing, and the like. Although an amplifier can be used as described, it is understood that amplification is secondary for the operation.

Figure 86:
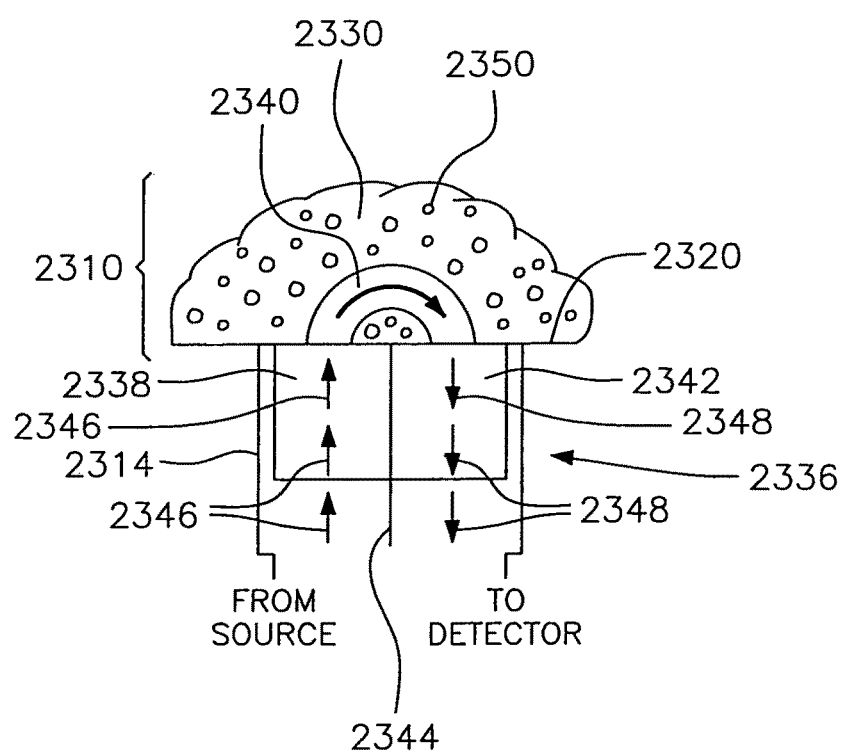
FIG. 86 is a schematic diagram of a sensor in accordance to a preferred embodiment of FIG. 85.

Now referring to FIG. 86, the apparatus includes a probe 2336 with a sensor head 2314 provided on its end with radiation source transmission fiber 2338 and radiation receiving collector fiber 2342 which are preferably side-by-side. The distance between the radiation transmission source 2338 and the radiation receiving collector 2342 is preferably around 0.5 mm, but determined such that the light path 2340 is mostly formed in the plasma interface 2330. Although only one collecting fiber 2342 is illustrated, it is understood that a plurality of collection fibers positioned at different distances from the source fiber 2338 can be used. Use of optical fibers enable optimization of delivery with the light 2346 being piped through optical fibers 2338 and delivered to the plasma/conjunctiva interface 2310.

Still with reference to FIG. 86, the end of source fiber 2338 directs radiation at the plasma interface 2330 where there is a high relative concentration of the substance of interest 2350. The radiation 2340 interacts with the substance of interest 2350 and the resulting radiation 2348 is collected by the collection fibers 2342 for subsequent measuring absorbencies at a wavelength selected for the substance of interest 2350 and determining the concentration of said substance of interest 2350. The sensor head 2314 can include a wall 2344 positioned between the light source 2338 and light collector 2342 to shield the collector 2342 from light 2346.

In a transparent, thin, and homogeneous structure like the conjunctiva/plasma interface 2310, Beer-Lambert's law can be applied to determine energy absorption.

As an example, glucose can be chosen as a substance of interest measured in the conjunctiva/plasma interface in accordance with a preferred embodiment of the invention. Near-infrared reflectance measurement of plasma glucose adjacent to the conjunctiva was done in association with conventional methods normally used in a laboratory to evaluate plasma glucose. The "overall setup" includes:

1. A light source generating multiple wavelengths of near infrared light.
2. Fiber optics. Fiber optics transmits the photons from the light source to the conjunctival site on the patient and from the conjunctival site to a detector. In general photons follow an elliptical path through the sample from the source to the detector. Fiber optic separation is important in determining the area of interrogation by the incident photons. The shorter the interoptode distance, the less deep is the penetration of light. In the probe arrangement (sensor head) for the conjunctiva, the optic fibers were separated by a distance of 0.5 mm. Alternatively, a distance of 0.1 mm was used for interrogating substances present in the superficial structure of the conjunctiva/plasma interface and thinner interface areas. The collecting optic fiber collected the resulting radiation. The resulting radiation contains spectral information for each plasma constituent and due to its optimal point of detection as disclosed in the invention there is no significant background spectral information.

3. Selective filters or diffraction grating systems. These filter systems are used for selecting wavelength of interest as well as eliminating wavelength which do not have a high correlation with the substance of interest. A reference filter can be used and consists of a narrow bandpass filter which pass wavelengths which have no correlation with the substance of interest.
4. Photon detection circuitry such as a photomultiplier and integration amplifier including a lead-sulfide photodetector which convert the resulting radiation into signals representative of the intensity of those wavelengths.
5. An A/D converter to convert the analog signals from the photon detection circuit to digital information.
6. A central processor with appropriate software (algorithms) to process the information obtained in the resulting radiation and compare it with the known amount of reference radiation.
7. An information display system to report the result.

A known amount of incident light is used to illuminate the conjunctiva using a probe in apposition to the conjunctiva. The amount of light recovered after the photons pass through the conjunctiva depend on the amount of light absorption by the substance of interest and the degree of light scatter and absorption by the tissue. Scattering as well as absorption by tissue and other interfering constituents are insignificant in the conjunctiva as previously described.

In more detail, the testing equipment included a 75 W halogen light source coupled to an optic fiber (available from Linos Photonics GmbH, Göttingen, Germany). An optical filter adjusted the wavelength to provide near-infrared radiation in the 1400-2500 nm spectral range. The radiation was delivered to the conjunctiva surface using a fiber optic probe arrangement (sensor head) supported by a Haag-Streit Goldmann tonometer piece and associated Haag-Streit slit-lamp 6E (Haag-Streit, Bern, Switzerland).

The sensor head was coupled to the conjunctival surface of the eye. Reflected radiation that interacted with the conjunctiva was collected by the collecting optic fiber. The optic fiber delivered the resulting radiation to a photodetector analyzer which performed the quantitative analysis.

The magnitude of the absorption peak is directly related to the concentration of glucose. Suitable analyzers include modified Fourier Transform Infrared (FTIR) spectrometers with chemometric software packages. Those are available from the PerkinElmer Corporation (Wellesley, Mass.) and Thermo Nicolet Company (Madison, Wis.).

The signal was digitized and the concentration of conjunctival plasma glucose determined by chemometric analysis algorithms with comparison of the unknown value with a standard reference to determine the conjunctival plasma glucose value. Blood was acquired and plasma glucose measured with conventional laboratory analysis using a Beckman analyzer system.

The mean value of conjunctival plasma glucose was 101.2 mg/dl and a correlation coefficient of 0.94 was achieved when compared to physical values by laboratory testing. The FTIR used allows evaluation of all incident wavelengths. The signal processing of the FTIR system can select for the final analysis the wavelength related to the substance of interest. Various substances of interest such as glucose, cholesterol, ethanol, can then be evaluated by using the different algorithms for each substance incorporated in the FTIR system.

Alternatively, a custom made system, as described in the "overall setup" above, was constructed using the above light source and selective bandpass filters centered around 2100 nm (available from CVI Laser Company, Albuquerque, N. Mex.) for selecting the wavelength for glucose. This alternative embodiment, provides a lower-cost and more compact system, but is capable of measuring only one substance of interest according to the wavelength selected.

In-vitro calibration models available commercially can be used accurately and precisely as a reference since there is no background interference. However, a simplified calculation and statistical method can be achieved since the conjunctiva/plasma sample obeys Beer-Lambert law and the background variables are eliminated. The resulting radiation acquired from the conjunctiva corresponds directly to plasma constituents. A quantitative measure of the glucose concentration using the resulting absorption intensity can be provided upon calculation using Beer-Lambert's law.

In addition, an in-vivo calibration method is used. The concentration of plasma glucose is obtained by invasive means and analyzed in the conventional laboratory setting. The range of glucose levels of usual interest in clinical practice (40 to 400 mg/dl) obtained invasively creates a reference database, which is then correlated to the resulting radiation obtained using conjunctival plasma. Considering a stable optical system as the conjunctiva/plasma interface, the amount of incident radiation (known) and the subsequent reflected radiation (measured) can be calculated for each wavelength related to the substance measured creating then a reference line. The concentration of the substance of interest is then determined by correlating the predicted value with the acquired (unknown) value using the predetermined calibration line.

An alternative embodiment and experiment involved using Attenuated Total Internal Reflection technique and incident radiation in the 9,000 to 10,000 nm wavelength region. This spectral region has high correlation with glucose and is strongly absorbed by glucose while avoiding absorption by interfering constituents. However this region is not used because large amounts of energy are needed which can cause damage to the tissue. The large amount of energy is needed because the sample of interest (glucose) is located deep and the far-infrared energy is readily absorbed by interfering constituents. Thus the radiation energy does not reach the substance of interest (glucose) present deep in the tissues.

Contrary to that, in the present invention a low power far-infrared incident radiation was used due to the insignificant absorption due to the characteristics of conjunctiva/plasma interface (as disclosed in the invention) and the plasma with glucose is present in the surface. Thus, no damage or discomfort was elicited during measurement. The conjunctiva/plasma interface allows measurement to be done in this region of the wavelength spectrum because the substance being interrogated is already separated and present in plasma in the surface of the sample.

Figure 87:
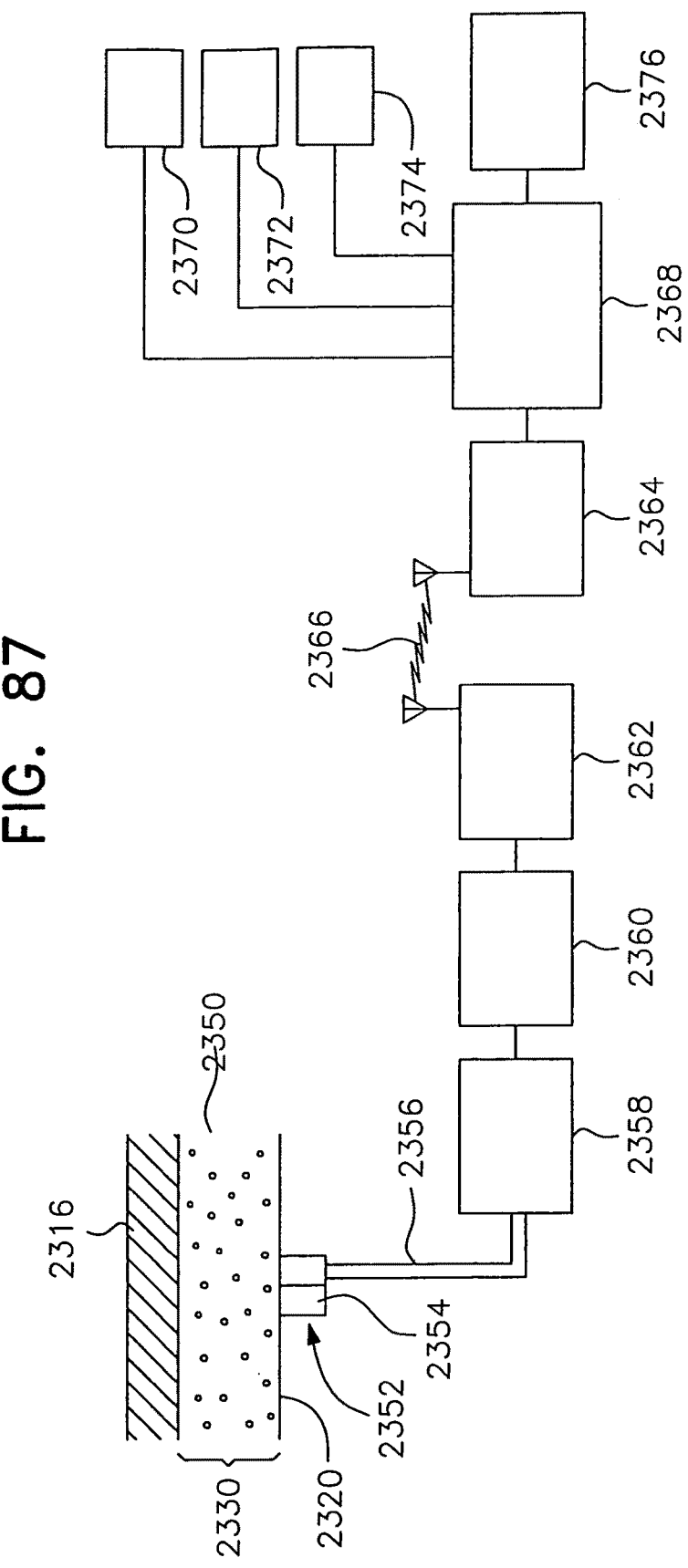
FIG. 87 is a schematic block diagram of an apparatus according to another preferred embodiment of the present invention.

FIG. 87 shows a schematic block diagram of one preferred embodiment of the present invention with wireless transmission of information to an external receiver. The apparatus includes a sensor head 2352 which has a light source 2354 such as LED and a light collector 2356 such as an optic fiber cable which is connected to a photodetector 2358. Radiation is transmitted from the source 2354 and directed at the plasma interface 2330, between the conjunctiva 2320 and sclera 2316. The resulting radiation is reflected back and collected by collecting optic fiber 2356 and transmitted to photodetector 2358. The signal is then converted to digitized information by the A/D converter 2360 and sent to the RF transceiver 2362 with the signal 2366 being transmitted to a remotely placed RF transceiver 2364.

The signal is then fed into the processor 2368 and memory 2376 which calculates the concentration of the substance of interest 2350 which is subsequently visualized in display 2370. The processor can also activate an alarm and audio transmitter 2372 that can alert the user about abnormal measurement levels and control the delivery of medication through delivery device 2374. The delivery device 2374 can include: contact lens dispensing systems, iontophoresis-based dispensing systems, infusion pumps as insulin infusion pump, glucagon pump for injection of glucagon when glucose levels are below 55 mg/dl, drug infusion devices, inhalers, and the like. The processor 2368 can make adjustments for delivery of medication through delivery device 2374 according to the identification or concentration of the substance of interest 2350.

Figure 88:
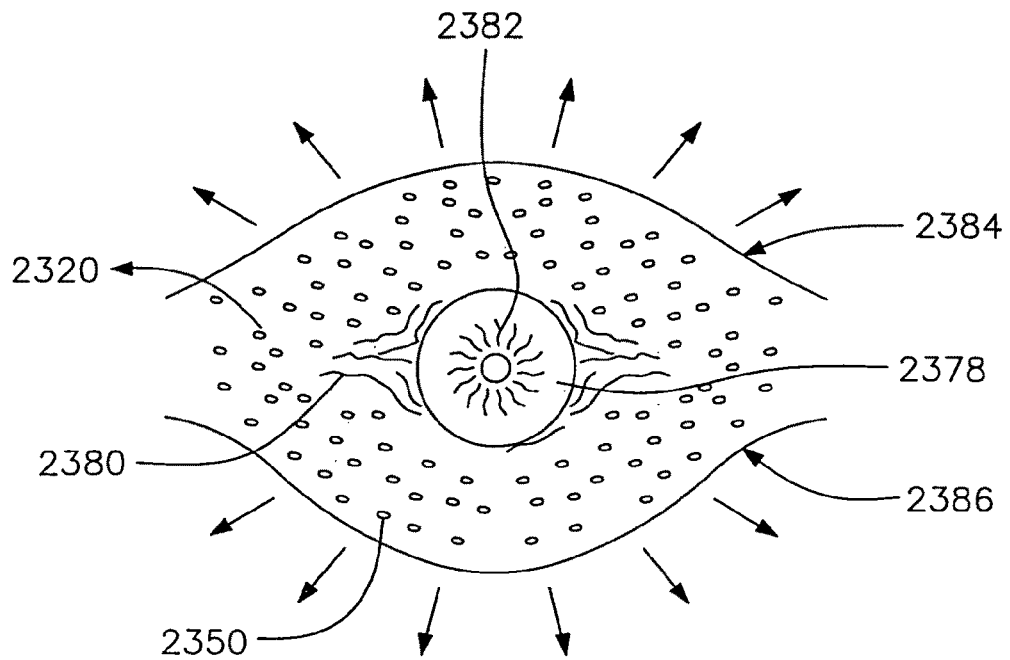
FIG. 88 is a schematic representation of the frontal view of the surface of the eye

FIG. 88 shows the front surface of the eye with cornea 2378, iris 2382, and conjunctival vessels 2380. The upper 2384 and lower 2386 eyelids were pulled away to show the conjunctival lining 2320 covering the eye surface and the substance of interest 2350 present in the surface of the eye. Most of the conjunctival area 2320 is hidden in the eyelid pocket both superior and inferior and not observable by an external viewer.

Figure 89A:
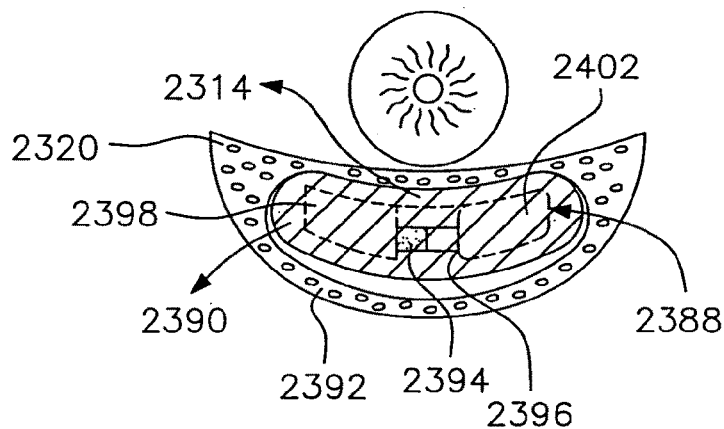
FIGS. 89A-D illustrates different positions for the location of sensor of FIG. 87.

FIG. 89(A) shows schematically a reflectance measuring system 2388 encased in the contact device 2390, the combination of which is referred to herein as a measuring Intelligent Contact Lens (ICL). The measuring ICL is placed in the eyelid pocket 2392 in apposition to the conjunctival lining 2320. The measuring ICL includes a sensor head 2314 with light source 2394 and light detector 2396, RF transceiver 2402 and other electronics 2398 previously described.

Figure 89B:
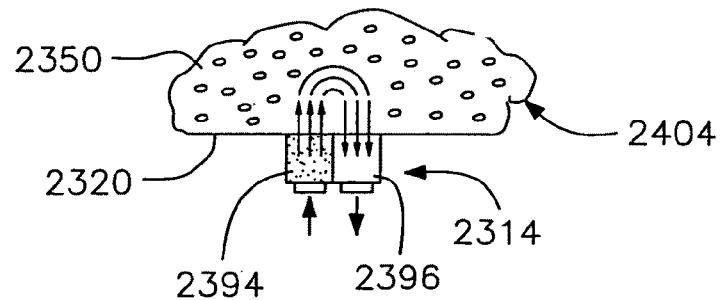

FIG. 89(B) shows in more detail the sensor head 2314 in apposition to the conjunctiva 2320 in the cul-de-sac 2404. The radiation emitted interacts with the substance of interest 2350 present underneath the conjunctiva 2320. Source 2394 and detector 2396 are mounted adjacent to each other in a way that light from the source 2394 reaches the substance of interest 2350 and is received by the detector 2396.

Figure 89C:
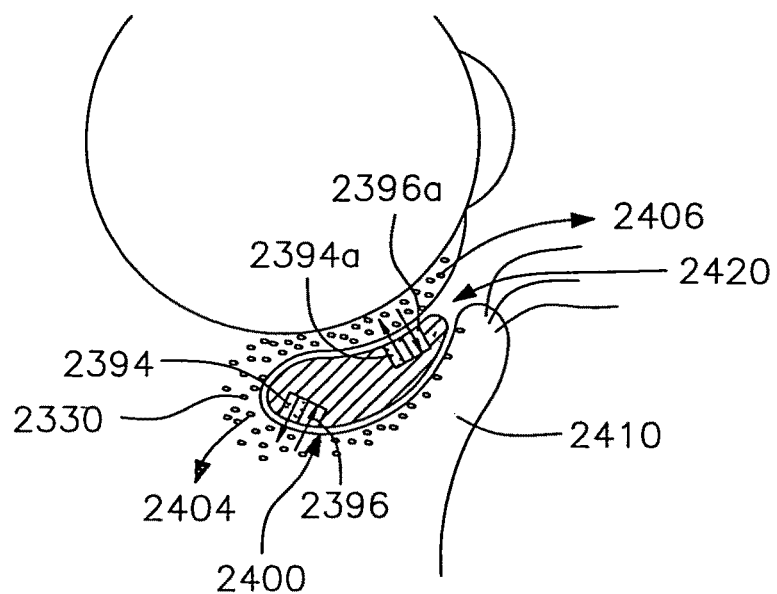

FIG. 89(C) shows a cross-section view of the eye and eyelid 2410 with the measuring ICL 2400 and its light source 2394 and light collector 2396 in apposition to the cul-de-sac 2404 of the conjunctiva 2320 which is free of blood vessels but has plasma 2330 collected underneath. FIG. 89(C) also shows another position for light source 2394a and collector 2396a as in apposition to the bulbar conjunctiva 2406.

Figure 89D:
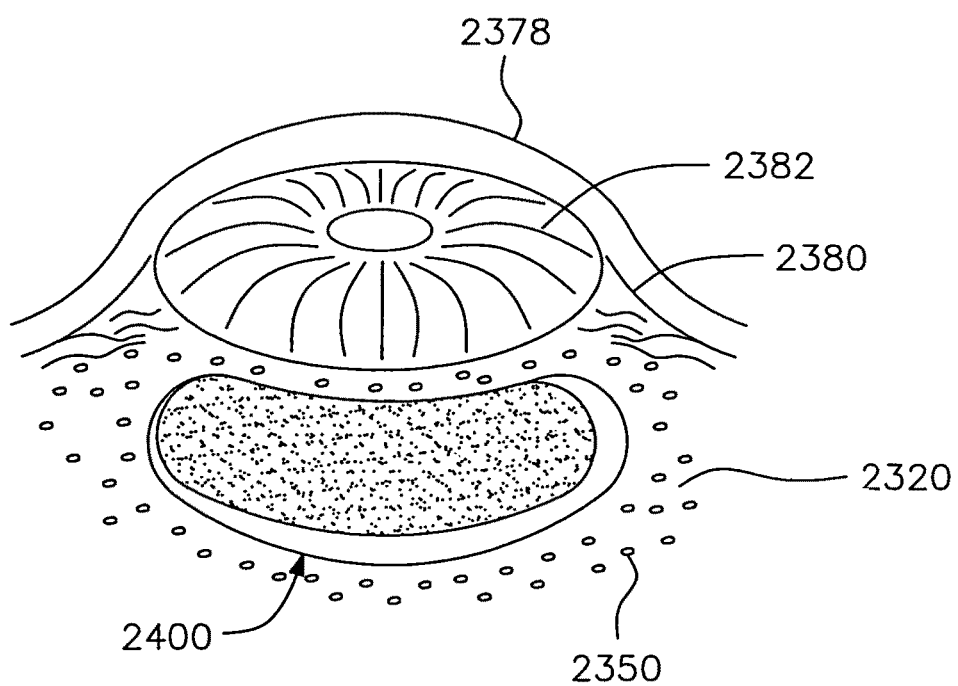

FIG. 89(D) shows a bird's eye view of the eye surface with cornea 2378, iris 2382, conjunctival vessels 2380, and measuring ICL 2400 in apposition to the conjunctiva 2320 and substance of interest 2350. The thickness of the measuring ICL 2400 is preferably less than 5 mm.

The contact device or measuring ICL 2400 allows appropriate interface with the sample in a reproducible location and with a reproducible amount of pressure and temperature on the sample surface. Normal eyelids exert a stable amount of pressure against the measuring ICL 2400 when the eyelid 2410 is in a relaxed state, meaning without squeezing the eyelids. The pressure applied by the eyelid 2410 in the resting state is fairly constant and equal in normal subjects with a horizontal force of 25,000 dynes, a tangential force of 50 dynes and pressure of 10 Torr. Muscles in the body can enlarge and become stronger by means of continuous exercising such as in body building. Contrary to that, the muscles in the eyelids have a special characteristic and do not hypertrophy by continuous blinking or eyelid exercising. The muscles in the eyelid remain with similar contractility and force throughout life unless affected by a disease. This similar and stable eyelid contractility and tone allows an ideal apposition of a source detector pair to the tissue surface. Positioning of the conjunctiva 2320 in apposition to the sensor head 2314 with the source-detector pair can be done naturally by the eyelid which leads to great reproducibility and reproducible degrees of pressure with very low inter- and intra-individual variability.

The eyelid pocket 2420 also provides good reproducibility as far as location of the measurement since the measuring ICL 2400 can be made to fit a particular pre-determined area of the eyelid pocket 2420 allowing to reproduce the same location for measurement. The eyelid structural arrangement provides the only superficial area in the body in which a true pocket is formed creating a natural confined environment in the surface of the body by said pocket. The conjunctiva as mentioned is a thin homogenous tissue located in a naturally confined area of the body forming a natural pocket and the lens dimensions can assure that the same site is taken for different measurements and centered on areas of high plasma 2330 concentration and minimal blood vessels such as in the lower part of the cul-de-sac 2404. Alternatively, the light 2302 can be directed to any point in the conjunctiva 2320.

The embodiments of the present invention provide a reproducible and stable degree of pressure and reproducible location which is achieved naturally according to the morphology and physiology of the eye and eyelids.

A contact device for placement on the surface of the eye and preferably in the eyelid pocket as shown in FIG. 101B was used. The contact device preferably contains an infrared LED (available from PerkinElmer Corporation) as a light source. Infrared LEDs (wavelength-specific LEDs) are the preferred light source for the embodiment using a contact device because they can emit light of known intensity and wavelength, are small in size, low-cost, and the light can be precisely focused in a small area of the conjunctiva. By using an infrared LED that emits a narrow bandwidth of radiation no filters are need to be coupled with the photodetector.

Alternatively, a miniature selective filter that transmits light within the 2,100 to 2,200 range of wavelengths is incorporated with the photodetector. The selective filter transmits wavelength which corresponds to absorption by glucose.

The preferred photodetector included a semiconductor photodiode with a 400 μm diameter photosensitive area coupled to an amplifier as an integrated circuit. The photodetector has spectral sensitivity in the range of the light transmitted. The photodetector receives an attenuated reflected radiation and converts the radiation into an electrical signal. The photodetector is connected to a low-power radio-frequency integrated circuit and the electrical signal is converted into an audio signal and transmitted to an external receiver.

An alternative embodiment used an A/D converter and a digital RF integrated circuit built in the contact device. The RF circuit then transmits the analog or binary signal corresponding to the intensity of radiation (resulting radiation) reflected from the conjunctiva/plasma interface. The remote RF transceiver receives the signal and sends it to a processor for signal processing and calculation of the concentration of glucose using a predetermined calibration reference. The detector output data is correlated to blood glucose levels using FTIR and statistical analysis previously described. Although one LED was described, multiple miniature LEDs can be used as light sources for simultaneous measurement of multiple substances using multiple pair source/detector.

Besides active RF transmission, passive RF devices built-in in the contact device can be used and receive the signal from the sensor. An external radiating antenna emits the excitation energy which powers the contact device. Such passive RF devices includes paper thin inductive and capacitive designs, for example Performa tags available from Check Point Systems, Inc. Thorofare, N.J. and BiStatix tags available from Motorola Inc., Schaumburg, Ill.

Figure 90:
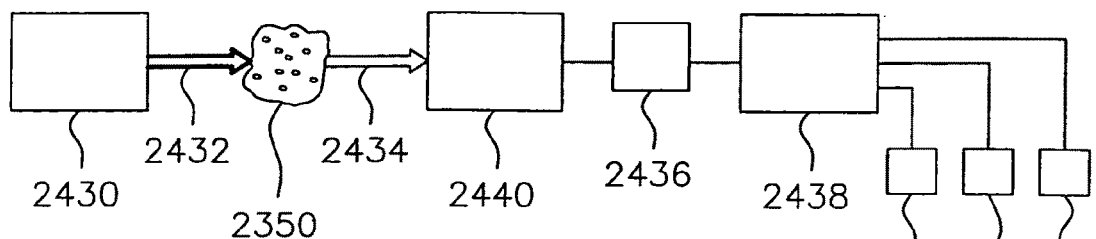
FIG. 90 is a schematic block diagram of an apparatus according to a preferred embodiment of the present invention.

FIG. 90 shows a schematic block diagram of one preferred transmission measuring apparatus of the present invention. In an exemplary embodiment, the system includes a source of light 2430 which emits light at a plurality of different wavelengths and a photodetector 2440 for detecting light 2432 emitted from said source 2430. The source 2430 and the detector 2440 are arranged diametrically opposed to each other and preferably including a forceps configuration. The arrangement is such that the light output 2432 from the source 2430 interacts with the eye fluid and substance of interest 2350-before being collected by the detector 2440. The resulting transmitted radiation 2434 includes the emitted radiation less the back scattered and absorbed radiation plus any forward scattering radiation. Since in the present invention there is insignificant scattering due to interfering constituents, the resulting radiation 2434 is the known emitted radiation less the absorbed radiation which corresponds to the substance of interest 2350. The resulting radiation 2434 is collected by the detector 2440 and contains the spectra of the eye fluid at each of the selected wavelengths. Since in the present invention the scattering is insignificant and there is a high signal, a small number wavelength is required and the resulting spectra relates to the substance of interest 2350. The resulting transmitted spectra is then converted by the A/D converter 2436 into digital information and the spectral information obtained is sent to the processor 2438 for spectral analysis to determine the concentration of the substance of interest 2350. The processor 2438 can be connected to a display 2442 for reporting the concentration of the substance of interest, to an alarm system 2444 to bring attention to abnormal and ominous values and to a medication delivery system 2446 which delivers medication according to the concentration of the substance of interest.

Figure 91A:
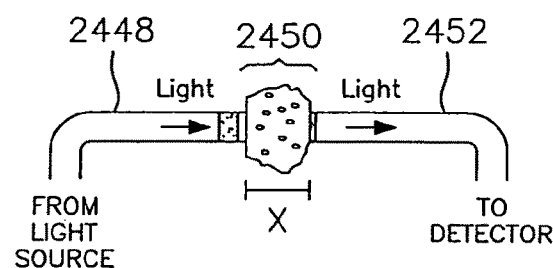
FIGS. 91A-C illustrates various sensing arrangements in accordance with the embodiment of FIG. 90.

In reference to FIG. 91(A), the radiation source fiber 2448 and collector fiber 2452 are positioned diametrically opposed to each other so that the output of the radiation source 2448 goes through the plasma/conjunctiva interface 2450 before being received by the collector 2452 and then sent to the detector (not shown). The space X from the radiation source 2448 to the collector 2452 can be changeable but is ultimately fixed in order to maintain a fixed optical distance between said source 2448 and collector 2452.

In one exemplary embodiment the distance X in the tip of the forceps device, meaning the distance between the light source and the light detector is preferably 1 mm, however various optical path distances that encompass the sample 2450 with the substance of interest 2350 can be used. The source can include the output end of an optical fiber cable connected to a light radiation source or a plurality of radiation sources. The detector can include the receiving end of a collection of optical fibers connected to one or a plurality of photodetectors.

Optical fibers encased in each arm of the forceps device are preferably used as a light delivery 2448 and light collection 2452 system for the light source and the light detector providing a more ergonomic design for the forceps configuration device. During measurement the conjunctiva/plasma interface 2450 is placed between the path of the optical beam from the source 2448 to detector 2452. The output of the light source and the input of the detector are in contact with the plasma/conjunctiva interface 2450 or in close proximity to such interface.

Figure 91B:
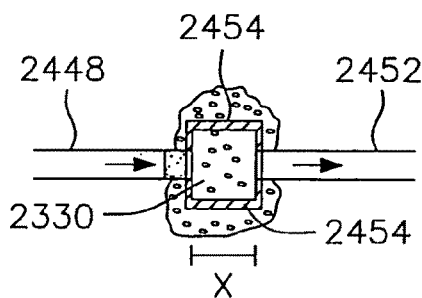
Figure 91C:
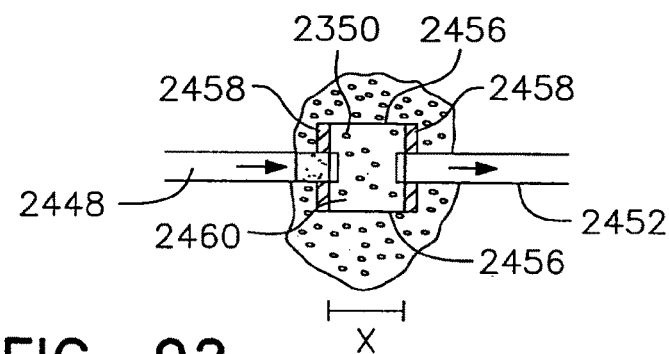

FIGS. 91(B) and 91(C) show alternative embodiments for the source-collector pair for exemplary transmission measuring systems. FIG. 91 (B) shows rigid arms 2454 connecting the light source end 2448 to the light collector end 2452 at a fixed distance X with plasma 2330 interposed between the two ends 2448, 2452. Although two arms, superior and inferior, are shown, it is understood that only one rigid arm is needed to keep distance X as a fixed distance.

FIG. 91(C) shows an alternative embodiment in which rigid arms 2458 are connected to semi-permeable membranes 2456. The membranes 2456 can be made permeable only to the substance of interest 2350 which then can enter a chamber 2460 formed by the membranes 2456 and interact with the radiation emitted by the light source 2448. The membranes 2456 can be coated with permeability enhancers which can enhance the flow of the substance of interest 2350 to the measuring chamber 2460. Rigid ends at prefixed distance X are used to maintain light source 2448 and collector 2452 at a prescribed space to define a measuring optical path length. The radiation from the source passes through the optical fiber 2448 which works as a guide path to the light. The radiation then interacts with the substance of interest 2350 selectively present in the sample fluid in the chamber 2460. The resulting radiation is incident upon the light receiving end and guided to the detector through fiber optic collector 2452. The embodiments of FIGS. 91(B) and 91(C) are better suited to use as an implantable measuring system.

Figure 92:
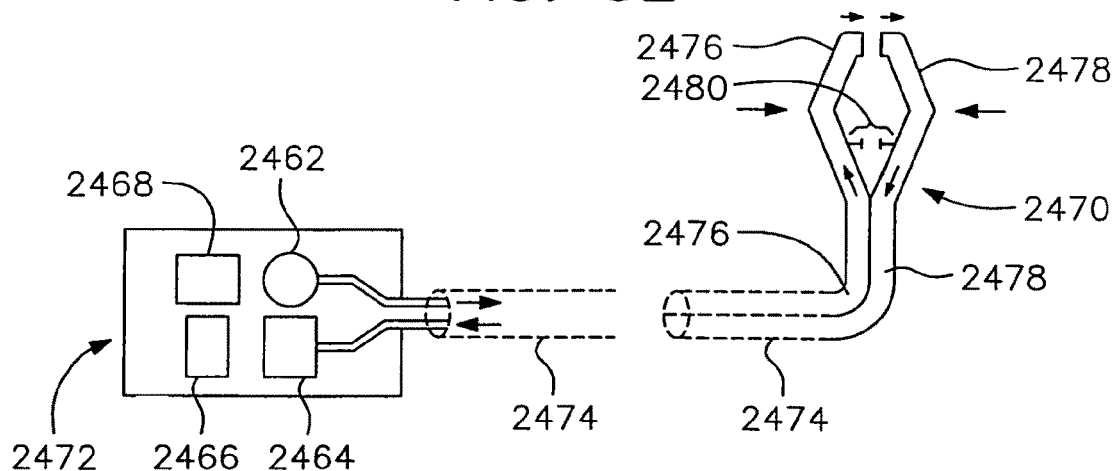
FIG. 92 schematically illustrates a preferred embodiment in accordance with the embodiment of FIG. 90.

FIG. 92 shows schematically one of the preferred embodiments using a forceps-like probe 2470 with wired transmission of resulting radiation signal to the processor 2468. The apparatus includes a main body housing 2472 which encases the light source 2462, photodetector 2464, A/D converter 2466, and a processing/controlling part 2468. In this exemplary embodiment, the light source 2462 and photodetectors 2464 can be located in the main body 2472 away from the forceps-like probe 2470. The main body housing 2472 is connected to the forceps-like probe 2470 by cable 2474 which contains fiber optics from the light source 2462 and fiber optics to the photodetector 2464. The forceps-like probe 2470 configuration includes spatially separated pairs of infrared light delivering fibers 2476 and light collecting fibers 2478. Arms of the forceps-like probe 2470 are moveable toward and away from each other. The gap between delivering fibers 2476 and collecting fibers 2478 can be adjusted into a fixed 1 mm position by a mechanical stop part 2480.

The conjunctival tissue and plasma are placed or grasped between the two faces of the infrared light source end 2476 and the infrared light detector end 2478 in the arms of the forceps 2470. The light source 2462 emits radiation which is focused onto fiber optic cable 2476. Each source and collector pair is spaced so that light from the light source 2462 and fiber optic cable 2476 passes through the conjunctiva/eye fluid interface (not shown) and is received by the collecting optic fiber cable 2478. The resulting radiation output of the collection optic fiber cable 2478 is provided through a second optical interface system to a the analyzer/detector 2464 housed in the main body housing 2472 of the unit. The signal is then converted to digital information by A/D converter 2466 and fed into the processor 2468 for determination of the concentration of the substance of interest.

A modified forceps probe similar to the one illustrated in FIG. 92 was used for transmission measurements. Conjunctiva in the cul-de-sac was grasped by the forceps. A halogen light source delivered radiation to the conjunctiva coupled to the input end of optic fibers in the arm of the forceps. The radiation passed through the interface conjunctiva-plasma-conjunctiva with the optical path set at 1 mm. The collecting fibers sent the resulting radiation to a detector associated with a narrow bandpass filter centered at 2120 nm to separate the glucose band. The digitized signal was fed to the processor. The processor is programmed to calculate the concentration of glucose using a calibration line obtained by a PLS regression analysis and a 0.93 correlation coefficient was obtained.

Alternatively as shown in FIG. 93(A) the measuring device 2482 can be implanted under the conjunctiva 2320 with said device 2482 being bathed by the surrounding plasma. In such embodiment the device 2482 is encased in biocompatible material as previously described with the optical surfaces encased by infrared transitive material such as sapphire or high-grade quartz. The system includes a main body 2484 and two arms located diametrically opposed to each other encasing the light source 2486 and detector 2488. The light detector 2488 collects the light emitted from the light source 2486 after it interacts with the substance of interest 2350.

During measurement the plasma 2330 located between the light source and detector is the source medium for measuring the substance of interest 2350 as shown in the enlarged view of FIG. 93(B). The dimensions of the detector 2488 are such that allows optimal acquisition of the light signal emitted from the light source 2486 with the detector 2488 being reactive to the spectrum of collected wavelengths for the substance of interest 2350. The output signal is converted into an electrical signal which is then transmitted as an audio signal by RF transceiver 2490 to a remotely placed receiving unit 2492. The signal is then converted by the A/D converter 2494 and then analyzed and processed by the analyzer/processor 2498 for obtaining the concentration of the substance of interest 2350 which is reported by display 2496, activates an audio transmitter 2502 that can alert the user about abnormal measurement levels, and controls the delivery of medication through a medication delivery device 2504 according to said measurement. The system can alternatively include a detector and A/D converter in the main body with the output signal of the detector being received by the A/D converter which converts the signal into digital information which is transmitted by RF transceiver to remotely placed RF transceiver.

Alternatively as shown in FIG. 94 the measuring device 2500 can penetrate the conjunctiva 2320 with one of its arms 2508 located underneath the conjunctiva lining and the other arm 2506 located above the conjunctival lining 2320. The conjunctiva 2320 can be easily penetrated with a very mildly sharp point or even a blunt end. Light is emitted through the conjunctiva 2320 by arm 2506 and collected by the opposing arm 2508. The conjunctiva is the only superficial area in the body that an incision can be done using only one drop of topical anesthetic. Although, less desirable, a reflector for infrared light can be implanted under the conjunctiva.

A further alternative embodiment as shown in FIG. 95(A) includes a forceps 2510 configuration to be used for grasping the edge of the eyelid 2410, shown in a cross-section of the eye and eyelid. The forceps 2510 of FIG. 95(A) is shown in the enlarged view of FIG. 95(B) and includes light source 2514 such as for example light emitting diodes or optic fibers in apposition to the red palpebral conjunctiva 2512 to radiate the conjunctiva/plasma interface 2310 and detectors 2516 positioned on the opposite external surface of the eyelid 2410 in apposition with the eyelid skin 2518. Detectors 2516 collect the resulting transmitted radiation which was directed through the eyelid 2410.

Eyelid 2410 is an ideal alternative for measurement since said eyelid 2410 is highly vascularized and one surface 2512 is transparent with plasma 2330 present while the opposing surface 2518 is comprised of a unique type of skin. Although there is interaction of the radiation with skin, which as described can be an important source of errors, the skin of the eyelid is uniquely fit for measurements because of its characteristics.

The skin 2518 covering the lower eyelid 2410 is the thinnest skin in the whole body. The skin 2518 of the eyelid 2410 is also the only skin area in the body which there is no fat layer. Since fat absorbs significant amounts of radiation over an important portion of the glucose absorbance spectrum, there is a significant reduction of signal when the substance of interest 2350 is glucose. This interference by the presence of a fat layer does not occur in the skin 2518 of the eyelid 2410.

This can be easily observed by pinching the skin of the lower eyelid. One can then easily feel that only a very thin skin is grasped. The same grasping in any other part of the body will show that a much thicker amount of skin is pinched. Those characteristics, contrary to the skin in the rest of the body, enable the acquisition of a good signal to noise ratio. However, the preferred way of the present invention includes complete elimination of the skin as, source of errors and variability.

The apparatus of this alternative embodiment 2510 can include a manual, spring, or automatic adjustment system for engagement and positioning of the device at the edge of the eyelid 2410, right above the eyelashes 2522. The apparatus can also include a fixed predetermined space between source 2514 and detector 2516 according to the individual characteristics of the eyelid 2410. Although one means to grasp the eyelid was described, it is understood that a variety of manual or automatic assemblies to grasp the edge of the eyelid 2410 can be used. In this embodiment, clinical calibration instead of analytical calibration can be used and the device 2510 is calibrated according to the fairly constant skin and tissue characteristics of said eyelid skin 2518.

As shown in FIG. 96, the forceps probe 2520 is grasping the bulbar conjunctiva and plasma interface 2310. The forceps probe 2520 can be wirelessly connected with the main body housing 2524 via RF transceiver 2526 in the probe 2520. The forceps probe 2520 can include the light source 2528 and detector 2530, optic fibers 2532 for directing radiation and optic fibers 2534 for collecting radiation which has interacted with the substance of interest 2350 present in the plasma 2330. The signal 2536 is wirelessly transmitted to the RF transceiver 2538 in the main body housing 2524. The main body 2524 also encases the display 2540, and memory and processor 2542 which makes a spectrum analysis of the collected resulting radiation and determine the concentration of the substance of interest 2350. Conventional statistical analysis and models can be used for the determination of concentration of the substance of interest 2350, but said analysis and models are simplified and less prone to errors since the majority of interfering constituents are eliminated in accordance with the principles of the present invention. The tip of the forceps probe 2520 serves to receive the conjunctiva/plasma interface 2310 with the substance of interest 2350 to be measured. The position of the forceps arms are arranged to adjust the proper spacing with respect to the conjunctiva/plasma medium 2310 to remain stable during the measurement.

A further embodiment as shown in FIGS. 97A and 97B can include a forceps-like system 2560 embedded in a contact device 2562 with two arms extending from the main body of the contact device 2562. A light source 2564 and a light detector 2566 are encased in said contact device 2562 and located diametrically opposed to each other, preferably at a fixed distance. In this embodiment the bottom part of the contact device 2562 lodges in the cul-de-sac 2404 of the eyelid pocket. The recess present between the two arms 2564 and 2566 in the bottom part of the contact device 2562 captures the plasma/conjunctiva interface 2310.

In this embodiment the output of the forceps-like system 2560 can be wirelessly communicated to the receiving unit/processor 2568. The processor 2568 is programmed to execute algorithm and functions needed to determine the concentration of the substance of interest 2350. FIG. 97(C) shows an alternative embodiment in which the contact device 2570 communicates the output by a micro wire 2572 connected to a receiver 2572a and to a processor and display (not shown), Radio transceiver 2572a can include an adhesive patch that is attached to the skin. The micro wires 2572 can comfortably exit the eye and be connected with the adhesive transceiver 2572a. The signal can then be transmitted to another receiver for further processing and display. Alternatively, transceiver 2572a can be comprised of processing and display means. A booster or transceiver placed around the ear can also be used to receive the signal from either contact device 2750 (wired) or 2400 (wireless) on the eye. Contact device can be used for measurement of temperature as well as evaluation of the concentration of the substance of interest.

Figure 98A:
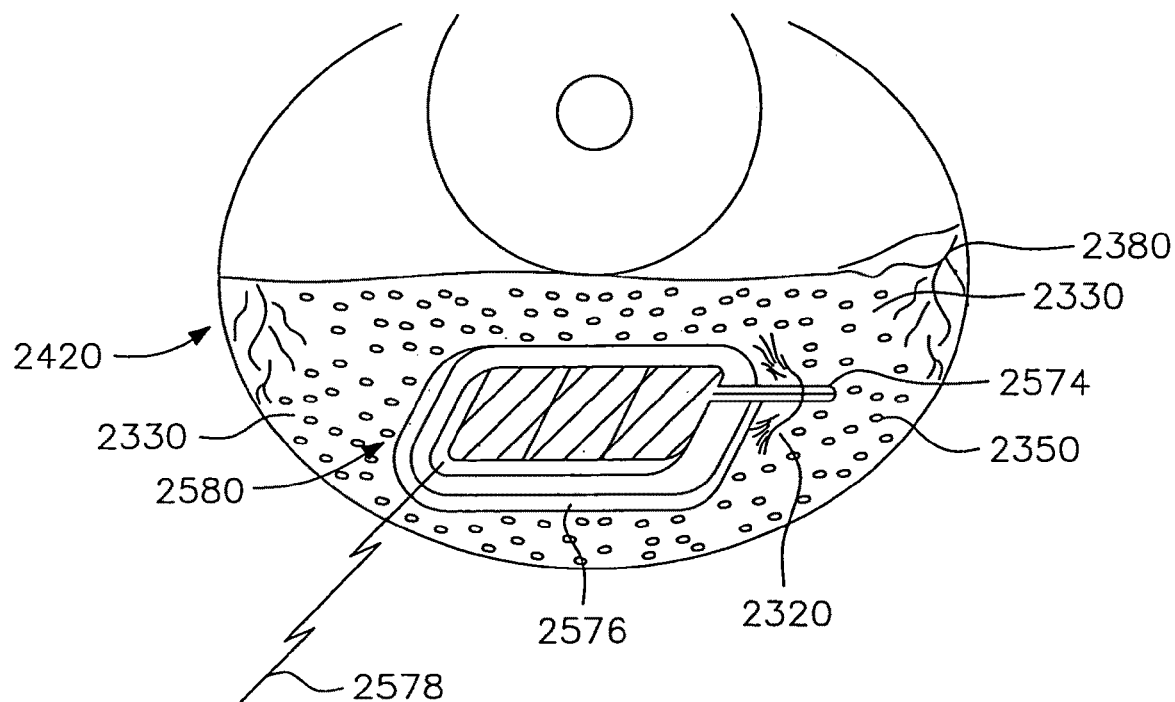
FIG. 98A schematically illustrates a preferred embodiment for implantation of the present invention.

FIG. 98(A) shows the measuring ICL 2580 in which only the tip of the sensor 2574 penetrates the conjunctiva 2320. The tip 2574 is bathed by the plasma 2330 with the substance of interest 2350 in direct contact with the sensor tip 2574. The tip 2574 can include an electrochemical sensor, an optical sensor, or the like. In addition, fiberoptic optodes can be used in the tip 2574 to continuously monitor pH; carbon dioxide-partial pressure, and oxygen partial pressure. The main body 2576 of the measuring ICL 2580 is located in the eyelid pocket 2420 and rests against the conjunctiva 2320. The signal 2578 can be wirelessly transmitted to an external receiver 2580. This embodiment provides a cost-effective away of achieving the measuring function since there is no need for the main body 2576 to be in intimate apposition to the conjunctiva for capturing flow of plasma 2330 with the substance of interest 2350 in case of using electrochemical techniques.

Figure 98B:
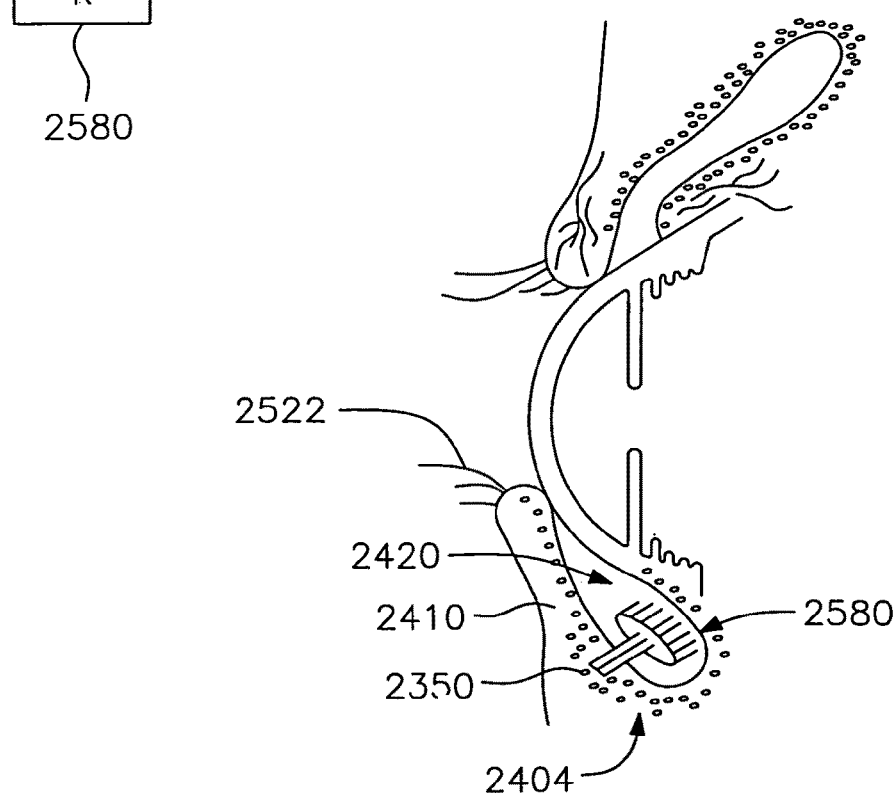
FIG. 98B shows a cross-sectional view of the embodiment shown in FIG. 98A.

The main body 2576 can be made with inexpensive biocompatible polymers that do not need to intimately interact with the surface of the conjunctiva 2320. The flow of plasma occurs directly into the sensing means of the tip 2574. The tip 2574 of the sensor is placed in intimate and immediate contact to the plasma 2330 flowing from the blood vessels. FIG. 98(B) shows a cross-sectional view of the eye, eyelid 2410, and eyelashes 2522. The measuring ICL 2580 is in the eyelid pocket 2420. The tip 2574 of the sensor penetrates the conjunctiva 2320 and is bathed by plasma 2330 and substance of interest 2350 in the cul-de-sac area 2404.

Figure 99A:
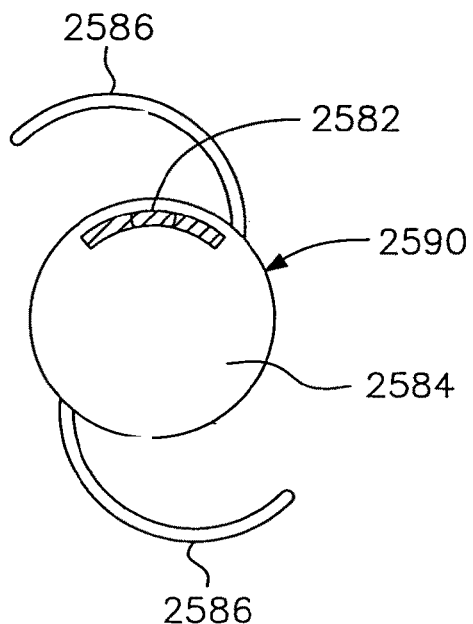
FIG. 99A-D schematically illustrates implantable sensors in accordance with an alternative embodiment of the present invention.

FIG. 99(A) shows an alternative embodiment in which the sensor 2582 is housed in an intraocular lens 2590. The measuring intraocular lens 2590 includes a transparent main body 2584 usually with optical properties. The measuring intraocular lens 2590 can be used as a replacement for the diseased natural lens of the eye during a cataract operation, an optical surface placed in addition to the natural lens of the eye for correction of refractive errors, and the like. The measuring intraocular lens 2590 is implanted surgically inside the eye. This intraocular lens 2590 then is bathed by the aqueous humor 2588 with its various substances of interest 2350.

Although this alternative embodiment requires a surgical procedure and the substance of interest 2350 is present in diluted quantities, this embodiment allows direct contact of the aqueous humor 2588 with the sensor surface 2582. Sensor 2582 can include electrochemical sensors, optical sensors, chemical sensors, or the like. The sensor 2582 can be encased in the main body 2584 and acquire the signal corresponding to the substance of interest 2350 as previously described.

The signal is then transmitted to a remote receiver and processor (not shown) for identification and determination of the concentration of the substance of interest. The apparatus can include a main body 2584 with or without optical properties with the sensor 2582 encased in said main body 2584 and the haptics 2586 of the intraocular lens 2590 being used as antennas. The sensor 2582 can also be attached to one of the haptics 2586.

Figure 99B:
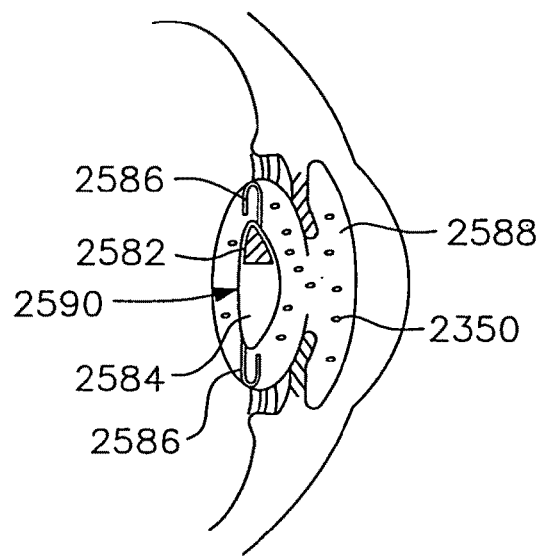

FIG. 99(B) shows a cross section of the eye with the intraocular lens 2590 implanted and placed in the capsular bag. The main body 2584 with sensor 2582 is positioned in the center with the haptics 2586 providing a supporting function. The substance of interest 2350 present in the eye fluid 2588 interacts with the surface of the sensor 2582.

Figure 99C:
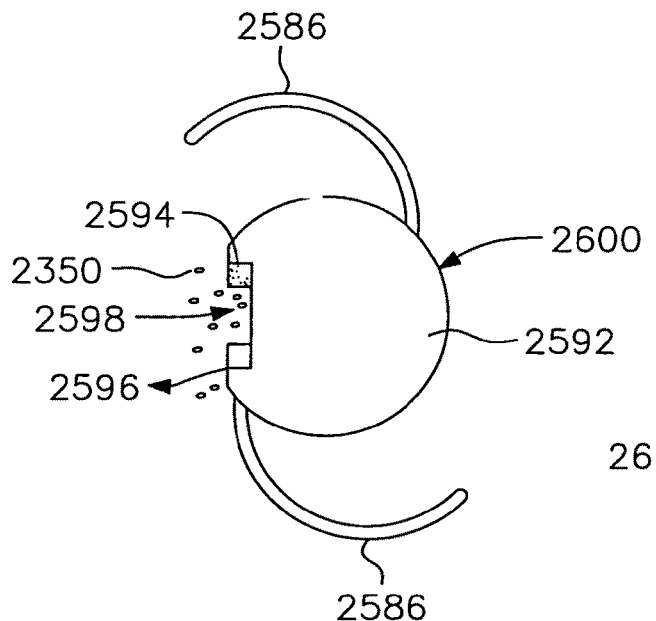

FIG. 99(C) shows an alternative embodiment with modified main body 2592 and haptics 2586. This modified main body 2592 houses in its periphery light source 2594 and light collectors 2596 diametrically opposed to each other. The substance of interest 2350 is present in the fluid 2588 that bathes the lens 2600 and the recess 2598 formed between light source 2594 and collector 2596. In this embodiment the sensor system can be powered using active or passive means including electromagnetic coupling, photoelectric cell using energy from the environment, biological sources, and the like.

Figure 99D:
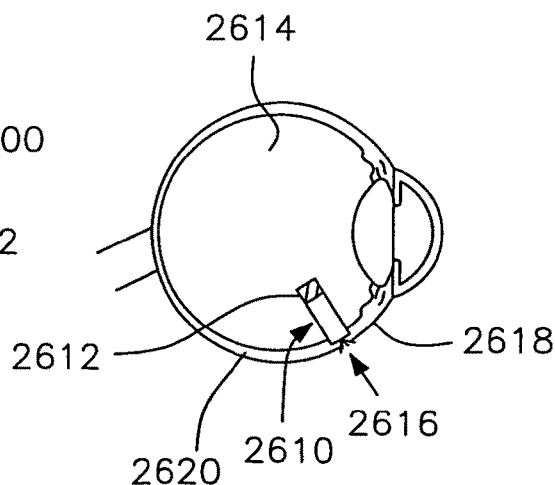

Alternatively as shown in FIG. 99(D), an intra-vitreal implant plate 2610 can be used. The sensor 2612, includes optical, electrochemical sensors or the like. The sensor 2612 can be placed in the vitreous cavity 2614 inside the eye using an incision around the pars plana 2616 area of the eye which is the area between the ciliary body 2618 and the retina 2620. In this embodiment the sensor 2612 is encased in a biocompatible plate 2610 and inserted inside the eye in the vitreous cavity 2614. The plate 2610 is secured with a stitch to the sclera and the sensor 2612 is in contact with the vitreous humor of the eye.

Besides reflectance and transmission spectroscopy, the methods and apparatus of the present invention provide optimal detection using other regions of the electromagnetic spectrum. Another preferred embodiment includes measurement of substances in eye fluid and plasma using far-infrared spectroscopy and will be described in detail below. For example but not by way of limitation two other techniques that can use other regions in the electromagnetic spectrum will be briefly described: radio wave impedance and fluorescent techniques.

Now with reference to FIG. 100(A), the temperature and far-infrared detection ICL 2650 includes a housing 2652 having the shape of a contact device to engage the surface of the eye and an infrared sensor 2654 which detects infrared radiation from the eye. The far-infrared detection ICL 2650 is preferably placed in the eyelid pocket 2420 which allows intimate and stable contact with the tissue in the eye.

Referring to FIG. 100(B), an infrared sensor 2654 is placed in apposition to the conjunctiva 2656 bulbar or palpebral, but preferably the bulbar conjunctiva in apposition to the sclera. Alternatively the face of the sensor 2654 can be placed in apposition to the red palpebral conjunctiva 2656, with said conjunctiva containing blood vessels superficially and being in apposition to the eyelid. The heat radiation 2660 emitted by the plasma 2658 in apposition to the sclera 2659 travels directly to the infrared sensor 2654. The heat radiation 2660 passes only through the thin conjunctiva 2656 with said infrared emission 2660 not being absorbed by the conjunctiva 2656.

The infrared emission 2660 from the blood/plasma 2658 in the conjunctival vessels is collected by the sensor 2654 which can include an infrared sensor or other conventional means to detect temperature on contact. The temperature sensor 2654, preferably a contact thermosensor, is positioned in the sealed environment provided by the eyelid pocket 2420, which eliminates spurious readings which can occur by accidental reading of ambient temperature. The sensor 2654 can measure the intensity of the infrared radiation 2660.

For example, a thermopile sensor which converts the infrared radiation 2660 into an electrical signal can be used or a temperature sensor as a thermistor-like element. The sensor 2654 coupled with a filter that correlates with the substance of interest converts said infrared energy 2660 into an electrical signal. The signal is then transmitted by wireless or wired transmission to a processor (not shown) which calculates the concentration of the substance of interest.

FIG. 100(C) shows a schematic block diagram of one preferred far-infrared spectroscopy measuring apparatus of the present invention. The apparatus includes a thermal infrared detector 2654 which has a filter 2662 and a sensing element 2664 with said sensing element 2664 being preferably a thermopile and responding to thermal infrared radiation 2660 naturally emitted by the eye. A variety of infrared sensors responsive to thermal radiation can be used as sensor 2664 besides a thermopile, such as for example, optoelectronic sensors including thermistor-based infrared sensor, temperature sensitive resistor, pyroelectric sensors, and the like, and preferably thin membrane sensors. The detector 2654 faces the conjunctiva 2656 and if the face of the detector 2654 is encased by the housing 2652 material, said material is preferably transparent to infrared radiation.

The far-infrared radiation 2660 emitted by the conjunctival blood/plasma 2658 (within the spectrum corresponding to thermal radiation from the body; from 4,000 to 14,000 nm) is partially absorbed by the substance of interest 2350 according to its band of spectral absorption and which is related in a linear fashion to the concentration of said substance of interest 2350. For example in the thermally sealed and thermally stable environment in the eyelid pocket 2420 (FIG. 102A), at 38 degrees Celsius spectral radiation 2660 emitted as heat by the eye in the 9,400 nm band is absorbed by glucose in a linear fashion according to the amount of the concentration of glucose. The resulting radiation from conjunctiva/plasma 2658 is the thermal emission 2660 minus the absorbed radiation by the substance of interest 2350.

This resulting radiation enters the infrared detector 2654 which generates an electrical signal corresponding to the spectral characteristic and intensity of said resulting radiation. The resulting radiation is then converted into digital information by converter 2666. The signal 2671 is then transmitted by RF transceiver 2668 to a remotely placed receiver 2670 connected to a processor 2672.

The processor 2672 then calculates the concentration of the substance of interest 2350 according to the amount of thermal energy absorbed in relation to the reference intensity absorption outside the substance of interest band. The output can be adapted to report the value on a display 2674, activate an audio transmitter 2676, and control dispensing means 2678 for the delivery of medications.

A variety of filters can be used to include the spectral region of correlation to the substance of interest. The apparatus can also include a heating induction element and cooling element as well as light radiation and collection means (not shown) to create an integrated far-infrared and near-infrared system. The front surface of contact device can have a coating to increase energy transfer in the spectral region of interest.

In reference to FIG. 100(D), the temperature and far-infrared detection ICL 2651 includes a housing 2653 having the shape of a contact device to engage the surface of the eye and a dual infrared detector arrangement 2654 which is selected to detect far-infrared radiation corresponding to the substance of interest, and sensor 2655 which is used as a reference and detects radiation outside the wavelength corresponding to the substance of interest. Filters are used to select a wavelength of interest and a reference wavelength to calculate the concentration of the substance of interest. The far-infrared detection ICL 2651 is preferably placed in the eyelid pocket 2420 which allows intimate and stable contact with the tissue and source of heat as found in the eye surface.

A contact device with a germanium coated selective filter coupled to a thermopile detector was constructed and used to non-invasively measure conjunctival plasma glucose emitted as thermal emission from the eye. The preferred embodiment comprised an arrangement which included the thermopile coupled to the germanium coated selective filter for passing a wavelength corresponding to a wavelength of high correlation with the substance of interest.

For this exemplary measurement of glucose, wavelength centered around 9,400 nm (glucose band) was used. There is a prominent absorption peak of glucose around 9,400 nm due to the carbon-oxygen-carbon bond in its pyrane ring present in the glucose molecule. The contact device filter system allowed passage of the glucose band which is used as a reference measuring point while simultaneously measuring thermal energy absorption outside the glucose band. The thermal energy absorption in the glucose band by plasma glucose is spectroscopically determined by comparing the measured and predicted radiation at the conjunctival surface.

The predicted amount of thermal energy radiated can be calculated by the Planck distribution function. The absorption of the thermal energy in the plasma glucose band is related in a linear fashion to glucose concentration and the percentage of thermal energy absorption is arithmetically converted to plasma glucose concentration. One preferred embodiment includes a dual detector arrangement in the same contact device. One detector has a filter for reference and the other has a narrow band pass filter for the substance of interest. The ratio of the two wavelengths is used to determine the concentration of the substance of interest.

The system and method of the invention using the conjunctiva/plasma interface solves all of the critical problems with the technique of using thermal emissions by the body for non-invasive analysis. One of the critical issues is related to the fact that the signal size of human thermal emissions is very small as occurs in the skin, mucosal areas, tympanic membrane and other surface areas in the body. This inability of acquiring a useful signal is in addition to the other drawbacks and interfering constituents previously mentioned. The present invention using its preferred embodiments achieves a high signal and correlation by providing a unique place in the body that combines a thermally sealed and stable environment as in the eyelid pocket with a contact device that provides direct contact of detector to the source of heat (blood and plasma) associated with measurement of core temperature, large area of the contact sensor to detector, no interfering constituents, and with active heat transfer from the tissue to the detector.

In addition, due to the characteristics of the conjunctiva/plasma interface as described and high signal obtained, other novel techniques can be easily achieved. One of them includes the use of a calibration line as another preferred embodiment. The concentration of plasma glucose can be obtained by invasive means and analyzed in the laboratory setting. The range of glucose levels of usual interest in clinical practice (40 to 400 mg/dl) obtained invasively creates a reference database to be correlated to the intensity of radiation obtained using the contact device in the eyelid pocket of the present invention. Planck's function can be used to convert temperature to intensities. This invasive reference is done for each clinically useful level of temperature, for example 35 to 41 degrees Celsius. For example, at 37 degrees Celsius, the concentration of glucose (e.g. 100 mg/dl was the glucose level) measured invasively correlated to the spectral intensity value detected at 9,400 nm by the contact device. The concentration of the substance of interest is then determined by correlating the predicted value with the acquired (unknown) value using the predetermined calibration line.

Alternatively, a temperature sensor can be included in the contact device and provide a correction factor according to the level of temperature thus avoiding a calibration table that requires different levels of reference temperature. Processing applies automatically the real time value of the temperature to determine the concentration of the substance of interest. Yet in another alternative embodiment, input means can be provided that allows the user to input the temperature value manually with processing applying that value when calculating the concentration.

Alternatively, a heating element is incorporated in the contact device. The increase in temperature creates a reference measurement which is correlated with the measurement achieved using the natural thermal emission. Moreover, a bandpass filter can be used to select one particular wavelength such as 11,000 nm that is used as a reference and compared to the wavelength of the substance of interest creating a dual detector system with narrow bandpass interference filter. One detector/filter passing a narrow range of radiation centered at 9400 nm and a second detector/filter passing radiation centered at 11000 nm. Selective filters are used to adjust passage of radiation related to the spectrum region of interest, in the case of glucose from 9,000 to 11,000 nm. For detection of ethanol levels the 3,200 to 3,400 nm region of the spectrum is selected. Alternatively, a heating and cooling of the surface of the conjunctiva can be used and the thermal gradient used to determine the concentration of the substance of interest.

Another preferred embodiment includes the use of Beer-Lambert's law in-vivo to determine the concentration of the substance of interest using thermal emissions. In other parts of the body, with the exception of the eyelid pocket and surface of the eye, various natural phenomena and structural characteristics occur that prevent the direct in-vivo use of Beer's law for the determination of the concentration of the substance of interest:

1. The optical path length cannot be determined. In standard spectroscopic calibration and in-vitro measurement, the optical path length comprises the length traversed by light in the sample being evaluated such as for example contained in a cuvette. In any part of the body the thermal emission travels an unknown path from the origin of heat deep in the body until it reaches the surface.
2. Self-absorption. This relates to the phenomena that deep layers of tissue selectively absorb wavelengths of infrared energy prior to emission at the surface. The amount and type of infrared energy self-absorbed is unknown. At the surface those preferred emissions are weak due to self-absorption by the other layers deriving insignificant spectral characteristic of the substance being analyzed. Self-absorption by the body thus naturally prevents useful thermal emission for measurement to be delivered at the surface.
3. Thermal gradient. The deeper layers inside the body are warmer than the superficial layers. The path length increases as the thermal gradient is produced. This third factor in addition to the two described above to further prevent undisturbed natural body heat to be used for determination of concentration of substances. Moreover, there is excessive and highly variable scattering of photons when passing through various layers such as in the skin and other solid organs. This scattering voids the Beer-Lambert law due to radiation that is lost and not accounted for in the measurement associated to an unknown extension of the optical path length and other thermal loss.

The characteristics of the conjunctiva/plasma interface as described fits with and obeys Beer-Lambert's law. The conjunctiva is a transparent surface covering a clear solution (plasma is clear which prevents multiple scattering) which contain a substance to be measured such as glucose. Due to the unique geometry of the conjunctiva/plasma interface, the method and apparatus of this preferred embodiment provide for a key variable in-vivo that allows direct use of Beer-Lambert's law, which is the optical path length. The embodiment provides the equivalent of an in-vivo "cuvette" since the conjunctiva/plasma interface thickness (d) is stable for each location in the eye. The mid to inferior third of the undisturbed bulbar conjunctiva/plasma interface measures 100 nm. Dimensions (d) are similar for each area but can vary greatly from area to area reaching a few millimeters in the lower parts and 20 micrometers in the upper third of the conjunctiva/plasma interface.

One face of the cuvette is the conjunctiva surface and the other face is the sclera with clear plasma in between. The sclera has tissue insulation characteristics that make this surface of the cuvette as the origin of the thermal radiation. The sclera accomplish that because it is a tissue completely avascular, white and cold in relation to the conjunctiva/plasma interface which has the heat source coming from the blood and plasma. The efficiency with which glucose absorbs light is called extinction coefficient (E). E is measured as the amount of absorption produced over 1 cm optical path length by 1 molar solution. Then, the radiation absorbed or Absorbance ($A=\log I_0/I$) by the dissolved material (e.g., glucose) equals the molar extinction coefficient (E) of the substance of interest for the particular wavelength employed times the concentration (c) times the optical path length (d). The equation can be written as:

$$A = \log(I_0/I) = E \cdot c \cdot d \qquad (1)$$

And rewritten to determine the unknown concentration (c)

$$c = A/E \cdot d \qquad (2)$$

where Io can be measured as the original intensity of the incident radiation, I is the transmitted intensity through the sample corresponding to the substance of interest according to the wavelength selected and can be detected with a photodetector.

The other two interfering problems above, self-absorption and thermal gradient, are also eliminated providing the accuracy and precision needed for clinical application. There is no self-absorption by tissues. The radiation (heat) is generated by the local blood/plasma flow and the only tissue traversed is the conjunctival lining which does not absorb the radiation. There is no other tissue interposed in the path from source (heat in the eye surface) to detector. In addition, there are no deep or superficial layers interposed and since the source of heat (blood/plasma) is in direct apposition to the detector, thermal gradient is insignificant.

Filters can limit the wavelength (thermal radiation) to the desired range. It is understood that multiple filters with different wavelength selectivity can be used for the simultaneous measurement of various substances of interest. For example a selective filter allows passage of 9,400 nm band when the substance of interest is glucose. The incident thermal energy traversing the detector, for example a thermopile detector, is proportional to the glucose concentration according to a calibration reference. Alternatively filters can be used to select a wavelength of interest and a reference wavelength to calculate the concentration of the substance of interest as previously described. Yet alternatively the ratio of the concentration of water to the substance of interest can be used to determine the concentration since the concentration of water is known (molecular weight of water is 18 forming a 55.6 molar solution with water band at 11000 nm).

The same principles disclosed above can be used for near-infrared transmission measurements as well as for continuous wave tissue oximeters, evaluation of hematocrit and other blood components. The substance of interest can be endogenous such as glucose or exogenous such as drugs including photosensitizing drugs.

Photosensitizing agents are a class of drugs used in Photo-Dynamic Therapy (PDT). PDT relies on photoactivation of an exogenously administered photosensitizing drug. A variety of cancers and age-related macular degeneration can be treated in this fashion. Those drugs are injected in the circulation of a patient and activated by light after reaching the target organ. The time point between the injection of the photosensitizing drug and exposure to light is critical. However, previously there was no way to determine the time according to real-time measurement of the concentration of the drug in the patient.

For example, in the treatment of macular degeneration in the eye, an arbitrary time of 15 minutes from the time of injection to applying light is chosen for all patients using verteporfin. This time relates to an attempt to achieve optimal concentration of the drug in the target tissue and presumes that all patients will have the same amount of the drug in the eye after 15 minutes. However, substantial variation in pharmacodynamics and pharmacokinetics of the drug can occur from patient to patient preventing an optimum time from injection to photoactivation to be achieved without actually measuring the concentration of the drug in plasma. If photoactivation is done too early it can damage the tissue, and if done too late has no therapeutic effect.

By knowing the concentration of the drug an optimum time for photoactivation can be achieved in addition to adjusting the amount of energy delivered in accordance to the concentration of the drug. In the case of the eye, an accurate concentration of the drug in the retina can be achieved by measuring the concentration of the drug in the conjunctiva. In addition, measurement of drug concentration in plasma present in the eye accurately reflects the concentration of the drug in other parts of the body.

The concentration of the drug can be determined in various ways. In the case of the eye using the drug verteporfin, photoactivation is achieved using a wavelength of 689 nm. A light source providing the same wavelength (689 nm) could be used but has the risk of photoactivation and damage of tissue. It is preferably then that an infrared LED of shorter wavelength, for example an AlInGaP LED, can be used to deliver radiation that interacts with the drug present in the conjunctival plasma.

The intensity of the reflected radiation is measured by photodetectors adjusted to receive the peak absorption radiation from the drug present in the conjunctival plasma. Determination of the concentration of the drug can be done by directly applying Beer-Lambert's law as described or comparing the measured value against a predetermined calibration line. The calibration consists of the relationship between the physical quantity measured to the signal obtained.

Other exemplary agents include purlytin (tin ethyl etiopurpurin) which is photoactivated at 664 nm. A determination of concentration achieved can be obtained in a similar manner as described for verteporfin.

Yet another exemplary agent includes lutetium texaphyrin. In this case photoactivation is achieved using a wavelength of 732 nm. In this case a light source in the contact device, such as a LED, illuminates the conjunctiva at a wavelength of 690 nm. When illuminated at 690 nm the lutetium texaphyrin fluoresces at 750 nm. A suitable detector for 750 nm is incorporated to detect the intensity of the reflected radiation which can be done with the detector being in direct contact with the tissue ors by non-contact means with an externally placed detector aimed at the conjunctiva.

The apparatus which is employed for single or continuous measurement of temperature, but not for determining concentration of the substance of interest can include a simpler arrangement than the embodiment for determination of the concentration of the substance of interest. In accordance with this exemplary embodiment for temperature measurement as shown in FIG. 101(A), the thermal energy 2682 emitted by the eye is sensed by the temperature sensor 2680 such as a miniature thermistor which produces a signal representing the thermal energy 2682 sensed. The signal is then transmitted by RF transmitter 2685 to a remotely placed receiver 2687. The signal is then converted to digital information by A/D converter 2684 and processed by processor 2686 using standard processing for determining the temperature. The temperature level can then be displayed in degrees Centigrade, Fahrenheit or Kelvin in display 2688.

The processor 2686 can also control activation of ICL system 2690 for detection of infectious agents during a temperature spike. If an infectious agent is identified as by microfluidic systems, the processor 2686 can control the delivery of antibiotics according to the infectious agent identified, or control chemotherapy if cancer markers are identified. Drug dispensing devices implanted in the eye (inside the globe or under the conjunctiva) can be used to deliver drugs according to the signal received.

The tear punctum area and inner canthal area of the eye are important for measuring substances non-invasively and for the measurement of core temperature. The punctum and inner canthal area is the hottest part of the body that is exposed (not in the eyelid pocket) to the environment and that reflects core temperature. A temperature sensor can be placed against the inner canthal area and tear punctum with the remaining RF transmitter and electronics placed inside the eyelid pocket.

FIG. 101(B) shows a cross-sectional view of the eye with a temperature measuring contact device 2681. The contact device thermometer includes two miniature temperature sensors 2683, 2689, for example a passive temperature sensor such as a thermocouple. Sensor 2689 is in apposition to the cornea facing the ambient and measuring cornea temperature. Sensor 2683 is inside the eyelid pocket and measuring core temperature. The signal from both sensors 2683, 2689 is transmitted to an external receiver 2687.

This embodiment can be used for measurement of temperature and the differential used to evaluate the presence of disorders such as cancer which increases temperature. Although two temperature sensors are shown it is understood that only one temperature sensor on the cornea can also be used as well as multiple temperature sensors encased in any part of the contact device disclosed.

A variety of temperature sensing elements can be used as a temperature sensor including a thermistor, NTC thermistor, thermocouple, or RTD (Resistance Temperature Detector). A temperature sensing element consisting of platinum wire or any temperature transducer including temperature sensitive resistors fabricated from semiconductor material are also suitable. Other sensing means that can change value over time and provide continuous measurement of temperature include: semiconductors, thermoelectric systems which measure surface temperature, temperature sensitive resistors in which the electrical resistance varies in accordance with the temperature, and the like. Those temperature sensors and resistance temperature device can be activated by closing or blinking of the eye.

Alternatively, a low mass black body coupled to an optic fiber which fluoresces according to the temperature can be used. The amount of light is proportional to the temperature. An alternative embodiment includes reversible temperature indicators including liquid crystal MYLAR sheets. External color detectors read the change in color which corresponds to the temperature.

Figure 102A:
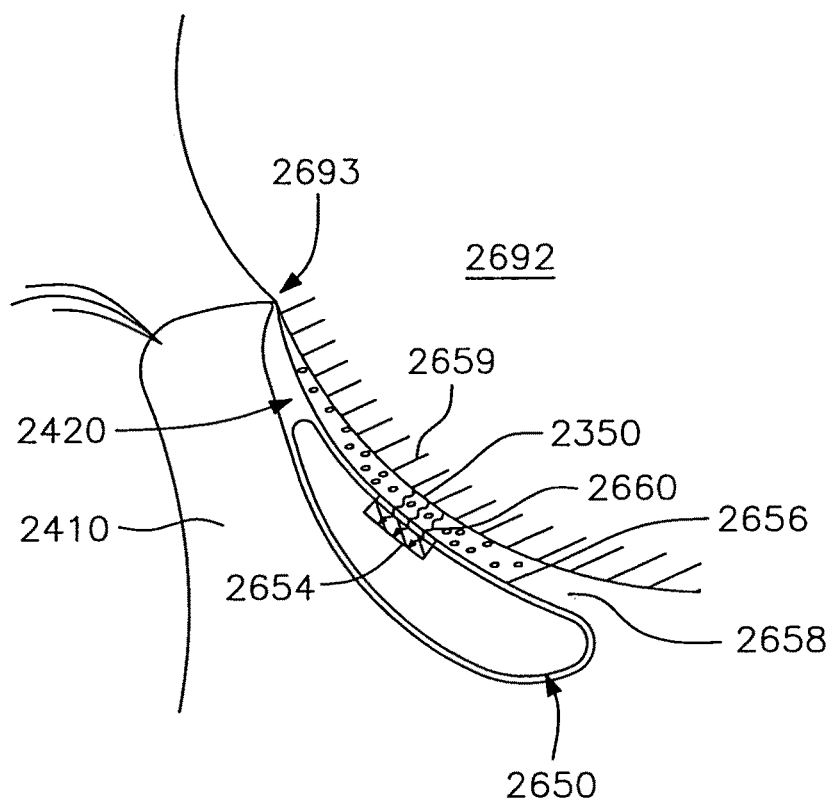
FIG. 102A-B shows a cross-sectional view of one preferred embodiment of the present invention.

FIG. 102(A) shows the far-infrared detection Intelligent Contact Lens 2650 in the eyelid pocket 2420 which provides non-invasive measurement of the substance of interest using natural eye emission as heat in addition to providing measurement of core temperature of the body. The sensor 2654, in contact with the conjunctiva 2656 and substance of interest 2350, draws thermal energy (heat) from said conjunctiva/plasma 2658 and maximizes the temperature detection function. There is no interference since the heat source which is the blood/plasma flow in the surface of the conjunctiva 2656 is in direct apposition to the sensor 2654. The eyelid pocket 2420 functions as a cavity since the eyelid edge 2693 is tightly opposed to the surface of the eyeball 2692. The eyelid pocket 2420 provides a sealed and homogeneous thermal environment. There is active heat transfer from the conjunctiva/plasma 2658 to the sensor 2654 caused by local blood/plasma flow which is in direct contact with said sensor 2654. The opposing surface, the sclera 2659, serves as an insulating element. The increasing surface-to-surface contact as occur naturally in the eyelid pocket 2420 (conjunctiva surface-to-sensor surface contact) increases the rate of heat energy 2660 transfer from conjunctiva 2656 to temperature sensor 2654.

Figure 102B:
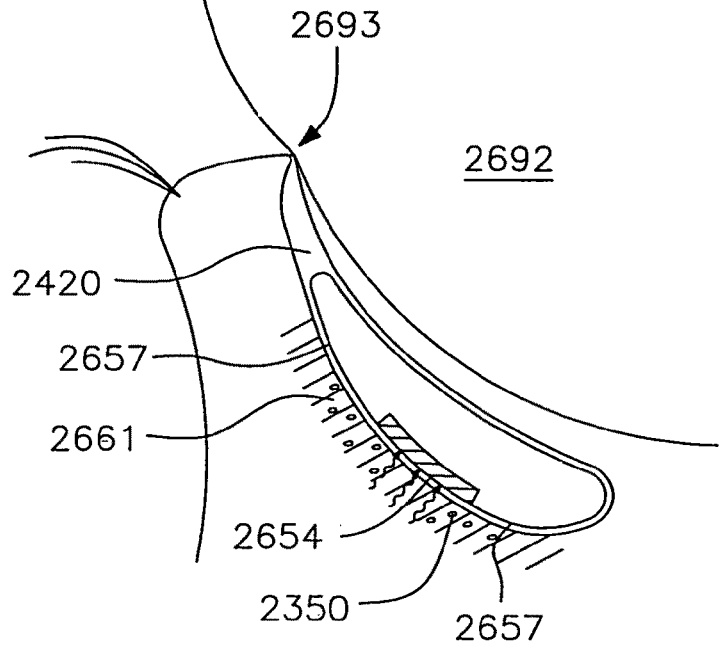

FIG. 102(B) shows the far-infrared detection Intelligent Contact Lens 2651 in the eyelid pocket 2420 which provides non-invasive measurement of the substance of interest using natural eye emission as heat in addition to providing measurement of core temperature of the body. The sensor 2654 in contact with the red palpebral conjunctiva 2657 and substance of interest 2350 draws energy from said conjunctiva 2657 and blood vessels 2661 to maximize temperature detection function. The heat source which is the blood/plasma flow in the surface of the conjunctiva 2657 is in direct apposition to the sensor 2654. The eyelid pocket 2420 functions as a cavity since the eyelid edge 2693 is tightly opposed to the surface of the eyeball 2692.

The eyelid pocket 2420 provides a sealed and homogeneous thermal environment with capillary level 2661 present in the surface. There is active heat transfer from the vessels 2661 to the sensor 2654 caused by local blood/plasma flow which is in direct contact with said sensor 2654: The increasing surface-to-surface contact as occur naturally in the eyelid pocket 2420 (conjunctiva surface-to-sensor surface contact) increases the rate of heat energy 2660 transfer from conjunctiva 2657 to temperature sensor 2654.

Figure 102C:
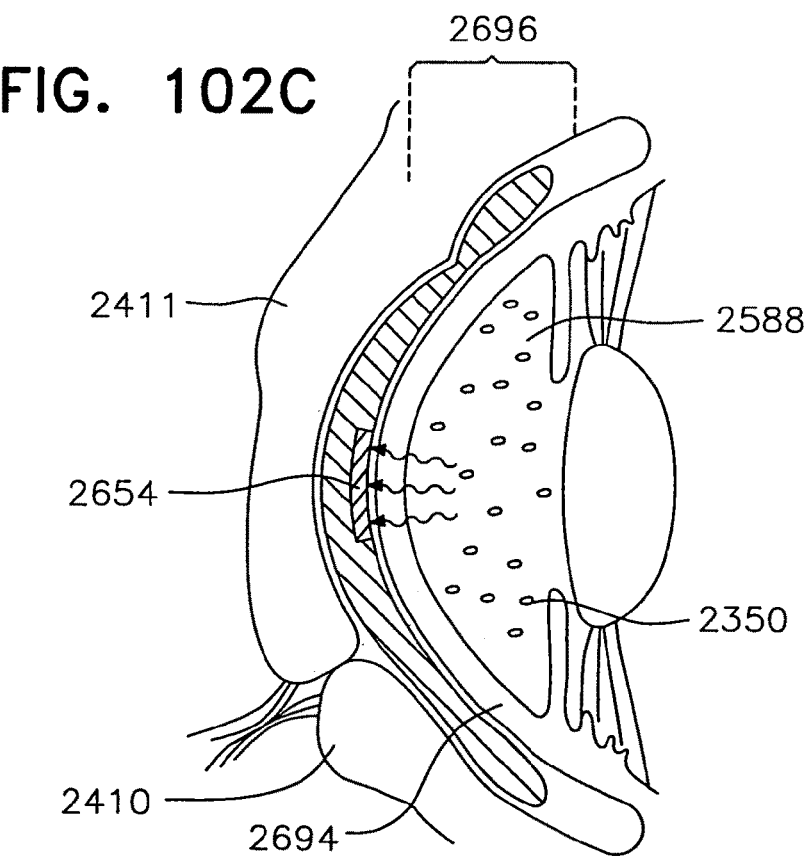
FIG. 102C shows a cross-sectional view of an alternative embodiment of the present invention.

FIG. 102(C) shows an alternative embodiment illustrating a cross-section view of the eye with cornea 2694, upper and lower eyelids 2410, 2411, anterior segment of the eye 2696 with aqueous humor 2588 and substance of interest 2350 in said anterior chamber 2696 of the eye. FIG. 102 (C) also shows the eyes closed with the thermal sensor 2654 located on the surface of the cornea 2694 and the substance of interest 2350 and thermal emission 2660 coming through the cornea 2694. When the eyelids are closed (during blinking or during sleeping), the thermal environment of the eye is exclusively internal corresponding to the core temperature of the body. This alternative embodiment can be preferably used for measurement of temperature or substance of interest 2350 during sleeping.

Radio wave impedance techniques can also be used and enhanced by the principles of the invention. Impedance is proportional to the differences in amplitude and phase of the wave compared to a reference wave. Radio waves promote excitation of molecular rotation. In reference to FIG. 103, the substance of interest 2350 interacts with the radio wave 2700 to attenuate the amplitude and shift the phase of the wave creating a resulting wave 2702. The resulting impedance 2702 is proportional to the concentration of the substance of interest 2350 which can be calculated using a conversion factor.

Figure 103:
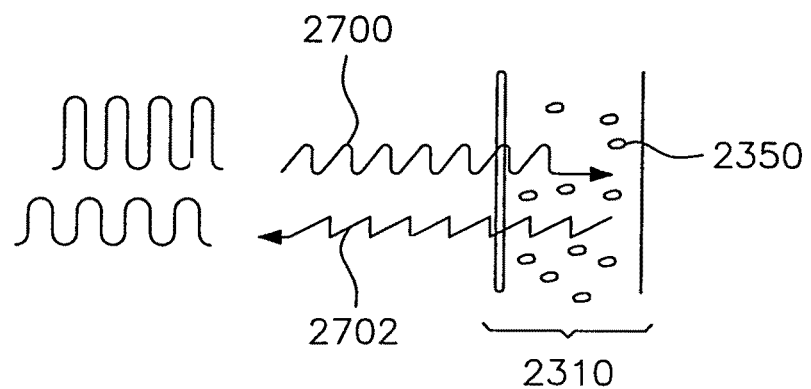
FIG. 103 schematically illustrates an alternative embodiment of the present invention.

FIG. 103 shows the substance of interest, for example a nonionic solute such as glucose, which interacts with a radio wave 2700 that is passed through the conjunctiva/plasma interface 2310. Since there are few interfering elements and glucose in plasma is in relative higher concentration compared to background, the concentration can be accurately and precisely obtained.

Light induced fluorescence can be used since the since the plasma with the analyte to be measured is present on the surface. A variety of fluorescent techniques can also be used to identify or quantify a substance or cellular constituent. A variety of disorders including bacterial infection, degenerative diseases such as Alzheimer, multiple sclerosis and the like can be identified by for example emitted light or fluorescent light generated by interaction with degenerated constituents (not shown). The radiation induced fluorescence depends on the biochemical and histomorphological characteristics of the sample including presence of cancerous cells which can be optically characterized in the surface of the eye and conjunctiva.

FIG. 104(A) shows a probe arrangement for reflectance measurement with a wired handle 2730 which contains the fiber optic bundles for delivery of and collection of radiation directed at the substance of interest 2350 present in the conjunctiva/plasma interface 2310. The probe can also work as a pen like device with the signal being wirelessly transmitted to an external receiver.

FIG. 104(B) shows a schematic illustration of another preferred embodiment using non-contact infrared detection of thermal radiation from the conjunctiva/plasma interface 2310. A penlight 2731 measuring device receives radiation 2660 which passes through filter 2733 corresponding to high correlation with the substance of interest 2350 and filter 2732 that works as a reference filter outside of the range corresponding to the substance of interest 2350. The pen 2731 contains the electronics and processing (not shown) needed to calculate and display the data. Display 2737 shows the concentration of the substance of interest, for example the glucose value and display 2735 shows the temperature value. FIG. 104(B1-B3) shows illustratively the different locations in the eye that measurement can be done, in the conjunctiva 2739, in the inner canthal area and tear punctum 2741, and in the cornea 2742.

FIG. 104(C) is a block diagram of a continuous measurement system of the invention in which the infrared detector is mounted preferably in the frame of eye glasses. A head-band and the like can also be used. The field of view of the infrared sensor is directed at the exposed conjunctival area when the eyes are open. The continuous signal of the infrared sensor is delivered to a RF transmitter which transmits the signal to an external receiver for subsequent processing and display.

FIG. 104(D) shows the measuring pen 2731 coupled with a telescope or lighting system which are in line with the area from which radiation is being emitted from the surface of the eye. This allows precise aim and indicates the area being measured for consistency.

FIG. 104(E) is a schematic view of the probe of pen 2731. The tip rests against the conjunctiva 2320 with a sensor arrangement located in a recess inside the tip of the probe. The sensor arrangement includes filter 2662a for the substance of interest and 2662b that is used as a reference and infrared detector 2664.

FIGS. 104(F-G) show a cross-sectional view for various positions of the probe of pen 2731 in relation to the conjunctiva. FIG. 104(F) show the probe resting on the conjunctiva 2320 and covered by disposable cover 2665 while FIG. 104 (G) shows the probe receiving thermal radiation 2660 away from the conjunctiva 2320.

FIG. 104 (H-J) show in more detail some arrangements for selecting substance of interest according to the wavelength. FIG. 104(I) shows filter 2662a corresponding to the substance of interest and filter 2662b used as a reference. FIG. 104(J) shows a similar arrangement as in FIG. 104(I) with an additional temperature sensor 2667. FIG. 104(H) shows a preferred embodiment with a selection arrangement consisting of infrared sensor 2662e receiving thermal radiation 2660 from conjunctiva 2320 at the body temperature. Infrared sensor 2662e has two junctions, a cold junction 2662d and a hot junction 2662c. The cold junction is covered with a membrane (not shown) to reduce the amount of heat reaching said cold junction 2662d. In addition, the cold junction 2662d is artificially cooled and thus receives the radiation from the conjunctiva 2320 at a lower temperature. The increased temperature gradient created increases the voltage signal of detector 2662e facilitating determination of the concentration of the substance of interest. Alternatively, the cold junction 2662d is mounted surrounding the hot junction 2662c (not shown) and an aperture is created to direct the heat toward the hot junction 2662c while avoiding the cold junction 2662d. The above arrangements which increase the temperature gradient in the infrared sensor helps said sensor 2662e to remain with a high signal since when the narrow band pass filter is placed in front of the infrared detector the signal is decreased. Narrow band pass filters such as found in rotatable filter 2673 are placed preferably in front of the hot junction and centered at the wavelength corresponding to the substance of interest. The signal can also be increased by increasing the number of junctions in the detector and increasing the resistance. A thermistor can be incorporated to measure the temperature in the cold junction in order to accurately measure the temperature of the conjunctiva. The probe head 2731a of pen 2731 can include a wall (not shown) positioned between sensor 2662c and sensor 2662d similar to the one described in FIG. 86.

A variety of means can be used to increase the temperature gradient between the hot and cold junctions of a thermopile and increase the signal including using a power source to bring the cold junction to a lower temperature. Besides using thermoelectric means, contact cooling with cold crystals or cold bodies can be used to decrease the temperature of the sensor. When using the contact device 2400 the cooling of the cold junction cools the conjunctiva in a very efficient manner since the conjunctiva is very thin and has a small thermal mass. When using the pen 2731 the cooling of the infrared sensor is carried from the surface of the sensor to the conjunctival surface with cooling of said conjunctival surface.

Due to the characteristics of the conjunctiva/plasma interface as described, with direct application of Beer-Lambert's law and determination of a precise calibration line, a reference filter may be eliminated. This simple and cost-effective arrangement is only possible in a place like the conjunctiva/plasma interface. The intensity, of the received radiation is evaluated against a predetermined calibration line and corrected according to the temperature detected.

The characteristics of the plasma-conjunctiva interface allows a variety of hardware arrangements and techniques to be used in order to determine the concentration of the substance of interest as has been described. One preferred embodiment is shown as a cross-sectional view in FIG. 104 (K-1). The arrangement of probe head of pen 2731 includes a rotatable filter 2763 for measurement of various substances according to selection of the appropriate filter corresponding to the substance of interest. FIG. 104 (K-2) shows a planar view of rotatable filter 2673 including three narrow bandpass filters. The rotatable filter 2763 contains filters 2663, 2669, 2671 corresponding to the wavelength of three different substances.

For example filter 2663 is centered at 9400 nm for measuring glucose, filter 2669 is centered at 8300 nm for measuring cholesterol and filter 2671 is centered at 9900 nm for measuring ethanol. Filter 2667 is centered at between 10.5 m and 11 m and is used as a reference filter. The filter being used is in apposition with detector 2664. The filters not being used, for example filter 2663 rests against a solid part 2773 of the probe not permeable to infrared radiation. Although only one reference filter is shown it is understood that a similar rotatable system with different reference filters can be used according to the substance being measured. Infrared detector 2664 can consist of passive detectors such as thermopile detectors. The electrical signal generated by detector 2664 is fed into the processor (not shown) for determination of the concentration of the substance of interest. A variety of focusing lens and collimating means known in the art including polyethylene lens or calcium fluoride lens can be used for better focusing radiation into infrared detector 2664.

By applying Beer-Lambert's law, the ratio of the reference and measured values is used to calculate the concentration of the substance of interest independent of the temperature value. One preferred method for determining the concentration of the substance of interest is to direct the field of view of the detector to capture radiation coming from the medial canthal area of the eye (corner of the eye), which is the hottest spot on the surface of the human body. The field of view of an infrared detector can also be directed at the eyelid pocket lining after the eyelid is pulled away.

FIG. 104(L) shows another preferred temperature measuring system 2675 in which the temperature detector 2677 rests against the canthal area (inner corner of the eye) and tear duct of the eye and the body 2679 of the contact device rests in the eyelid pocket. FIG. 104(M) shows an alternative embodiment for measurement of concentration of substances using far infrared thermal emission from the eye and a temperature gradient. The contact device 2703 includes infrared sensor 2704. Infrared sensor 2704 has a superior half 2704a exposed to ambient temperature above the eyelid pocket and the inferior half 2704b remains inside the eyelid pocket measuring core temperature. Alternatively, one sensor can be placed against the skin and another one in the eyelid pocket.

FIG. 104(N) shows a device 2705 for measuring substances of interest or temperature using a band or ring-like arrangement including both the upper and lower eyelid pockets.

FIG. 104(O) shows the pen 2706 connected to an arm 2707 at a fixed distance. The tip of the pen or probe 2706 has an angled tip to fit with the curvature of the sclera with a radius of approximately 11.5 mm. The filed of view of the pen 2706 is in accordance with the distance of the eye surface to the sensor. The arm 2707 can be used to push the lower lid down and expose the conjunctival area to be measured. This facilitates exposing the conjunctiva and provides measurement of the same location and same distance. Fresnell lenses can be added to measure temperature at a longer distances. An articulated arm or flexible shaft can also be used to facilitate reaching the area of interest.

Other alternative means to determine the concentration of the substance of interest using the conjunctiva/plasma interface includes using an actual reference cell with a known amount of the substance being measured incorporated in the pen 2731 which is used as a reference. In addition, stimulating an enzymatic reaction to process glucose can be used. Since processing of glucose can cause an exothermic reaction, the amount of heat generated can be correlated with the amount of glucose.

FIG. 104(P) shows simultaneous measurement of temperature of the right and left eye with a non-contact infrared system 2693. Arm 2695 carries a sensor measuring temperature for the right eye which is displayed on display 2701. Arm 2697 carries a sensor measuring temperature for the left eye which is displayed on display 2669. The difference in temperature (left eye is 101° F. and right eye 97° F.) can be indicative of a disorder. An asymmetric eye temperature also can corresponds with carotid disease and nervous system abnormalities. Although temperature was used as an illustration, the device can also be used for detecting asymmetry in the concentration of chemical substances.

FIG. 104(Q1-Q4) shows a series of photographs for evaluation and measurement of thermal radiation from the eye and conjunctiva/plasma interface. The images were acquired using a computerized high-resolution infrared imaging system which measures the far-infrared energy emitted by the eye and displays the images. In the photographs, the amount of thermal energy goes from highest to intermediate and lowest. In the black and white images the white digital points correspond to the areas of highest thermal energy, black indicates the coolest part and gray intermediate. The hottest external point in the human body is located in the inner canthal area. This area corresponds to an exposed conjunctiva and reflects the thermal energy in the eyelid pocket. This is easily observed by looking at the eye and noticing the red area in the eye by the nose which is continuous with the lining in the eyelid pocket.

FIG. 104(Q1A) shows an image of the thermal energy present in the eye before applying a fan and cold immersion of hands FIG. 104Q1B shows the image after applying a fan/immersion of hands in cold in order to try to cool down the conjunctiva/plasma interface Note that there is virtually no change in the amount of thermal energy demonstrating the stability of the thermal emission of the area.

FIG. 104(Q2A-B) shows black and white images with the hottest point appearing as white dots. FIG. 104(Q2A) shows the thermal emission from the red superficial conjunctiva/plasma interface located by the nose with the eyes closed. FIG. 104(Q2B) shows the enormous amount of thermal energy present in the conjunctival area and margin of the eyelid pocket (B) with the eyes open. Note that the points are of same color and characteristics indicating same thermal energy present on theses surfaces. Note that the cornea (A) is cold (dark color) in relation to the conjunctiva (bright white points).

FIG. 104 (Q3) shows the symmetry of thermal energy between the two eyes and the hottest spot located in the canthal area. Note that the remaining portion of the face is cold in relation to the conjunctiva. There are no bright white points on the face with the exception of the inner canthal area.

FIG. 104 (Q4) shows a close-up view of the lower eyelid being pulled down by the finger. This maneuver exposes the eyelid pocket lining and conjunctiva/plasma interface showing the high amount of thermal energy present in the area. Note the great concentration of bright white points in the surface of the eyelid pocket representing the thermal energy being emitted from the area. The great amount, consistency and reproducibility of thermal energy in the conjunctiva/plasma interface and eyelid pocket allows obtaining a high signal to noise ratio and accurate and precise determination of the substance of interest using far-infrared emission from the eye.

FIG. 104(Q5) shows a close-up view of the face and eyes with the symmetric and great amount of infrared radiation being emitted by the corner of both eyes which are seen as bright white spots. Note that the only place in which bright spots can be seen is in the corner of the eye indicating the highest amount of infrared energy being radiated. The darker the area the lesser amount of infrared energy being emitted. The great amount, consistency and reproducibility of thermal energy in the corner of the eye allows obtaining a high signal to noise ratio and accurate and precise determination of the substance of interest using far-infrared emission from the corner of the eye.

Illustrative resonance absorption peak for some exemplary substances of interest (wavelength in nm)
Albumin 2170
Bilirubin 460
Carbon dioxide 4200
Cholesterol 2300
Creatinine 2260
Cytochromes 700
Ethanol 3300
Glucose 2120
Hemoglobin 600
Ketones 2280
Lutetium texaphyrin 732
L-aspartyl chlorin e6 664
Oxygen 770
Photoporphyrin 690
Porphyrins 350
Purlytin 664
Triglycerides 1715
Urea 2190
Verteporfin 689
Water 11000

The body maintains ocular blood flow constant, whereas skin, muscle, and splancnic blood flow varies with changing cardiac output and ambient conditions. Oxygen in the eye can continuously monitor perfusion and detect early hemodynamic changes. In addition, the oxygen levels found in the eyelid pocket reflects central oxygenation. The oxygen monitoring in the eye can be representative of the general hemodynamic state of the body. Many critical conditions such as sepsis (disseminated infection) or heart problems can alter perfusion in most of the body and it is thus difficult to evaluate adequacy of organ perfusion.

The eye though, remains with unaltered perfusion in such disease states and can provide a good indication of the level of oxygenation. FIG. 105(A) shows a simplified block diagram of ICL 2710 with oxygen sensor 2712 and RF transceiver 2714 wirelessly connected to a pacemaker 2716 and an internal cardiac defibrillator 2718. The contact device 2710 for oxygen monitoring can be used for activating lifesaving equipment such as pacemakers 2716, internal cardiac defibrillators 2718, and the like. The defibrillator 2718 or pacemaker 2716 can be activated if the levels of oxygen are within critical levels, for example during sleeping when the user is not capable to react to the life-threatening condition. The activation of the pacemaker 2716 or defibrillator 2718 is preferably done when both the oxygen sensor 2710 and the heart tracing sensor 2720 indicate a life-threatening condition. Other systems such as implanted conventional plethysmography can also work in association with the eye monitoring systems to provide a more comprehensive monitoring.

The eye also provides a direct indication of heart beating and rhythm. FIG. 105(B) shows a tracing of heart beat achieved by using a contact device and transducer placed on the eye. The tracing gives a waveform corresponding to heart rhythm that can be used to monitor cardiac arrhythmia and cardiac contractility. The beating of the heart can be detected and a change in heart rhythm used to activate or regulate lifesaving equipment.

FIG. 105(C) shows a block diagram in which the Intelligent Contact Lens 2720 is used as heart monitor and coupled to an implanted pacemaker 2716, an internal cardiac defibrillator 2718, an alarm system 2722, and a medication delivery system 2724 that can deliver for instance heart medication to increase heart contractility or medication to correct an abnormal heart rate in order to meet oxygenation and perfusion needs of the patient.

The monitoring system can also be used as an intraoperative awareness device. The phenomenon of intraoperative awareness occurs when a patient awakes during surgery and experiences pain. The anesthetic wears off but because of muscle paralyzing drugs the patient, although awake, cannot react to the pain, speak, or move. However, the eye muscles are activated when one awakens and the reverse Bell phenomena can be used to gauge how awake the patient is. The reverse Bell phenomena relates to the eyes moving from a superotemporal position to a straight gaze position when the individual awakens. The monitoring function can be accomplished by identifying the changes that occur with the movement of the eye when the patient is awake. For instance, a motion or pressure sensor can be encased in the contact device and transmit the information to an external receiver. In addition, the change in rhythm as identified by the tracing in FIG. 105(B) can be combined with the above reverse Bell phenomena monitoring means and used to gauge the degree of anesthesia.

With reference to FIG. 105(D1-D7), a HTSD (Heat Stimulation Transmission Device) is shown. Although the HSTD herein is described for the eye, it is understood that the system can be used in the other parts and organs of the body. The HSTD 2711 is an arc shaped band with a radius of approximately 11.5 mm to fit in apposition to the sclera 2659. FIG. 105(D1) shows a cross-sectional view of the eye with the HSTD 2711 implanted on the surface of the eye in apposition to the sclera 2659. The HSTD 2711 includes a heating element 2713, a temperature sensor 2715 such as a thermocouple and a RF transceiver 2719 connected to the thermocouple 2715 by cable 2717. The heating element 2713 is located adjacent to the neovascular membrane 2729 being treated and located in the most posterior part of the eye. The heating element 2713 emits heat ranging from 40 to 41 degrees Celsius. This amount of heat delivered over 12 hours restores function of abnormal vessels and closes leaking vessels with reabsorption of liquid leaking from the vessels. This HSTD 2711 can be surgically implanted in the back of the eye in apposition to the sclera 2659 or inside the sclera 2659, for treating cancer, macular degeneration, diabetic retinopathy, neovascular membranes, vein occlusion, glaucoma, and any other vascular abnormalities present in the eye and the body. Besides surgical implantation, the HSTD can be noninvasively placed on the surface of the eye.

An LED, laser or other light sources delivering radiation in the infrared region can also be used in the device 2711 as a substitute for heating element 2713. The use of the infrared wavelength including the use of LEDs results in delivering radiation that is minimally absorbed by photoreceptors in the retina. The diameter of the LED, light source or heating element can preferably vary between 0.5 mm to 6 mm depending on the size of the lesion being treated. A thermocouple 2715 can be incorporated to measure temperature real time which is transmitted to an external receiver 2725 via transceiver 2719.

The apparatus is based on the physiologic and anatomic characteristics of the eye. The eye has the largest supply of blood per gram of tissue and has the unique ability to be overperfused when there is an increase in temperature. For each degree Celsius of increase in temperature there is an increase of about 7% in the oxygen levels in the eye. This increase in temperature causes dilation of the capillary bed and increased delivery of oxygen and can be used in situations in which there is hypoxia (decreased oxygenation) such as in diabetes, vascular occlusions, carotid artery disease, and the like. A higher increase in temperature and long term exposure causing localized hyperthermia leads to vascular sclerosis and reabsorption of liquid and can be used in the treatment of neovascular membranes as it occurs in age-related macular degeneration. A further increase in temperature causes obliteration of vessels and necrosis of rapidly duplicating cells and can be used for treating tumors.

Besides surface electrodes, one exemplary and preferred way for generating heat for the HSTD is by using conductive polymers with self-regulating properties. Conductive polymers are made from a blend of specially formulated plastics and conductive particles. At predetermined temperatures the polymer assumes a crystalline structure through which the conductive particles form low-resistance chains in the polymer material that carry the current. With increased temperature the polymer's structure changes to an amorphous state breaking the conductive chains and rapidly increasing the device's resistance. When the temperature returns to its preset value the polymer returns to its crystalline state and the conductive chains reform, returning the resistance to its normal value. At the preset temperature levels, not enough heat is generated to change the polymer to an amorphous state. When there is an excess heat the resistance rapidly increases with a corresponding decrease in the current and consequent decreased heat formation.

The apparatus of the present invention allows the tissue being treated to be maintained at a predetermined temperature. In addition minimum and maximum temperature can be set. The internal temperature and resistance depends on the chemical composition of that specific polymer. For any conductive polymer, there is a current that will raise the polymer's internal temperature high enough to cause it to change from a crystalline to a non-crystalline or amorphous state. As current passes through the conductive polymer heat is generated. As the temperature drops, the number of electrical paths through the core increases and more heat is produced. Conversely, as the temperature rises, the core has fewer electrical paths and less heat is produced keeping the temperature at a set predetermined level. The apparatus responds continuously to temperature increasing their heat output as the temperature drops and decreasing heat output as the temperature rises. Such conductive polymers are available from the Raychem Corporation, Menlo Park, Calif.

The apparatus of the invention provides precisely the right amount of heat at the predetermined location and time. The system design can be adjusted to accommodate any type of disorder ranging from lower temperature (less heat) for treating diabetic-retinopathy to medium range temperature (38.5 to 40 degrees Celsius) to treat neovascular membranes and higher temperature for treating cancer in the eye or any location in the body. The apparatus of the invention is low-cost and adjusts automatically to temperature changes. There is no need for special controls and no moving parts. Although the apparatus was described using polymers, ceramic, conductive paste, polymer thick films and a variety of polymeric positive temperature coefficient devices, and the like can be used in the HSTD of the present invention. When using such conductive polymers a lower cost system can be achieved. In this embodiment the HSTD can include a power source and controller coupled to the conductive polymer. There is no need for a temperature detector nor RF transmitter.

Another preferred embodiment, besides heating, includes the use of a radioactive source. The radioactive source can also be used in the device 2711 as a substitute for heating element 2713. For example an active seed such as Iodine-125 (I-125) or Paladium-103 (Pd-103) emitting x-rays and gamma rays can be used. A fiber-based delivery system for delivering radiation which is encased in the HSTD 2711 can also be used.

Besides I-125 and Pd-103 other isotopes and Iridium can be used. Although, I-125 has a half-life of 59.61 days which would-take about one year for complete inactivation, the device 2711 with the seed can be easily removed at any time according to the response of the tissue. Exemplary seeds are available from North American Scientific, Inc., Chatsworth, Calif.

The device 2711 with radioactive seeds can be used to treat neovascular membranes, vascular abnormalities, cancers, and the like and length of implantation done according to the disease being treated. For treating neovascular membranes the device 2711 should be removed in less than 7 days with longer periods for treating cancer.

FIG. 105(D2) shows a side view of the arc-shaped HSTD 2711 with its elements 2713, 2715, 2719 encased in it.

FIG. 105 (D3) shows a frontal view of the HSTD 2711 shaped as a band and with two small arms 2721 with holes 2721a for fixating the device 2711 against the sclera 2659. Suture 2725 is passed through the hole 2721a of arms 2721 to secure the device 2711 in a stable position. Multiple arms in different positions can be incorporated for fixating the device 2711 in a more stable position. The arc length of the device 2711 is dependent upon the location of the lesion being treated.

FIG. 105(D4-D6) show exemplary steps used for implantation. The patient looks down and a drop of anesthetic is placed on the eye. Then an incision 2723 is made in the conjunctiva and device 2711 is slid over the sclera 2659 toward the back of the eye. While the patient is still looking down, a couple of sutures 2725 are placed for fixation of device 2711 to the sclera 2659 using the side arms 2721.

FIG. 105(D6) shows the device 2711 and microscopic sutures covered by the conjunctiva 2320 and the upper eyelid 2411. After completion of the procedure the device 2711 is not visible and no discomfort elicited. After the lesion is treated the device 2711 can be easily removed with one drop of anesthetic with subsequent cutting the sutures 2725 and pulling the device 2711 out.

FIG. 105(D7) shows a frontal view of the HSTD 2711 shaped as a cross and with two holes 27211a for fixating the device 2711 against the sclera 2659. This preferred HSTD is a low cost device only comprising the heating element 2713, cables 2717, and power source/controller 2717a. Multiple arms in different positions can be incorporated for delivering a more widespread heat to the organ. The arms preferably embrace the organ for achieving an intimate apposition. The arms are shaped according to the shape of the organ being treated.

Besides the sensor being encased in a conventional contact lens configuration as described above, the sensor part can be placed in the eye and subsequent to that a polymer that solidifies when in contact with the eye is placed the eyelid pocket. This alternative embodiment can be used for creating the housing for the sensor in-situ, meaning in the eye pocket.

Additional Dispensing Capabilities:

Many patients go blind even after diagnosis and treatment for the disease has been instituted. One classic example is glaucoma. The treatment of glaucoma requires the patient to instill eye drops on a daily basis in order to preserve their sight. Even after being prescribed sight-saving eye drops, patients still go blind. Sometimes patients need to instill drops several times a day for a variety of diseases. Studies have shown that close to 60% of patients had difficulties with self-administration of eye drops. Current means to administer topical ocular drugs requires skills. The patient must not only administer the drops with a correct amount, but also master a rather difficult technique.

The technique recommended and most used for instilling eye drops was described in the paper "How best to apply topical ocular medication". The process is not simple which explains the difficulties related to using eye drops. The steps include: bending the neck, looking up, looking away from the tip of the bottle to avoid fright reaction, pulling the lower eyelid down and away from the globe, positioning the inverted bottle over the eye but not touching any part of the eye, squeezing the bottle and placing the drop on the eye without touching the tip to the eye, to eyelids, or to eyelashes and yet without blinking or lid squeezing when-compressing the bottle. The problems described by patients included: raising their arms above their heads, tilting their heads, holding the bottle and squeezing the bottle with the arms raised, directing the bottle on top of the eye without touching the eye, fear of hitting the eye leading the bottle to the held too high or away from the eye, involuntary blinking or closing eyes after squeezing the bottle, placing the correct number of eye drops, and poor view of the tip of the bottle.

With the dispensing ICL of the present invention, the user does not have to bend their neck in addition to not having to perform all of the other maneuvers described above. This ICL dispensing device and applicator system of the present invention eliminates or substantially minimizes these difficulties and the consequent vision loss that occur due to inability of instilling eye drops correctly.

The user can comfortably place the dispensing ICL on the eye according to the following method and steps. The dispensing ICL is placed on the eye under direct view and looking straight ahead. The user holds the handle in the ICL, place said dispensing ICL in the edge of the lower eyelid pocket while looking at a mirror. The remainder of the dispensing ICL then engages the surface of the cornea and the patient closes his/her eye. The closure of the eye or blinking provides the actuating force to deform a reservoir and release the medication from the reservoir. The patient keeps the eye closed for 15 seconds to allow better absorption of the medication, then open the eyes, grasps the handle and removes the dispensing ICL from the eye.

In FIG. 106(A), the Intelligent Contact Lens dispensing device 2750 includes a self-contained substance source 2752 which is released by the physical displacement of a portion of the reservoir 2760 thereof whereupon substance 2752 is forced to the outside and directed to the surface of the eye. The substance 2752 self-contained in the reservoir can include liquid, gel, ointment, powder, pastes, gas, and the like.

Still with reference to FIG. 106(A), the apparatus include a dispensing Intelligent Contact Lens 2750 adapted to facilitate the dispensing of substances 2752 such as eye drops, and preferably actuated by eyelid motion. The apparatus is preferably utilized as a single use and is disposable. The Intelligent Contact Lens in FIG. 106(A) includes a main body 2754 to engage the surface of the eye and a reservoir 2760. The reservoir 2760 has the distal end 2756 partially covered with three membranes 2758, 2762, 2764. The closure-seal membranes 2758, 2762, 2764 are applied to the open distal end 2756 of the reservoir 2760 facing the eye surface. Illustratively, the membrane 2764 spans a hole 2766 in the open distal end 2756 of the reservoir 2760 to encapsulate the liquid or powder inside said reservoir 2760. The membranes 2758, 2762, 2764 and walls 2768 of the reservoir 2760 ensure leak-proof retention of the substance 2752 inside said reservoir 2760. The reservoir 2760 can be made of elastic material which is compressible. The reservoir 2760 component and surrounding main body structure 2754 is made to be deformable by pressure applied against said reservoir.

FIG. 106(B) shows the main body 2754 joined by a shaft 2772 which is connected to a handle 2774. The handle 2774 is used to facilitate placement and removal of the dispensing ICL 2750 to and from the eye.

In reference to FIG. 107(A), the actuating element to cause deformation of the reservoir 2760 with extrusion of its contents is preferably provided by pressure applied by the eyelid 2770 during blinking or closure of the eye. The eyelid motion provides the most universal and natural actuating force. Everybody without disease blinks in the same manner. People from difference races blink in the same manner. The process of blinking in a normal person does not age and a 70 year old person blinks in the same manner as a 20 year old. The closure of the eye or blinking produces a 10 mmHg increase in pressure and applies a force of 25,000 dynes against the exterior surface of the main body 2754 and reservoir 2760.

FIG. 107(A) also shows this squeezing pressure by the eyelid 2770 which exceeds the bursting strength of the membrane portion 2764 and the membrane 2764 is then ruptured. FIG. 107(A) yet shows the dispensing ICL 2750 partially compressed in its upper part encompassing membrane 2764 by the squeezing pressure of the eyelid 2770. The liquid 2752 is expelled from reservoir 2760 and directed toward the surface of the eye and absorbed by the eye. The liquid permeates the cornea 2776 and can be seen in the anterior chamber 2778 of the eye.

FIG. 107(B) shows the dispensing ICL 2750 completely compressed by the eyelid 2770 with the medication 2752 absorbed by the eye and present in large quantities in the anterior chamber 2778 of the eye. The main body 2754 of the compressed dispensing ICL 2750 serves as a surface to increase retention time.

Another advantage of the present dispensing means is the ability of increasing retention time by interposing a surface such as the main body 2754 against the fluid 2752 which increases penetration. One important problem when administering topical eye drops is that the medication is drained through the lacrimal canal and absorbed by the circulation in the nose and throat. This is experienced when applying eye drops, when one can taste the drops. A serious problem, including death reported in the literature, occur due to the absorption of eye drops by the naso-pharingeal circulation.

By increasing retention time as provided with the methods and apparatus described herein, there is elimination or reduction of unwanted drainage and systemic absorption of medications designed to be used in the eye. The increased retention time and surface barrier by the main body 2754 of the dispensing ICL 2750 prevents the unwanted drainage of the eye medication. Thus, the dispensing ICL provides a much safer way for the delivery of medications to the eye. In addition, the ICL dispensing system 2750 provides a more cost-effective solution. The increased retention time increases absorption of medication by the eye, and thus less medication is wasted.

Although, the preferred embodiment includes a reservoir with membranes that can be broken, it is understood that the dispensing function can be accomplished without the rupture of the membrane. The pressure applied by the eyelid during closure of the eye can cause increased permeation of the wall and membranes to the medication present inside the reservoir. The medication can then reach the eye surface through intact walls of the reservoir and without fracture of the seal to initiate passage of the liquid. Although the cornea was described as a preferred embodiment, other parts in the surface of the eye can be used for placement of the dispensing ICL with the actuation means preferably provided by the squeezing pressure of the eyelid. Although a permanently fixed shaft 2772 and handle 2774 was described, it is understood that a detachable shaft 2772 and handle 2774 can be used.

It is also understood that although reservoirs were used, a sponge-like material that absorbs fluid a certain predetermined amount over a set period of time can be used. The sponge dispensing ICL is then placed on the eye in a similar fashion. The pressure of the eyelid during closure of the eye can then squeeze the fluid present in the sponge structure. Multiple membranes can also be used to allow the medication to be in contact with a large surface of the eye for better absorption as well as a combination of multiple membranes and a sponge part.

Although the preferred embodiment relates to using blinking as the actuating force, it is understood that squeezing of the eyelids or applying pressure from the outside can be used as actuating means. FIG. 108 shows pressure being applied by an external source 2880 such as a finger or massage motion against the closed eyelids 2770 with the dispensing ICL 2750 underneath said eyelid 2770. This alternative embodiment can be used by patients with severe disorders of the muscles of the eyelid or with eyelid nerve damage as means to enhance pressure applied by said diseased eyelid. Pressing with the finger or massaging the dispensing ICL is less desirable due to the enormous variation in force applied and risk of injury.

Although, the preferred embodiment uses a membrane that can be fractured under pressure, it is understood that a one way valve, single or multiple, alone or in combination with fracturable membranes can be used. Any other means, valves, or membranes that retain the substance in the reservoir and which release the substance upon deformation can be used in the dispensing ICL.

FIG. 109 shows a dispensing ICL 2750 with a dual reservoir 2882, 2884, for example, with two different medications including timolol gel 2886 and latanoprost 2888 which are medications used for glaucoma treatment. A single or multiple reservoir configuration can be used for single or multiple delivery of medications.

In order to facilitate placement, handles can be included and grasped by fingers or forceps for insertion without touching the main body. Alternatively the body can be made out of magnetic material and a magnetic applicator used for placement and removal of the dispensing ICL. In addition, part of the main body can be made of rigid material to allow securely grasping of the dispensing ICL without touching the reservoirs.

An alternating embodiment for the dispensing ICL is shown in FIGS. 110(A) and 110(B). This alternative embodiment isolates the liquid from the main body of the contact device engaging the eye. The apparatus includes a liquid containing squeezable bulb 2890 joined by a conduit 2892 to a main body contact device 2900 in apposition to the eye 2894. A rupturable membrane or seal 2896 contains and isolates the liquid 2752 from the main body contact device 2900 and keep said liquid 2752 confined to the storage bulb 2890. The contact device 2900 is connected by a conduit 2892 to the storage bulb 2890. The contact device 2900 has multiple openings 2902 in its concave surface through which the liquid 2752 from the conduit 2892 flows to the surface of the eye 2894. The contact device 2900 serves to direct the liquid 2752 to the surface of the eye 2894 and to increase retention time for the liquid 2752 being applied to the eye 2894.

In use the patient places the contact device 2900 on the surface of the eye 2894 and squeezes the bulb 2890. FIG. 110(B) shows the bulb 2890 partially squeezed by pressure P to illustrate the dynamics of the dispensing process. This pressure P directs the liquid 2752 against the seal 2896 to cause its rupture and force the liquid 2752 through the conduit 2892. The liquid 2752 then travels to the contact device 2900, enters the channel 2904 and is delivered to the surface of the eye 2894, which includes the cornea and/or conjunctiva. The dimensions of bulb 2890 and contact device 2900 are made to deliver the appropriate amount of medication according to the prescribed dosage by the doctor.

Although one storage area in the bulb was described, it is understood that multiple storage areas in the bulb can be used. Besides, the storage bulb can be of a detachable type. The storage bulb can have two compartments, one with air and one with liquid and a dual membrane seal. The first membrane seal is interposed between the air and liquid storage areas and the second membrane seal between the liquid storage area and the conduit. This embodiment allows delivery of the total amount of liquid in the storage liquid compartment as the air fills the remainder of the conduit and contact device. In addition, tubular means connected to the storage bulb or a medication dispenser can be used to create a gap in the eyelid pocket and precisely deliver the medication into said eyelid pocket. This can be done with the tubular fluid delivery means alone or coupled to a member that facilitate positioning and/or opening of the eyelid pocket.

The reservoir with the medication can be encased in the main body during manufacturing or assembly of the ICL by conventional contact lens manufacturing means. A variety of conventional manufacturing processes for contact lens can be used including injection molding, light-cured polymerization, casting process, sheet forming, compression, automatic or manual lathe cutting techniques, and the like. An exemplary way can include placement in the molding cavity of a pellet which has the medication sealed with a membrane. The polymer injected in the cavity surrounding the pellet forms the body of the dispensing ICL. The pellet containing medication encased by the surrounding polymer turns into the reservoir in the dispensing ICL.

While several embodiments of the present invention have been shown and described, alternate embodiments and combination of embodiments and/or features will be apparent to those skilled in the art and are within the intended scope of the present invention.

I claim:

1. An apparatus for noninvasive measurement of the concentration of at least one substance in conjunctival tissue of the eye, said apparatus comprising:
    a source of electromagnetic radiation optically coupled to a remote transmitter, said remote transmitter being configured to irradiate one side of the conjuctival tissue of the eye,
    a detecting device optically coupled with a remote receiver, said remote receiver being configured to be located on an opposite side from the one side of the conjuctival tissue and exteriorly of the eye and collecting electromagnetic radiation emitted by the substance being measured in the conjuctival tissue,
    said detecting device being configured for detecting an intensity of the electromagnetic radiation and providing an output signal representative of the detected intensity of said radiation,
    the remote receiver and the remote transmitter being maintained spaced from each other and located diametrically opposed to each other at corresponding terminal ends of two arms, said two arms extending from the source of electromagnetic radiation and from the detecting device, respectively, said two arms being bent outwardly from the source of electromagnetic radiation and from said detecting device, said two arms then being bent inwardly and terminating at said remote receiver and said remote transmitter, respectively, in a forceps configuration to space the remote receiver and said remote transmitter from each other, and
    an analyzer/processor configured to calculate a concentration of the substance of interest in the conjunctival tissue of the eye from the output signal.

2. The apparatus of claim 1, wherein said at least one substance includes at least one of glucose, cholesterol and ethanol.

3. The apparatus of claim 1, further comprising a filter for selecting a wavelength corresponding to absorption of infrared energy by the substance being measured.

4. The apparatus of claim 3, wherein the filter has a bandwidth centered on about 2,120 nm.

5. The apparatus of claim 3, wherein the filter has a bandwidth centered on about 2,300 nm.

6. The apparatus of claim 3, wherein the filter has a bandwidth centered on about 3,300 nm.

7. The apparatus of claim 1, wherein the remote receiver is an infrared sensor.

8. The apparatus of claim 1, wherein electromagnetic radiation from the source of electromagnetic radiation is transmitted by an optical fiber cable to the remote transmitter.

9. The apparatus of claim 8, wherein the remote receiver includes a collection of optical fibers.

10. A method for noninvasive measurement of at least one substance in a plasma/conjunctiva interface of the eye, said method comprising the steps of:
    irradiating one side of the plasma/conjunctiva interface of the eye with electromagnetic radiation exteriorly of the eye from a source of electromagnetic radiation,
    positioning a collector of electromagnetic radiation diametrically opposed to the source of electromagnetic radiation on an opposite side from the one side of the plasma/conjunctiva interface exteriorly of the eye, said collector of electromagnetic radiation and said source of electromagnetic radiation being spaced apart in a forceps configuration, collecting by the collector electromagnetic radiation emitted by the substance in the plasma/conjunctiva interface of the eye, detecting an intensity of electromagnetic radiation emitted by the substance being measured in the plasma/conjunctiva interface of the eye and collected by the collector, and providing an output signal representative of the intensity of said radiation collected by the collector and calculating a concentration of the substance in the plasma/conjunctiva interface of the eye from the output signal in the absence of surgical intervention.

11. The method of claim 10, wherein an output of the source of electromagnetic radiation and an input of the collector of radiation are in contact with the eyelid of the eye.

* * * * *